United States Patent
Ham et al.

(10) Patent No.: US 8,003,658 B2
(45) Date of Patent: Aug. 23, 2011

(54) QUINAZOLINE DERIVATIVES FOR INHIBITING CANCER CELL GROWTH AND METHOD FOR THE PREPARATION THEREOF

(75) Inventors: Young Jin Ham, Seoul (KR); Ji Hyeon Gong, Osan-si (KR); Mi Young Cha, Suwon-si (KR); Jong Woo Kim, Seoul (KR); Maeng Sup Kim, Seoul (KR); Eun Young Kim, Suwon-si (KR); Ji Yeon Song, Suwon-si (KR); Chang In Kim, Seoul (KR); Se Young Kim, Seongnam-si (KR); Gwan Sun Lee, Seoul (KR)

(73) Assignee: Hanmi Holdings Co., Ltd., Seoul (KR)

( * ) Notice: Subject to any disclaimer, the term of this patent is extended or adjusted under 35 U.S.C. 154(b) by 1071 days.

(21) Appl. No.: 11/722,096

(22) PCT Filed: Dec. 20, 2005

(86) PCT No.: PCT/KR2005/004395
§ 371 (c)(1),
(2), (4) Date: Jun. 19, 2007

(87) PCT Pub. No.: WO2006/071017
PCT Pub. Date: Jul. 6, 2006

(65) Prior Publication Data
US 2008/0009509 A1    Jan. 10, 2008

(30) Foreign Application Priority Data
Dec. 29, 2004 (KR) .......... 10-2004-0114839
Nov. 22, 2005 (KR) .......... 10-2005-0111724

(51) Int. Cl.
*A61K 31/517* (2006.01)
*C07D 239/72* (2006.01)

(52) U.S. Cl. ............... 514/266.1; 514/266.2; 514/266.4; 544/235

(58) Field of Classification Search .................. None
See application file for complete search history.

(56) References Cited

U.S. PATENT DOCUMENTS

2002/0082270 A1    6/2002    Himmelsbach et al.

FOREIGN PATENT DOCUMENTS

| EP | 602851 A1 | 6/1994 |
|---|---|---|
| WO | WO 97/30034 A1 | 8/1997 |
| WO | WO 99/09016 A1 | 2/1999 |
| WO | WO 01/85760 | * 11/2001 |
| WO | WO 02/068396 A1 | 9/2002 |

OTHER PUBLICATIONS

Cha et al. Journal of Medicinal Chemistry, 2009, 52, 6880-6888.*
Cancer definition:, http://www.medterms.com/script/main/art.asp?articlekey=2580, accessed Nov. 27, 2007.*
Albuschat, R., et al., "4-Anilinoquinazolines with Lavendustin A subunit as inhibitors of epidermal growth factor receptor tyrosine kinase: syntheses, chemical and pharmacological properties," European J. of Medicinal Chemistry, 2004, 39, pp. 1001-1011.

* cited by examiner

*Primary Examiner* — Noble Jarrell
(74) *Attorney, Agent, or Firm* — Sughrue Mion, PLLC

(57) ABSTRACT

The present invention relates to a novel quinazoline derivative and a pharmaceutically acceptable salt thereof for inhibiting the growth of cancer cells, a method for the preparation thereof and a pharmaceutical composition comprising same as an active ingredient.

11 Claims, No Drawings

QUINAZOLINE DERIVATIVES FOR INHIBITING CANCER CELL GROWTH AND METHOD FOR THE PREPARATION THEREOF

This is a National Stage under 35 U.S.C. §371 of PCT/KR2005/004395 filed Dec. 20, 2005, which claims benefit from Korean Patent Application 10-2004-0114839 filed Dec. 29, 2004 and Korean Patent Application 10-2005-0111724 filed Nov. 22, 2005, the entire disclosures of which are incorporated by reference.

FIELD OF THE INVENTION

The present invention relates to a novel quinazoline derivative and a pharmaceutically acceptable salt thereof for inhibiting the growth of cancer cells, a method for the preparation thereof and a pharmaceutical composition comprising same as an active ingredient.

BACKGROUND OF THE INVENTION

Most of the traditional drugs used for treating cancers, e.g., taxanes such as paclitaxel and doxetaxel; vinca alkaloid such as vincristine, vinblastine and vinorelbin; anthracyclines such as daunomycin and doxorubicin; camptothecins such as topotecan, irinotecan; actinomycin; and etopocid are based on selective cytotoxicity, but such selectivity against cancer cells has been unsatisfactory to cause many side effects.

To overcome such a problem, recent studies have focused on specific molecular level targets in the cell to maximize the therapeutic effect of an anticancer agent without causing adverse side effects.

In cells, there are many signal transduction systems, which are functionally linked to each other to control the proliferation, growth, metastasis and apoptosis of cells. A breakdown of the intracellular controlling system by genetic and environmental influences may cause abnormal amplification or destruction of the signal transduction system so that the possibility for tumor cell generation occurs.

Protein tyrosine kinases play important roles in such cellular regulation, and their abnormal expression or mutation has been observed in cancer cells. Protein tyrosine kinase is an enzyme which catalyzes the transportation of phosphate groups from ATP to tyrosines located on the protein substrate. Many growth factor receptor proteins function as tyrosine kinases to transport cellular signals. The interaction between growth factors and their receptors normally controls the cellular growth, but abnormal signal transduction caused by the mutation or overexpression of any of the receptors may induce tumor cells or cancers.

Protein tyrosine kinases have been classified into many families in terms of growth factors, and epithelial cell growth factors (EGFs)-related EGF receptor (EGFR) tyrosine kinase have been intensely studied. An EGFR tyrosine kinase is composed of a receptor and tyrosine kinase, and delivers extracellular signals to the cell nuclear through the cellular membrane. The EGFR tyrosine kinases are classified by their structural differences into EGFR (Erb-B1), Erb-B2, Erb-B3, Erb-B4, and all of the above members can form a homodimer- or heterodimer-signal delivery complex. Also, overexpression of more than one member of the above mentioned homodimers is often observed in malignant cells.

Therefore, the inhibition of mutated or overexpressed EGFR tyrosine kinases has been considered to be useful for treating tumors, and many drugs have been developed therefor, e.g., Gefitinib, Erlotinib, Camertinib, Lapatinib.

International Patent Publications WO 96/033981, WO 96/033979, WO 97/038994 and WO 96/033980 each discloses a quinazoline derivative substituted with an alkoxyalkylamino or alkylaminoalkoxy group, International Patent Publications WO 97/030034 and WO 96/016960 each discloses quinazoline substituted with aryl or heteroaryl, and International Patent Publications WO 2003/040109 and WO 2003/040108 disclose compounds having aminoalkoxy substituents at position 5 of quinazoline (Nomenclature of quinazoline is according to a reference [J. A. Joule, Chapman & Hall, *Heterocyclic chemistry*, 3rd Ed., 189]).

International Patent Publication WO 95/019970 and U.S. Pat. Nos. 5,654,307 and 5,679,683 each discloses various tricyclic heteroaryl compounds, International Patent Publications WO 99/006396, WO 99/006378, WO 97/038983, WO 2000/031048, WO 98/050038, WO 99/024037 and WO 2000/006555, and European Patent 787722 each discloses quinazoline compounds that inhibit the tyrosine kinase irreversably, U.S. Pat. No. 6,225,318, European Patents 0387063 and 01292591, and International Patent Publications WO 2001/098277, WO 2003/045939 and WO 2003/049740 each discloses compounds having various alkenyl or alkynyl substituents at position 6 of quinazoline.

Also, International Patent Publications WO 98/043960, WO 2000/018761, WO 2001/047892, WO 2001/072711, WO 2003/050090, WO 99/09016, WO 2000/018740 and WO 2000/66583 disclose 3-cyanoquinoline compounds, International Patent Publications WO 98/002434, WO 98/002437, WO 99/035132, WO 99/035146, WO 2001/004111 and WO 2002/002552 each discloses various quinazoline compounds substituted with furan having various sulfonealkylamino substituents, and International Patent Publications WO 2003/053466 and WO 2001/094353 disclose specific thienopyrimidine compounds.

Further, International Patent Publications WO 2001/012227, WO 2004/014386, WO 2004/035057 and WO 2001/076586 disclose various methods for treating tumors that employ specific drugs that interact with EGFR tyrosine kinase in combination with radiation therapy.

However, the above mentioned conventional quinazoline derivatives have to be taken in large dose for intended treatments, which causes such side effects such as diarrhea and skin eruption. Accordingly, there has continued to exist a need to develop an effective drug that gives no adverse side effect.

SUMMARY OF THE INVENTION

Accordingly, it is an object of the present invention to provide a novel quinazoline derivative which selectively inhibits the cancer cell growth caused by epitherial growth factor without any side effects, and a method for the preparation thereof.

It is another object of the present invention to provide a phamarceutical composition for inhibiting cancer cell growth comprising the quinazoline derivative as an active ingredient.

In accordance with one aspect of the present invention, there is provided a quinazoline derivative of formula (I) or a pharmaceutically acceptable salt thereof:

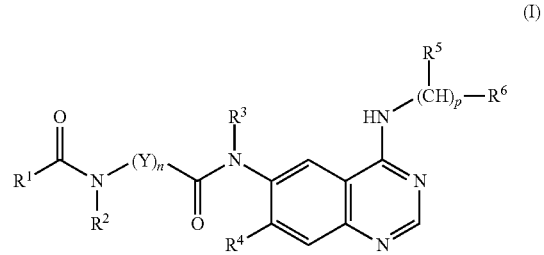

wherein, $R^1$ is hydrogen, $C_{1-6}$alkyl, $C_{3-7}$cycloalkyl, $C_{2-6}$alkenyl, $C_{2-6}$alkynyl, $C_{1-6}$alkoxy, $C_{1-6}$alkylamino, $C_{1-6}$dialkylamino, $C_{1-6}$alkylthio, aryl or heteroaryl which is optionally substituted with X;

$R^2$ and $R^3$ are each independently hydrogen, hydroxy, $C_{1-6}$alkyl, $C_{3-7}$cycloalkyl, hydroxy$C_{1-5}$alkyl, $C_{1-6}$alkoxy $C_{1-6}$alkyl, amino$C_{1-6}$alkyl, $C_{1-6}$alkylamino$C_{1-6}$alkyl or $C_{1-6}$dialkylamino$C_{1-6}$alkyl;

Y is —$(CR^{11}R^{12})$—, aryl or heteroaryl, $R^{11}$ and $R^{12}$ being each independently hydrogen, halogen, hydroxy, amino, nitro, cyano, thiol, carboxylic acid, carbamoyl; $C_{1-6}$alkyl, $C_{1-6}$alkylamino, $C_{1-6}$dialkylamino, $C_{1-6}$alkoxy, $C_{1-6}$alkylthio, $C_{1-6}$alkylsulfinyl, $C_{1-6}$alkylsulfonyl, $C_{1-6}$alkyloxysulfonyl, $C_{1-6}$alkylaminosulfonyl, $C_{1-6}$dialkylaminosulfonyl, $C_{1-6}$alkanoyl, $C_{1-6}$alkoxycarbonyl, $C_{1-6}$alkylcarbamoyl, $C_{1-6}$dialkylcarbamoyl, $C_{1-6}$alkylthiocarbonyl, $C_{1-6}$alkanoyloxy, $C_{1-6}$alkyloxycarbonyloxy, $C_{1-6}$alkylaminocarbonyloxy, $C_{1-6}$dialkylaminocarbonyloxy, $C_{1-6}$alkylthiocarbonyloxy, $C_{1-6}$alkanoylamino, $C_{1-6}$alkoxycarbonylamino, $C_{1-6}$alkyl or $C_{1-6}$dialylureido, $C_{1-6}$alkyl, $C_{1-6}$dialkylguanidino, aryl, or heteroaryl which is optionally substituted with substituent Z; or optionally fused to each other to form a 3 to 8-membered non-aromatic ring, or $R^{11}$ or $R^{12}$ may be fused to $R^2$ or $R^3$ to form together with the carbon and nitrogen they are attached to a 4 to 8-membered non-aromatic ring;

$R^4$ is hydrogen, halogen, hydroxy, amino, or $C_{1-6}$alkyl, $C_{1-6}$alkoxy or $C_{1-6}$alkylamino optionally substituted with $R^{13}$, $R^{13}$ being halogen, cyano, trifluoromethyl, trifluoromethoxy, $C_{1-6}$alkoxy, $C_{1-6}$alkylamino, $C_{1-5}$dialkylamino, aryl or heteroaryl);

$R^5$ is hydrogen or $C_{1-3}$alkyl;

$R^6$ is $R^{14}$, aryl or heteroaryl optionally substituted with $R^{15}$, $R^{14}$ and $R^{15}$ being each independently hydrogen, halogen, trifluoromethyl, trifluoromethoxy, nitro, $C_{1-6}$alkyl, $C_{1-6}$alkoxy, $C_{1-6}$alkylamino, $C_{1-6}$dialkylamino, or aryl, heteroaryl, arylalkyl, heteroarylalkyl, arylalkoxy, heteroarylalkoxy, aryloxy, heteroaryloxy, aryloxycarbonyl, heteroaryloxycarbonyl, arylcarbonyl, heteroarylcarbonyl, arylcarbamoyl, heteroarylcarbamoyl, arylsulfonyl or heteroarylsulfonyl optionally substituted with $R^{16}$, wherein $R^{16}$ is halogen, nitro, $C_{1-6}$alkyl, $C_{1-6}$alkoxy, $C_{1-6}$alkylamino or $C_{1-6}$dialkylamino;

n is an integer in the range of 1 to 6;

p is 0 or 1;

X and Z are each independently hydrogen, halogen, nitro, hydroxy, amino, cyano, thiol, carboxylic acid, carbamoyl, trifluoromethyl, trifluoromethoxy, $C_{1-6}$alkyl, $C_{3-7}$cycloalkyl, $C_{2-6}$alkenyl, $C_{2-6}$alkynyl, $C_{1-6}$alkoxy, $C_{1-6}$alkylamino, $C_{1-6}$dialkylamino, $C_{1-6}$alkylthio, $C_{1-6}$alkylsulfinyl, $C_{1-6}$alkylsulfonyl, $C_{1-6}$alkylsulfonylamino, $C_{1-6}$alkylcarbonyl, $C_{1-6}$alkylthiocarbonyl, $C_{1-6}$alkyloxycarbonyl, $C_{1-6}$alkylcarbamoyl, $C_{1-6}$dialkylcarbamoyl, $C_{1-6}$alkanoyl, $C_{1-6}$alkanoyloxy, $C_{1-6}$alkoxycarbonyloxy, $C_{1-6}$alkylaminocarbonyloxy, $C_{1-6}$dialkylaminocarbonyloxy, $C_{1-6}$alkylthiocarbonyloxy, $C_{1-6}$alkanoylamino, $C_{1-6}$alkoxycarbonylamino, $C_{1-6}$alkylureido, $C_{1-6}$dialkylureido, $C_{1-6}$alkylguanidino, $C_{1-6}$dialkylguanidino, $C_{1-6}$alkoxysulfonyl, $C_{1-6}$alkylaminosulfonyl, $C_{1-6}$dialkylaminosulfonyl, $C_{1-6}$alkylsulfamoyl, $C_{1-6}$alkylaminosulfamoyl, $C_{1-6}$dialkylaminosulfamoyl, aryl or heteroaryl; wherein aryl is $C_{5-12}$ monocylic or bicyclic aryl;

heteroaryl is a 5 to 13-membered heteroaromatic or non-aromatic group containing one or more of the elements selected from the group consisting of N, O, S, SO and $SO_2$; and The optionally substituted aryl and heteroaryl each has one or more substituents selected from the group consisting of halogen, hydroxy, amino, nitro, cyano, $C_{1-6}$alkyl, $C_{1-6}$alkoxy, $C_{1-6}$alkylamino and $C_{1-6}$dialkylamino.

DETAILED DESCRIPTION OF THE INVENTION

In the quinazoline derivative of formula (I) of the present invention, $R^1$ is preferably methyl, cyclopropyl, trifluoromethyl, cyanomethyl, chloromethyl, phenyl, methoxy, phenoxy, benzyloxy, methoxymethyl, acetoxymethyl, dimethylaminoethoxymethyl, methoxyethoxymethyl, methylthiomethyl, methanesulfinylmethyl, methanesulfonylmethyl, dimethylaminomethyl, morpholinomethyl, 4-methylpiperazinylmethyl, methanesulfonylethylaminomethyl, methoxyethylaminomethyl, ethoxycarbonyl, ethylamino, furan-3-yl, furan-2-yl-methylamino, benzamino, benzylamino, t-buthoxy, 3-methyl-isoxazol-5-yl, 5-methyl-isoxazol-4-yl, 1H-pyrazol-4-yl, vinyl, penta-1,3-dienyl, cyclopentenyl, 2-phenylvinyl, 2-methylvinyl, 2,2-dimethylvinyl, 1-methylvinyl, 2-phenylethynyl, 2-methylethynyl, 2-(bromomethyl)vinyl, 2-(dimethylaminomethyl)vinyl, 2-(morpholinomethyl)vinyl, 2-(4-methylpiperazinylmethyl)vinyl, 2-((N-methyl-(2-hydroxyethyl)amino)methyl)vinyl or 2-(methanesulfonylethylaminomethyl)vinyl;

$R^2$ and $R^3$ are preferably each independently hydrogen, methyl, ethyl or 3-(N,N-dimethylamino)propyl;

$R^4$ is preferably hydrogen, amino, hydroxyl, fluoro, chloro, methoxy, ethoxy, methoxyethoxy, methoxypropoxy, ethylsulfanyl, cyclopropylmethoxy, cyclopentyloxy, 2,2,2-trifluoroethoxy, 2-fluoroethoxy, N,N-dimethylamino, morpholinopropoxy or 4-methylpiperadinylmethoxy;

$R^5$ is preferably hydrogen;

$R^6$ is preferably 1-phenyl-ethyl, 3-ethynyl-phenyl, biphenyl, 3-chloro-4-fluoro-phenyl, 3-chloro-4-(3-fluoro-benzyloxy)-phenyl, 3-methyl-4-(6-methyl-pyridin-3-yloxy)-phenyl, 4-[2-(6,7-dimethoxy-3,4-dihydro-1H-isoquinolin-2-yl)-ethyl]-phenyl, N-phenyl-benzamid-4-yl, 3-chloro-4-(pyridin-2-ylmethoxy)-phenyl, 3-chloro-4-(pyridin-3-ylmethoxy)-phenyl, 3-chloro-4-(6-methyl-pyridin-2-ylmethoxy)-phenyl, 3-chloro-4-(pyridin-4-ylmethoxy)-phenyl, 3-methyl-4-(pyridin-2-ylmethoxy)-phenyl, 1-pyridin-2-ylmethyl-1H-indazol-5-yl, 1-(3-fluoro-benzyl)-1H-indazol-5-yl, 1-penta-2,4-dienyl-1H-indazol-5-yl, 3-chloro-4-(2-fluoroethoxy)-phenyl, 2-methyl-1H-indol-5-yl or 1-benzyl-1H-indazol-5-yl;

Y is preferably —$(CR^{11}R^{12})$—, aryl or heteroaryl, $R^{11}$ and $R^{12}$ being each independently hydrogen, amino, hydroxyl, halogen, $C_{1-6}$alkyl, $C_{1-3}$alkenyl, $C_{1-6}$alkyl$C_{1-6}$alkyl, hydroxyl$C_{1-3}$alkyl, di$C_{1-3}$alkylamino$C_{1-3}$alkyl, $C_{1-3}$alkoxy$C_{1-3}$alkyl, $C_{1-3}$alkylsulfonyl$C_{1-3}$alkyl, $C_{1-3}$alkylsulfinyl$C_{1-3}$alkyl, $C_{1-3}$alkylsulfanyl$C_{1-3}$alkyl, carboxy$C_{1-3}$alkyl, $C_{1-3}$alkoxycarbonyl$C_{1-3}$-yl, di$C_{1-3}$alkylamino, $C_{1-3}$alkoxy, $C_{1-6}$alkanoyloxy, $C_{1-6}$alkylcarbamoyl, aryl, heteroaryl, or $C_{1-3}$alkyl substituted with aryl or heteroaryl, the aryl or heteroaryl is phenyl, naphtyl, furan, thiophene, imidazole, triazole, pyridine, oxazole, isoxazole, thiazole, indole, quinoline, isoquinoline, quinazoline, aziridine, azetidine, pyrrolidine, piperidine, morpholine, piperazine, thiomorpholine or 4-pyridone, or optionally fused to each other to form a 3 to 8-membered non-aromatic ring, or $R^{11}$ or $R^{12}$ may be fused to $R^2$ or $R^3$ to form together with the carbon and nitrogen they are attached to a 4 to 8-membered non-aromatic ring; and Preferable n is an integer in the range of 1 to 4.

In the present invention, the term 'halo' refers to fluoro, chloro, bromo or iodo, unless otherwise indicated.

In the present invention, the term 'alkyl' refers to a monovalent saturated hydrocarbon compound having linear, circular or branched residue, 'alkenyl' and 'alkynyl' refer to the said alkyl compound having carbon-carbon double bond and triple bond, respectively, when the alkyl is composed of 2 or more carbon atoms.

In the present invention, the term 'alkoxy' refers to an oxygen derivative of the said alkyl, unless otherwise indicated.

In the present invention, the term 'aryl' refers to an aromatic hydrocarbon such as phenyl or naphtyl, unless otherwise indicated.

Examples of more preferred compounds of formula (I) according to the present invention are:

1) ({4-[3-chloro-4-(3-fluoro-benzyloxy)-phenylamino]-quinazolin-6-ylcarbamoyl}-methyl)-carbamic acid t-butylester;
2) N-({4-[3-chloro-4-(3-fluoro-benzyloxy)-phenylamino]-quinazolin-6-ylcarbamoyl}-methyl)-2-methoxy-acetamide;
3) N-({4-[3-chloro-4-(3-fluoro-benzyloxy)-phenylamino]-quinazolin-6-ylcarbamoyl}-methyl)-2-methanesulfonyl-acetamide;
4) N-({4-[3-chloro-4-(3-fluoro-benzyloxy)-phenylamino]-quinazolin-6-ylcarbamoyl}-methyl)-acrylamide;
5) (2S)—N-{4-[3-chloro-4-(3-fluoro-benzyloxy)-phenylamino]-quinazolin-6-yl}-2-(2-methoxy-acetylamino)-3-phenyl-propionamide;
6) (1S)-(1-{4-[3-chloro-4-(3-fluoro-benzyloxy)-phenylamino]-quinazolin-6-ylcarbamoyl}-3-methanesulfanyl-propyl)-carbamic acid t-butylester;
7) (2S)—N-{4-[3-chloro-4-(3-fluoro-benzyloxy)-phenylamino]-quinazolin-6-yl}-2-(2-methoxy-acetylamino)-4-methanesulfanyl-butyramide;
8) (2S)—N-{4-[3-chloro-4-(3-fluoro-benzyloxy)-phenylamino]-quinazolin-6-yl}-2-(2-methanesulfonyl-acetamino)-4-methanesulfanyl-butyramide;
9) (2S)-2-acryloylamino-N-{4-[3-chloro-4-(3-fluoro-benzyloxy)-phenylamino]-quinazolin-6-yl}-4-methanesulfanyl-butyramide;
10) (1-{4-[3-chloro-4-(3-fluoro-benzyloxy)-phenylamino]-quinazolin-6-ylcarbamoyl}-cyclopropyl)-carbamic acid t-butylester;
11) (2S)—N-{4-[3-chloro-4-(3-fluoro-benzyloxy)-phenylamino]-quinazolin-6-yl}-2-(2-methoxy-acetylamino)-2-phenyl-acetamide;
12) (4S)-4-t-buthoxycarbonylamino-4-{4-[3-chloro-4-(3-fluoro-benzyloxy)-phenylamino]-quinazolin-6-ylcarbamoyl}-butyric acid methylester;
13) 4-{4-[3-chloro-4-(3-fluoro-benzyloxy)-phenylamino]-quinazolin-6-ylcarbamoyl}-4-(2-methoxy-acetylamino)-butyric acid methylester;
14) 4-{4-[3-chloro-4-(3-fluoro-benzyloxy)-phenylamino]-quinazolin-6-ylcarbamoyl}-4-(2-methoxy-acetylamino)-butyric acid;
15) 2-{4-[3-chloro-4-(3-fluoro-benzyloxy)-phenylamino]-quinazolin-6-ylcarbamoyl}-pyrrolidine-1-carboxylic acid t-butylester;
16) 1-(2-methoxy-acetyl)-pyrrolidine-2-carboxylic acid {4-[3-chloro-4-(3-fluoro-benzyloxy)-phenylamino]-quinazolin-6-yl}-amide;
17) 1-(2-methanesulfonyl-acetyl)-pyrrolidine-2-carboxylic acid {4-[3-chloro-4-(3-fluoro-benzyloxy)-phenylamino]-quinazolin-6-yl}-amide;
18) 1-acryloyl-pyrrolidine-2-carboxylic acid {4-[3-chloro-4-(3-fluoro-benzyloxy)-phenylamino]-quinazolin-6-yl}-amide;
19) (2-{4-[3-chloro-4-(3-fluoro-benzyloxy)-phenylamino]-quinazolin-6-ylcarbamoyl}-ethyl)-carbamic acid t-butylester;
20) N-{4-[3-chloro-4-(3-fluoro-benzyloxy)-phenylamino]-quinazolin-6-yl}-3-(2-methoxy-acetylamino)-propionamide;
21) N-{4-[3-chloro-4-(3-fluoro-benzyloxy)-phenylamino]-quinazolin-6-yl}-3-(2-methanesulfonyl-acetylamino)-propionamide;
22) N-(2-{4-[3-chloro-4-(3-fluoro-benzyloxy)-phenylamino]-quinazolin-6-ylcarbamoyl}-ethyl)-acrylamide;
23) 3-phenyl-propionylic acid (2-{4-[3-chloro-4-(3-fluoro-benzyloxy)-phenylamino]-quinazolin-6-ylcarbamoyl}-ethyl)-amide;
24) hexa-2,4-dienonylic acid (2-{4-[3-chloro-4-(3-fluoro-benzyloxy)-phenylamino]-quinazolin-6-ylcarbamoyl}-ethyl)-amide;
25) cyclopent-1-en carboxylic acid (2-{4-[3-chloro-4-(3-fluoro-benzyloxy)-phenylamino]-quinazolin-6-ylcarbamoyl}-ethyl)-amide;
26) N-(2-{4-[3-chloro-4-(3-fluoro-benzyloxy)-phenylamino]-quinazolin-6-ylcarbamoyl}-ethyl)-3-phenyl-acrylamide;
27) but-2-ynoylic acid(2-{4-[3-chloro-4-(3-fluoro-benzyloxy)-phenylamino]-quinazolin-6-ylcarbamoyl}-ethyl)-amide;
28) but-2-enonylic acid (2-{4-[3-chloro-4-(3-fluoro-benzyloxy)-phenylamino]-quinazolin-6-ylcarbamoyl}-ethyl)-amide;
29) 3-methyl-but-2-enonylic acid (2-{4-[3-chloro-4-(3-fluoro-benzyloxy)-phenylamino]-quinazolin-6-ylcarbamoyl}-ethyl)-amide;
30) N-(2-{4-[3-chloro-4-(3-fluoro-benzyloxy)-phenylamino]-quinazolin-6-ylcarbamoyl}-ethyl)-2-methyl-acrylamide;
31) N-(2-{4-[3-chloro-4-(3-fluoro-benzyloxy)-phenylamino]-quinazolin-6-ylcarbamoyl}-ethyl)-2-cyano-acetamide;
32) 3-methyl-isoxazol-5-carboxylic acid (2-{4-[3-chloro-4-(3-fluoro-benzyloxy)-phenylamino]-quinazolin-6-ylcarbamoyl}-ethyl)-amide;
33) furan-3-carboxylic acid (2-{4-[3-chloro-4-(3-fluoro-benzyloxy)-phenylamino]-quinazolin-6-ylcarbamoyl}-ethyl)-amide;
34) 1H-pyrazol-4-carboxylic acid (2-{4-[3-chloro-4-(3-fluoro-benzyloxy)-phenylamino]-quinazolin-6-ylcarbamoyl}-ethyl)-amide;
35) N-(2-{4-[3-chloro-4-(3-fluoro-benzyloxy)-phenylamino]-quinazolin-6-ylcarbamoyl}-ethyl)-benzamide;
36) N-(2-{4-[3-chloro-4-(3-fluoro-benzyloxy)-phenylamino]-quinazolin-6-ylcarbamoyl}-ethyl)-oxalamic acid ethylester;
37) cyclopropylcarboxylic acid (2-{4-[3-chloro-4-(3-fluoro-benzyloxy)-phenylamino]-quinazolin-6-ylcarbamoyl}-ethyl)-amide;
38) acetic acid 2-t-buthoxycarbonylamino-1-{4-[3-chloro-4-(3-fluoro-benzyloxy)-phenylamino]-quinazolin-6-ylcarbamoyl}-ethylester;
39) acetic acid 1-{4-[3-chloro-4-(3-fluoro-benzyloxy)-phenylamino]-quinazolin-6-ylcarbamoyl}-2-(2-methoxy-acetylamino)-ethylester;
40) N-{4-[3-chloro-4-(3-fluoro-benzyloxy)-phenylamino]-quinazolin-6-yl}-2-hydroxyl-3-(2-methoxy-acetylamino)-propionamide;
41) (2-{4-[3-chloro-4-(3-fluoro-benzyloxy)-phenylamino]-quinazolin-6-ylcarbamoyl}-propyl)-carbamic acid t-butylester;

42) N-{4-[3-chloro-4-(3-fluoro-benzyloxy)-phenylamino]-quinazolin-6-yl}-3-(2-methoxy-acetylamino)-2-methyl-propionamide;
43) N-{4-[3-chloro-4-(3-fluoro-benzyloxy)-phenylamino]-quinazolin-6-yl}-3-(2-methanesulfonyl-acetylamino)-2-methyl-propionamide;
44) N-(2-{4-[3-chloro-4-(3-fluoro-benzyloxy)-phenylamino]-quinazolin-6-ylcarbamoyl}-propyl)-acrylamide;
45) (2-{4-[3-chloro-4-(3-fluoro-benzyloxy)-phenylamino]-quinazolin-6-ylcarbamoyl}-1-phenyl-ethyl)-carbamic acid t-butylester;
46) N-{4-[3-chloro-4-(3-fluoro-benzyloxy)-phenylamino]-quinazolin-6-yl}-3-(2-methoxy-acetylamino)-3-phenyl-propionamide;
47) N-{4-[3-chloro-4-(3-fluoro-benzyloxy)-phenylamino]-quinazolin-6-yl}-3-(2-methanesulfonyl-acetylamino)-3-phenyl-propionamide;
48) 3-(2-methoxy-acetylamino)-thiophene-2-carboxylic acid {4-[3-chloro-4-(3-fluoro-benzyloxy)-phenylamino]-quinazolin-6-yl}-amide;
49) (2-{4-[3-methyl-4-(6-methyl-pyridin-3-yloxy)-phenylamino]-quinazolin-6-ylcarbamoyl}-ethyl)-carbamic acid t-butylester;
50) 3-(2-methanesulfonyl-acetylamino)-N-{4-[3-methyl-4-(6-methyl-pyridin-3-yloxy)-phenylamino]-quinazolin-6-yl}-propionamide;
51) N-(2-{4-[3-methyl-4-(6-methyl-pyridin-3-yloxy)-phenylamino]-quinazolin-6-ylcarbamoyl}-ethyl)-acrylamide;
52) {2-[4-(3-chloro-4-fluoro-phenylamino)-quinazolin-6-ylcarbamoyl]-ethyl}-carbamic acid t-butylester;
53) N-[4-(3-chloro-4-fluoro-phenylamino)-quinazolin-6-yl]-3-(2-methanesulfonyl-acetylamino)-propionamide;
54) N-{2-[4-(3-chloro-4-fluoro-phenylamino)-quinazolin-6-ylcarbamoyl]-ethyl}-acrylamide;
55) 4-bromo-but-2-enonylic acid (2-{4-[3-chloro-4-(3-fluoro-benzyloxy)-phenylamino]-quinazolin-6-ylcarbamoyl}-ethyl)-amide;
56) 4-dimethylamino-but-2-enonylic acid (2-{4-[3-chloro-4-(3-fluoro-benzyloxy)-phenylamino]-quinazolin-6-ylcarbamoyl}-ethyl)-amide;
57) 4-morpholin-4-yl-but-2-enonylic acid (2-{4-[3-chloro-4-(3-fluoro-benzyloxy)-phenylamino]-quinazolin-6-ylcarbamoyl}-ethyl)-amide;
58) 4-(4-methyl-piperazin-1-yl)-but-2-enonylic acid (2-{4-[3-chloro-4-(3-fluoro-benzyloxy)-phenylamino]-quinazolin-6-ylcarbamoyl}-ethyl)-amide;
59) 4-[(2-hydroxyl-ethyl)-methyl-amino]-but-2-enonylic acid (2-{4-[3-chloro-4-(3-fluoro-benzyloxy)-phenylamino]-quinazolin-6-ylcarbamoyl}-ethyl)-amide;
60) 4-(2-methanesulfonyl-ethylamino)-but-2-enonylic acid (2-{4-[3-chloro-4-(3-fluoro-benzyloxy)-phenylamino]-quinazolin-6-ylcarbamoyl}-ethyl)-amide;
61) 3-(2-chloro-acetylamide)-N-{4-[3-chloro-4-(3-fluoro-benzyloxy)-phenylamino]-quinazolin-6-yl}-propionamide;
62) N-{4-[3-chloro-4-(3-fluoro-benzyloxy)-phenylamino]-quinazolin-6-yl}-3-(2-morpholin-4-yl-acetylamino)-propionamide;
63) N-{4-[3-chloro-4-(3-fluoro-benzyloxy)-phenylamino]-quinazolin-6-yl}-3-(2-dimethylamino-acetylamino)-propionamide;
64) N-{4-[3-chloro-4-(3-fluoro-benzyloxy)-phenylamino]-quinazolin-6-yl}-3-[2-(4-methyl-piperazin-1-yl)-acetylamino]-propionamide;
65) N-{4-[3-chloro-4-(3-fluoro-benzyloxy)-phenylamino]-quinazolin-6-yl}-3-[2-(2-methoxy-ethylamino)-acetylamino]-propionamide;
66) N-{4-[3-chloro-4-(3-fluoro-benzyloxy)-phenylamino]-quinazolin-6-yl}-3-[2-(2-methanesulfonyl-ethylamino)-acetylamino]-propionamide;
67) 3-(2-chloro-acetylamino)-N-{4-[3-methyl-4-(6-methyl-pyridin-3-yloxy)-phenylamino]-quinazolin-6-yl}-propionamide;
68) N-{4-[3-methyl-4-(6-methyl-pyridin-3-yloxy)-phenylamino]-quinazolin-6-yl}-3-(2-morpholin-4-yl-acetylamino)-propionamide;
69) 3-(2-dimethylamino-acetylamino)-N-{4-[3-methyl-4-(6-methyl-pyridin-3-yloxy)-phenylamino]-quinazolin-6-yl}-propionamide;
70) N-{4-[3-methyl-4-(6-methyl-pyridin-3-yloxy)-phenylamino]-quinazolin-6-yl}-3-[2-(4-methyl-piperazin-1-yl)-acetylamino]-propionamide;
71) 3-[2-(2-methoxy-ethylamino)-acetylamino]-N-{4-[3-methyl-4-(6-methyl-pyridin-3-yloxy)-methylamino]-quinazolin-6-yl}-propionamide;
72) 3-[2-(2-methanesulfonyl-ethylamino)-acetylamino]-N-{4-[3-methyl-4-(6-methyl-pyridin-3-yloxy)-phenylamino]-quinazolin-6-yl}-propionamide;
73) N-{2-[4-(2-methyl-1H-indol-5-ylamino)-quinazolin-6-ylcarbamoyl]-ethyl}-acrylamide;
74) 3-(2-methanesulfonyl-acetylamino)-N-[4-(1-phenyl-ethylamino)-quinazolin-6-yl]-propionamide;
75) N-{2-[4-(1-phenyl-ethylamino)-quinazolin-6-ylcarbamoyl]-ethyl}-acrylamide;
76) N-[2-(4-{4-[2-(6,7-dimethoxy-3,4-dihydro-1H-isoquinolin-2-yl)-ethyl]-phenylamino}-quinazolin-6-ylcarbamoyl)-ethyl]-acrylamide;
77) {2-[4-(1-benzyl-1H-indazol-5-ylamino)-quinazolin-6-ylcarbamoyl]-ethyl}-carbamic acid t-butylester;
78) N-[4-(1-benzyl-1H-indazol-5-ylamino)-quinazolin-6-yl]-3-(2-methanesulfonyl-acetylamino)-propionamide;
79) N-{2-[4-(1-benzyl-1H-imidazol-5-ylamino)-quinazolin-6-ylcarbamoyl]-ethyl}-acrylamide;
80) {2-[4-(4-phenylcarbamoyl-phenylamino)-quinazolin-6-ylcarbamoyl]-ethyl}-carbamic acid t-butylester;
81) 4-{6-[3-(2-methanesulfonyl-acetylamino)-propionylamino]-quinazolin-4-ylamino}-N-phenyl-benzamide;
82) 4-[6-(3-acryloylamino-propionylamino)-quinazolin-4-ylamino]-N-phenyl-benzamide;
83) N-[4-(biphenyl-4-ylamino)-quinazolin-6-yl]-3-(2-methanesulfonyl-acetylamino)-propionamide;
84) N-{2-[4-(biphenyl-4-ylamino)-quinazolin-6-ylcarbamoyl]-ethyl}-acrylamide;
85) N-{2-[4-[3-chloro-4-(3-fluoro-benzyloxy)-phenylamino]-7-(3-morpholin-4-yl-propoxy)-quinazolin-6-ylcarbamoyl]-ethyl}-acrylamide;
86) (3-{4-[3-chloro-4-(3-fluoro-benzyloxy)-phenylamino]-quinazolin-6-ylcarbamoyl}-propyl)-carbamic acid t-butylester;
87) N-{4-[3-chloro-4-(3-fluoro-benzyloxy)-phenylamino]-quinazolin-6-yl}-4-(2-methoxy-acetylamino)-butyramide;
88) N-{4-[3-chloro-4-(3-fluoro-benzyloxy)-phenylamino]-quinazolin-6-yl}-4-(2-methanesulfonyl-acetylamino)-butyramide;
89) 4-acryloylamino-N-{4-[3-chloro-4-(3-fluoro-benzyloxy)-phenylamino]-quinazolin-6-yl}-butyramide;
90) N-(3-{4-[3-chloro-4-(3-fluoro-benzyloxy)-phenylamino]-quinazolin-6-ylcarbamoyl}-propyl)-benzamide;
91) N-(3-{4-[3-chloro-4-(3-fluoro-benzyloxy)-phenylamino]-quinazolin-6-ylcarbamoyl}-propyl)-oxalamic acid ethylester;

92) cyclopropylcarboxylic acid (3-{4-[3-chloro-4-(3-fluoro-benzyloxy)-phenylamino]-quinazolin-6-ylcarbamoyl}-propyl)-amide;
93) N-{4-[3-chloro-4-(3-fluoro-benzyloxy)-phenylamino]-quinazolin-6-yl}-4-(2-cyano-acetylamino)-butyramide;
94) furan-3-carboxylic acid (3-{4-[3-chloro-4-(3-fluoro-benzyloxy)-phenylamino]-quinazolin-6-ylcarbamoyl}-propyl)-amide;
95) 1H-pyrazol-4-carboxylic acid (3-{4-[3-chloro-4-(3-fluoro-benzyloxy)-phenylamino]-quinazolin-6-ylcarbamoyl}-propyl)-amide;
96) {3-[4-(3-chloro-4-fluoro-phenylamino)-quinazolin-6-ylcarbamoyl]-propyl}-carbamic acid t-butylester;
97) N-[4-(3-chloro-4-fluoro-phenylamino)-quinazolin-6-yl]-4-(2-methanesulfonyl-acetylamino)-butyramide;
98) 4-acryloylamino-N-[4-(3-chloro-4-fluoro-phenylamino)-quinazolin-6-yl]-butyramide;
99) (3-{4-[3-methyl-4-(6-methyl-pyridin-3-yloxy)-phenylamino]-quinazolin-6-ylcarbonyl}-propyl)-carbamic acid t-butylester;
100) 4-(2-methanesulfonyl-acetylamino)-N-{4-[3-methyl-4-(6-methyl-pyridin-3-yloxy)-phenylamino]-quinazolin-6-yl}-butyramide;
101) 4-acryloylamino-N-{4-[3-methyl-4-(6-methyl-pyridin-3-yloxy)-phenylamino]-quinazolin-6-yl}-butyramide;
102) 4-(2-chloro-acetylamino)-N-{4-[3-chloro-4-(3-fluoro-benzyloxy)-phenylamino]-quinazolin-6-yl}-butyramide;
103) N-{4-[3-chloro-4-(3-fluoro-benzyloxy)-phenylamino]-quinazolin-6-yl}-4-(2-morpholin-4-yl-acetylamino)-butyramide;
104) N-{4-[3-chloro-4-(3-fluoro-benzyloxy)-phenylamino]-quinazolin-6-yl}-4-(2-dimethylamino-acetylamino)-butyramide;
105) N-{4-[3-chloro-4-(3-fluoro-benzyloxy)-phenylamino]-quinazolin-6-yl}-4-[2-(4-methyl-piperazin-1-yl)-acetylamino]-butyramide;
106) N-{4-[3-chloro-4-(3-fluoro-benzyloxy)-phenylamino]-quinazolin-6-yl}-4-[2-(2-methoxy-ethylamino)-acetylamino]-butyramide;
107) N-{4-[3-chloro-4-(3-fluoro-benzyloxy)-phenylamino]-quinazolin-6-yl}-4-[2-(2-methanesulfonyl-ethylamino)-acetylamino]-butyramide;
108) 4-(2-chloro-acetylamino)-N-{4-[3-methyl-4-(6-methyl-pyridin-3-yloxy)-phenylamino]-quinazolin-6-yl}-butyramide;
109) N-{4-[3-methyl-4-(6-methyl-pyridin-3-yloxy)-phenylamino]-quinazolin-6-yl}-4-(2-morpholin-4-yl-acetylamino)-butyramide;
110) 4-(2-dimethylamino-acetylamino)-N-{4-[3-methyl-4-(6-methyl-pyridin-3-yloxy)-phenylamino]-quinazolin-6-yl}-butyramide;
111) N-{4-[3-methyl-4-(6-methyl-pyridin-3-yloxy)-phenylamino]-quinazolin-6-yl}-4-[2-(4-methyl-piperazin-1-yl)-acetylamino]-butyramide;
112) 4-[2-(2-methanesulfonyl-ethylamino)-acetylamino]-N-{4-[3-methyl-4-(6-methyl-pyridin-3-yloxy)-phenylamino]-quinazolin-6-yl}-butyramide;
113) 4-[2-(2-methoxy-ethylamino)-acetylamino]-N-{4-[3-methyl-4-(6-methyl-pyridin-3-yloxy)-phenylamino]-quinazolin-6-yl}-butyramide;
114) (4-{4-[3-chloro-4-(3-fluoro-benzyloxy)-phenylamino]-quinazolin-6-ylcarbamoyl}-butyl)-carbamic acid t-butylester;
115) 5-(2-methoxy-acetylamino)-pentanoic acid {4-[3-chloro-4-(3-fluoro-benzyloxy)-phenylamino]-quinazolin-6-yl}-amide;
116) 5-(2-methanesulfonyl-acetylamino)-pentanoic acid {4-[3-chloro-4-(3-fluoro-benzyloxy)-pentylamino]-quinazolin-6-yl}-amide;
117) N-{4-[3-chloro-4-(3-fluoro-benzyloxy)-phenylamino]-quinazolin-6-yl}-3-(2-methanesulfanyl-acetylamino)-propionamide;
118) N-{4-[3-chloro-4-(3-fluoro-benzyloxy)-phenylamino]-quinazolin-6-yl}-3-(2-methanesulfinyl-acetylamino)-propionamide;
119) N-{4-[3-chloro-4-(3-fluoro-benzyloxy)-phenylamino]-quinazolin-6-yl}-3-(2,2,2-trifluoro-acetylamino)-propionamide;
120) 3-acetylamino-N-{4-[3-chloro-4-(3-fluoro-benzyloxy)-phenylamino]-quinazolin-6-yl}-propionamide;
121) acetic acid (2-{4-[3-chloro-4-(3-fluoro-benzyloxy)-phenylamino]-quinazolin-6-ylcarbamoyl}-ethylcarbamoyl)-methylester;
122) N-{4-[3-chloro-4-(3-fluoro-benzyloxy)-phenylamino]-quinazolin-6-yl}-3-[2-(2-dimethylamino-ethoxy)-acetylamino]-propionamide;
123) N-{4-[3-chloro-4-(3-fluoro-benzyloxy)-phenylamino]-quinazolin-6-yl}-3-(3-ethyl-ureido)-propionamide;
124) N-{4-[3-chloro-4-(3-fluoro-benzyloxy)-phenylamino]-quinazolin-6-yl}-3-(3-phenyl-ureido)-propionamide;
125) N-{4-[3-chloro-4-(3-fluoro-benzyloxy)-phenylamino]-quinazolin-6-yl}-3-(3-furan-2-ylmethyl-ureido)-propionamide;
126) (2-{4-[3-chloro-4-(3-fluoro-benzyloxy)-phenylamino]-quinazolin-6-ylcarbamoyl}-ethyl)-carbamic acid methylester;
127) (2-{4-[3-chloro-4-(3-fluoro-benzyloxy)-phenylamino]-quinazolin-6-ylcarbamoyl}-ethyl)-carbamic acid phenylester;
128) (2-{4-[3-chloro-4-(3-fluoro-benzyloxy)-phenylamino]-quinazolin-6-ylcarbamoyl}-ethyl)-carbamic acid benzylester;
129) N-{4-[3-chloro-4-(pyridin-2-ylmethoxy)-phenylamino]-quinazolin-6-yl}-3-(2-methoxy-acetylamino)-propionamide;
130) N-{4-[3-chloro-4-(pyridin-2-ylmethoxy)-phenylamino]-quinazolin-6-yl}-3-(2-methanesulfonyl-acetylamino)-propionamide;
131) N-(2-{4-[3-chloro-4-(pyridin-2-ylmethoxy)-phenylamino]-quinazolin-6-ylcarbamoyl}-ethyl)-acrylamide;
132) N-{4-[3-chloro-4-(pyridin-3-ylmethoxy)-phenylamino]-quinazolin-6-yl}3-(2-methoxy-acetylamino)-propionamide;
133) N-{4-[3-chloro-4-(pyridin-3-ylmethoxy)-phenylamino]-quinazolin-6-yl}-3-(2-methanesulfonyl-acetylamino)-propionamide;
134) N-(2-{4-[3-chloro-4-(pyridin-3-ylmethoxy)-phenylamino]-quinazolin-6-ylcarbamoyl}-ethyl)-acrylamide;
135) N-{4-[3-chloro-4-(3-fluoro-benzyloxy)-phenylamino]-quinazolin-6-yl}-3-[2-(2-methoxy-ethoxy)-acetylamino]-propionamide;
136) 5-methyl-isoxazol-4-carboxylic acid (2-{4-[3-chloro-4-(3-fluoro-benzyloxy)-phenylamino]-quinazolin-6-ylcarbamoyl}-ethyl)-amide;
137) N-{4-[3-chloro-4-(3-fluoro-benzyloxy)-phenylamino]-quinazolin-6-yl}-4-(2-methanesulfanyl-acetylamino)-butyramide;
138) N-{4-[3-chloro-4-(3-fluoro-benzyloxy)-phenylamino]-quinazolin-6-yl}-4-(2-methanesulfinyl-acetylamino)-butyramide;
139) N-[2-({4-[3-chloro-4-(3-fluoro-benzyloxy)-phenylamino]-quinazolin-6-yl}-methyl-carbamoyl)-ethyl]-acrylamide;

140) N-[2-({4-[3-chloro-4-(3-fluoro-benzyloxy)-phenylamino]-quinazolin-6-yl}-ethyl-carbamoyl)-ethyl]-acrylamide;
141) N-{2-[{4-[3-chloro-4-(3-fluoro-benzyloxy)-phenylamino]-quinazolin-6-yl}-(3-dimethylamino-propyl)-carbamoyl]-ethyl}-acrylamide;
142) N-(2-{4-[3-chloro-4-(3-fluoro-benzyloxy)-phenylamino]-quinazolin-6-ylcarbamoyl}-ethyl)-N-methyl-acrylamide;
143) N-(2-{4-[3-chloro-4-(pyridin-2-ylmethoxy)-phenylamino]-quinazolin-6-ylcarbamoyl}-ethyl)-N-methyl-acrylamide;
144) N-(2-{4-[3-chloro-4-(6-methyl-pyridin-2-ylmethoxy)-phenylamino]-quinazolin-6-ylcarbamoyl}-ethyl)-acrylamide;
145) (2S)-1-acryloyl-pyrrolidin-2-carboxylic acid {4-[3-chloro-4-(pyridin-2-ylmethoxy)-phenylamino]-quinazolin-6-yl}-amide;
146) (2S)-1-(1-oxo-butyn-2-yl)-pyrrolidin-2-carboxylic acid {4-[3-chloro-4-(pyridin-2-ylmethoxy)-phenylamino]-7-methoxy-quinazolin-6-yl}-amide;
147) (2S)-1-acryloyl-pyrrolidine-2-carboxylic acid {4-[3-chloro-4-(6-methyl-pyridin-2-ylmethoxy)-phenylamino]-quinazolin-6-yl}-amide;
148) (3R,5S)-acetic acid 1-acryloyl-5-{4-[3-chloro-4-(pyridin-2-ylmethoxy)-phenylamino]-quinazolin-6-ylcarbamoyl}-pyrrolidin-3-ylester;
149) (2S,4R)-1-acryloyl-4-hydroxyl-pyrrolidine-2-carboxylic acid {4-[3-chloro-4-(pyridin-2-ylmethoxy)-phenylamino]-quinazolin-6-yl}-amide;
150) (2S,4R)-1-acryloyl-4-ethylsulfanyl-pyrrolidine-2-carboxylic acid {4-[3-chloro-4-(pyridin-2-ylmethoxy)-phenylamino]-quinazolin-6-yl}-amide;
151) (2S,4R)-1-acryloyl-4-dimethylamino-pyrrolidine-2-carboxylic acid {4-[3-chloro-4-(pyridin-2-ylmethoxy)-phenylamino]-quinazolin-6-yl}-amide;
152) (2S)-1-acryloyl-pyrrolidine-2-carboxylic acid {4-[3-chloro-4-(pyridin-3-ylmethoxy)-phenylamino]-quinazolin-6-yl}-amide;
153) (2S)-1-acryloyl-pyrrolidine-2-carboxylic acid {4-[3-chloro-4-(pyridin-4-ylmethoxy)-phenylamino]-quinazolin-6-yl}-amide;
154) 2-(1-acryloyl-pyrrolidin-2-yl)-N-{4-[3-chloro-4-(pyridin-2-ylmethoxy)-phenylamino]-quinazolin-6-yl}-acetamide;
155) 1-acryloyl-pyrrolidine-3-carboxylic acid {4-[3-chloro-4-(pyridin-2-ylmethoxy)-phenylamino]-quinazolin-6-yl}-amide;
156) 1-acryloyl-piperidine-4-carboxylic acid {4-[3-chloro-4-(pyridin-2-ylmethoxy)-phenylamino]-quinazolin-6-yl}-amide;
157) (2S)-1-acryloyl-pyrrolidine-2-carboxylic acid {4-[3-methyl-4-(6-methyl-pyridin-3-yloxy)-phenylamino]-quinazolin-6-yl}-amide;
158) (2S)-1-acryloyl-pyrrolidine-2-carboxylic acid [4-(3-ethynyl-phenylamino)-quinazolin-6-yl]-amide;
159) (2S)-1-acryloyl-pyrrolidine-2-carboxylic acid [4-(3-chloro-4-fluoro-phenylamino)-quinazolin-6-yl]-amide;
160) (2S,4R)-1-acryloyl-4-ethanesulfonyl-pyrrolidine-2-carboxylic acid {4-[3-chloro-4-(pyridin-2-ylmethoxy)-phenylamino]-quinazolin-6-yl}-amide;
161) (2S,4R)-1-acryloyl-4-methoxy-pyrrolidine-2-carboxylic acid {4-[3-chloro-4-(pyridin-2-ylmethoxy)-phenylamino]-quinazolin-6-yl}-amide;
162) 1-acryloyl-piperidine-3-carboxylic acid {4-[3-chloro-4-(pyridin-2-ylmethoxy)-phenylamino]-quinazolin-6-yl}-amide;
163) 1-acryloyl-azetidine-3-carboxylic acid {4-[3-chloro-4-(pyridin-2-ylmethoxy)-phenylamino]-quinazolin-6-yl}-amide;
164) 1-acryloyl-piperidine-2-carboxylic acid {4-[3-chloro-4-(pyridin-2-ylmethoxy)-phenylamino]-quinazolin-6-yl}-amide;
165) (2S)-1-acryloyl-pyrrolidine-2-carboxylic acid {4-[3-chloro-4-(pyridin-2-ylmethoxy)-phenylamino]-7-fluoro-quinazolin-6-yl}-amide;
166) (2S)-1-acryloyl-pyrrolidine-2-carboxylic acid {4-[3-chloro-4-(pyridin-2-ylmethoxy)-phenylamino]-7-methoxy-quinazolin-6-yl}-amide;
167) N-(2-{4-[3-chloro-4-(pyridin-2-ylmethoxy)-phenylamino]-7-methoxy-quinazolin-6-ylcarbamoyl}-ethyl)-acrylamide;
168) (2S)-1-acryloyl-pyrrolidin-2-carboxylic acid {7-methoxy-4-[3-methyl-4-(pyridin-2-ylmethoxy)-phenylamino]-quinazolin-6-yl}-amide;
169) 2-(1-acryloyl-pyrrolidin-2-yl)-N-{4-[3-chloro-4-(pyridin-2-ylmethoxy)-phenylamino]-7-methoxy-quinazolin-6-yl}-acetamide;
170) (2S)-1-acryloyl-pyrrolidine-2-carboxylic acid {4-[3-chloro-4-(pyridin-2-ylmethoxy)-phenylamino]-7-ethoxy-quinazolin-6-yl}-amide;
171) (2S)-1-acryloyl-pyrrolidine-2-carboxylic acid {4-[3-chloro-4-(pyridin-2-ylmethoxy)-phenylamino]-7-ethyl-sulfanyl-quinazolin-6-yl}-amide;
172) (2S)-1-acryloyl-pyrrolidine-2-carboxylic acid {4-[3-chloro-4-(pyridin-2-ylmethoxy)-phenylamino]-7-cyclopropylmethoxy-quinazolin-6-yl}-amide;
173) (2S)-1-acryloyl-pyrrolidine-2-carboxylic acid {4-[3-chloro-4-(pyridin-2-ylmethoxy)-phenylamino]-7-cyclopentyloxy-quinazolin-6-yl}-amide;
174) N-(2-{4-[3-chloro-4-(pyridin-4-ylmethoxy)-phenylamino]-quinazolin-6-ylcarbamoyl}-ethyl)-acrylamide;
175) (2S)-1-(4-dimethylamino-buten-2-oyl)-pyrrolidine-2-carboxylic acid {4-[3-chloro-4-(pyridin-2-ylmethoxy)-phenylamino]-7-methoxy-quinazolin-6-yl}-amide;
176) (2S)-1-acryloyl-pyrrolidine-2-carboxylic acid {7-chloro-4-[3-chloro-4-(pyridin-2-ylmethoxy)-phenylamino]-quinazolin-6-yl}-amide;
177) (2S)-1-acryloyl-pyrrolidine-2-carboxylic acid {7-fluoro-4-[3-methyl-4-(pyridin-2-ylmethoxy)-phenylamino]-quinazolin-6-yl}-amide;
178) N-(2-{7-fluoro-4-[3-methyl-4-(pyridin-2-ylmethoxy)-phenylamino]-quinazolin-6-ylcarbamoyl}-ethyl)-acrylamide;
179) (2S)-1-acryloyl-2,5-dihydro-1H-pyrrol-2-carboxylic acid {4-[3-chloro-4-(pyridin-2-ylmethoxy)-phenylamino]-7-methoxy-quinazolin-6-yl}-amide;
180) (4R)-3-acryloyl-thiazolidin-4-carboxylic acid {4-[3-chloro-4-(pyridin-2-ylmethoxy)-phenylamino]-7-methoxy-quinazolin-6-yl}-amide;
181) 1-acryloyl-azetidine-2-carboxylic acid {4-[3-chloro-4-(pyridin-2-ylmethoxy)-phenylamino]-quinazolin-6-yl}-amide;
182) 1-acryloyl-azetidine-2-carboxylic acid {4-[3-chloro-4-(pyridin-2-ylmethoxy)-phenylamino]-7-methoxy-quinazolin-6-yl}-amide;
183) (2S)-1-acryloyl-pyrrolidine-2-carboxylic acid [4-[3-chloro-4-(pyridin-2-ylmethoxy)-phenylamino]-7-(2,2,2-trifluoro-ethoxy)-quinazolin-6-yl]-amide;
184) (2S)-1-acryloyl-pyrrolidine-2-carboxylic acid {4-[3-chloro-4-(pyridin-2-ylmethoxy)-phenylamino]-7-dimethylamino-quinazolin-6-yl}-amide;

185) (2S)-1-acryloyl-pyrrolidine-2-carboxylic acid [7-methoxy-4-(1-pyridin-2-ylmethyl-1H-indazol-5-ylamino)-quinazolin-6-yl]-amide;

186) (2S)-1-acryloyl-pyrrolidine-2-carboxylic acid {4-[3-methyl-4-(pyridin-2-ylmethoxy)-phenylamino]-7-ethoxy-quinazolin-6-yl}-amide;

187) (2S)-1-acryloyl-pyrrolidine-2-carboxylic acid [4-[3-chloro-4-(pyridin-2-ylmethoxy)-phenylamino]-7-(2-fluoro-ethoxy)-quinazolin-6-yl]-amide;

188) (2S)-1-acryloyl-pyrrolidine-2-carboxylic acid {4-[1-(3-fluoro-benzyl)-1H-indazol-5-ylamino]-7-methoxy-quinazolin-6-yl}-amide;

189) (1R)—N-(1-{4-[3-chloro-4-(pyridin-2-ylmethoxy)-phenylamino]-7-methoxy-quinazolin-6-ylcarbamoyl}-ethyl)-acrylamide;

190) (1S)—N-1-{4-[3-chloro-4-(pyridin-2-ylmethoxy)-phenylamino]-7-methoxy-quinazolin-6-ylcarbamoyl}-ethyl)-acrylamide;

191) (1S)—N-(1-{4-[3-chloro-4-(pyridin-2-ylmethoxy)-phenylamino]-7-methoxy-quinazolin-6-ylcarbamoyl}ethyl)-N-methyl-acrylamide;

192) N-(2-{4-[3-chloro-4-(pyridin-2-ylmethoxy)-phenylamino]-7-fluoro-quinazolin-6-ylcarbamoyl}-ethyl)-acrylamide;

193) (2S)-1-acryloyl-pyrrolidine-2-carboxylic acid [7-methoxy-4-(1-penta-2,4-dienyl-1H-indazol-5-ylamino)-quinazolin-6-yl]-amide;

194) (2S)-1-acryloyl-pyrrolidine-2-carboxylic acid {4-[3-chloro-4-(6-methyl-pyridin-2-ylmethoxy)-phenylamino]-7-methoxy-quinazolin-6-yl}-amide;

195) 1-acryloyl-azetidine-2-carboxylic acid {4-[3-chloro-4-(pyridin-2-ylmethoxy)-phenylamino]-7-fluoro-quinazolin-6-yl}-amide;

196) 1-acryloyl-piperidine-2-carboxylic acid {4-[3-chloro-4-(pyridin-2-ylmethoxy)-phenylamino]-7-methoxy-quinazolin-6-yl}-amide;

197) 1-acryloyl-piperidine-4-carboxylic acid {4-[3-chloro-4-(pyridin-2-ylmethoxy)-phenylamino]-7-methoxy-quinazolin-6-yl}-amide;

198) 1-acryloyl-pyrrolidine-3-carboxylic acid {4-[3-chloro-4-(pyridin-2-ylmethoxy)-phenylamino]-7-methoxy-quinazolin-6-yl}-amide;

199) 1-acryloyl-azetidine-2-carboxylic acid {4-[3-chloro-4-(pyridin-2-ylmethoxy)-phenylamino]-7-ethoxy-quinazolin-6-yl}-amide;

200) 1-acryloyl-azetidine-3-carboxylic acid {4-[3-chloro-4-(pyridin-2-ylmethoxy)-phenylamino]-7-methoxy-quinazolin-6-yl}-amide;

201) (3S)-1-acryloyl-piperidine-3-carboxylic acid {4-[3-chloro-4-(pyridin-2-ylmethoxy)-phenylamino]-7-methoxy-quinazolin-6-yl}-amide;

202) N-((1S)-1-{4-[3-chloro-4-(pyridin-2-ylmethoxy)-phenylamino]-7-methoxy-quinazolin-6-ylcarbamoyl}-ethyl)-N-ethyl-acrylamide;

203) (2S)-1-acryloyl-pyrrolidine-2-carboxylic acid {4-[3-chloro-4-(2-fluoro-ethoxy)-phenylamino]-7-methoxy-quinazolin-6-yl}-amide;

204) (2S)-1-acryloyl-pyrrolidine-2-carboxylic acid {4-[3-chloro-4-(pyridin-3-ylmethoxy)-phenylamino]-7-methoxy-quinazolin-6-yl}-amide;

205) (2S)-2-acryloylamino-N-{4-[3-chloro-4-(pyridin-2-ylmethoxy)-phenylamino]-7-methoxy-quinazolin-6-yl}-butyramide;

206) N-(2-{4-[3-chloro-4-(pyridin-2-ylmethoxy)-phenylamino]-7-methoxy-quinazolin-6-ylcarbamoyl}-2-fluoro-ethyl)-acrylamide;

207) (2S)-1-acryloyl-pyrrolidine-2-carboxylic acid {4-[3-chloro-4-(pyridin-3-ylmethoxy)-phenylamino]-7-(1-methyl-piperidin-4-ylmethoxy)-quinazolin-6-yl}-amide;

208) (1R)—N-(1-{4-[3-chloro-4-(pyridin-2-ylmethoxy)-phenylamino]-7-(2-methoxy-ethoxy)-quinazolin-6-ylcarbamoyl}-ethyl)-acrylamide;

209) (2S)-1-acryloyl-pyrrolidine-2-carboxylic acid {4-[3-chloro-4-(pyridin-3-ylmethoxy)-phenylamino]-7-(3-morpholin-4-yl-propoxy)-quinazolin-6-yl}-amide;

210) N-({4-[3-chloro-4-(pyridin-2-ylmethoxy)-phenylamino]-7-methoxy-quinazolin-6-ylcarbamoyl}-methyl)-acrylamide 211) N-({4-[3-chloro-4-(3-fluoro-benzyloxy)-phenylamino]-7-methoxy-quinazolin-6-ylcarbamoyl}-methyl)-acrylamide;

212) (3S)-3-acryloylamino-N-{4-[3-chloro-4-(pyridin-2-ylmethoxy)-phenylamino]-7-methoxy-quinazolin-6-yl}-butyramide;

213) (2S)-1-acryloyl-pyrrolidine-2-carboxylic acid [4-[3-chloro-4-(pyridin-2-ylmethoxy)-phenylamino]-7-(2-methoxyethoxy)-quinazolin-6-yl]-amide;

214) (1S)—N-{1-[4-[3-chloro-4-(3-fluoro-benzyloxy)-phenylamino]-7-(2-methoxyethoxy)-quinazolin-6-ylcarbamoyl]-ethyl}-acrylamide;

215) (2S)-1-acryloyl-pyrrolidine-2-carboxylic acid [4-[3-chloro-4-(3-fluoro-benzyloxy)-phenylamino]-7-(2-methoxyethoxy)-quinazolin-6-yl]-amide;

216) (1S)—N-(1-{4-[3-chloro-4-(pyridin-2-ylmethoxy)-phenylamino]-7-methoxy-quinazolin-6-ylcarbamoyl}-ethyl)-acrylamide;

217) N-{[4-[3-chloro-4-(3-fluoro-benzyloxy)-phenylamino]-7-(2-methoxyethoxy)-quinazolin-6-ylcarbamoyl]-methyl}-acrylamide;

218) N-({4-[3-chloro-4-(pyridin-2-ylmethoxy)-phenylamino]-7-(2-methoxyethoxy)-quinazolin-6-ylcarbamoyl}-methyl]-acrylamide;

219) (1S)—N-(1-{4-[3-chloro-4-(pyridin-2-ylmethoxy)-phenylamino]-7-(3-morpholin-4-yl-propoxy)-quinazolin-6-ylcarbamoyl}-ethyl-acrylamide;

220) (1S)—N-(1-{4-[3-chloro-4-(pyridin-2-ylmethoxy)-phenylamino]-7-(3-methoxypropoxy)-quinazolin-6-ylcarbamoyl}-ethyl)-acrylamide;

221) (2S)-2-acryloylamino-N-{4-[3-chloro-4-(3-fluoro-benzyloxy)-phenylamino]-7-methoxy-quinazolin-6-yl}-4-methylsulfanyl-butyramide;

222) (2S)-2-acryloylamino-N-{4-[3-chloro-4-(3-fluoro-benzyloxy)-phenylamino]-7-(2-methoxyethoxy)-quinazolin-6-yl}-4-methylsulfanyl-butyramide;

223) (2S)-2-acryloylamino-N-{4-[3-chloro-4-(3-fluoro-benzyloxy)-phenylamino]-7-methoxy-quinazolin-6-yl}-4-methylsulfinyl-butyramide;

224) (2S)-2-acryloylamino-N-{4-[3-chloro-4-(pyridin-2-ylmethoxy)-phenylamino]-quinazolin-6-yl}-3-methyl-butyramide; and 225) (2S)-2-acryloylamino-4-methyl-pentanoic acid {4-[3-chloro-4-(pyridin-2-ylmethoxy)-phenylamino]-quinazolin-6-yl}-amide.

The compound of formula (I) of the present invention may be prepared by the procedure shown in Reaction Scheme (I):
Reaction Scheme (I)
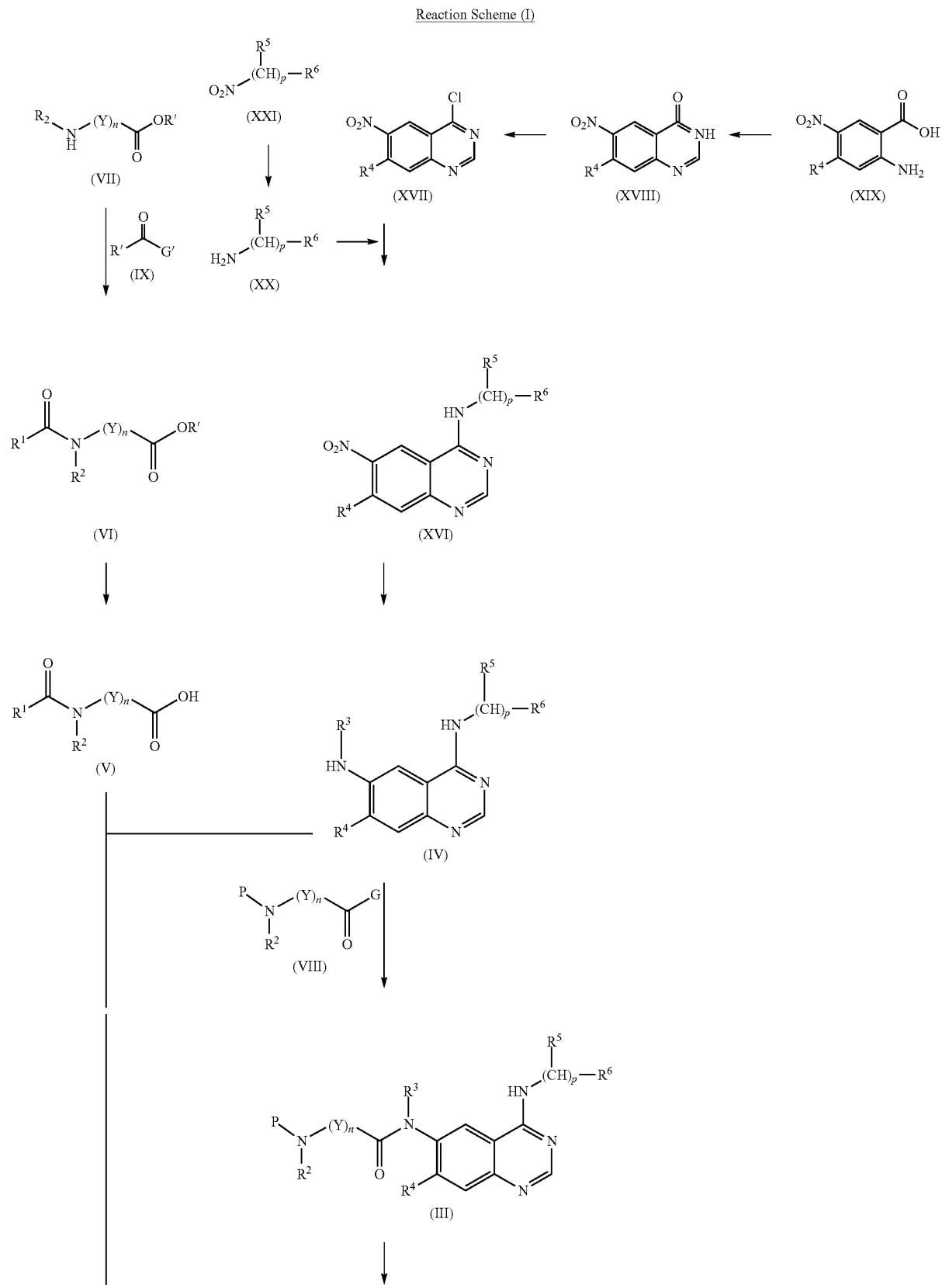

-continued

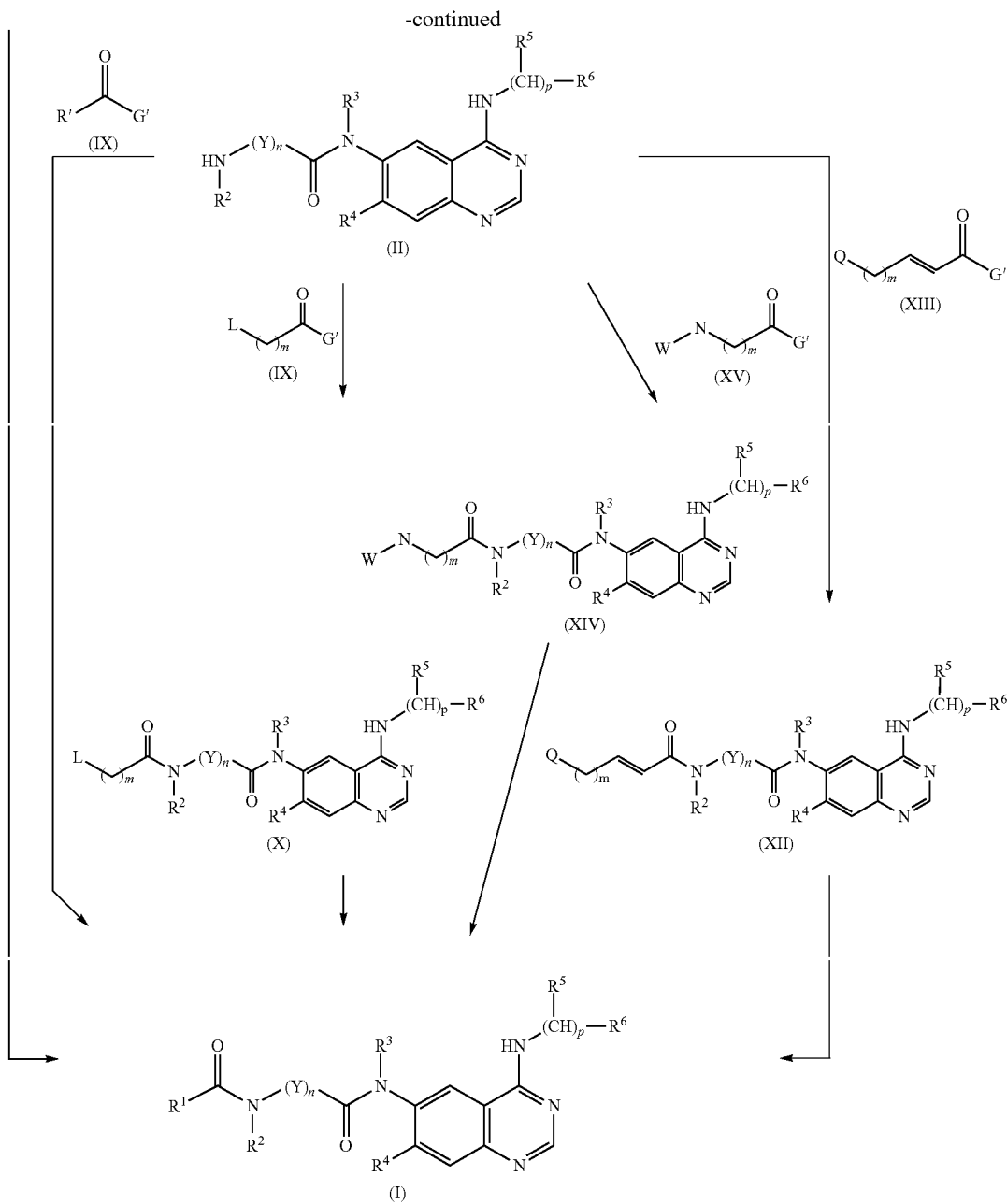

wherein, $R^1$, $R^2$, $R^3$, $R^4$, $R^5$, $R^6$, Y, n and p have the same meanings as defined previously while;

R' and W are each independently $C_{1-6}$alkyl;

G, G' and G'' are each independently halogen, hydroxy or $C_{1-6}$alkanoyloxy;

L is halogen, $C_{1-6}$alkylsulfonyloxy or arylsulfonyloxy;

Q is halogen;

G''' is halogen, hydroxy or tri($C_{1-6}$alkyl)silyloxy;

P is a t-buthoxycarbonyl or benzyloxycarbonylate amine protecting group; and

M is an integer in the range of 1 to 5.

Specifically, The compound of formula (I) of the present invention may be prepared by the procedure shown in Reaction Schemes (II) to (VI):

Reaction Scheme (II)

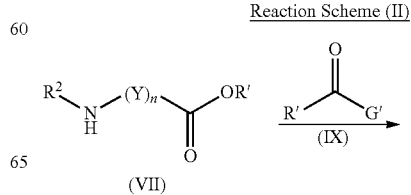

-continued (VI) → (V)

(IV)

(I)

wherein,
$R^1$, $R^2$, $R^3$, $R^4$, $R^5$, $R^6$, Y, n, p, R' and G' have same meanings as defined above.

In Reaction Scheme (II), a compound of formula (IV), the preparative procedure thereof is explained in Reaction Scheme (VII) in detail, is subjected to a condensation reaction with a compound of formula (V) to obtain a compound of formula (I). The condensation agent which may be used in this reaction is 1-(3-dimethylaminopropyl)-3-ethylcarbodiimide, N,N-dicyclohexyldiimide, $C_{1-6}$alkylchloroformate, carbonyldiimidazole or O-(1H-benzotriazol-1-yl)-N,N,N'N'-tetramethyluronium tetrafluoroborate, and the agent may be employed in an amount of 1 to 10 equivalentss, preferably 1 to 5 equivalentss based on the compound of formula (IV). The compound of formula (V) may be employed in an amount of 1 to 10 equivalentss, preferably 1 to 4 equivalentss based on the compound of formula (IV).

N,N-dimethylaminopyridine, N,N-hydroxysuccinimide or N-hydroxybenzotriazole can be added as a catalyst in an amount of 0.05 to 1 equivalent based on the compound of formula (IV). Also, triethylamine, N,N-diisopropylethylamine, pyridine or N-methylmorpholine can be added as a base in an amount of 1 to 5 equivalentss based on the compound of formula (IV).

The solvent used in this reaction may be methylene chloride, chloroform, N,N-dimethylformamide, tetrahydrofuran (THF), 1,4-dioxane or acetonitrile, and the reaction can be carried out at a temperature ranging from −20° C. to the boiling point of the solvent used, preferably 0 to 40° C.

The compound of formula (V) is commercially available and it can be prepared by hydrolysis of the compound of formula (VI). In this hydrolysis step, lithium hydroxide, sodium hydroxide, potassium hydroxide or barium hydroxide may be used in an amount of 1 to 20 equivalentss, preferably 1 to 10 equivalentss based on the compound of formula (VI). The hydrolysis can be carried out at a temperature ranging from −20° C. to 100° C., preferably 0 to 30° C. in a solvent selected from the group consisting of water, alcohol, ether and a mixture thereof.

The compound of formula (VII) is subjected to a condensation reaction with the compound of formula (IX) to obtain the compound of formula (VI), and the compound of formula (IX) may be employed in an amount of 1 to 10 equivalents, preferably 1 to 3 equivalents based on the compound of formula (VII). In case that the G' is halogen or alkanoyloxy, the compound of formula (VI) may be prepared by just adding a base without a condensation reagent, and in ease that the G' is hydroxy, the compound of formula (VI) may be prepared by using a condensation reagent selected from the group consisting of 1-(3-dimethylaminopropyl)-3-ethylcarbodiimide, N,N-dicyclohexyldiimide, $C_{1-6}$alkylchloroformate and O-(1H-benzotriazol-1-yl)-N,N,N',N'-tetramethyluronium tetrafluoroborate in an amount of 1 to 10 equivalents, preferably 1 to 5 equivalents based on the compound of formula (VII).

In this reaction, a solvent such as N,N-dimethylaminopyridine, N,N-hydroxysuccinimide and N-hydroxybenzotriazole may be optionally used in an amount of 0.05 to 1 equivalent based on the compound of formula (VII). Further, a base such as triethylamine, N,N-diisopropylethylamine, pyridine and N-methylmorpholine may be optionally used in an amount of 1 to 5 equivalents. The solvent used in this reaction may be selected from the group consisting of methylene chloride, chloroform, N,N-dimethylformamide, THF, 1,4-dioxane, acetonitrile and a mixture thereof, and the reaction can be carried out at a temperature ranging from −20° C. to the boiling point of the solvent used, preferably 10 to 40° C.

The compound of formula (VII) is commercially available and it can be prepared in accordance with the method described by Dieter Seebach et al., [*Helvetica Chimica Acta*, 2003, 86:1852].

The compound of formula (IX) is commercially available and it can be prepared in accordance with the method described by Hwei-Ru Tsou et al., [*Journal of Medicinal Chemistry*, 2001, 44:2719].

Reaction Scheme (III)

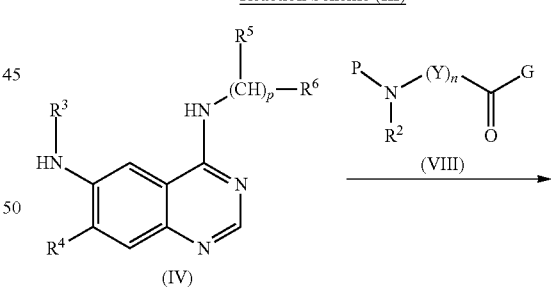

(IV) + (VIII) →

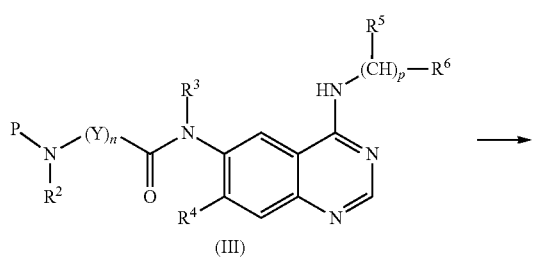

(III)

-continued

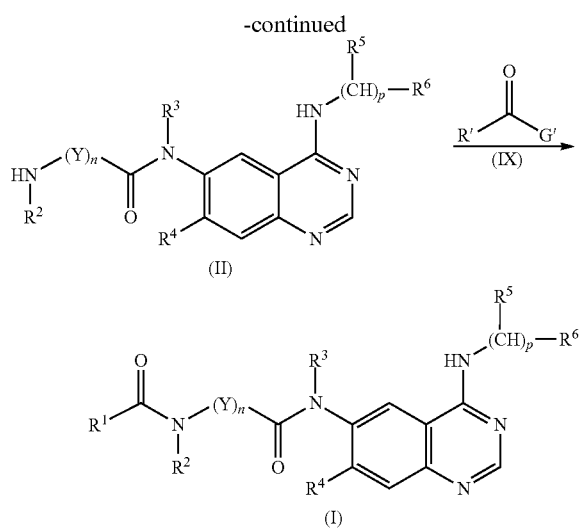

wherein,
R$^1$, R$^2$, R$^3$, R$^5$, R$^6$, Y, n, p, G, G' and P have same meanings as defined above.

In Reaction Scheme (III), the compound of formula (II) is subjected to a condensation reaction with a compound of formula (IX) to obtain the compound of formula (I). The compound of formula (IX) may be employed in an amount of 1 to 10 equivalents, preferably 1 to 5 equivalents based on the compound of formula (II). In case that the G' is halogen or alkanoyloxy, the compound of formula (I) may be prepared by just adding a base without a condensation reagent, and in case that the G' is hydroxy, the compound of formula (I) may be prepared by using a condensation reagent selected from the group consisting of 1-(3-dimethylaminopropyl)-3-ethylcarbodiimide, N,N-dicyclohexyldiimide, C$_{1-6}$alkylchloroformate and O-(1H-benzotriazol-1-yl)-N,N,N',N'-tetramethyluronium tetrafluoroborate in an amount of 1 to 10 equivalents, preferably 1 to 5 equivalents based on the compound of formula (II).

In this reaction, a solvent such as N,N-dimethylaminopyridine, N,N-hydroxysuccinimide and N-hydroxybenzotriazole may be optionally used in an amount of 0.05 to 1 equivalent based on the compound of formula (II). Further, a base such as triethylamine, N,N-diisopropylethylamine, pyridine and N-methylmorpholine may be optionally used in an amount of 1 to 5 equivalents. The solvent used in this reaction may be selected from the group consisting of methylene chloride, chloroform, N,N-dimethylformamide, THF, 1,4-dioxane, acetonitrile and a mixture thereof, and the reaction can be carried out at a temperature ranging from −20° C. to the boiling point of the solvent used, preferably 0 to 40° C.

The compound of formula (IV), the preparative procedure thereof is explained in Reaction Scheme (VII) in detail, is subjected to a condensation reaction with a compound of formula (VIII) to obtain a compound of formula (III). Then, the compound of formula (III) is subjected to the deprotection (removing the protecting group 'P') to obtain the compound of formula (II).

The compound of formula (VIII) is commercially available and it can be prepared in accordance with the method described by Dieter Seebach et al., [*Helvetica Chimica Acta*, 2003, 86:1852].

The condensation agents which may be used in this reaction is 1-(3-dimethylaminopropyl)-3-ethylcarbodiimide, N,N-dicyclohexyldiimide, C$_{1-6}$alkylchloroformate, carbonyldiimidazole or O-(1H-benzotriazol-1-yl)-N,N,N',N'-tetramethyluronium tetrafluoroborate. The compound of formula (VIII) may be employed in an amount of 1 to 10 equivalents, preferably 1 to 3 equivalents based on the compound of formula (IV). In case that the G' is halogen or alkanoyloxy, the compound of formula (VI) may be prepared by just adding a base without a condensation reagent, and in case that the G' is hydroxy, the compound of formula (VI) may be prepared by using the said condensation reagent. In this reaction, a solvent such as N,N-dimethylaminopyridine, N,N-hydroxysuccinimide and N-hydroxybenzotriazole may be optionally used in an amount of 0.05 to 1 equivalent based on the compound of formula (IV). Also, triethylamine, N,N-diisopropylethylamine, pyridine and N-methylmorpholine can be optionally added as a base in an amount of 1 to 5 equivalents based on the compound of formula (IV). The solvent used in this reaction may be selected from the group consisting of methylene chloride, chloroform, N,N-dimethylformamide, THF, 1,4-dioxane, acetonitrile and a mixture thereof, and the reaction can be carried out at a temperature ranging from −20° C. to the boiling point of the solvent used, preferably 0 to 40° C.

While subjecting the compound of formula (III) to deprotection to obtain the compound of formula (II), hydrochloric acid, phosphoric acid, sulfuric acid or trifluoroacetic acid as a deprotecting agent can be added or used as a solvent. Further, the compound of formula (II) can be obtained by using metal (for example, palladium, platinum or nickel) or metal oxide, carrying the reaction under hydrogen gas, or adding cyclohexene or cyclodihexene. The deprotection can be carried out at a temperature ranging from 0° C. to 10° C., preferably room temperature to 50° C. in accordance with the method described by Greene Wuts, [*Protective Groups in Organic Synthesis*, 3rd Ed., Wiley-Interscience].

Reaction Scheme (IV)

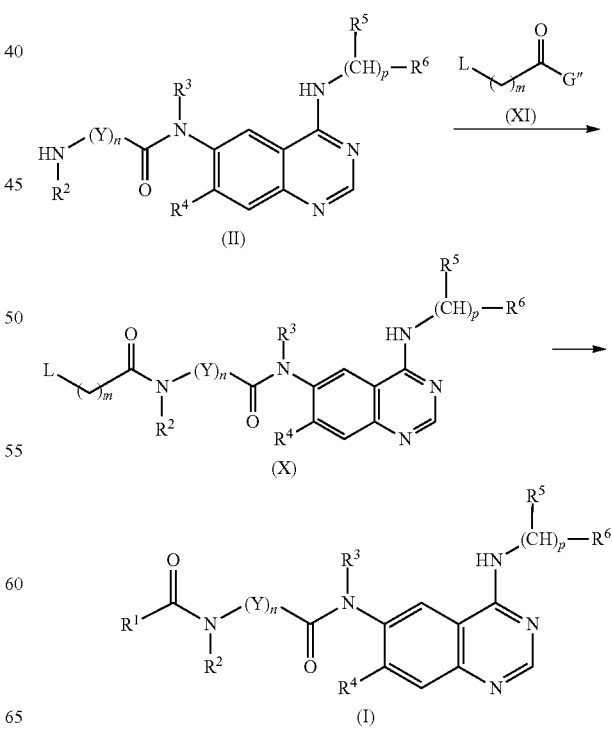

wherein,

R$^1$, R$^2$, R$^3$, R$^4$, R$^5$, R$^6$, Y, n, p, L, G″ and m have same meanings as defined above.

In Reaction Scheme (IV), when the R$^1$ is C$_{1-6}$alkylaminoC$_{1-6}$alkyl, C$_{1-6}$dialkylaminoC$_{1-6}$alkyl, C$_{1-6}$alkoxyC$_{1-6}$alkyl or C$_{1-6}$alkylthioC$_{1-6}$alkyl, the compound of formula (X) may be prepared by subjecting the compounds of formula (II) and (XI) to condensation reaction, and then the compound of formula (I) may be prepared by adding amine, alcohol or thiol corresponding to R$^1$.

The condensation reaction to obtain the compound (II) is carried out in similar condition of reaction to prepare the compound of formula (III) or by applying the reaction. The compound of formula (XI) is commercially available and it can be prepared in accordance with conventional methods.

The amine, alcohol or thiol added to the compound of formula (X) is commercially available and it can be prepared in accordance with conventional methods, and the compounds may be employed in an amount of 1 to 10 equivalents, preferably 1 to 3 equivalents based on the compound of formula (X). Further, an inorganic or organic base such as potassium carbonate, sodium carbonate, sodium hydride, triethylamine, 1,8-diazabicyclo[5.4.0]undec-7-en (DBU) and N,N-diisopropylethylamine may be used in an amount of 1 to 5 equivalents based on the compound of formula (X). The solvent used in this reaction may be selected from the group consisting of THF, 1,4-dioxane, toluene, N,N-dimethylformamide, dimethoxyethane and a mixture thereof, and the reaction can be carried out at a temperature ranging from 0° C. to 150° C., preferably 0° C. to 100° C.

Reaction Scheme (V)

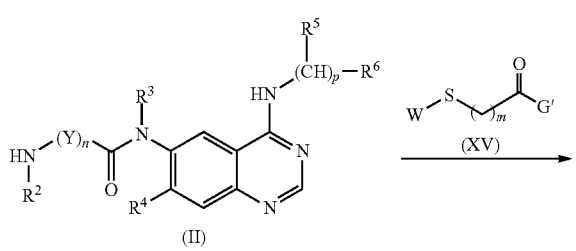

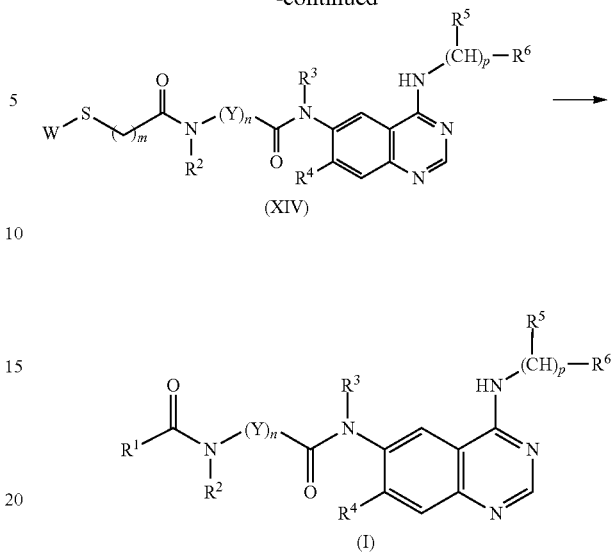

wherein,

R$^1$, R$^2$, R$^3$, R$^4$, R$^5$, R$^6$, Y, n, p, W, G′ and m have same meanings as defined above.

In Reaction Scheme (V), when the R$^1$ is C$_{1-6}$alkylsulfinyl or C$_{1-6}$alkylsulfonyl, the compound of formula (XIV) may be prepared by subjecting the compounds of formula (II) and (XV) to condensation reaction, and then the compound of formula (I) may be prepared by oxidizing the compound of formula (XIV) in the presence of an oxidizing agent such as m-chloroperoxybenzoic acid (CPBA) or OXONE (Koichiro Matsumoto) in an amount of 1 to 5 equivalents based on the compound of formula (XIV), and as occasion demands, an inorganic base such as sodium carbonate or an aqueous solution thereof can be used. The reaction can be carried out at a temperature ranging from −20° C. to 50° C.

Reaction Scheme (VI)

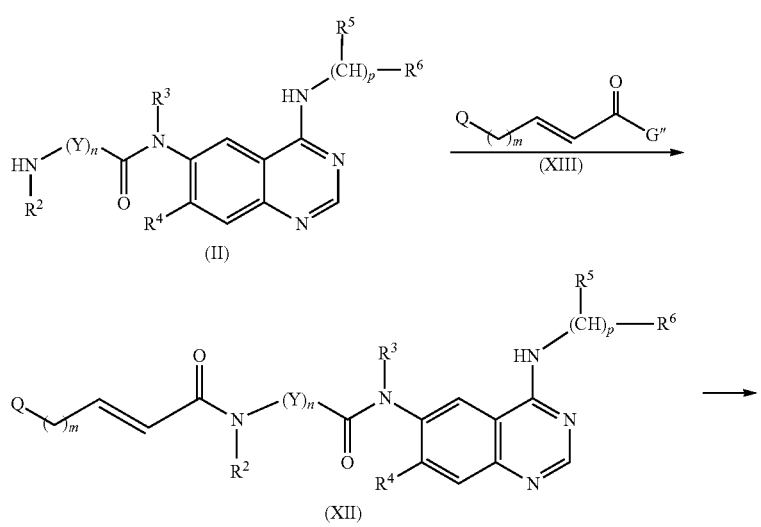

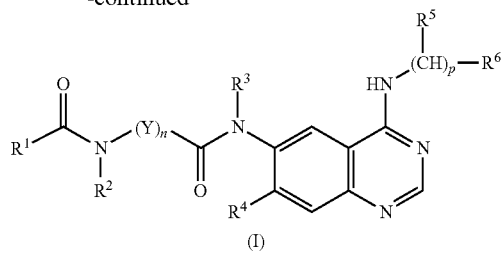

wherein,

R¹, R², R³, R⁴, R⁵, R⁶, Y, n, p, Q, G''' and m have same meanings as defined above.

In Reaction Scheme (VI), when the R¹ is $C_{1-6}$alkenyl, the compound of formula (XII) may be prepared by subjecting the compounds of formula (II) and (XIII) to condensation reaction, and then the compound of formula (I) may be prepared by adding amine, alcohol or thiol corresponding to R¹.

The compound of formula (XIII) is commercially available and it can be prepared in accordance with the conventional method [*Synthesis*, 1983, 745]. In case that the G''' is halogen, the compound of formula (VI) may be prepared by just adding a base, and in case that the G''' is hydroxy or trialkylsilyloxy, the compound of formula (VI) may be prepared by using the base after substituting the G''' to halogen by using thionylchloride, oxalylchloride or phosphorousoxychloride at a temperature ranging from 0° C. to room temperature. Further, during the substitution, N,N-dimethylformamide can be optionally added in an catalytic amount, and the compound of formula (XIII) may be employed in an amount ranging from 1 to 3 equivalents based on the compound of formula (II). In this reaction, the base such as triethylamine, N,N-diisopropylethylamine, pyridine or N-methylmorpholine may be employed in an amount ranging from 1 to 5 equivalents. The solvent used in this reaction may be selected from the group consisting of methylene chloride, chloroform, N,N-dimethylformamide, THF, 1,4-dioxane, acetonitrile and a mixture thereof, and the reaction can be carried out at a temperature ranging from −20° C. to 50° C., preferably 0 to room temperature.

The amine, alcohol or thiol added to the compound of formula (XII) is commercially available and it can be prepared in accordance with conventional methods, and the compounds may be employed in an amount of 1 to 10 equivalents, preferably 1 to 3 equivalents based on the compound of formula (XII). Further, an inorganic or organic base such as potassium carbonate, sodium carbonate, sodium hydride, triethylamine, 1,8-diazabicyclo[5.4.0]undec-7-en (DBU) and N,N-diisopropylethylamine may be used in an amount of 1 to 5 equivalents based on the compound of formula (XII). The solvent used in this reaction may be selected from the group consisting of THF, 1,4-dioxane, toluene, N,N-dimethylformamide, dimethoxyethane and a mixture thereof, and the reaction can be carried out at a temperature ranging from 0° C. to 150° C., preferably 0° C. to 60° C.

The compound of formula (IV) forementioned in Reaction Schemes (II) and (III) can be prepared by reducing the compound of formula (XVI) after reacting compounds of formula (XVII) and (XVIII) to obtain the compound of formula (XVI).

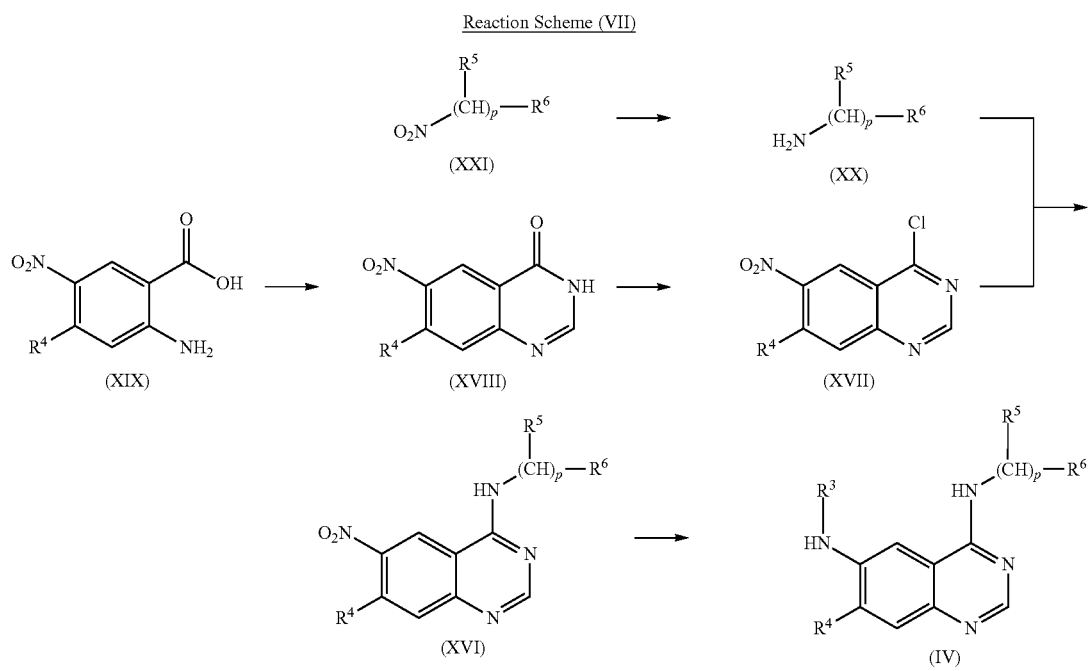

wherein,

R³, R⁴, R⁵, R⁶ and p have same meanings as defined above.

In Reaction Scheme (VII), the compound of formula (XVI) can be prepared by reacting compounds of formula (XVII) and (XVIII) to substitute a chloride of the compound of formula (XVII) to the compound of formula (XX). In this reaction, a base such as N,N-dimethylaniline can be added, and the reaction can be carried out in a solvent such as isopropanol and acetonitrile at a temperature ranging from 0° C. to 150° C., preferably room temperature to 100° C.

The reducing agent which used in this reaction may be selected from the group consisting of indium, palladium, platinum, iron, tartar, and oxide or chloride thereof, and employed in an amount of 1 to 5 equivalents based on the compound of formula (XVI). The reducing reaction can be carried out in the presence of hydrogen gas, and cyclohexene or cyclohexadien, or an inorganic or organic acid such as acetic acid, hydrochloric acid can be added thereto. The solvent used in this reaction may be selected from the group consisting of THF, 1,4-dioxane, ethylacetate, $C_{1-6}$alcohol, methylene chloride, chloroform, water, hexane, toluene and a mixture thereof.

The compound of formula (XX) is commercially available and it can be prepared in accordance with similar or identical method preparing the compound of formula (IV) from the compound of formula (XXI).

The compound of formula (XXI) is commercially available and it can be prepared in accordance with the method described by Yue-Mei Zhang et al., [*Bioorganic and Medicinal Chemistry Letters*, 2004 14:111].

The compound of formula (XVII) can be prepared from the compound of formula (XIX) via the compound of formula (XVIII) ([Alexander J. Bridges et al., *Journal of Medicinal Chemistry*, 1996 39:267]).

The compound of formula (I) of the present invention can also be used in the form of a pharmaceutically acceptable salt formed with an inorganic or organic acid, such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The inventive compound or a pharmaceutically acceptable salt thereof selectively inhibits the growth of cancer cells induced by epithelial cell growth factors, and provides enhanced anticancer effects when combined with other anticancer agents. Namely, the inventive compound or a pharmaceutically acceptable salt thereof is useful for enhancing the effects of anticancer agents selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents and antiandrogen.

Therefore, the present invention provides a pharmaceutical composition for inhibiting cancer cell growth comprising the compound of formula (I) or a pharmaceutically acceptable salt thereof as an active ingredient The inventive compound or a pharmaceutically acceptable salt thereof may be administered orally or parenterally as an active ingredient in an effective amount ranging from about 0.01 to 100 mg/kg, preferably 0.2 to 50 mg/kg body weight per day in case of mammals including human in a single dose or in divided doses. However, the foregoing dosage should be monitored, and change in consideration of idiosyncrasy and weight of the patient, kind and seriousness of illnesses, characteristics of the drug and interval and duration of drug.

The pharmaceutical composition of the present invention may be formulated for oral and parenteral administration, including intravenous, intraperitoneal, subcutaneous, rectal and topical routes of administration in accordance with conventional methods. The composition for administration may take various forms such as tablets, powder, soft and hard gelatin capsules, aqueous solutions, suspensions, emulsions, syrups, granules, aerosol elixirs, sterilized aqueous solution, sterilized powder, non-aqueous solution and lyophilized agent, and additionally includes conventional additives such as a diluent, lubricant, filler, extender, wetting agent, absorbent, colorant, flavor, sweetener, preservative, emulsifier and the like.

The inventive pharmaceutical composition for oral administration may be prepared by mixing the active ingredient with a carrier, diluent or excipient. Examples of the carrier, excipient and diluent are a disintegrator (e.g., starch, sugar and mannitol); a filler and extender (e.g., calcium phosphate and silicate derivatives); a binder (e.g., carboxymethylcellulose and a derivative thereof, gelatin, and polyvinylpyrrolidone); and a lubricant (e.g., talc, calcium stearate and magnesium stearate, and polyethylene glycol(s)).

Examples of the carrier employed in the injectable composition of the present invention is a water, saline solution, glucose solution, alcohol, glycol, ether (e.g., polyethylene glycol 400), oil, fatty acid, fatty acid ester, glyceride, surfactant, suspension or emulsifier.

The following Examples are intended to further illustrate the present invention without limiting its scope.

Example 1

Preparation of ({4-[3-chloro-4-(3-fluoro-benzyloxy)-phenylamino]-quinazolin-6-ylcarbamoyl}-methyl)-carbamic acid t-butylester (1-1) Preparation of 6-nitro-3H-quinazolin-4-one 150 g of 2-amino-5-nitro-benzoylic acid was added to 200 ml of formamide, the resulting solution was heated to 170° C. for 4 hours, and cooled to 100° C. 500 ml of ice water was added thereto, stirred for 1 hour, and the resulting mixture was filtered under a reduced pressure. The resulting residue was washed with water to obtain a solid, which was dried at 40° C. for 15 hours to obtain the title compound of formula (140 g, 90%).

¹H-NMR (DMSO-$d_6$, 300 MHz): δ 8.77 (d, J=2.7 Hz, 1H), 8.55 (dd, J=6.9 Hz, 1H), 8.36 (s, 1H), 7.84 (d, J=9 Hz, 1H).

(1-2) Preparation of 4-chloro-6-nitro-quinazoline hydrochloride 415 ml of thionylchloride and 123 ml of phosphorousoxy chloride were added to 80 g of the compound obtained in (1-1), and the mixture was stirred at 120° C. for 10 hours after adding 3 ml of N,N-dimethylformamide. The reacted solution was cooled to room temperature, concentrated under a reduced pressure, 240 ml of toluene was added thereto, and the resulting solution was concentrated under a reduced pressure again to obtain the title compound of formula (72 g, 69%).

¹H-NMR (DMSO-$d_6$, 300 MHz): δ 8.80 (d, J=2.6 Hz, 1H), 8.57 (dd, J=3.9 Hz, 1H), 8.35 (s, 1H), 7.89 (d, J=9 Hz, 1H).

(1-3) Preparation of [3-chloro-4-(3-fluoro-benzyloxy)-phenyl]-(6-nitro-quinazolin-4-yl)-amine hydrochloride 72 g of the compound obtained in (1-2) and 74 g of 3-chloro-4-(3-fluoro-benzyloxy)-phenylamine were added to 1,000 ml of isopropanol, and the solution was stirred at 100° C. for 17 hours. The mixture was cooled to room temperature and concentrated under a reduced pressure. The concentrate was washed with acetone and dried at 40° C. for 15 hours to obtain the tile compound (118 g, 91%).

$^1$H-NMR (DMSO-$d_6$, 300 MHz): δ 9.82 (d, J=2 Hz, 1H), 8.97 (d, J=3 Hz, 1H), 8.75 (dd, J=6, 9 Hz, 1H), 8.14 (d, J=9 Hz, 1H), 7.93 (d, J=3 Hz, 1H), 7.70 (dd, J=2.6, 9 Hz, 1H), 7.45-7.48 (m, 1H), 7.29-7.36 (m, 311), 7.18 (t, J=6 Hz, 1H), 5.29 (s, 2H).

(1-4) Preparation of $N^4$-[3-chloro-4-(3-fluoro-benzyloxy)-phenyl]-quinazolin-4,6-diamine 700 ml of THF and 1,400 ml of water were added to 118 g of the compound obtained in (1-3), and 92 g of indium and 192 ml of HCl were added thereto sequentially. The reacted solution was stirred at room temperature for 10 hours, distilled under a reduced pressure to remove THF, and left at 0° C. for 30 mins. The resulting solid was filtered and stirred for 30 mins in 1,000 ml of saturated aqueous sodium bicarbonate solution. The resulting mixture was filtered under a reduced pressure, and the residue was washed with water and dried at 40° C. to obtain the title compound (80 g, 83%).

$^1$H-NMR (DMSO-$d_6$, 300 MHz): δ 9.42 (s, 1H), 8.40 (s, 1H), 8.03 (d, J=2 Hz, 1H), 7.73 (dd, J=2.4, 9 Hz, 1H), 7.43-7.53 (m, 2H), 7.29-7.33 (m, 3H), 7.18-7.25 (m, 3H), 5.61 (s, 2H), 5.24 (s, 2H).

(1-5) Preparation of ({4-[3-chloro-4-(3-fluoro-benzyloxy)-phenylamino]-quinazolin-6-ylcarbamoyl}-methyl)-carbamic acid t-butylester 297 mg of 1-hydroxylbenzotriazole and 959 mg of 1-(3-dimethylaminopropyl)-3-ethylcarbodiimide hydrochloride were added to 664 mg of t-buthoxycarbonylacetic acid dissolved in 10 ml of THF, and the solution was reacted at room temperature for 2 hours after adding 1 g of the compound obtained in (1-4). The reacted solution was washed with distilled water, dried over magnesium sulfate, filtered and distilled under a reduced pressure to obtain impure residue, and the resulting residue was subjected to column chromatography (column-silica gel 60 (Merck, 107719); eluent-methylene chloride:methanol=20:1) to obtain the title compound (1.35 g, 97%).

$^1$H-NMR (CDCl$_3$, 300 MHz): δ 9.40 (br s, 1H), 8.67 (s, 1H), 8.34 (br s, 1H), 8.02 (d, 1H), 7.73 (m, 3H), 7.48 (m, 2H), 7.35 (m, 2H), 7.15 (t, 1H), 7.07 (d, 1H), 5.63 (t, 1H), 5.26 (s, 2H), 4.16 (d, 2H), 1.59 (s, 9H).

Example 2

Preparation of N-({4-[3-chloro-4-(3-fluoro-benzyloxy)-phenylamino]-quinazolin-6-ylcarbamoyl}-methyl)-2-methoxy-acetamide

(2-1) Preparation of (2-methoxy-acetylamino)-acetic acid ethylester 1.5 ml of triethylamine was added to 500 mg of aminoacetic acid ethylester hydrochloride dissolved in 5 ml of chloroform, and the solution was cooled to −78° C. 0.34 ml of methoxyacetylchloride diluted with 3 ml of chloroform was slowly added thereto, and the resulting solution was heated slowly to room temperature and reacted for 6 hours. The reacted solution was washed with distilled water, adjusted to pH 8 to 9 by adding saturated sodium bicarbonate solution, extracted with organic solvent, dried over magnesium sulfate, and filtered and distilled under a reduced pressure to obtain the title compound (595 mg, 75%).

$^1$H-NMR (CDCl$_3$, 300 MHz): δ 7.15 (br s, 1H), 4.26 (q, 2H), 4.11 (d, 2H), 3.98 (s, 2H), 3.48 (s, 3H), 1.33 (t, 3H).

(2-2) Preparation of (2-methoxy-acetylamino)-acetic acid 229 mg of lithium hydroxide was added to 595 mg of the compound obtained in (2-1) dissolved in 6 ml of 50% aqueous THF solution, and the solution was reacted for 4 hours. The reacted solution was washed with distilled water, adjusted to pH 2 by adding 1 N HCl solution, extracted with organic solvent several times, dried over magnesium sulfate, and filtered and distilled under a reduced pressure to obtain the title compound (110 mg, 21%).

$^1$H-NMR (CDCl$_3$, 300 MHz): δ 4.09 (s, 2H), 3.50 (s, 3H), 3.45 (d, 2H).

(2-3) Preparation of 2-amino-N-{4-[3-chloro-4-(3-fluoro-benzyloxy)-phenylamino]-quinazolin-6-yl}-acetamide 25 ml of trifluoroacetic acid was added to 1.3 g of the compound obtained in (1-5) of Example 1 dissolved in 25 ml of methylene chloride, and the solution was reacted at room temperature for 2 hours. The residue obtained from distillation of the reacted solution under a reduced pressure was dissolved in distilled water, washed with saturated sodium bicarbonate solution. The organic layer was dried over magnesium sulfate, and filtered and distilled under a reduced pressure to obtain the title compound (394 mg, 36%).

$^1$H-NMR (CDCl$_3$, 300 MHz): δ 9.96 (s, 1H), 8.93 (d, 1H), 8.80 (s, 1H), 7.99 (m, 2H), 7.66 (dd, 1H), 7.60 (dd, 1H), 7.44 (m, 1H), 7.35 (m, 2H), 7.08 (m, 2H), 5.27 (s, 2H), 3.67 (s, 2H).

(2-4) Preparation of N-({4-[3-chloro-4-(3-fluoro-benzyloxy)-phenylamino]-quinazolin-6-ylcarbamoyl}-methyl)-2-methoxy-acetamide 110 mg of the compound obtained in (2-2) and 0.4 ml of triethylamine were dissolved in 5 ml of THF, and the solution was cooled to 0° C. 0.18 ml of isobutylchloroformate was added thereto, and the resulting solution was stirred for 20 mins. 134 mg of the compound obtained in (1-4) of Example 1 diluted with 2 ml of THF was added thereto, and the solution was reacted at −20° C. for 8 hours. The reacted solution was adjusted to pH 9 by adding saturated sodium bicarbonate solution, dried over magnesium sulfate, filtered and distilled under a reduced pressure, and the resulting residue was subjected to column chromatography (eluent-chloroform:methanol=15:1) to obtain the title compound (10 mg, 6%).

$^1$H-NMR (CDCl$_3$, 300 MHz): δ 8.73 (m, 2H), 8.52 (s, 1H), 7.87 (m, 2H), 7.62 (s, 1H), 7.51 (td, 2H), 7.35 (m, 1H), 7.23 (m, 1H), 7.00 (m, 2H), 5.16 (s, 2H), 4.09 (s, 2H), 3.56 (s, 3H), 3.50 (m, 2H).

Example 3

Preparation of N-({4-[3-chloro-4-(3-fluoro-benzyloxy)-phenylamino]-quinazolin-6-ylcarbamoyl}-methyl)-2-methanesulfonyl-acetamide 16 mg of 1-hydroxylbenzotriazole and 53 mg of 1-(3-dimethylaminopropyl)-3-ethylcarbodiimide hydrochloride were added to 18 mg of methanesulfonylacetic acid dissolved in 3 ml of THF, and the solution was reacted at room temperature for 2 hours after adding 50 mg of the compound obtained in (2-1) of Example 2. The reacted solution was extracted with distilled water, and the resulting residue was filtered under a reduced pressure to obtain the title compound (44 mg, 70%).

$^1$H-NMR (CDCl$_3$, 300 MHz): δ 8.60 (s, 1H), 8.52 (s, 1H), 7.82 (d, 1H), 7.69 (m, 2H), 7.54 (dd, 1H), 7.31 (m, 2H), 7.21 (t, 2H), 6.97 (m, 2H), 5.12 (s, 2H), 4.12 (s, 2H), 4.03 (s, 2H), 3.14 (s, 3H).

Example 4

Preparation of N-({4-[3-chloro-4-(3-fluoro-benzyloxy)-phenylamino]-quinazolin-6-ylcarbamoyl}-methyl)-acrylamide 22 µl of acrylic acid dissolved in 2 ml of THF was cooled to 0° C., and 30 µl of pyridine was added thereto. 70 mg of the compound (2-1) of Example 2 and 59 mg of 1-(3-dimethylaminopropyl)-3-ethylcarbodiimide hydrochloride were added thereto, and the solution was reacted at 0° C. for 7.5 hours. The reacted solution was washed with saturated sodium bicarbonate solution, dried over sodium sulfate, filtered and distilled under a reduced pressure, and the resulting residue was subjected to column chromatography (eluent-chloroform:methanol=15:1) to obtain the title compound (14.8 mg, 19%).

$^1$H-NMR (CD$_3$OD, 300 MHz): δ 8.51 (d, 1H), 8.35 (s, 1H), 7.78 (d, 1H), 7.64 (m, 2H), 7.48 (m, 1H), 7.29 (m, 2H), 7.18 (m, 2H), 7.04 (d, 1H), 6.95 (t, 1H), 6.27 (d, 1H), 6.20 (dd, 1H), 5.64 (dd, 1H), 5.11 (s, 2H), 4.07 (s, 2H).

Example 5

Preparation of (2S)—N-{4-[3-chloro-4-(3-fluoro-benzyloxy)-phenylamino]-quinazolin-6-yl}-2-(2-methoxy-acetylamino)-3-phenyl-propionamide (5-1) Preparation of (2S)-2-(2-methoxy-acetylamino)-3-phenyl-propionic acid methylester 500 mg of 2-amino-3-phenyl-propionic acid methylester hydrochloride dissolved in 10 ml of chloroform was cooled to −78° C., 0.96 ml of triethylamine and 0.23 ml of methoxyacetylchloride were added thereto, and the solution was reacted at room temperature for 2 hours. The reacted solution dissolved in distilled water was adjusted to pH 9 by adding saturated sodium bicarbonate solution, extracted with organic solvent, dried over magnesium sulfate, and filtered and distilled under a reduced pressure to obtain the title compound (427 mg, 73%).

$^1$H-NMR (CDCl$_3$, 300 MHz): δ 7.27 (m, 5H), 7.13 (d, 2H), 6.92 (d, 1H), 4.92 (m, 1H), 3.88 (s, 2H), 3.72 (s, 3H), 3.35 (s, 3H), 3.14 (m, 2H).

(5-2) Preparation of (2S)-(2-methoxy-acetylamino)-3-phenyl-propionic acid 122 mg of lithium hydroxide was added to 427 mg of the compound obtained in (5-1) dissolved in 10 ml of 50% aqueous THF solution, and the solution was reacted for 2 hours. The reacted solution was diluted with distilled water, adjusted to pH 3 to 4 by adding 1 N HCl solution, extracted with organic solvent, dried over magnesium sulfate, and filtered and distilled under a reduced pressure to obtain the title compound (120 mg, 100%).

$^1$H-NMR (CDCl$_3$, 300 MHz): δ 7.28 (m, 3H), 7.19 (d, 2H), 6.95 (d, 1H), 4.91 (q, 1H), 3.89 (s, 2H), 3.34 (s, 3H), 3.25 (dd, 1H), 3.15 (dd, 1H).

(5-3) Preparation of (2S)—N-{4-[3-chloro-4-(3-fluoro-benzyloxy)-phenylamino]-quinazolin-6-yl}-2-(2-methoxy-acetylamino)-3-phenyl-propionamide 76 mg of 1-hydroxylbenzotriazole, 244 mg of 1-(3-dimethylaminopropyl)-3-ethylcarbodiimide hydrochloride, and 200 mg of the compound obtained in (1-4) of Example 1 were added to 120 mg of the compound obtained in (5-2) dissolved in 8 ml of THF, and the solution was reacted at room temperature for 15 hours. The reacted solution was washed with distilled water, dried over magnesium sulfate, filtered and distilled under a reduced pressure, and the resulting residue was subjected to column chromatography (eluent-chloroform:methanol=15:1) to obtain the title compound (94 mg, 30%).

$^1$H-NMR (CDCl$_3$, 300 MHz): δ 9.30 (br s, 1H), 8.58 (d, 1H), 8.08 (d, 1H), 7.86 (m, 2H), 7.63 (m, 2H), 7.48 (m, 1H), 7.29 (m, 7H), 7.00 (m, 2H), 5.15 (s, 2H), 4.93 (m, 1H), 3.93 (m, 2H), 3.37 (s, 3H), 3.30 (m, 1H), 3.16 (m, 1H).

Example 6

Preparation of (1S)-(1-{4-[3-chloro-4-(3-fluoro-benzyloxy)-phenylamino]-quinazolin-6-ylcarbamoyl}-3-methanesulfanyl-propyl)-carbamic acid t-butylester The procedure of (5-3) of Example 5 was repeated except for using 126 mg of 2-t-buthoxycarbonylamino-4-methanesulfanyl-butyric acid instead of the compound obtained in (5-2) of Example 5 to obtain the title compound (80 mg, 25%).

$^1$H-NMR (CD$_3$OD, 300 MHz): δ 8.64 (br s, 1H), 8.48 (s, 1H), 7.91 (d, 1H), 7.79 (m, 2H), 7.60 (dd, 1H), 7.42 (m, 1H), 7.34 (m, 3H), 7.18 (d, 1H), 7.08 (t, 1H), 5.24 (s, 2H), 4.40 (m, 1H), 2.67 (m, 2H), 2.14 (s, 3H), 2.08 (m, 2H), 1.46 (s, 9H); MS (ESI): [M+H+] 626.

Example 7

Preparation of (2S)—N-{4-[3-chloro-4-(3-fluoro-benzyloxy)-phenylamino]-quinazolin-6-yl}-2-(2-methoxy-acetylamino)-4-methanesulfanyl-butyramide (7-1) Preparation of (2S)-2-amino-N-{4-[3-chloro-4-(3-fluoro-benzyloxy)-phenylamino]-quinazolin-6-yl}-4-methanesulfanyl-butyramide 10 ml of trifluoroacetic acid was added to 527 mg of the compound obtained in Example 6 dissolved in 10 ml of methylene chloride, and the solution was reacted at room temperature for 3 hours. The residue obtained from distillation of the reacted solution under a reduced pressure was adjusted to pH 9 by adding saturated aqueous sodium bicarbonate solution, dried over magnesium sulfate, and filtered and distilled under a reduced pressure to obtain the title compound (370 mg, 84%).

$^1$H-NMR (CDCl$_3$, 300 MHz): δ 9.97 (br s, 1H), 8.82 (d, 1H), 8.68 (s, 1H), 7.85 (m, 2H), 7.51 (m, 2H), 7.37 (m, 1H), 7.23 (m, 2H), 7.00 (m, 2H), 5.16 (s, 2H), 3.74 (m, 1H), 2.70 (m, 2H), 2.35 (m, 1H), 2.15 (s, 3H), 1.88 (m, 1H).

(7-2) Preparation of (2S)—N-{4-[3-chloro-4-(3-fluoro-benzyloxy)-phenylamino]-quinazolin-6-yl}-2-(2-methoxy-acetylamino)-4-methanesulfanyl-butyramide 108 mg of the compound obtained in (7-1) dissolved in 3 ml of chloroform was cooled to −78° C. after adding 70 µl of triethylamine, and 70 µl of methoxyacetylchloride dissolved in 2 ml of chloroform was added thereto. The reacted solution was washed with saturated aqueous sodium bicarbonate solution, dried over magnesium sulfate, filtered and distilled under a reduced pressure, and the resulting residue was subjected to column chromatography (eluent-chloroform:methanol=15:1) to obtain the title compound (16 mg, 16%).

$^1$H-NMR (CDCl$_3$, 300 MHz): δ 9.27 (s, 1H), 8.62 (s, 1H), 8.32 (m, 1H), 7.86 (m, 1H), 7.75 (m, 2H), 7.60 (m, 2H), 7.34 (m, 1H), 7.15 (m, 1H), 6.89 (m, 3H), 5.16 (s, 2H), 4.85 (m, 1H), 3.98 (m, 2H), 3.47 (s, 2H), 3.45 (s, 3H), 2.65 (m, 2H), 2.14 (s, 3H); MS (ESI): [M+H+] 598.

Example 8

Preparation of (2S)—N-{4-[3-chloro-4-(3-fluoro-benzyloxy)-phenylamino]-quinazolin-6-yl}-2-(2-methanesulfonyl-acetamino)-4-methanesulfanyl-butyramide 43 mg of 1-hydroxylbenzotriazole, 103 mg of 1-(3-dimethylaminopropyl)-3-ethylcarbodiimide hydrochloride and 150 mg of the compound obtained in (7-1) of Example 7 were added to 47.2 mg of methanesulfonylacetic acid dissolved in 6 ml of methylene chloride, and the solution was reacted at room temperature for 6 hours. The reacted solution was washed with distilled water, dried over magnesium sulfate, filtered and distilled under a reduced pressure, and the resulting residue was subjected to column chromatography (eluent-chloroform:methanol=15:1) to obtain the title compound (40 mg, 22%).

$^1$H-NMR (CDCl$_3$, 300 MHz): δ 9.31 (s, 1H), 8.51 (s, 1H), 8.39 (d, 1H), 8.24 (s, 1H), 7.72 (d, 1H), 7.52 (m, 3H), 7.33 (m, 1H), 7.18 (t, 2H), 7.00 (t, 1H), 6.83 (d, 1H), 5.03 (s, 2H), 4.85 (m, 1H), 4.18 (m, 2H), 3.15 (s, 3H), 2.61 (t, 2H), 2.18 (m, 2H), 2.03 (s, 3H); MS (ESI): [M+H+] 647.

Example 9

Preparation of (2S)-2-acryloylamino-N-{4-[3-chloro-4-(3-fluoro-benzyloxy)-phenylamino]-quinazolin-6-yl}-4-methanesulfanyl-butyramide 5 µl of acrylic acid dissolved in 5 ml of methylene chloride was cooled to 0° C., 20 µl of N,N-diisopropylethylamine, 27 mg of O-(1H-benzotriazol-1-yl)-N,N,N',N'-tetramethyluronium tetrafluoroborate and 30 mg of the compound obtained in (7-1) of Example 7 were added thereto, and reacted for 2 hours. The reacted solution was washed with distilled water, dried over magnesium sulfate, filtered and distilled under a reduced pressure, and the resulting residue was subjected to column chromatography (eluent-chloroform:methanol=15:1) to obtain the title compound (6 mg, 19%).

$^1$H-NMR (CDCl$_3$, 300 MHz): δ 10.13 (s, 1H), 8.49 (s, 1H), 7.79 (d, 2H), 7.69 (d, 1H), 7.54 (m, 3H), 7.34 (m, 1H), 7.20 (m, 2H), 7.01 (t, 1H), 6.88 (d, 1H), 6.30 (dd, 2H), 5.71 (dd, 1H), 5.09 (s, 2H), 5.02 (m, 1H), 2.72 (t, 2H), 2.02 (m, 2H), 2.13 (s, 3H).

Example 10

Preparation of (1-{4-[3-chloro-4-(3-fluoro-benzyloxy)-phenylamino]-quinazolin-6-ylcarbamoyl}-cyclopropyl)-carbamic acid t-butylester 76 mg of 1-hydroxylbenzotriazole, 244 mg of 1-(3-dimethylaminopropyl)-3-ethylcarbodiimide hydrochloride and 200 mg of the compound obtained in (1-4) of Example 1 were added to 180 mg of 1-t-buthoxycarbonylamino-cyclopropylcarboxylic acid dissolved in 15 ml of methylene chloride, and reacted at room temperature for 6 hours. The reacted solution was washed with distilled water, dried over magnesium sulfate, filtered and distilled under a reduced pressure, and the resulting residue was subjected to column chromatography (eluent-chloroform:methanol=15:1) to obtain the title compound (160 mg, 55%).

$^1$H-NMR (CDCl$_3$, 300 MHz): δ 8.92 (br s, 1H), 8.66 (m, 2H), 7.83 (m, 2H), 7.54 (dd, 1H), 7.39 (m, 2H), 7.22 (m, 2H), 6.98 (m, 2H), 5.15 (s, 2H), 1.70 (m, 2H), 1.50 (s, 9H), 1.18 (m, 2H).

Example 11

Preparation of (2S)—N-{4-[3-chloro-4-(3-fluoro-benzyloxy)-phenylamino]-quinazolin-6-yl}-2-(2-methoxy-acetylamino)-2-phenyl-acetamide 38 mg of 1-hydroxylbenzotriazole and 121 mg of 1-(3-dimethylaminopropyl)-3-ethylcarbodiimide hydrochloride were added to 68 mg of (2-methoxy-acetylamino)-phenylacetic acid dissolved in 5 ml of methylene chloride, and reacted at room temperature for 28 hours after adding 100 mg of the compound obtained in (1-4) of Example 1. The reacted solution was washed with distilled water, dried over magnesium sulfate, filtered and distilled under a reduced pressure, and the resulting residue was subjected to column chromatography (eluent-chloroform:methanol=15:1) to obtain the title compound (22 mg, 15%).

$^1$H-NMR (CDCl$_3$, 300 MHz): δ 8.52 (s, 1H), 8.44 (s, 1H), 7.74 (m, 2H), 7.54 (m, 1H), 7.45 (m, 2H), 7.30 (m, 3H), 7.13 (m, 3H), 6.94 (m, 2H), 6.81 (m, 1H), 5.03 (s, 2H), 3.91 (s, 1H), 3.83 (s, 2H), 3.34 (s, 3H); MS (ESI): [M+H+] 602.

Example 12

Preparation of (4S)-4-t-buthoxycarbonylamino-4-{4-[3-chloro-4-(3-fluoro-benzyloxy)-phenylamino]-quinazolin-6-ylcarbamoyl}-butyric acid methylester 109 mg of 1-hydroxylbenzotriazole and 350 mg of 1-(3-dimethylaminopropyl)-3-ethylcarbodiimide hydrochloride were added to 230 mg of 2-t-buthoxycarbonylamino-pentanedionic acid-5-methylester dissolved in 10 ml of methylene chloride, and reacted at room temperature for 13 hours after adding 289 mg of the compound obtained in (1-4) of Example 1. The reacted solution was washed with distilled water, dried over magnesium sulfate, filtered and distilled under a reduced pressure, and the resulting residue was subjected to column chromatography (eluent-chloroform:methanol=15:1) to obtain the title compound (87 mg, 19%).

$^1$H-NMR (CDCl$_3$, 300 MHz): δ 8.57 (s, 1H), 8.38 (s, 1H), 7.80 (d, 1H), 7.71 (d, 1H), 7.56 (m, 1H), 7.46 (m, 2H), 7.26

(m, 2H), 7.12 (m, 1H), 6.92 (m, 2H), 5.08 (s, 2H), 4.27 (m, 1H), 3.65 (s, 3H), 2.18 (m, 2H), 1.98 (m, 2H), 1.38 (s, 9H).

Example 13

Preparation of 4-{4-[3-chloro-4-(3-fluoro-benzyloxy)-phenylamino]-quinazolin-6-ylcarbamoyl}-4-(2-methoxy-acetylamino)-butyric acid methylester (13-1) Preparation of (4S)-4-amino-4-{4-[3-chloro-4-(3-fluoro-benzyloxy)-phenylamino]-quinazolin-6-ylcarbamoyl}-butyric acid methylester 4.6 ml of trifluoroacetic acid was added to 80 mg of the compound obtained in Example 12 dissolved in 4.6 ml of methylene chloride, and reacted at room temperature for 4 hours. The reacted solution was distilled under a reduced pressure to obtain residue, and the residue was washed with saturated sodium bicarbonate, dried over magnesium sulfate, and filtered and distilled under a reduced pressure to obtain the title compound (76 mg, 99%).
$^1$H-NMR (CDCl$_3$, 300 MHz): δ 8.83 (s, 1H), 8.70 (s, 1H), 7.89 (m, 2H), 7.59 (m, 2H), 7.37 (m, 2H), 7.25 (m, 1H), 6.98 (m, 2H), 5.18 (s, 2H), 3.73 (s, 3H), 2.60 (t, 1H), 2.32 (m, 2H), 2.06 (m, 2H).

(13-2) Preparation of 4-{4-[3-chloro-4-(3-fluoro-benzyloxy)-phenylamino]-quinazolin-6-ylcarbamoyl}-4-(2-methoxy-acetylamino)-butyric acid methylester 17 mg of 1-hydroxylbenzotriazole and 53 mg of 1-(3-dimethylaminopropyl)-3-ethylcarbodiimide hydrochloride were added to 20 μl of methoxyacetic acid dissolved in 5 ml of methylene chloride, and the solution was reacted at room temperature for 8 hours after adding 60 mg of the compound obtained in (13-1). The reacted solution was washed with distilled water, dried over magnesium sulfate, filtered and distilled under a reduced pressure, and the resulting residue was subjected to column chromatography (eluent-chloroform:methanol=15:1) to obtain the title compound (20 mg, 29%).
$^1$H-NMR (CDCl$_3$, 300 MHz): δ 9.67 (s, 1H), 8.50 (s, 1H), 8.07 (s, 1H), 7.80 (d, 1H), 7.57 (d, 3H), 7.43 (d, 1H), 7.29 (m, 1H), 7.16 (t, 2H), 6.88 (m, 2H), 5.08 (s, 2H), 4.56 (m, 1H), 3.92 (d, 2H), 3.65 (s, 3H), 3.40 (s, 3H), 2.50 (m, 2H), 2.25 (m, 2H).

Example 14

Preparation of 4-{4-[3-chloro-4-(3-fluoro-benzyloxy)-phenylamino]-quinazolin-6-ylcarbamoyl}-4-(2-methoxy-acetylamino)-butyric acid 8 mg of the compound obtained in (13-2) of Example 13 dissolved in 2.4 ml of 50% aqueous THF solution was reacted for 13 hours after adding 1 mg of lithium hydroxide. The reacted solution was diluted with distilled water, adjusted to pH 4.8 by adding 1 N HCl aqueous solution, and filtered under a reduced pressure to obtain the title compound (6.2 mg, 80%).
$^1$H-NMR (CD$_3$OD, 300 MHz): δ 8.53 (d, 1H), 8.37 (s, 1H), 7.81 (d, 1H), 7.75 (d, 1H), 7.67 (d, 1H), 7.50 (dd, 1H), 7.32 (m, 1H), 7.19 (m, 2H), 7.07 (d, 1H), 6.96 (t, 1H), 5.13 (s, 2H), 4.52 (m, 1H), 4.47 (s, 2H), 3.37 (s, 3H), 2.34 (t, 2H), 2.14 (m, 2H); MS (ESI): [M+H+] 596.

Example 15

Preparation of 2-{4-[3-chloro-4-(3-fluoro-benzyloxy)-phenylamino]-quinazolin-6-ylcarbamoyl}-pyrrolidine-1-carboxylic acid t-butylester 187 mg of 1-hydroxylbenzotriazole and 604 mg of 1-(3-dimethylaminopropyl)-3-ethylcarbodiimide hydrochloride were added to 299 mg of proline-1,2-dicarboxylic acid-1-t-butylester dissolved in 5 ml of THF, and reacted at room temperature for 5 hours after adding 500 mg of the compound obtained in (1-4) of Example 1. The reacted solution was washed with distilled water, dried over magnesium sulfate, filtered and distilled under a reduced pressure, and the resulting residue was subjected to column chromatography (eluent-chloroform:methanol=15:1) to obtain the title compound (459 mg, 61%).
$^1$H-NMR (CDCl$_3$, 300 MHz): δ 10.24 (s, 1H), 8.47 (s, 1H), 7.93 (s, 1H), 7.73 (m, 4H), 7.35 (m, 2H), 7.24 (m, 1H), 7.00 (m, 2H), 5.15 (s, 2H), 4.66 (m, 1H), 3.68 (m, 1H), 3.53 (m, 1H), 2.25 (m, 4H), 1.46 (s, 9H).

Example 16

Preparation of 1-(2-methoxy-acetyl)-pyrrolidine-2-carboxylic acid {4-[3-chloro-4-(3-fluoro-benzyloxy)-phenylamino]-quinazolin-6-yl}-amide (16-1) Preparation of pyrrolidine-2-carboxylic acid {4-[3-chloro-4-(3-fluoro-benzyloxy)-phenylamino]-quinazolin-6-yl}-amide The procedure of (13-1) of Example 13 was repeated except for using 448 mg of the compound obtained in Example 15 instead of the compound obtained in Example 12 to obtain the title compound (297 mg, 82%).
$^1$H-NMR (CDCl$_3$, 300 MHz): δ 10.39 (br s, 1H), 8.93 (s, 1H), 8.83 (s, 1H), 8.06 (d, 1H), 7.79 (d, 1H), 7.69 (m, 2H), 7.54 (m, 1H), 7.40 (m, 2H), 7.18 (m, 2H), 5.33 (s, 2H), 4.20 (m, 1H), 3.31 (m, 2H), 2.46 (m, 1H), 2.28 (m, 1H), 2.02 (m, 2H).

(16-2) Preparation of 1-(2-methoxy-acetyl)-pyrrolidine-2-carboxylic acid {4-[3-chloro-4-(3-fluoro-benzyloxy)-phenylamino]-quinazolin-6-yl}-amide 21 mg of 1-hydroxylbenzotriazole and 68 mg of 1-(3-dimethylaminopropyl)-3-ethylcarbodiimide hydrochloride were added to 19 mg of methoxyacetic acid dissolved in 5 ml of THF, and reacted at room temperature for 9 hours after adding 70 mg of the compound obtained in (16-1). The reacted solution was washed with distilled water, dried over magnesium sulfate, filtered and distilled under a reduced pressure, and the resulting residue was subjected to column chromatography (eluent-chloroform:methanol=15:1) to obtain the title compound (73 mg, 91%).
$^1$H-NMR (CDCl$_3$, 300 MHz): δ 8.51 (s, 1H), 7.96 (s, 1H), 7.83 (d, 1H), 7.67 (m, 2H), 7.56 (d, 1H), 7.26 (m, 1H), 7.17 (m, 1H), 6.93 (m, 2H), 5.09 (s, 2H), 4.84 (m, 1H), 4.11 (d, 2H), 3.68 (m, 2H), 3.51 (m, 2H), 3.40 (s, 3H), 2.19 (m, 2H).

Example 17

Preparation of 1-(2-methanesulfonyl-acetyl)-pyrrolidine-2-carboxylic acid {4-[3-chloro-4-(3-fluoro-benzyloxy)-phenylamino]-quinazolin-6-yl}-amide 21 mg of 1-hydroxylbenzotriazole and 67 mg of 1-(3-dimethylaminopropyl)-3-ethylcarbodiimide hydrochloride were added to 30 mg of methanesulfonylacetic acid dissolved in 5 ml of THF, and reacted at room temperature for 9 hours after adding 70 mg of the compound obtained in (16-1) of Example 16. The reacted solution was washed with distilled water, dried over magnesium sulfate, filtered and distilled under a reduced pressure, and the resulting residue was subjected to column chromatography (eluent-chloroform:methanol=15:1) to obtain the title compound (66 mg, 76%).

$^1$H-NMR (CDCl$_3$, 300 MHz): δ 8.59 (s, 1H), 8.57 (s, 1H), 7.82 (d, 1H), 7.75 (d, 1H), 7.54 (m, 2H), 7.29 (m, 1H), 7.19 (m, 2H), 6.91 (m, 2H), 5.09 (s, 2H), 4.79 (m, 1H), 4.10 (dd, 2H), 3.92 (m, 1H), 3.69 (m, 1H), 3.13 (s, 3H), 2.41 (m, 1H), 2.12 (m, 3H).

Example 18

Preparation of 1-acryloyl-pyrrolidine-2-carboxylic acid {4-[3-chloro-4-(3-fluoro-benzyloxy)-phenylamino]-quinazolin-6-yl}-amide 40 μl of pyridine and 100 mg of the compound obtained in (16-1) of Example 16 dissolved in 4 ml of THF were added to 30 μl of acrylic acid dissolved in 1 ml of THF at 0° C., and reacted with 82 mg of the compound obtained in (16-1) of Example 16 for 6 hours. The reacted solution was washed with distilled water, dried over magnesium sulfate, filtered and distilled under a reduced pressure, and the resulting residue was subjected to column chromatography (eluent-chloroform:methanol=15:1) to obtain the title compound (30 mg, 27%).

$^1$H-NMR (CDCl$_3$, 300 MHz): δ 10.56 (s, 1H), 8.49 (s, 1H), 7.90 (d, 1H), 7.75 (m, 3H), 7.44 (d, 1H), 7.37 (m, 1H), 7.25 (m, 2H), 7.05 (t, 1H), 7.10 (d, 1H), 6.60 (dd, 1H), 6.45 (dd, 1H), 5.81 (dd, 1H), 5.15 (s, 2H), 5.00 (m, 1H), 3.93 (m, 1H), 3.76 (m, 1H), 2.26 (m, 4H).

Example 19

Preparation of (2-{4-[3-chloro-4-(3-fluoro-benzyloxy)-phenylamino]-quinazolin-6-ylcarbamoyl}-ethyl)-carbamic acid t-butylester 0.29 g of 3-t-buthoxycarbonylamino-propionic acid, 0.6 g of 1-(3-dimethylaminopropyl)-3-ethylcarbodiimide hydrochloride 0.6 g and 0.2 g of hydroxylbenzotriazole dissolved in 20 ml of methylene chloride were stirred at room temperature for 13 hours after adding 0.5 g of the compound obtained in (1-4) of Example 1 at room temperature for 13 hours. The reacted solution was extracted with methylene chloride 2 times after adding saturated sodium bicarbonate solution, washed with distilled saturated saline solution, dried over magnesium sulfate, filtered and distilled under a reduced pressure, and the resulting residue was subjected to column chromatography (eluent-chloroform:methanol=15:1) to obtain the title compound (0.3 g, 42%).

$^1$H-NMR (DMSO-d$_6$, 300 MHz): δ 10.20 (s, 1H), 9.73 (s, 1H), 8.64 (s, 1H), 8.48 (s, 1H), 7.92 (d, 1H), 7.74 (m, 2H), 7.45 (d, 2H), 7.18 (m, 4H), 6.84 (t, 1H), 5.20 (s, 2H), 3.40 (t, 2H), 2.42 (t, 2H), 1.33 (s, 9H); MS (ESI): [M+H+] 566.

Example 20

Preparation of N-{4-[3-chloro-4-(3-fluoro-benzyloxy)-phenylamino]-quinazolin-6-yl}-3-(2-methoxy-acetylamino)-propionamide (20-1) Preparation of 3-amino-N-{4-[3-chloro-4-(3-fluoro-benzyloxy)-phenylamino]-quinazolin-6-yl}-propionamide 0.42 g of the compound obtained in Example 19 dissolved in 13 ml of methylene chloride and 13 ml of trifluoroacetic acid was stirred at room temperature for 2 hours. The residue obtained from distillation of the reacted solution under a reduced pressure was melted in 10 ml of methylene chloride while adding 20 ml of saturated sodium bicarbonate slowly, and filtered under a reduced pressure to obtain the title compound as solid (0.34 g, 98%).

$^1$H-NMR (CD$_3$OD, 300 MHz): δ 8.67 (s, 1H), 8.47 (s, 1H), 7.90 (d, 1H), 7.76 (m, 2H), 7.60 (dd, 1H), 7.42 (m, 1H), 7.30 (m, 2H), 7.16 (d, 1H), 7.06 (t, 1H), 5.22 (s, 2H), 3.08 (m, 2H), 2.68 (t, 2H).

(20-2) Preparation of N-{4-[3-chloro-4-(3-fluoro-benzyloxy)-phenylamino]-quinazolin-6-yl}-3-(2-methoxy-acetylamino)-propionamide 0.07 ml of triethylamine was added to 0.08 g of the compound obtained in (20-1) dissolved in 3 ml of methylene chloride, and reacted with 0.03 ml of methoxyacetylchloride at −70° C. for 30 mins and at room temperature for 4 hours. The reacted solution was extracted with methylene chloride 2 times after adding saturated sodium bicarbonate solution, washed with distilled saturated saline solution, dried over magnesium sulfate, filtered and distilled under a reduced pressure, and the resulting residue was subjected to column chromatography (eluent-chloroform:methanol=15:1) to obtain the title compound (0.04 g, 44%).

$^1$H-NMR (CD$_3$OD, 300 MHz): δ 8.64 (s, 1H), 8.47 (s, 1H), 7.87 (d, 1H), 7.80 (s, 1H), 7.73 (s, 2H), 7.58 (dd, 1H), 7.36 (m, 1H), 7.30 (m, 2H), 7.13 (d, 1H), 7.04 (t, 1H), 5.21 (s, 2H), 3.90 (s, 2H), 3.66 (t, 2H), 3.42 (s, 3H), 2.72 (t, 2H).

Example 21

Preparation of N-{4-[3-chloro-4-(3-fluoro-benzyloxy)-phenylamino]-quinazolin-6-yl}-3-(2-methanesulfonyl-acetylamino)-propionamide 0.12 g of methanesulfonylacetic acid, 0.34 g of 1-(3-dimethylaminopropyl)-3-ethylcarbodiimide hydrochloride and 0.12 g of methylene chloride dissolved in 2 ml of methylene chloride was stirred at room temperature for 2 hours after adding 0.2 g of the compound obtained in (20-1) of Example 20. The reacted solution was filtered under a reduced pressure after adding saturated sodium bicarbonate to obtain the title compound as solid (0.2 g, 80%).

$^1$H-NMR (DMSO-d$_6$, 300 MHz): δ 10.35 (s, 1H), 9.83 (s, 1H), 8.66 (s, 1H), 8.50 (m, 2H), 7.95 (s, 1H), 7.86 (d, 1H), 7.65 (m, 2H), 7.48 (m, 1H), 7.32 (m, 2H), 7.18 (m, 2H), 5.23 (s, 2H), 4.08 (s, 2H), 3.44 (m, 2H), 3.11 (s, 3H), 2.58 (t, 2H).

Example 22

Preparation of N-(2-{4-[3-chloro-4-(3-fluoro-benzyloxy)-phenylamino]-quinazolin-6-ylcarbamoyl}-ethyl)-acrylamide 0.03 ml of acrylic acid, 0.1 ml of diisopropylethylamine and 0.15 g of O-(1H-benzotriazolyl-1-yl)-N,N,N',N'-tetramethyluronium tetrafluoroborate dissolved in 10 ml of methylene chloride at 0° C. was reacted with 0.14 g of the compound obtained in (20-1) of Example 20 for 10 mins and at room temperature for 15 hours. The reacted solution was extracted with methylene chloride 2 times after adding saturated sodium bicarbonate solution, washed with distilled saturated saline solution, dried over magnesium sulfate, filtered and distilled under a reduced pressure, and the resulting residue was subjected to column chromatography (eluent-chloroform:methanol=15:1) to obtain the title compound (0.05 g, 37%).

$^1$H-NMR (CD$_3$OD, 300 MHz): δ 8.59 (s, 1H), 8.37 (s, 1H), 7.84 (d, 1H), 7.70 (s, 1H), 7.60 (d, 1H), 7.51 (m, 1H), 7.37 (m, 1H), 7.21 (m, 2H), 7.04 (m, 2H), 6.23 (d, 2H), 5.65 (t, 1H), 5.17 (s, 2H), 3.66 (t, 2H), 2.72 (t, 2H); MS (ESI): [M+H+] 520.2.

Example 23

Preparation of 3-phenyl-propionylic acid (2-{4-[3-chloro-4-(3-fluoro-benzyloxy)-phenylamino]-quinazolin-6-ylcarbamoyl}-ethyl)-amide 32.2 mg of phenylpropagylic acid dissolved in 1 ml of THF was cooled to 0° C., and reacted with 22 μl of pyridine, 50 mg of the compound obtained (20-1) of Example 20 and 41 mg of 1-(3-dimethylaminopropyl)-3-ethylcarbodiimide hydrochloride for 15 hours. The reacted solution was diluted with distilled water, washed with saturated sodium bicarbonate solution, dried over magnesium sulfate, filtered and distilled under a reduced pressure, and the resulting residue was subjected to column chromatography (eluent-chloroform:methanol=15:1) to obtain the title compound (16.9 mg, 26%).

$^1$H-NMR (CD$_3$OD, 300 MHz): δ 8.46 (s, 1H), 8.24 (s, 1H), 7.67 (d, 1H), 7.53 (s, 2H), 7.34 (dd, 1H), 7.30 (m, 2H), 7.20 (m, 4H), 7.05 (m, 2H), 6.94 (d, 1H), 6.83 (t, 1H), 5.00 (s, 2H), 3.45 (t, 2H), 2.52 (t, 2H); MS (ESI): [M+H+] 594.

Example 24

Preparation of hexa-2,4-dienonylic acid (2-{4-[3-chloro-4-(3-fluoro-benzyloxy)-phenylamino]-quinazolin-6-ylcarbamoyl}-ethyl)-amide The procedure of Example 23 was repeated except for using 25 mg of 2,4-hexadienonylic acid instead of phenyl-propagylic acid. The resulting solution was poured into ice water after adding 4 droplets of saturated sodium bicarbonate solution to obtain solid. The solid was dissolved in a mixture of methylene chloride and methanol, and the solution was recrystallized with hexane to obtain the title compound (36.1 mg, 58.2%).

$^1$H-NMR (CD$_3$OD, 300 MHz): δ 8.77 (s, 1H), 8.58 (s, 1H), 8.01 (d, 1H), 7.87 (d, 2H), 7.72 (dd, 1H), 7.53 (m, 1H), 7.43 (m, 2H), 7.26 (m, 2H), 7.18 (m, 1H), 6.25 (m, 3H), 6.01 (d, 1H), 5.34 (s, 2H), 3.77 (t, 2H), 2.83 (t, 2H), 1.94 (d, 3H); MS (ESI): [M+H+] 560.

Example 25

Preparation of cyclopent-1-en carboxylic acid (2-{4-[3-chloro-4-(3-fluoro-benzyloxy)-phenylamino]-quinazolin-6-ylcarbamoyl}-ethyl)-amide The procedure of Example 23 was repeated except for using 25 mg of 1-cyclopentene carboxylic acid instead of phenylpropagylic acid. 2 ml of distilled water was added to the resulting solution to obtain solid. The solid was dissolved in a mixture of methylene chloride and methanol, and the solution was recrystallized with hexane to obtain the title compound (29.3 mg, 47.3%).

$^1$H-NMR (CD$_3$OD, 300 MHz): δ 8.55 (s, 1H), 8.30 (s, 1H), 7.80 (d, 1H), 7.66 (s, 2H), 7.51 (dd, 1H), 7.31 (m, 1H), 7.19 (m, 2H), 7.08 (d, 1H), 6.96 (m, 1H), 6.47 (s, 1H), 5.13 (s, 2H), 3.55 (t, 2H), 2.63 (t, 2H), 2.41 (m, 4H), 1.87 (t, 2H); MS (ESI): [M+H+] 560.

Example 26

Preparation of N-(2-{4-[3-chloro-4-(3-fluoro-benzyloxy)-phenylamino]-quinazolin-6-ylcarbamoyl}-ethyl)-3-phenyl-acrylamide The procedure of Example 23 was repeated except for using 32.3 mg of cinnamic acid instead of phenylpropagylic acid. The resulting solution was poured into ice water after adding 4 droplets of saturated sodium bicarbonate solution to obtain solid. The solid was dissolved in a mixture of methylene chloride and methanol, and the solution was recrystallized with hexane to obtain the title compound (35.6 mg, 56%).

$^1$H-NMR (CD$_3$OD, 300 MHz): δ 8.87 (s, 1H), 8.66 (s, 1H), 8.09 (d, 1H), 7.94 (m, 2H), 7.77 (m, 4H), 7.56 (m, 5H), 7.37 (d, 1H), 7.26 (m, 1H), 6.82 (d, 2H), 5.43 (s, 2H), 3.91 (t, 2H), 2.96 (t, 2H); MS (ESI): [M+H+] 596.

Example 27

Preparation of but-2-ynoylic acid(2-{4-[3-chloro-4-(3-fluoro-benzyloxy)-phenylamino]-quinazolin-6-ylcarbamoyl}-ethyl)-amide The procedure of Example 23 was repeated except for using 19 mg of 2-butenoylic acid instead of phenylpropagylic acid to obtain the title compound (11.8 mg, 20%).

$^1$H-NMR (CD$_3$OD, 300 MHz): δ 8.54 (s, 1H), 8.34 (s, 1H), 7.77 (s, 1H), 7.62 (s, 2H), 7.46 (dd, 1H), 7.28 (m, 1H), 7.17 (m, 2H), 7.04 (d, 1H), 6.93 (t, 1H), 5.10 (s, 2H), 3.47 (t, 2H), 2.57 (t, 2H), 1.82 (s, 3H); MS (ESI): [M+H+] 532.

Example 28

Preparation of but-2-enonylic acid (2-{4-[3-chloro-4-(3-fluoro-benzyloxy)-phenylamino]-quinazolin-6-ylcarbamoyl}-ethyl)-amide 0.64 ml of pyridine was added to 50 mg of the compound obtained (20-1) of Example 20, cooled to 0° C., and reacted with 12.5 μl of crotonylchloride dissolved in 0.26 ml of diethylether for 4 hours. The residue obtained from distillation of the reacted solution under a reduced pressure was dissolved in distilled water, washed with saturated sodium bicarbonate solution, dried over magnesium sulfate, filtered and distilled under a reduced pressure, and the resulting residue was subjected to column chromatography (eluent-chloroform:methanol=15:1) to obtain the title compound (12.6 mg, 22%).

$^1$H-NMR (CD$_3$OD, 300 MHz): δ 8.56 (s, 1H), 8.37 (s, 1H), 7.80 (d, 1H), 7.65 (d, 2H), 7.51 (dd, 1H), 7.31 (m, 1H), 7.21 (m, 2H), 7.07 (d, 1H), 6.96 (td, 1H), 6.70 (dd, 1H), 5.84 (dd, 1H), 5.13 (s, 2H), 3.54 (t, 2H), 2.61 (t, 2H), 1.74 (dd, 2H); MS (ESI): [M+H] 534.

Example 29

Preparation of 3-methyl-but-2-enonylic acid (2-{4-[3-chloro-4-(3-fluoro-benzyloxy)-phenylamino]-quinazolin-6-ylcarbamoyl}-ethyl)-amide The procedure of Example 28 was repeated except for using 14.3 μl of 3,3-dimethylacryloylchloride instead of crotonylchloride. The residue obtained from distillation of the reacted solution under a reduced pressure was stirred after adding distilled water, and filtered under a reduced pressure to obtain the title compound (47.9 mg, 81.2%).

$^1$H-NMR (CD$_3$OD, 300 MHz)): δ 8.87 (s, 1H), 8.66 (s, 1H), 7.98 (d, 1H), 7.95 (dd, 1H), 7.86 (d, 1H), 7.69 (dd, 1H), 7.50 (m, 1H), 7.36 (m, 2H), 7.29 (d, 1H), 7.13 (t, 1H), 5.77 (s, 1H), 5.34 (d, 2H), 3.69 (t, 2H), 2.79 (t, 2H), 2.19 (d, 3H), 1.92 (d, 3H); MS (ESI): [M+H+] 548.

Example 30

Preparation of N-(2-{4-[3-chloro-4-(3-fluoro-benzyloxy)-phenylamino]-quinazolin-6-ylcarbamoyl}-ethyl)-2-methyl-acrylamide The procedure of Example 28 was repeated except for using 13 μl of metacryloy chloride instead of crotonylchloride to obtain the title compound (14.6 mg, 25.5%).

$^1$H-NMR (CD$_3$OD, 300 MHz): δ 8.86 (s, 1H), 8.66 (s, 1H), 8.09 (d, 1H), 7.95 (s, 2H), 7.80 (dd, 1H), 7.59 (m, 1H), 7.49 (m, 2H), 7.37 (d, 1H), 7.26 (t, 1H), 5.90 (s, 1H), 5.57 (s, 1H), 5.41 (s, 2H), 3.84 (t, 2H), 2.92 (t, 2H), 2.14 (s, 3H); MS (ESI): [M+H] 534.

Example 31

Preparation of N-(2-{4-[3-chloro-4-(3-fluoro-benzyloxy)-phenylamino]-quinazolin-6-ylcarbamoyl}-ethyl)-2-cyano-acetamide The procedure of Example 21 was repeated except for using cyano acetic acid instead of methanesulfonylacetic acid and 0.09 g of the compound obtained in (20-1) of Example 20 to obtain the title compound (0.09 g, 88%).

$^1$H-NMR (DMSO-d$_6$, 300 MHz): δ 10.28 (s, 1H), 9.76 (s, 1H), 8.66 (s, 1H), 8.49 (s, 1H), 8.35 (t, 1H), 7.97 (d, 1H), 7.83 (dd, 1H), 7.73 (d, 1H), 7.68 (dd, 1H), 7.45 (m, 1H), 7.29 (m, 2H), 7.23 (d, 1H), 7.17 (t, 1H), 5.24 (s, 2H), 3.61 (s, 2H), 3.41 (q, 2H), 2.59 (t, 2H).

Example 32

Preparation of 3-methyl-isoxazol-5-carboxylic acid (2-{4-[3-chloro-4-(3-fluoro-benzyloxy)-phenylamino]-quinazolin-6-ylcarbamoyl}-ethyl)-amide The procedure of Example 21 was repeated except for using 3-methyl-isoxazol-5-carboxylic acid instead of methanesulfonylacetic acid and 0.09 g of the compound obtained in (20-1) of Example 20 to obtain the title compound (0.04 g, 58%).

$^1$H-NMR (CD$_3$OD, 300 MHz): δ 8.67 (s, 1H), 8.46 (s, 1H), 7.90 (d, 1H), 7.40 (d, 2H), 7.60 (dd, 1H), 7.40 (m, 1H), 7.29 (m, 2H), 7.17 (d, 1H), 7.05 (t, 1H), 6.81 (s, 1H), 5.23 (s, 2H), 3.77 (t, 2H), 2.80 (t, 2H), 2.32 (s, 3H).

Example 33

Preparation of furan-3-carboxylic acid (2-{4-[3-chloro-4-(3-fluoro-benzyloxy)-phenylamino]-quinazolin-6-ylcarbamoyl}-ethyl)-amide The procedure of Example 21 was repeated except for using furan-3-carboxylic acid instead of methanesulfonylacetic acid and 0.09 g of the compound obtained in (20-1) of Example 20 to obtain the title compound (0.06 g, 56%).

$^1$H-NMR (DMSO-d$_6$, 300 MHz): δ 10.30 (s, 1H), 9.77 (s, 1H), 8.67 (d, 1H), 8.50 (s, 1H), 8.33 (t, 1H), 8.17 (t, 1H), 7.98 (d, 1H), 7.83 (dd, 1H), 7.72 (m, 3H), 7.47 (m, 1H), 7.31 (m, 2H), 7.24 (d, 1H), 7.18 (t, 1H), 6.85 (t, 1H), 5.25 (s, 2H), 3.55 (q, 2H), 2.68 (t, 2H).

Example 34

Preparation of 1H-pyrazol-4-carboxylic acid (2-{4-[3-chloro-4-(3-fluoro-benzyloxy)-phenylamino]-quinazolin-6-ylcarbamoyl}-ethyl)-amide The procedure of Example 21 was repeated except for using 1H-pyrazol-4-carboxylic acid and 0.09 g of the compound obtained in (20-1) of Example 20 instead of methanesulfonylacetic acid to obtain the title compound (0.07 g, 65%).

$^1$H-NMR (CD$_3$OD, 300 MHz): δ 8.89 (d, 1H), 8.69 (s, 1H), 8.03 (m, 3H), 7.86 (d, 1H), 7.81 (d, 1H), 7.60 (dd, 1H), 7.38 (m, 1H), 7.25 (m, 2H), 7.17 (d, 1H), 7.04 (t, 1H), 5.22 (s, 2H), 3.76 (t, 2H), 2.81 (t, 2H).

Example 35

Preparation of N-(2-{4-[3-chloro-4-(3-fluoro-benzyloxy)-phenylamino]-quinazolin-6-ylcarbamoyl}-ethyl)-benzamide The procedure of (20-2) of Example 20 was repeated except for using benzoic acid and 0.05 g of the compound obtained in (20-1) of Example 20 instead of methoxyacetic acid to obtain the title compound (0.03 g, 49%).

$^1$H-NMR (CD$_3$OD, 300 MHz): δ 8.82 (d, 1H), 8.61 (s, 1H), 7.88 (dd, 1H), 7.75 (d, 1H), 7.68 (m, 3H), 7.48 (dd, 1H), 7.38 (m, 1H), 7.30 (m, 3H), 7.13 (m, 3H), 6.95 (t, 1H), 5.12 (s, 2H), 3.70 (t, 2H), 2.73 (t, 2H); MS (ESI): [M+H+] 569.

Example 36

Preparation of N-(2-{4-[3-chloro-4-(3-fluoro-benzyloxy)-phenylamino]-quinazolin-6-ylcarbamoyl}-ethyl)-oxalamic acid ethylester The procedure of (20-2) of Example 20 was repeated except for using oxalic acid monoethylester and 0.09 g of the compound obtained in (20-1) of Example 20 instead of methoxyacetic acid, and subjecting column chromatography (eluent-chloroform:methanol=15:1) to obtain the title compound (0.04 g, 37%).

$^1$H-NMR (CD$_3$OD, 300 MHz): δ 8.93 (s, 1H), 8.47 (d, 1H), 7.88 (m, 2H), 7.38 (d, 1H), 7.28 (m, 1H), 7.13 (m, 3H), 7.06 (d, 1H), 6.95 (t, 1H), 5.09 (s, 2H), 4.19 (q, 2H), 3.53 (t, 2H), 2.61 (t, 2H), 1.22 (t, 3H)

Example 37

Preparation of cyclopropylcarboxylic acid (2-{4-[3-chloro-4-(3-fluoro-benzyloxy)-phenylamino]-quinazolin-6-ylcarbamoyl}-ethyl)-amide The procedure of (20-2) of Example 20 was repeated except for using cyclopropylcarboxylic acid and 0.09 g of the compound obtained in (20-1) of Example 20 instead of methoxyacetic acid, and subjecting column chromatography (eluent-chloroform:methanol=15:1) to obtain the title compound (0.05 g, 49%).

¹H-NMR (CD₃OD, 300 MHz): δ 8.59 (s, 1H), 8.39 (s, 1H), 7.83 (d, 1H), 7.68 (s, 2H), 7.53 (dd, 1H), 7.33 (m, 1H), 7.23 (m, 2H), 7.10 (d, 1H), 6.99 (t, 1H), 5.16 (s, 2H), 3.52 (t, 2H), 2.61 (t, 2H), 1.49 (m, 1H), 0.77 (m, 2H), 0.68 (m, 2H).

Example 38

Preparation of acetic acid 2-t-buthoxycarbony-lamino-1-{4-[3-chloro-4-(3-fluoro-benzyloxy)-phenylamino]-quinazolin-6-ylcarbamoyl}-ethylester 1.83 g of 2-acetoxy-3-t-buthoxycarbonylamino-propionic acid, 2.83 g of 1-(3-dimethylaminopropyl)-3-ethylcarbodiimide hydrochloride and 1 g of 1-hydroxylbenzotriazole dissolved in 30 ml of methylene chloride was reacted with 1.46 g of the compound obtained in (1-4) of Example 1 at room temperature for 22 hours. The reacted solution was extracted with methylene chloride 2 times after adding saturated sodium bicarbonate solution, washed with distilled saturated saline solution, dried over magnesium sulfate, filtered and distilled under a reduced pressure, and the resulting residue was subjected to column chromatography (eluent-chloroform:methanol=15:1) to obtain the title compound (1.08 g, 47%).
¹H-NMR (CDCl₃, 300 MHz): δ 9.37 (s, 1H), 8.55 (s, 1H), 8.15 (s, 2H), 7.76 (d, 1H), 7.50 (m, 3H), 7.32 (m, 1H), 7.22 (m, 2H), 6.99 (t, 1H), 6.86 (d, 1H), 5.53 (t, 1H), 5.29 (t, 1H), 5.07 (s, 2H), 3.72 (m, 2H), 2.19 (s, 3H), 1.40 (s, 9H).

Example 39

Preparation of acetic acid 1-{4-[3-chloro-4-(3-fluoro-benzyloxy)-phenylamino]-quinazolin-6-ylcarbamoyl}-2-(2-methoxy-acetylamino)-ethylester (39-1) Preparation of acetic acid 2-amino-1-{4-[3-chloro-4-(3-fluoro-benzyloxy)-phenylamino]-quinazolin-6-ylcarbamoyl}-ethyl ester 0.12 g of the compound obtained in Example 38 dissolved in 3 ml of methylene chloride and 3 ml of trifluoroacetic acid was stirred at room temperature for 1.5 hours. The residue obtained from distillation of the reacted solution under a reduced pressure was stirred in 3 ml of methylene chloride while adding 10 ml of saturated sodium bicarbonate slowly and filtered under a reduced pressure to obtain the title compound (0.08 g, 84%).
¹H-NMR (CDCl₃, 300 MHz): δ 8.53 (m, 2H), 7.81 (d, 1H), 7.76 (d, 1H), 7.63 (dd, 1H), 7.56 (dd, 1H), 7.30 (m, 1H), 7.15 (m, 2H), 6.96 (m, 2H), 5.08 (s, 2H), 4.28 (m, 1H), 3.65 (m, 2H), 2.02 (s, 3H).

(39-2) Preparation of acetic acid 1-{4-[3-chloro-4-(3-fluoro-benzyloxy)-phenylamino]-quinazolin-6-ylcarbamoyl}-2-(2-methoxy-acetylamino)-ethylester 0.4 g of metonym acetic acid, 1.69 g of 1-(3-dimethylaminopropyl)-3-ethylcarbodiimide hydrochloride and 0.6 g of 1-hydroxylbenzotriazole dissolved in 20 ml of methylene chloride were reacted with 1.14 g of the compound obtained in (39-1) at room temperature for 6.5 hours. The reacted solution was filtered under a reduced pressure after adding saturated sodium bicarbonate solution to obtain the title compound as solid (0.7 g, 54%).
¹H-NMR (DMSO-d₆, 300 MHz): δ 10.62 (s, 1H), 9.93 (s, 1H), 8.74 (s, 1H), 8.58 (s, 1H), 8.17 (t, 1H), 8.07 (d, 1H), 7.98 (d, 1H), 7.77 (m, 2H), 7.52 (m, 1H), 7.40 (m, 2H), 7.31 (d, 1H), 7.24 (t, 1H), 5.31 (s, 2H), 4.26 (m, 2H), 3.72 (m, 2H), 3.56 (m, 1H), 3.42 (s, 3H), 1.90 (s, 3H), Example 40

Preparation of N-{4-[3-chloro-4-(3-fluoro-benzyloxy)-phenylamino]-quinazolin-6-yl}-2-hydroxyl-3-(2-methoxy-acetylamino)-propionamide 0.5 ml of ammonia water was added to 0.1 g of the compound obtained in (39-2) of Example 39 dissolved in 10 ml of methanol, and the solution was stirred at room temperature for 1.5 hours. The reacted solution was filtered under a reduced pressure after adding distilled water to obtain the title compound as solid (0.08 g, 86%).
¹H-NMR (DMSO-d₆, 300 MHz): δ 10.00 (s, 1H), 9.80 (s, 1H), 8.72 (d, 1H), 8.58 (s, 1H), 8.14 (dd, 1H), 8.05 (m, 2H), 7.79 (m, 2H), 7.54 (m, 1H), 7.39 (m, 2H), 7.34 (d, 1H), 7.23 (t, 1H), 6.22 (d, 1H), 5.31 (s, 2H), 4.26 (m, 1H), 3.61 (m, 1H), 3.36 (s, 3H), 3.28 (m, 1H), 1.90 (s, 2H).

Example 41

Preparation of (2-{4-[3-chloro-4-(3-fluoro-benzyloxy)-phenylamino]-quinazolin-6-ylcarbamoyl}-propyl)-carbamic acid t-butylester 0.44 g of 3-t-buthoxycarbonylamino-2-methyl-propionic acid, 0.83 g of 1-(3-dimethylaminopropyl)-3-ethylcarbodiimide hydrochloride and 0.29 g of 1-hydroxylbenzotriazole dissolved in 20 ml of methylene chloride were reacted with 0.43 g of the compound obtained in (1-4) of Example 1 at room temperature for 18 hours. The reacted solution was extracted with methylene chloride 3 times after adding saturated sodium bicarbonate solution, washed with saturated saline solution, dried over magnesium sulfate, filtered and distilled under a reduced pressure, and the resulting residue was subjected to column chromatography (eluent-chloroform:methanol=15:1) to obtain the title compound (0.32 g, 52%).
¹H-NMR (DMSO-d₆, 300 MHz): δ 10.17 (s, 1H), 9.70 (s, 1H), 8.64 (s, 1H), 8.41 (s, 1H), 7.88 (d, 1H), 7.73 (t, 1H), 7.59 (m, 2H), 7.38 (m, 1H), 7.24 (m, 2H), 7.17 (d, 1H), 7.10 (t, 1H), 6.83 (t, 1H), 5.17 (s, 2H), 2.93 (m, 1H), 1.30 (s, 9H), 1.04 (d, 2H), 0.95 (d, 2H).

Example 42

Preparation of N-{4-[3-chloro-4-(3-fluoro-benzyloxy)-phenylamino]-quinazolin-6-yl}-3-(2-methoxy-acetylamino)-2-methyl-propionamide (42-1) Preparation of 3-amino-N-{4-[3-chloro-4-(3-fluoro-benzyloxy)-phenylamino]-quinazolin-6-yl}-2-methyl-propionamide 0.24 g of the compound obtained in Example 41 dissolved in 7 ml of methylene chloride and 7 ml of trifluoroacetic acid was stirred at room temperature for 8 hours. The residue obtained from distillation of the reacted solution under a reduced pressure was stirred in 4 ml of methylene chloride while adding 20 ml of saturated sodium bicarbonate slowly and filtered under a reduced pressure to obtain the title compound as solid (0.19 g, 96%).
¹H-NMR (CD₃OD, 300 MHz): δ 9.84 (s, 1H), 8.71 (s, 1H), 8.49 (s, 1H), 7.99 (d, 1H), 7.88 (dd, 1H), 7.72 (m, 2H), 7.46

(m, 1H), 7.32 (m, 2H), 7.26 (d, 1H), 7.15 (t, 1H), 5.25 (s, 2H), 2.75 (m, 2H), 2.40 (m, 1H), 1.12 (d, 3H); MS (ESI): [M+H]+ 480.2.

(42-2) Preparation of N-{4-[3-chloro-4-(3-fluoro-benzyloxy)-phenylamino]-quinazolin-6-yl}-3-(2-methoxy-acetylamino)-2-methyl-propionamide 0.02 g of methoxy acetic acid, 0.08 g of 1-(3-dimethylaminopropyl)-3-ethylcarbodiimide hydrochloride and 0.03 g of 1-hydroxylbenzotriazole dissolved in 3 ml of methylene chloride were reacted with 0.05 g of the compound obtained in (42-1) at room temperature for 46 hours. The reacted solution was filtered under a reduced pressure after adding saturated sodium bicarbonate solution to obtain the title compound as solid (0.4 g, 70%).

$^1$H-NMR (DMSO-$d_6$, 300 MHz): δ 10.29 (s, 1H), 9.82 (s, 1H), 8.74 (d, 1H), 8.52 (s, 1H), 8.00 (d, 1H), 7.84 (m, 2H), 7.75 (m, 2H), 7.50 (m, 1H), 7.35 (m, 2H), 7.27 (d, 1H), 7.21 (t, 1H), 5.28 (s, 2H), 3.83 (s, 2H), 3.40 (m, 2H), 3.31 (s, 3H), 2.85 (m, 1H), 1.17 (d, 3H).

Example 43

Preparation of N-{4-[3-chloro-4-(3-fluoro-benzyloxy)-phenylamino]-quinazolin-6-yl}-3-(2-methanesulfonyl-acetylamino)-2-methyl-propionamide 0.03 g of methanesulfonylacetic acid, 0.08 g of 1-(3-dimethylaminopropyl)-3-ethylcarbodiimide hydrochloride and 0.03 g of 1-hydroxylbenzotriazole dissolved in 3 ml of methylene chloride were reacted with 0.05 g of the compound obtained in (42-1) of Example 42 at room temperature for 46 hours. The reacted solution was filtered under a reduced pressure after adding saturated sodium bicarbonate solution to obtain the title compound as solid (0.4 g, 64%).

$^1$H-NMR (DMSO-$d_6$, 300 MHz): δ 10.29 (s, 1H), 9.79 (s, 1H), 8.71 (d, 1H), 8.49 (m, 2H), 7.98 (d, 1H), 7.85 (d, 1H), 7.73 (m, 2H), 7.46 (m, 1H), 7.25 (m, 4H), 5.25 (s, 1H), 4.10 (s, 2H), 3.11 (s, 3H), 2.75 (m, 2H), 2.20 (m, 1H), 1.18 (d, 3H).

Example 44

Preparation of N-(2-{4-[3-chloro-4-(3-fluoro-benzyloxy)-phenylamino]-quinazolin-6-ylcarbamoyl}-propyl)-acrylamide 0.02 g of acrylic acid, 0.1 g of 1-(3-dimethylaminopropyl)-3-ethylcarbodiimide hydrochloride and 0.04 g of 1-hydroxylbenzotriazole dissolved in 5 ml of methylene chloride were reacted with 0.06 g of the compound obtained in (42-1) of Example 42 at room temperature for 24 hours. The reacted solution was extracted with methylene chloride 2 times after adding saturated sodium bicarbonate solution, washed with saturated saline solution, dried over magnesium sulfate, filtered and distilled under a reduced pressure, and the resulting residue was subjected to column chromatography (eluent-chloroform:methanol=15:1) to obtain the title compound (0.01 g, 15%).

$^1$H-NMR (CD$_3$OD, 300 MHz): δ 8.50 (s, 1H), 8.31 (s, 1H), 7.74 (d, 1H), 7.60 (m, 2H), 7.44 (dd, 1H), 7.24 (m, 1H), 7.15 (m, 2H), 7.01 (d, 1H), 6.90 (t, 1H), 6.09 (m, 2H), 5.49 (m, 1H), 5.07 (s, 2H), 3.50 (m, 2H), 2.75 (m, 1H), 1.13 (d, 3H).

Example 45

Preparation of (2-{4-[3-chloro-4-(3-fluoro-benzyloxy)-phenylamino]-quinazolin-6-ylcarbamoyl}-1-phenyl-ethyl)-carbamic acid t-butylester 1.35 g of 3-t-buthoxycarbonylamino-3-phenyl-propionic acid, 1.95 g of 1-(3-dimethylaminopropyl)-3-ethylcarbodiimide hydrochloride and 0.69 g of 1-hydroxylbenzotriazole dissolved in 30 ml of methylene chloride were reacted with 1 g of the compound obtained in (1-4) of Example 1 at room temperature for 12 hours. The reacted solution was extracted with methylene chloride 2 times after adding saturated sodium bicarbonate solution, washed with saturated saline solution, dried over magnesium sulfate, filtered and distilled under a reduced pressure, and the resulting residue was subjected to column chromatography (eluent-chloroform:methanol=15:1) to obtain the title compound (0.7 g, 43%).

$^1$H-NMR (DMSO-$d_6$, 300 MHz): δ 9.18 (s, 1H), 8.77 (s, 1H), 7.62 (s, 1H), 7.45 (s, 1H), 6.92 (d, 1H), 6.70 (m, 3H), 6.40 (m, 2H), 6.25 (m, 8H), 4.22 (s, 2H), 4.04 (m, 1H), 1.79 (d, 2H), 0.30 (s, 9H).

Example 46

Preparation of N-{4-[3-chloro-4-(3-fluoro-benzyloxy)-phenylamino]-quinazolin-6-yl}-3-(2-methoxy-acetylamino)-3-phenyl-propionamide (46-1) Preparation of 3-amino-N-{4-[3-chloro-4-(3-fluoro-benzyloxy)-phenylamino]-quinazolin-6-yl}-3-phenyl-propionamide 0.64 g of the compound obtained in Example 45 dissolved in 20 ml of methylene chloride and 20 ml of trifluoroacetic acid was stirred at room temperature for 4 hours. The residue obtained from distillation of the reacted solution under a reduced pressure was stirred in 5 ml of methylene chloride while adding 20 ml of saturated sodium bicarbonate slowly and filtered under a reduced pressure to obtain the title compound as solid (0.53 g, 98%).

$^1$H-NMR (DMSO-$d_6$, 300 MHz): δ 10.46 (s, 1H), 9.77 (s, 1H), 8.55 (s, 1H), 8.50 (s, 1H), 8.10 (bs, 2H), 7.95 (d, 1H), 7.79 (dd, 1H), 7.72 (d, 1H), 7.70 (dd, 1H), 7.53 (d, 2H), 7.40 (m, 3H), 7.31 (m, 2H), 7.26 (d, 1H), 7.21 (t, 1H), 5.25 (s, 2H), 4.73 (t, 1H), 3.08 (d, 2H).

(46-2) Preparation of N-{4-[3-chloro-4-(3-fluoro-benzyloxy)-phenylamino]-quinazolin-6-yl}-3-(2-methoxy-acetylamino)-3-phenyl-propionamide 0.03 g of methoxyacetic acid, 0.14 g of 1-(3-dimethylaminopropyl)-3-ethylcarbodiimide hydrochloride and 0.05 g of 1-hydroxylbenzotriazole dissolved in 5 ml of methylene chloride were reacted with 0.1 g of the compound obtained in (46-1) at room temperature for 23 hours. The reacted solution was extracted with methylene chloride 2 times after adding saturated sodium bicarbonate solution, washed with saturated saline solution, dried over magnesium sulfate, filtered and distilled under a reduced pressure, and the resulting residue was subjected to column chromatography (eluent-chloroform:methanol=15:1) to obtain the title compound (0.05 g, 45%).

$^1$H-NMR (DMSO-$d_6$, 300 MHz): δ 10.25 (s, 1H), 9.78 (s, 1H), 8.61 (s, 1H), 8.46 (s, 1H), 8.42 (d, 1H), 7.93 (d, 1H), 7.70

(m, 3H), 7.43 (m, 3H), 7.29 (m, 3H), 7.20 (m, 2H), 5.40 (m, 1H), 5.23 (s, 2H), 3.80 (s, 2H), 3.28 (s, 3H), 2.94 (m, 2H).

Example 47

Preparation of N-{4-[3-chloro-4-(3-fluoro-benzyloxy)-phenylamino]-quinazolin-6-yl}-3-(2-methanesulfonyl-acetylamino)-3-phenyl-propionamide 0.08 g of methanesulfonylacetic acid, 0.21 g of 1-(3-dimethylaminopropyl)-3-ethylcarbodiimide hydrochloride and 0.08 g of 1-hydroxylbenzotriazole dissolved in 10 ml of methylene chloride were reacted with 0.15 g of the compound obtained in (46-1) of Example 46 at room temperature for 24 hours. The reacted solution was extracted with methylene chloride 2 times after adding saturated sodium bicarbonate solution, washed with saturated saline solution, dried over magnesium sulfate, filtered and distilled under a reduced pressure, and the resulting residue was subjected to column chromatography (eluent-chloroform:methanol=15:1) to obtain the title compound (0.1 g, 55%).
$^1$H-NMR (DMSO-d$_6$, 300 MHz): δ 10.29 (s, 1H), 9.76 (s, 1H), 8.94 (d, 1H), 8.59 (s, 1H), 8.47 (s, 1H), 7.94 (d, 1H), 7.71 (m, 3H), 7.30 (m, 8H), 5.36 (m, 1H), 5.23 (s, 2H), 4.10 (m, 2H), 3.36 (m, 2H), 3.04 (s, 3H); MS (ESI): [M+H+] 662.17.

Example 48

Preparation of 3-(2-methoxy-acetylamino)-thiophene-2-carboxylic acid {4-[3-chloro-4-(3-fluoro-benzyloxy)-phenylamino]-quinazolin-6-yl}-amide 0.11 g of 3-(2-methoxy-acetylamino)-thiophene-2-carboxylic acid, 0.19 g of 1-(3-dimethylaminopropyl)-3-ethylcarbodiimide hydrochloride and 0.1 g of 1-hydroxylbenzotriazole dissolved in 10 ml of methylene chloride were reacted with 0.1 g of the compound obtained in (1-4) of Example 1 at room temperature for 3 hours. The reacted solution was extracted with methylene chloride 2 times after adding saturated sodium bicarbonate solution, washed with saturated saline solution, dried over magnesium sulfate, filtered and distilled under a reduced pressure, and the resulting residue was subjected to column chromatography (eluent-chloroform:methanol=15:1) to obtain the title compound (0.02 g, 14%).
$^1$H-NMR (CDCl$_3$, 300 MHz): δ 8.58 (d, 1H), 8.46 (d, 1H), 8.15 (d, 1H), 7.83 (m, 2H), 7.73 (m, 2H), 7.57 (d, 1H), 7.33 (m, 1H), 7.22 (m, 2H), 7.01 (m, 2H), 5.16 (s, 2H), 4.05 (s, 2H), 3.53 (s, 3H).

Example 49

Preparation of (2-{4-[3-methyl-4-(6-methyl-pyridin-3-yloxy)-phenylamino]-quinazolin-6-ylcarbamoyl}-ethyl)-carbamic acid t-butylester (49-1) Preparation of N$^4$-[3-methyl-4-(6-methyl-pyridin-3-yloxy)-phenyl]-quinazolin-4,6-diamine The procedures of (1-1) to (1-4) of Example 1 were repeated except for using 3-methyl-4-(6-methyl-pyridin-3-yloxy)-phenylamine instead of 3-chloro-4-(3-fluoro-benzyloxy)-phenylamine to obtain the title compound (0.38 g, 56%).

$^1$H-NMR (CDCl$_3$, 300 MHz): δ 8.62 (s, 1H), 8.28 (d, 1H), 7.77 (d, 1H), 7.64 (d, 1H), 7.53 (dd, 1H), 7.24 (dd, 1H), 7.12 (m, 3H), 6.94 (m, 2H), 4.06 (bs, 2H), 2.55 (s, 3H), 2.30 (s, 3H).

(49-2) Preparation of (2-{4-[3-methyl-4-(6-methyl-pyridin-3-yloxy)-phenylamino]-quinazolin-6-ylcarbamoyl}-ethyl)-carbamic acid t-butylester The procedure of Example 19 was repeated except for using 0.36 g of the compound obtained in (49-1) instead of the compound obtained in (1-4) of Example 1 to obtain the title compound (0.28 g, 53%).
$^1$H-NMR (CDCl$_3$, 300 MHz): δ 8.92 (bs, 1H), 8.77 (s, 1H), 8.68 (s, 1H), 8.26 (s, 1H), 7.82 (d, 1H), 7.61 (s, 1H), 7.53 (m, 2H), 7.12 (m, 2H), 6.90 (d, 1H), 5.23 (m, 1H), 3.57 (m, 2H), 2.70 (m, 2H), 2.51 (s, 3H), 2.24 (s, 3H), 1.37 (s, 9H).

Example 50

Preparation of 3-(2-methanesulfonyl-acetylamino)-N-{4-[3-methyl-4-(6-methyl-pyridin-3-yloxy)-phenylamino]-quinazolin-6-yl}-propionamide (50-1) Preparation of 3-amino-N-{4-[3-methyl-4-(6-methyl-pyridin-3-yloxy)-phenylamino]-quinazolin-6-yl}-propionamide The procedure of (20-1) of Example 20 was repeated except for using 1 g of the compound obtained in Example 49 instead of the compound obtained in (1-4) of Example 1 to obtain the title compound (0.79 g, 98%).
$^1$H-NMR (DMSO-d$_6$, 300 MHz): δ 10.63 (s, 2H), 8.81 (s, 1H), 8.70 (s, 1H), 8.21 (s, 1H), 8.01 (d, 1H), 7.82 (m, 3H), 7.70 (s, 1H), 7.59 (d, 1H), 7.29 (s, 2H), 6.98 (d, 1H), 3.14 (m, 2H), 2.81 (t, 2H), 2.46 (s, 3H), 2.24 (s, 3H).

(50-2) Preparation of 3-(2-methanesulfonyl-acetylamino)-N-{4-[3-methyl-4-(6-methyl-pyridin-3-yloxy)-phenylamino]-quinazolin-6-yl}-propionamide The procedure of Example 21 was repeated except for using 0.03 g of the compound obtained in (50-1) instead of the compound obtained in (1-4) of Example 1 to obtain the title compound (0.02 g, 52%).
$^1$H-NMR (DMSO-d$_6$, 300 MHz): δ 10.20 (s, 1H), 9.73 (s, 1H), 8.66 (s, 1H), 8.48 (s, 1H), 8.15 (bt, 1H), 8.14 (d, 1H), 7.72 (m, 4H), 7.20 (m, 2H), 6.90 (d, 1H), 4.02 (s, 2H), 3.20 (m, 2H), 3.05 (s, 3H), 2.39 (s, 3H), 2.18 (s, 3H), 1.98 (m, 2H); MS (ESI): [M+H+] 549.25.

Example 51

Preparation of N-(2-{4-[3-methyl-4-(6-methyl-pyridin-3-yloxy)-phenylamino]-quinazolin-6-ylcarbamoyl}-ethyl)-acrylamide The procedure of Example 22 was repeated except for using 0.08 g of the compound obtained in (50-1) of Example 50 instead of the compound obtained in (1-4) of Example 1 to obtain the title compound (0.03 g, 34%).
$^1$H-NMR (DMSO-d$_6$, 300 MHz): δ 8.74 (s, 1H), 8.68 (s, 1H), 8.26 (s, 1H), 7.82 (m, 1H), 7.60 (m, 2H), 7.53 (dd, 1H), 7.40 (d, 1H), 7.09 (m, 2H), 6.91 (d, 1H), 6.30 (m, 3H), 2.52 (s, 3H), 2.27 (m, 5H), 1.80 (m, 2H); MS (ESI): [M+H+] 483.22.

Example 52

Preparation of {2-[4-(3-chloro-4-fluoro-phenylamino)-quinazolin-6-ylcarbamoyl]-ethyl}-carbamic acid t-butylester

(52-1) Preparation of N$^4$-[3-methyl-4-(6-methyl-pyridin-3-yloxy)-phenyl]-quinazolin-4,6-diamine The procedures of (1-1) to (1-4) of Example 1 were repeated except for using 3-chloro-4-fluoro-phenylamine instead of 3-chloro-4-(3-fluoro-benzyloxy)-phenylamine to obtain the title compound (1.1 g, 48%).

1H-NMR (DMSO-d$_6$, 300 MHz): δ 9.49 (s, 1H), 8.36 (s, 1H), 8.21 (dd, 1H), 7.80 (m, 1H), 7.55 (d, 1H), 7.41 (t, 1H), 7.31 (s, 1H), 7.25 (dd, 1H), 5.65 (bs, 2H).

(52-2) Preparation of {2-[4-(3-chloro-4-fluoro-phenylamino)-quinazolin-6-ylcarbamoyl]-ethyl}-carbamic acid t-butylester The procedure of Example 19 was repeated except for using 1 g of the compound obtained in (52-1) instead of the compound obtained in (1-4) of Example 1 to obtain the title compound (0.7 g, 44%).

$^1$H-NMR (DMSO-d$_6$, 300 MHz): δ 10.27 (s, 1H), 9.90 (s, 1H), 8.70 (s, 1H), 8.52 (s, 1H), 8.10 (dd, 1H), 7.78 (m, 3H), 7.44 (t, 1H), 6.87 (bt, 1H), 3.24 (m, 2H), 2.54 (t, 2H), 1.36 (s, 9H); MS (ESI): [M+H+] 460.02.

Example 53

Preparation of N-[4-(3-chloro-4-fluoro-phenylamino)-quinazolin-6-yl]-3-(2-methanesulfonyl-acetylamino)-propionamide

(53-1) Preparation of 3-amino-N-[4-(3-chloro-4-fluoro-phenylamino)-quinazolin-6-yl]-propionamide The procedure of (20-1) of Example 20 was repeated except for using 0.55 g of the compound obtained in Example 52 instead of the compound obtained in (1-4) of Example 1 to obtain the title compound (0.4 g, 93%).

$^1$H-NMR (DMSO-d$_6$, 300 MHz): δ 8.69 (s, 1H), 8.51 (s, 1H), 8.11 (d, 1H), 7.79 (m, 3H), 7.40 (t, 1H), 2.88 (m, 2H), 2.55 (m, 2H).

(53-2) Preparation of N-[4-(3-chloro-4-fluoro-phenylamino)-quinazolin-6-yl]-3-(2-methanesulfonyl-acetylamino)-propionamide The procedure of Example 21 was repeated except for using 0.08 g of the compound obtained in (53-1) instead of the compound obtained in (20-1) of Example 20 to obtain the title compound (0.06 g, 57%).

$^1$H-NMR (DMSO-d$_6$, 300 MHz): δ 10.36 (s, 1H), 9.92 (s, 1H), 8.70 (s, 1H), 8.52 (s, 1H), 8.47 (bt, 1H), 8.11 (d, 1H), 7.80 (m, 3H), 7.40 (t, 1H), 4.05 (s, 2H), 3.41 (m, 2H), 3.09 (s, 3H), 2.53 (m, 2H); MS (ESI): [M+H+] 480.04.

Example 54

Preparation of N-{2-[4-(3-chloro-4-fluoro-phenylamino)-quinazolin-6-ylcarbamoyl]-ethyl}-acrylamide The procedure of Example 22 was repeated except for using 0.1 g of the compound obtained in (53-1) of Example 53 instead of the compound obtained in (20-1) of Example 20 to obtain the title compound (0.09 g, 79%).

$^1$H-NMR (DMSO-d$_6$, 300 MHz): δ 10.96 (s, 1H), 10.19 (s, 1H), 9.01 (s, 1H), 8.50 (s, 1H), 8.34 (m, 2H), 8.05 (m, 3H), 7.39 (t, 1H), 6.03 (m, 1H), 6.04 (m, 1H), 5.52 (dd, 1H), 3.19 (m, 2H), 2.60 (t, 2H); MS (ESI): [M+H+] 414.05.

Example 55

Preparation of 4-bromo-but-2-enonylic acid (2-{4-[3-chloro-4-(3-fluoro-benzyloxy)-phenylamino]-quinazolin-6-ylcarbamoyl}-ethyl)-amide 293 mg of 4-bromo-2-butenoylic acid trimethylsilylester dissolved in 3 ml of methylene chloride was stirred for 2 hours after adding 0.12 ml of oxalylchloride and 1 droplet of N,N-dimethylformamide, and the solution was distilled under a reduced pressure. The resulting residue dissolved in 5 ml of THF was reacted with 500 mg of the compound obtained (20-1) of Example 20 and 0.21 ml of N,N-diisopropylethylamine dissolved in 10 ml of THF at 0° C. for 4 hours. The residue obtained from distillation of the reacted solution under a reduced pressure was dissolved in distilled water, washed with saturated sodium bicarbonate solution, dried over magnesium sulfate, filtered and distilled under a reduced pressure, and the resulting residue was subjected to column chromatography (eluent-chloroform:methanol=15:1) to obtain the title compound (393 mg, 60%).

$^1$H-NMR (CD$_3$OD, 300 MHz): δ 8.57 (s, 1H), 8.37 (s, 1H), 7.80 (d, 1H), 7.66 (s, 2H), 7.51 (dd, 1H), 7.31 (m, 1H), 7.19 (m, 2H), 7.08 (d, 1H), 6.95 (t, 1H), 6.74 (m, 1H), 6.12 (d, 1H), 5.13 (s, 2H), 4.13 (dd, 1H), 3.56 (t, 2H), 2.63 (t, 2H).

Example 56

Preparation of 4-dimethylamino-but-2-enonylic acid (2-{4-[3-chloro-4-(3-fluoro-benzyloxy)-phenylamino]-quinazolin-6-ylcarbamoyl}-ethyl)-amide 1.6 ml of 2 M dimethylamine dissolved in 1 ml of THF was cooled to 0° C., and reacted for 19 hours after adding 100 mg of the compound obtained in Example 55 dissolved in 3 ml of THF. The reacted solution was washed with saturated sodium bicarbonate solution, dried over magnesium sulfate, filtered and distilled under a reduced pressure, and the resulting residue was subjected to column chromatography (eluent-chloroform:methanol=15:1) to obtain the title compound (20.5 mg, 22%).

$^1$H-NMR (CD$_3$OD, 300 MHz): δ 8.67 (s, 1H), 8.48 (s, 1H), 7.91 (d, 1H), 7.77 (s, 2H), 7.62 (dd, 1H), 7.43 (m, 1H), 7.31 (m, 2H), 7.19 (d, 1H), 7.08 (t, 1H), 6.76 (m, 1H), 5.25 (s, 2H), 3.67 (t, 2H), 3.11 (d, 2H), 2.74 (t, 2H), 2.28 (s, 6H).

Example 57

Preparation of 4-morpholin-4-yl-but-2-enonylic acid (2-{4-[3-chloro-4-(3-fluoro-benzyloxy)-phenylamino]-quinazolin-6-ylcarbamoyl}-ethyl)-amide 100 mg of the compound obtained in Example 55 dissolved in 3 ml of THF was cooled to 0° C., and reacted at room temperature for 16 hours after adding 0.3 ml of morpholine. The reacted solution was washed with saturated sodium bicarbonate solution, dried over magnesium sulfate, filtered and distilled under a reduced pressure, and the resulting residue was subjected to column chromatography (eluent-chloroform:methanol=15:1) to obtain the title compound (41 mg, 41%).

$^1$H-NMR (CD$_3$OD, 300 MHz): δ 8.55 (s, 1H), 8.36 (s, 1H), 7.79 (d, 1H), 7.64 (s, 2H), 7.50 (dd, 1H), 7.30 (m, 1H), 7.18 (m, 2H), 7.06 (d, 1H), 6.95 (t, 1H), 6.65 (m, 1H), 6.01 (d, 1H), 3.55 (m, 6H), 2.99 (d, 2H), 2.61 (t, 2H), 2.34 (br s, 4H).

Example 58

Preparation of 4-(4-methyl-piperazin-1-yl)-but-2-enonylic acid (2-{4-[3-chloro-4-(3-fluoro-benzyloxy)-phenylamino]-quinazolin-6-ylcarbamoyl}-ethyl)-amide The procedure of Example 57 was repeated except for using 0.18 ml of 1-methylpiperazine instead of morpholine to obtain the title compound (20 mg, 38%).

$^1$H-NMR (CD$_3$OD, 300 MHz): δ 8.55 (s, 1H), 8.37 (s, 1H), 7.80 (d, 1H), 7.65 (s, 2H), 7.51 (dd, 1H), 7.30 (m, 1H), 7.19 (m, 2H), 7.08 (d, 1H), 6.96 (t, 1H), 6.65 (m, 1H), 6.01 (d, 1H), 3.56 (t, 2H), 3.04 (d, 2H), 2.62 (t, 2H), 2.39 (br s, 4H), 2.17 (s, 3H).

Example 59

Preparation of 4-[(2-hydroxyl-ethyl)-methyl-amino]-but-2-enonylic acid (2-{4-[3-chloro-4-(3-fluoro-benzyloxy)-phenylamino]-quinazolin-6-ylcarbamoyl}-ethyl)-amide The procedure of Example 57 was repeated except for using 0.13 ml of 2-(methylamino) ethanol instead of morpholine to obtain the title compound (10 mg, 20%).

$^1$H-NMR (CD$_3$OD, 300 MHz): δ 8.56 (s, 1H), 8.37 (s, 1H), 7.80 (d, 1H), 7.66 (s, 2H), 7.51 (dd, 1H), 7.31 (m, 1H), 7.19 (m, 2H), 7.08 (d, 1H), 6.96 (t, 1H), 6.67 (m, 1H), 6.01 (d, 1H), 5.13 (s, 2H), 3.50 (m, 4H), 3.13 (d, 2H), 2.62 (t, 2H), 2.46 (t, 2H), 2.18 (s, 3H).

Example 60

Preparation of 4-(2-methanesulfonyl-ethylamino)-but-2-enonylic acid (2-{4-[3-chloro-4-(3-fluoro-benzyloxy)-phenylamino]-quinazolin-6-ylcarbamoyl}-ethyl)-amide The procedure of Example 57 was repeated except for using 12 mg of 2-methanesulfonyl-ethylamine instead of morpholine to obtain the title compound (11 mg, 21%).

$^1$H-NMR (CD$_3$OD, 300 MHz): δ 8.82 (s, 1H), 8.48 (s, 1H), 7.92 (d, 1H), 7.77 (s, 2H), 7.60 (dd, 1H), 7.42 (m, 1H), 7.33 (m, 2H), 7.20 (d, 1H), 7.07 (m, 1H), 6.79 (m, 1H), 6.11 (d, 1H), 5.24 (s, 2H), 3.67 (t, 2H), 3.39 (m, 2H), 3.32 (m, 2H), 3.07 (d, 2H), 3.02 (s, 3H), 2.73 (t, 2H).

Example 61

Preparation of 3-(2-chloro-acetylamide)-N-{4-[3-chloro-4-(3-fluoro-benzyloxy)-phenylamino]-quinazolin-6-yl}-propionamide 0.7 g of the compound obtained in (20-1) of Example 20 dissolved in 10 ml of THF was cooled to 0° C., and the solution was reacted at room temperature for 2 hours after adding 0.25 ml of pyridine and 0.18 ml of chloroacetylchloride. The reacted solution was extracted with ethylacetate, washed with saturated sodium bicarbonate solution, dried over magnesium sulfate, removed solvent under a reduced pressure, and vacuum dried to obtain the title compound (0.68 g, 84%).

$^1$H-NMR (CD$_3$OD, 300 MHz): δ 8.64 (s, 1H), 8.45 (s, 1H), 7.88 (d, 1H), 7.73 (s, 2H), 7.58 (dd, 1H), 7.38 (m, 1H), 7.27 (m, 2H), 7.15 (d, 1H), 7.04 (t, 1H), 5.21 (s, 2H), 4.05 (s, 2H), 3.62 (t, 2H), 2.70 (t, 2H).

Example 62

Preparation of N-{4-[3-chloro-4-(3-fluoro-benzyloxy)-phenylamino]-quinazolin-6-yl}-3-(2-morpholin-4-yl-acetylamino)-propionamide 0.07 g of the compound obtained in Example 61 dissolved in 5 ml of N,N-dimethylformamide was reacted with 0.04 ml of morpholine and 0.04 g of potassium carbonate for 2 hours while heating to 100° C. The reacted solution was diluted with distilled water, extracted with ethylacetate, washed with saturated saline solution, dried over magnesium sulfate, filtered and distilled under a reduced pressure, and the resulting residue was subjected to column chromatography (eluent-chloroform:methanol=15:1) to obtain the title compound (0.07 mg, 92%).

$^1$H-NMR (CD$_3$OD, 300 MHz): δ 8.51 (s, 1H), 8.36 (s, 1H), 7.78 (d, 1H), 7.63 (s, 2H), 7.49 (dd, 1H), 7.30 (m, 1H), 7.17 (m, 2H), 7.03 (d, 1H), 6.95 (t, 1H), 5.10 (s, 2H), 3.55 (m, 6H), 2.92 (s, 2H), 2.61 (t, 2H), 2.38 (m, 4H).

Example 63

Preparation of N-{4-[3-chloro-4-(3-fluoro-benzyloxy)-phenylamino]-quinazolin-6-yl}-3-(2-dimethylamino-acetylamino)-propionamide The procedure of Example 62 was repeated except for using 0.25 ml of dimethylamine 2 M THF solution instead of morpholine to obtain the title compound (0.08 g, 88%).

$^1$H-NMR (CDCl$_3$, 300 MHz): δ 8.49 (s, 1H), 8.47 (d, 1H), 7.79 (d, 1H), 7.68 (d, 1H), 7.53 (m, 2H), 7.25 (m, 1H), 7.12 (m, 2H), 6.87 (m, 2H), 5.06 (s, 2H), 3.53 (t, 2H), 2.85 (s, 2H), 2.58 (t, 2H), 2.15 (s, 6H).

Example 64

Preparation of N-{4-[3-chloro-4-(3-fluoro-benzyloxy)-phenylamino]-quinazolin-6-yl}-3-[2-(4-methyl-piperazin-1-yl)-acetylamino]-propionamide The procedure of Example 62 was repeated except for using 0.06 ml of 1-methylpiperazine instead of morpholine to obtain the title compound (0.07 g, 70%).

$^1$H-NMR (CD$_3$OD, 300 MHz): δ 8.48 (d, 1H), 8.33 (s, 1H), 7.76 (d, 1H), 7.59 (m, 2H), 7.47 (dd, 1H), 7.28 (m, 1H), 7.13 (m, 2H), 6.94 (m, 2H), 5.04 (s, 2H), 3.55 (t, 2H), 2.92 (s, 2H), 2.60 (t, 2H), 2.38 (bd, 8H), 2.06 (s, 3H)

Example 65

Preparation of N-{4-[3-chloro-4-(3-fluoro-benzyloxy)-phenylamino]-quinazolin-6-yl}-3-[2-(2-methoxy-ethylamino)-acetylamino]-propionamide The procedure of Example 62 was repeated except for using 0.07 ml of 2-methoxyethylamine instead of morpholine to obtain the title compound (0.08 g, 83%).

¹H-NMR (CD₃OD, 300 MHz): δ 8.57 (s, 1H), 8.40 (s, 1H), 7.83 (d, 1H), 7.66 (s, 2H), 7.54 (dd, 1H), 7.36 (m, 1H), 7.23 (m, 2H), 7.07 (d, 1H), 7.03 (t, 1H), 5.14 (s, 2H), 3.59 (t, 2H), 3.38 (t, 2H), 3.24 (s, 3H), 3.21 (s, 2H), 2.66 (m, 4H).

Example 66

Preparation of N-{4-[3-chloro-4-(3-fluoro-benzyloxy)-phenylamino]-quinazolin-6-yl}-3-[2-(2-methanesulfonyl-ethylamino)-acetylamino]-propionamide The procedure of Example 62 was repeated except for using 0.1 g of 2-methanesulfonyl-ethylamine instead of morpholine to obtain the title compound (0.1 g, 96%).
¹H-NMR (CD₃OD, 300 MHz): δ 8.56 (s, 1H), 8.36 (s, 1H), 7.80 (m, 1H), 7.65 (s, 2H), 7.49 (dd, 1H), 7.32 (m, 1H), 7.18 (m, 2H), 7.07 (d, 1H), 6.96 (t, 1H), 5.13 (s, 2H), 3.54 (t, 2H), 3.25 (m, 5H), 2.96 (t, 2H), 2.86 (s, 2H), 2.62 (t, 2H); MS (ESI): [M+H+] 629.11.

Example 67

Preparation of 3-(2-chloro-acetylamino)-N-{4-[3-methyl-4-(6-methyl-pyridin-3-yloxy)-phenylamino]-quinazolin-6-yl}-propionamide The procedure of Example 61 was repeated except for using 0.88 g of the compound obtained in (50-1) of Example 50 and 0.3 ml of chloroacetylchloride instead of the compound obtained in (20-1) of Example 20 to obtain the title compound (0.6 g, 58%).
¹H-NMR (CDCl₃, 300 MHz): δ 8.71 (s, 1H), 8.68 (s, 1H), 8.46 (s, 1H), 8.26 (s, 1H), 7.86 (d, 1H), 7.58 (m, 3H), 7.14 (m, 2H), 6.92 (d, 1H), 4.08 (s, 2H), 3.74 (q, 2H), 2.80 (t, 2H), 2.54 (s, 3H), 2.29 (s, 3H), 2.17 (s, 2H).

Example 68

Preparation of N-{4-[3-methyl-4-(6-methyl-pyridin-3-yloxy)-phenylamino]-quinazolin-6-yl}-3-(2-morpholin-4-yl-acetylamino)-propionamide The procedure of Example 62 was repeated except for using 0.09 g of the compound obtained in Example 67 and 0.05 ml of morpholine instead of the compound obtained in Example 61 to obtain the title compound (0.08 g, 81%).
¹H-NMR (CDCl₃, 300 MHz): δ 9.94 (s, 1H), 8.60 (m, 2H), 8.38 (bs, 1H), 8.19 (s, 1H), 7.78 (t, 1H), 7.67 (m, 2H), 7.57 (s, 1H), 7.50 (d, 1H), 7.08 (m, 2H), 6.82 (d, 1H), 3.63 (m, 6H), 2.98 (s, 2H), 2.68 (t, 2H), 2.49 (s, 3H), 2.44 (m, 4H), 2.20 (s, 3H); MS (ESI): [M+H+] 556.24.

Example 69

Preparation of 3-(2-dimethylamino-acetylamino)-N-{4-[3-methyl-4-(6-methyl-pyridin-3-yloxy)-phenylamino]-quinazolin-6-yl}-propionamide The procedure of Example 62 was repeated except for using 0.08 g of the compound obtained in Example 67 and 0.24 ml of dimethylamine 2 M THF instead of the compound obtained in Example 61 to obtain the title compound (0.04 g, 50%).
¹H-NMR (CDCl₃, 300 MHz): δ 9.85 (s, 1H), 8.65 (s, 1H), 8.62 (s, 1H), 8.22 (d, 1H), 7.80 (t, 1H), 7.70 (m, 2H), 7.61 (s, 1H), 7.51 (d, 1H), 7.12 (m, 2H), 6.86 (d, 1H), 3.68 (m, 2H), 2.99 (s, 2H), 2.72 (t, 2H), 2.44 (s, 3H), 2.26 (s, 6H), 2.23 (s, 3H).

Example 70

Preparation of N-{4-[3-methyl-4-(6-methyl-pyridin-3-yloxy)-phenylamino]-quinazolin-6-yl}-3-[2-(4-methyl-piperazin-1-yl)-acetylamino]-propionamide The procedure of Example 62 was repeated except for using 0.07 g of the compound obtained in Example 67 and 0.05 ml of 1-methylpiperazine instead of the compound obtained in Example 61 to obtain the title compound (0.04 g, 51%).
¹H-NMR (CDCl₃, 300 MHz): δ 9.83 (s, 1H), 8.64 (s, 2H), 8.21 (s, 1H), 7.75 (m, 2H), 7.58 (m, 3H), 7.10 (m, 2H), 6.87 (d, 1H), 3.66 (m, 2H), 3.01 (s, 2H), 2.72 (m, 2H), 2.51 (bs, 8H), 2.38 (s, 3H), 2.24 (s, 3H), 2.18 (s, 3H).

Example 71

Preparation of 3-[2-(2-methoxy-ethylamino)-acetylamino]-N-{4-[3-methyl-4-(6-methyl-pyridin-3-yloxy)-methylamino]-quinazolin-6-yl}-propionamide The procedure of Example 62 was repeated except for using 0.07 g of the compound obtained in Example 67 and 0.06 ml of 2-methoxyethylamine instead of the compound obtained in Example 61 to obtain the title compound (0.04 g, 54%).
¹H-NMR (CDCl₃, 300 MHz): δ 9.87 (s, 1H), 8.61 (s, 2H), 8.21 (d, 1H), 8.01 (t, 1H), 7.71 (s, 2H), 7.61 (m, 1H), 7.50 (d, 1H), 7.12 (m, 2H), 6.86 (d, 1H), 3.66 (q, 2H), 3.40 (m, 2H), 3.37 (s, 2H), 3.30 (s, 3H), 2.72 (m, 4H), 2.52 (s, 3H), 2.20 (s, 3H); MS (ESI): [M+H+] 544.23.

Example 72

Preparation of 3-[2-(2-methanesulfonyl-ethylamino)-acetylamino]-N-{4-[3-methyl-4-(6-methyl-pyridin-3-yloxy)-phenylamino]-quinazolin-6-yl}-propionamide The procedure of Example 62 was repeated except for using 0.09 g of the compound obtained in Example 67 and 0.11 g of 2-methanesulfonyl-ethylamine instead of the compound obtained in Example 61 to obtain the title compound (0.03 g, 29%).
¹H-NMR (CDCl₃, 300 MHz): δ 8.50 (m, 2H), 8.10 (m, 1H), 7.97 (s, 1H), 7.59 (s, 1H), 7.53 (m, 1H), 7.41 (d, 1H), 7.05 (m, 2H), 6.76 (m, 1H), 3.56 (m, 2H), 3.10 (m, 2H), 2.98 (m, 2H), 2.91 (s, 3H), 2.84 (s, 3H), 2.59 (m, 2H), 2.45 (s, 3H), 2.12 (s, 2H).

Example 73

Preparation of N-{2-[4-(2-methyl-1H-indol-5-ylamino)-quinazolin-6-ylcarbamoyl]-ethyl}-acrylamide (73-1) Preparation of 3-amino-N-[4-(2-methyl-1H-indol-5-ylamino)-quinazolin-6-yl]-propionamide 150 mg of 2-[4-(2-methyl-1H-indol-5-ylamino)-quinazolin-6-ylcarbamoyl]-ethyl-carbamic acid t-butylester dissolved in 5 ml of methylene chloride was reacted with 5 ml of trifluoroacetic acid at room temperature for 4 hours. The residue obtained from distillation of the reacted solution under a reduced pressure was stirred in 50 ml of saturated aqueous sodium bicarbonate solution for 30 mins, filtered under a reduced pressure, and dried to obtain the title compound (100 mg, 82%).

$^1$H-NMR (CD$_3$OD, 300 MHz): δ 8.66 (s, 1H), 8.32 (s, 1H), 7.82 (dd, J=2.9 Hz, 1H) 7.79 (d, J=9 Hz, 1H), 7.63 (s, 1H), 7.34 (d, J=8 Hz, 1H), 7.21 (dd, J=2.9 Hz, 1H), 6.16 (s, 1H), 3.32 (m, 2H), 2.72 (m, 2H), 2.44 (s, 3H).

(73-2) Preparation of N-{2-[4-(2-methyl-1H-indol-5-ylamino)-quinazolin-6-ylcarbamoyl]-ethyl}-acrylamide 106 mg of 1-(3-dimethylaminopropyl)-3-ethylcarbodiimide hydrochloride and 58 μl of pyridine were added to 40 μl of acrylic acid dissolved in 3 ml of THF at 0° C., reacted with 50 mg of the compound obtained in (73-1) for 30 mins while heating to room temperature, and the resulting solution was stirred at room temperature for 2 hours. The reacted solution was extracted with 9 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (5.2 mg, 9%).

$^1$H-NMR (CD$_3$OD, 300 MHz): δ 8.66 (s, 1H), 8.32 (s, 1H), 7.81 (dd, J=2.9 Hz, 1H), 7.73 (d, J=9 Hz, 1H), 7.63 (s, 1H), 7.34 (d, J=8 Hz, 1H), 7.21 (dd, J=2.9 Hz, 1H), 6.24-6.60 (m, 2H), 6.16 (s, 1H), 5.64-5.68 (m, 1H), 3.69 (t, J=7 Hz, 2H), 2.75 (t, J=7 Hz, 2H), 2.44 (s, 3H).

Example 74

Preparation of 3-(2-methanesulfonyl-acetylamino)-N-[4-(1-phenyl-ethylamino)-quinazolin-6-yl]-propionamide (74-1) Preparation of 3-amino-N-[4-(1-phenyl-ethylamino)-quinazolin-6-yl]-propionamide 250 mg of 2-[4-(1-phenyl-ethylamino)-quinazolin-6-ylcarbamoyl]-ethyl-carbamic acid t-butylester dissolved in 5 ml of methylene chloride was reacted with 5 ml of trifluoroacetic acid at room temperature for 4 hours. The residue obtained from distillation of the reacted solution under a reduced pressure was stirred in 50 ml of saturated aqueous sodium bicarbonate solution for 30 mins, filtered under a reduced pressure, and dried to obtain the title compound (90 mg, 52%).

$^1$H-NMR (CD$_3$OD, 300 MHz): δ 8.54 (s, 1H), 8.37 (s, 1H), 7.79 (dd, J=2.9 Hz, 1H), 7.70 (d, J=9 Hz, 1H), 7.47 (d, J=7 Hz, 2H), 7.35 (t, J=7 Hz, 2H), 7.25 (t, J=7 Hz, 1H), 3.26 (m, 3H), 2.90 (t, J=6 Hz, 2H), 1.7 (d, J=7 Hz, 3H).

(74-2) Preparation of 3-(2-methanesulfonyl-acetylamino)-N-[4-(1-phenyl-ethylamino)-quinazolin-6-yl]-propionamide 40 mg of 1-hydroxylbenzotriazole and 114 mg of 1-(3-dimethylaminopropyl)-3-ethylcarbodiimide hydrochloride were added to 41 mg of methanesulfonylacetic acid dissolved in 2 ml of THF, and reacted with 50 mg of the compound obtained in (74-1) at room temperature for 12 hours. The reacted solution was extracted with 6 ml of ethylacetate 3 times after adding 4 ml of water, dried over anhydrous magnesium sulfate, and filtered and distilled under a reduced pressure. 5 ml of diethylether was added to the resulting residue dissolved in 0.5 ml of methanol to obtain solid, and the solid was filtered under a reduced pressure and dried to obtain the title compound (3 mg, 6%).

$^1$H-NMR (CD$_3$OD, 300 MHz): δ 8.59 (s, 1H), 8.39 (s, 1H), 7.79-7.68 (m, 2H), 7.22-7.46 (m, 5H), 4.04 (s, 2H), 3.65 (m, 3H), 2.73 (t, J=6 Hz, 2H), 1.70 (d, J=7 Hz, 3H).

Example 75

Preparation of N-{2-[4-(1-phenyl-ethylamino)-quinazolin-6-ylcarbamoyl]-ethyl}-acrylamide 62 μl of pyridine and 114 mg of 1-(3-dimethylaminopropyl)-3-ethylcarbodiimide hydrochloride were added to 41 μl of acrylic acid dissolved in 3 ml of THF at 0° C., reacted with 50 mg of the compound obtained in (74-2) of Example 74 for 30 mins while heating to room temperature, and the resulting solution was stirred at room temperature for 2 hours. The reacted solution was extracted with 9 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (4.8 mg, 10%).

$^1$H-NMR (CD$_3$OD, 300 MHz): δ 8.54 (s, 1H), 8.37 (s, 1H), 7.69 (s, 2H), 7.47 (d, J=7.5 Hz, 2H), 7.32 (t, J=7 Hz, 2H), 7.23 (t, J=7 Hz, 1H), 6.29 (m, 2H), 5.67 (m, 1H), 3.66 (m, 2H), 2.66-2.76 (m, 3H), 1.7 (d, J=7 Hz, 3H).

Example 76

Preparation of N-[2-(4-{4-[2-(6,7-dimethoxy-3,4-dihydro-1H-isoquinolin-2-yl)-ethyl]-phenylamino}-quinazolin-6-ylcarbamoyl)-ethyl]-acrylamide (76-1) Preparation of 3-amino-N-(4-{4-[2-(6,7-dimethoxy-3,4-dihydro-1H-isoquinolin-2-yl)-ethyl]-phenylamino}-quinazolin-6-yl)-propionamide 800 mg of [2-(4-{4-[2-(6,7-dimethoxy-3,4-dihydro-1H-isoquinolin-2-yl)-ethyl]phenylamino}-quinazolin-6-ylcarbamoyl)-ethyl]-carbamic acid t-butylester dissolved in 16 ml of methylene chloride was reacted with 16 ml of trifluoroacetic acid at room temperature for 4 hours. The residue obtained from distillation of the reacted solution under a reduced pressure was stirred in 200 ml of saturated aqueous sodium bicarbonate solution for 30 mins, filtered under a reduced pressure and dried to obtain the title compound (310 mg, 46%).

$^1$H-NMR (CD$_3$OD, 300 MHz): δ 8.64 (s, 1H), 8.46 (s, 1H), 7.8 (d, J=9 Hz, 1H), 7.69-7.75 (m, 3H), 7.33 (d, J=7.5 Hz, 2H), 6.71 (d, J=9 Hz, 2H), 3.8 (s, 2H), 3.67 (s, 2H), 3.37 (m, 2H), 2.72-2.92 (m, 10H).

(76-2) Preparation of N-[2-(4-{4-[2-(6,7-dimethoxy-3,4-dihydro-1H-isoquinolin-2-yl)-ethyl]-phenylamino}-quinazolin-6-ylcarbamoyl)-ethyl]-acrylamide 59 μl of pyridine and 109 mg of 1-(3-dimethylaminopropyl)-3-ethylcarbodiimide hydrochloride were added to 39 μl of acrylic acid dissolved in 3 ml of THF, and the solution was reacted with 150 mg of the compound obtained in (76-1) at 0° C. for 30 mins and for 2 hours while heating to room temperature. The reacted solution was extracted with 6 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (22 mg, 20%).

$^1$H-NMR (CD$_3$OD, 300 MHz): δ 8.66 (s, 1H), 8.43 (s, 1H), 7.74 (s, 2H), 7.68 (d, J=9 Hz, 2H), 7.33 (d, J=9 Hz, 2H), 6.70 (d, J=9 Hz, 2H), 6.71 (d, J=9 Hz, 2H), 6.22-6.24 (m, 2H), 5.67 (m, 1H), 3.79 (s, 6H), 3.78 (s, 2H), 3.67 (t, J=7 Hz, 2H), 2.81-2.93 (m, 8H), 2.71 (t, J=7 Hz, 2H).

Example 77

Preparation of {2-[4-(1-benzyl-1-indazol-5-ylamino)-quinazolin-6-ylcarbamoyl]-ethyl}-carbamic acid t-butylester 1.1 g of 2-[3-cyano-4-(dimethylamino-methylene amino)-phenylcarbamoyl]-ethyl-carbamic acid t-butylester (see, *Journal of Medicinal Chemistry* 2004, 44:2719) dissolved in 6 ml of acetic acid was reacted with 1.05 g of 1-benzyl-1H-indazol-5-ylamine at 60° C. for 3 hours, and the resulting residue was stirred in 100 ml of saturated aqueous sodium bicarbonate solution at room temperature for 30 mins. The reacted solution was extracted with 30 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (810 mg, 66%).

$^1$H-NMR (CD$_3$OD, 300 MHz): δ 8.70 (s, 1H), 8.39 (s, 1H), 8.07-8.11 (m, 2H), 7.73 (s, 2H), 7.55-7.64 (m, 2H), 7.21-7.32 (m, 5H), 5.66 (s, 2H), 3.47 (t, J=7 Hz, 2H), 2.67 (t, J=7 Hz, 2H), 1.4 (s, 9H).

Example 78

Preparation of N-[4-(1-benzyl-1H-indazol-5-ylamino)-quinazolin-6-yl]-3-(2-methanesulfonyl-acetylamino)-propionamide (78-1) Preparation of 3-amino-N-[4-(1-benzyl-1H-indazol-5-ylamino)-quinazolin-6-yl]-propionamide 815 mg of the compound obtained in Example 77 dissolved in 16 ml of methylene chloride was reacted with 16 ml of trifluoroacetic acid at room temperature for 4 hours. The residue obtained from distillation of the reacted solution under a reduced pressure was stirred in 100 ml of saturated aqueous sodium bicarbonate for 30 mins, filtered under a reduced pressure, and dried to obtain the title compound (490 mg, 53%).

$^1$H-NMR (CD$_3$OD, 300 MHz): δ 8.70 (s, 1H), 8.40 (s, 1H), 8.11 (d, J=8 Hz, 2H), 7.76-7.79 (m, 2H), 7.56-7.63 (m, 2H), 7.22-7.33 (m, 5H), 5.67 (s, 2H), 3.32 (m, 2H), 2.73 (m, 2H).

(78-2) Preparation of N-[4-(1-benzyl-1H-indazol-5-ylamino)-quinazolin-6-yl]-3-(2-methanesulfonyl-acetylamino)-propionamide 50 μl of pyridine and 87 mg of 1-(3-dimethylaminopropyl)-3-ethylcarbodiimide hydrochloride were added to 63 mg of methanesulfonylacetic acid dissolved in 3 ml of THF at 0° C., reacted with 50 mg of the compound obtained in (78-1) at for 30 mins while heating to room temperature and the resulting solution was stirred at room temperature for 2 hours. The reacted solution was extracted with 6 ml of ethylacetate 3 times after adding 4 ml of water, dried over anhydrous magnesium sulfate, and filtered and distilled under a reduced pressure. 5 ml of diethylether was added to the resulting residue dissolved in 0.5 ml of methanol to obtain solid, and the solid was filtered under a reduced pressure and dried to obtain the title compound (11 mg, 17%).

$^1$H-NMR (CD$_3$OD, 300 MHz): δ 8.76 (s, 1H), 8.46 (s, 1H), 8.09-8.12 (m, 3H), 7.76-7.79 (m, 2H), 7.59-7.65 (m, 2H), 7.25-7.32 (m, 5H), 5.69 (s, 2H), 4.05 (s, 2H), 3.58 (m, 2H), 3.24 (s, 3H), 2.90 (m, 2H).

Example 79

Preparation of N-{2-[4-(1-benzyl-1H-imidazol-5-ylamino)-quinazolin-6-ylcarbamoyl]-ethyl}-acrylamide 71 μl of pyridine and 132 mg of 1-(3-dimethylaminopropyl)-3-ethylcarbodiimide hydrochloride were added to 47 μl of acrylic acid dissolved in 3 ml of THF at 0° C., reacted with 150 mg of the compound obtained in (78-1) of Example 78 for 30 mins while heating to room temperature, and the resulting solution was stirred at room temperature for 2 hours. The reacted solution was extracted with 6 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (13 mg, 8%).

$^1$H-NMR (CD$_3$OD, 300 MHz): δ 8.63 (s, 1H), 8.32 (s, 1H), 7.99-8.02 (m, 3H), 7.68-7.70 (m, 2H), 7.56-7.52 (m, 2H), 7.14-7.123 (m, 5H), 6.08-6.18 (m, 2H), 5.56-5.60 (m, 3H), 3.61 (t, J=7 Hz, 2H), 2.68 (t, J=7 Hz, 2H).

Example 80

Preparation of {2-[4-(4-phenylcarbamoyl-phenylamino)-quinazolin-6-ylcarbamoyl]-ethyl}-carbamic acid t-butylester 1 g of 2-[3-cyano-4-(dimethylamino-methylene amino)-phenylcarbamoyl]-ethyl-carbamic acid t-butylester (see, *Journal of Medicinal Chemistry* 2004, 44:2719) dissolved in 6 ml of acetic acid was reacted with 650 mg of 4-amino-N-phenyl-benzamide at 60° C. for 3 hours, and the resulting residue was stirred in 100 ml of saturated aqueous sodium bicarbonate solution at room temperature for 30 mins. The reacted solution was extracted with 30 ml of ethylacetate 3 times, dried over anhydrous magnesium sulfate, filtered and distilled under a reduced pressure, and the resulting residue was subjected to column chromatography (eluent-chloroform:methanol=15:1) to obtain the title compound (350 mg, 25%).

$^1$H-NMR (CD$_3$OD, 300 MHz): δ 8.64 (s, 1H), 8.51 (s, 1H), 7.92-8.01 (m, 3H), 7.87 (s, 1H), 7.67-7.69 (m, 4H), 7.36 (t, J=7.5 Hz, 2H), 7.14 (t, J=7.5 Hz, 1H), 3.47 (t, J=4 Hz, 2H), 2.65 (t, J=7 Hz, 2H), 1.4 (s, 9H).

Example 81

Preparation of 4-{6-[3-(2-methanesulfonyl-acetylamino)-propionylamino]-quinazolin-4-ylamino}-N-phenyl-benzamide (81-1) Preparation of 4-[6-(3-amino-propionylamino)-quinazolin-4-ylamino]-N-phenyl-benzamide 350 mg of the compound obtained in Example 80 dissolved in 7 ml of methylene chloride was reacted with 7 ml of trifluoroacetic acid at room temperature for 4 hours. The residue obtained from distillation of the reacted solution under a reduced pressure was stirred in 50 ml of saturated aqueous sodium bicarbonate for 30 mins, filtered under a reduced pressure, and dried to obtain the title compound (250 mg, 89%).

$^1$H-NMR (CD$_3$OD, 300 MHz): δ 8.75 (s, 1H), 8.59 (s, 1H), 8.00-8.07 (m, 4H), 7.80 (s, 2H), 7.73 (d, J=9 Hz, 2H), 7.40 (t, J=7.5 Hz, 2H), 7.18 (t, J=7.5 Hz, 1H), 3.31 (m, 2H), 2.71 (t, J=7 Hz, 2H).

(81-2) Preparation of 4-{6-[3-(2-methanesulfonyl-acetylamino)-propionylamino]-quinazolin-4-ylamino}-N-phenyl-benzamide 32 mg of hydroxyl-benzotriazole and 90 mg of 1-(3-dimethylaminopropyl)-3-ethylcarbodiimide hydrochloride were added to 32 mg of methanesulfonylacetic acid dissolved in 2 ml of THF, and reacted with 50 mg of the compound obtained in (81-1) at room temperature for 2 hours. The reacted solution was extracted with 6 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (10 mg, 16%).

$^1$H-NMR (CD$_3$OD, 300 MHz): δ 8.77 (s, 1H), 8.62 (s, 1H), 8.00-8.07 (m, 4H), 7.82 (s, 2H), 7.73 (d, J=9 Hz, 2H), 7.41 (t, J=7.5 Hz, 2H), 7.17 (t, J=7.5 Hz, 1H), 4.08 (s, 2H), 3.67 (t, J=7 Hz, 2H), 3.14 (s, 3H) 2.77 (t, J=7 Hz, 2H).

Example 82

Preparation of 4-[6-(3-acryloylamino-propionylamino)-quinazolin-4-ylamino]-N-phenyl-benzamide 124 μl of pyridine and 228 mg of 1-(3-dimethylaminopropyl)-3-ethylcarbodiimide hydrochloride were added to 82 μl of acrylic acid dissolved in 6 ml of THF at 0° C., reacted with 127 mg of the compound obtained in (81-1) of Example 81 for 30 mins while heating to room temperature, and the resulting solution was stirred at room temperature for 2 hours. The reacted solution was extracted with 6 ml of ethylacetate 3 times after adding 5 ml of water, dried over anhydrous magnesium sulfate, and filtered and distilled under a reduced pressure. 10 ml of diethylether was added to the resulting residue dissolved in 0.5 ml of methanol to obtain solid, and the solid was filtered under a reduced pressure and dried to obtain the title compound (15 mg, 10%).

$^1$H-NMR (CD$_3$OD, 300 MHz): δ 8.74 (s, 1H), 8.59 (s, 1H), 8.00-8.07 (m, 4H), 7.82 (s, 2H), 7.72 (d, J=9 Hz, 2H), 7.40 (t, J=7.5 Hz, 2H), 7.16 (t, J=7.5 Hz, 1H), 6.25-6.27 (m, 2H), 5.61-5.69 (m, 1H), 3.68 (t, J=7 Hz, 2H), 2.73 (t, J=7 Hz, 2H).

Example 83

Preparation of N-[4-(biphenyl-4-ylamino)-quinazolin-6-yl]-3-(2-methanesulfonyl-acetylamino)-propionamide

(83-1) Preparation of 3-amino-N-[4-(biphenyl-4-ylamino)-quinazolin-6-yl]-propionamide 480 mg of 2-[4-(biphenyl-4-ylamino)-quinazolin-6-ylcarbamoyl]-ethyl-carbamic acid t-butylester (prepared in accordance with the procedure of Example 80) dissolved in 10 ml of methylene chloride was reacted with 10 ml of trifluoroacetic acid at room temperature for 4 hours. The residue obtained from distillation of the reacted solution under a reduced pressure was stirred in 50 ml of saturated aqueous sodium bicarbonate for 30 mins, filtered under a reduced pressure, and dried to obtain the title compound (400 mg, 99%).

$^1$H-NMR (CD$_3$OD, 300 MHz): δ 8.71 (s, 1H), 8.50 (s, 1H), 7.89 (d, J=9 Hz, 2H), 7.78-7.80 (m, 2H), 7.65-7.75 (m, 4H), 7.43 (t, J=7.5 Hz, 2H), 7.34 (t, J=7.5 Hz, 1H) 3.32 (t, J=7 Hz, 2H), 2.71 (t, J=7 Hz, 2H).

(83-2) Preparation of N-[4-(biphenyl-4-ylamino)-quinazolin-6-yl]-3-(2-methanesulfonyl-acetylamino)-propionamide 56 mg of hydroxyl-benzotriazole and 160 mg of 1-(3-dimethylaminopropyl)-3-ethylcarbodiimide hydrochloride were added to 58 mg of methanesulfonylacetic acid dissolved in 5 ml of THF, and reacted with 80 mg of the compound obtained in (83-1) at room temperature for 12 hours. The reacted solution was extracted with 10 ml of ethylacetate 3 times after adding 5 ml of water, dried over anhydrous magnesium sulfate, and filtered and distilled under a reduced pressure. 5 ml of diethylether was added to the resulting residue dissolved in 0.5 ml of methanol to obtain solid, and the solid was filtered under a reduced pressure and dried to obtain the title compound (30 mg, 76%).

$^1$H-NMR (CD$_3$OD, 300 MHz): δ 8.76 (s, 1H), 8.56 (s, 1H), 7.84-7.89 (m, 3H), 7.63-7.73 (m, 5H), 7.42 (t, J=7.5 Hz, 2H), 7.34 (t, J=7.5 Hz, 1H), 4.1 (s, 2H), 3.68 (t, J=7 Hz, 2H), 3.16 (s, 3H), 2.77 (t, J=7 Hz, 2H).

Example 84

Preparation of N-{2-[4-(biphenyl-4-ylamino)-quinazolin-6-ylcarbamoyl]-ethyl}-acrylamide 54 μl of pyridine and 100 mg of 1-(3-dimethylaminopropyl)-3-ethylcarbodiimide hydrochloride were added to 36 μl of acrylic acid dissolved in 3 ml of THF at 0° C., reacted with 100 mg of the compound obtained in (83-1) of Example 83 for 30 mins while heating to room temperature, and the resulting solution was stirred at room temperature for 2 hours. The reacted solution was extracted with 6 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (11 mg, 10%).

$^1$H-NMR (CD$_3$OD, 300 MHz): δ 8.64 (s, 1H), 8.42 (s, 1H), 7.78 (d, J=8 Hz, 2H), 7.69-7.71 (m, 2H), 7.57-7.62 (m, 4H), 7.39 (t, J=7.5 Hz, 2H), 7.25 (t, J=7.5 Hz, 1H), 6.16-6.18 (m, 2H), 5.66-5.71 (m, 1H), 3.60 (t, J=7 Hz, 2H), 2.69 (t, J=7 Hz, 2H).

Example 85

Preparation of N-{2-[4-[3-chloro-4-(3-fluoro-benzyloxy)phenylamino]-7-(3-morpholin-4-yl-propoxy)-quinazolin-6-ylcarbamoyl]-ethyl}-acrylamide

(85-1) Preparation of N-[3-chloro-4-(3-fluoro-benzyloxy)-phenyl]-7-(3-morpholin-4-yl-propoxy)-quinazolin-4,6-diamine 353 mg of iron dissolved in aqueous 5% acetic acid solution was activated at 100° C. 450 mg of [3-chloro-4-(3-fluoro-benzyloxy)-phenyl]-[7 (3-morpholin-4-yl-propoxy)-6-nitroquinazolin-4-yl]-amine (see, *Journal of Medicinal Chemistry* 2000, 43, 1380) dissolved in a mixture of ethylacetate and acetic acid (1:1) was added thereto dropwise, and refluxed. The hot reacted solution was filtered under a reduced pressure through celite pad, and the pad was washed with ethylacetate. The washed solvent was washed with saturated sodium bicarbonate solution several times. The organic layer was dried over magnesium sulfate, and filtered and distilled under a reduced pressure to obtain the title compound (353 mg, 83%).

$^1$H-NMR (DMSO-$d_6$, 300 MHz): δ 9.22 (s, 1H), 8.32 (s, 1H), 8.03 (d, 1H), 7.71 (dd, 1H), 7.46 (m, 1H), 7.39 (s, 1H), 7.32 (m, 2H), 7.19 (m, 2H), 7.06 (s, 1H), 5.28 (br s, 2H), 5.23 (s, 2H), 4.19 (t, 2H), 3.59 (t, 4H), 2.50 (t, 2H), 2.40 (br s, 4H), 1.99 (m, 2H); MS (ESI): [M+H+] 537.

(85-2) Preparation of N-{2-[4-[3-chloro-4-(3-fluoro-benzyloxy)-phenylamino]-7-(3-morpholin-4-yl-propoxy)-quinazolin-6-ylcarbamoyl]-ethyl}-acrylamide The procedure of Example 4 was repeated except for using 250 mg of the compound obtained in Example (85-1) and 60 μL of acrylic acid instead of the compound obtained in (2-3) of Example 2 to obtain the title compound (10 mg, 4%).

$^1$H-NMR (CD$_3$OD, 300 MHz): δ 8.73 (s, 1H), 8.40 (s, 1H), 7.82 (d, 1H), 7.53 (dd, 1H), 7.39 (m, 1H), 7.29 (m, 2H), 7.09 (m, 3H), 6.25 (m, 2H), 5.66 (dd, 1H), 5.19 (s, 2H), 4.24 (t, 2H), 3.71 (t, 4H), 3.67 (t, 2H), 2.80 (t, 2H), 2.60 (t, 2H), 2.53 (br s, 4H), 2.12 (m, 2H); MS (ESI): [M+H+] 662.

Example 86

Preparation of (3-{4-[3-chloro-4-(3-fluoro-benzyloxy)-phenylamino]-quinazolin-6-ylcarbamoyl}-propyl)-carbamic acid t-butylester 1.54 g of 4-t-buthoxycarbonylamino-butyric acid, 2.9 g of 1-(3-dimethylaminopropyl)-3-ethylcarbodiimide hydrochloride and 1.03 g of 1-hydroxylbenzotriazole dissolved in 25 ml of methylene chloride was reacted with 1.5 g of the compound obtained in (1-4) of Example 1 at room temperature for 14 hours. Saturated sodium bicarbonate solution was added to the reacted solution, and the resulting solution was filtered under a reduced pressure to obtain the title compound as solid (0.9 g, 41%).

$^1$H-NMR (DMSO-$d_6$, 300 MHz): δ 10.20 (s, 1H), 9.76 (s, 1H), 8.68 (d, 1H), 8.48 (s, 1H), 7.96 (d, 1H), 7.70 (m, 3H), 7.45 (m, 1H), 7.31 (m, 4H), 6.86 (m, 1H), 5.24 (s, 2H), 2.99 (q, 2H), 2.37 (t, 2H), 1.73 (m, 2H), 1.37 (s, 9H).

Example 87

Preparation of N-{4-[3-chloro-4-(3-fluoro-benzyloxy)-phenylamino]-quinazolin-6-yl}-4-(2-methoxy-acetylamino)-butyramide (87-1) Preparation of 4-amino-N-{4-[3-chloro-4-(3-fluoro-benzyloxy)-phenylamino]-quinazolin-6-yl}-butyramide 0.76 g of the compound obtained in Example 86 dissolved in 22 ml of methylene chloride and 22 ml of trifluoroacetic acid was stirred at room temperature for 4 hours. The residue obtained from distillation of the reacted solution under a reduced pressure was stirred in 5 ml of methylene chloride while adding 50 ml of saturated aqueous sodium bicarbonate slowly, and filtered under a reduced pressure to obtain the title compound as solid (0.62 g, 99%).

$^1$H-NMR (DMSO-$d_6$, 300 MHz): δ 8.58 (s, 1H), 8.38 (s, 1H), 7.87 (s, 1H), 7.73 (d, 1H), 7.62 (m, 2H), 7.35 (m, 1H), 7.20 (m, 2H), 7.15 (d, 1H), 7.08 (t, 1H), 5.15 (s, 2H), 2.56 (m, 2H), 2.33 (t, 2H), 1.65 (m, 2H).

(87-2) Preparation of N-{4-[3-chloro-4-(3-fluoro-benzyloxy)-phenylamino]-quinazolin-6-yl}-4-(2-methoxy-acetylamino)-butyramide The procedure of (20-2) of Example 20 was repeated except for using 0.1 g of the compound obtained in (87-1) instead of 4-amino-N-{4-[3-chloro-4-(3-fluoro-benzyloxy)-phenylamino]-quinazolin-6-yl}-propionamide, and the resultant was filtered under a reduced pressure to obtain the title compound as solid (0.06 g, 53%).

$^1$H-NMR (DMSO-$d_6$, 300 MHz): δ 10.28 (s, 1H), 9.78 (bs, 1H), 8.67 (d, 1H), 8.44 (s, 1H), 7.95 (d, 1H), 7.84 (m, 2H), 7.67 (m, 2H), 7.43 (m, 1H), 7.26 (m, 2H), 7.20 (d, 1H), 7.12 (t, 1H), 5.21 (s, 2H), 3.76 (s, 2H), 3.26 (s, 3H), 3.15 (q, 2H), 2.38 (t, 2H), 1.77 (m, 2H).

Example 88

Preparation of N-{4-[3-chloro-4-(3-fluoro-benzyloxy)-phenylamino]-quinazolin-6-yl}-4-(2-methanesulfonyl-acetylamino)-butyramide The procedure of Example 21 was repeated except for using 0.1 g of the compound obtained in (87-1) of Example 87 instead of 4-amino-N-{4-[3-chloro-4-(3-fluoro-benzyloxy)-phenylamino]-quinazolin-6-yl}-propionamide, and the resultant was filtered under a reduced pressure to obtain the title compound as solid (0.05 g, 40%).

$^1$H-NMR (DMSO-$d_6$, 300 MHz): δ 10.41 (s, 1H), 9.85 (bs, 1H), 8.72 (s, 1H), 8.48 (m, 1H), 7.99 (s, 1H), 7.87 (d, 1H), 7.68 (m, 2H), 7.46 (m, 1H), 7.33 (m, 2H), 7.24 (d, 1H), 7.17 (t, 1H), 5.23 (s, 2H), 4.06 (s, 2H), 3.18 (m, 2H), 3.11 (s, 3H), 2.43 (t, 2H), 1.79 (m, 2H).

Example 89

Preparation of 4-acryloylamino-N-{4-[3-chloro-4-(3-fluoro-benzyloxy)-phenylamino]-quinazolin-6-yl}-butyramide 36 μl of pyridine, 100 mg of the compound obtained in (87-1) of Example 87 and 80 mg of 1-(3-dimethylaminopropyl)-3-ethylcarbodiimide hydrochloride were added to 30 μl of acrylic acid dissolved in 2 ml of THF, and reacted at 0° C. for 5 hours. The reacted solution was washed with saturated sodium bicarbonate, dried over sodium sulfate, filtered and distilled under a reduced pressure, and the resulting residue was subjected to column chromatography (eluent-chloroform:methanol=15:1) to obtain the title compound (14 mg, 13%).

$^1$H-NMR (CD$_3$OD, 300 MHz): δ 8.61 (s, 1H), 8.45 (s, 1H), 7.87 (d, 1H), 7.73 (m, 2H), 7.58 (dd, 1H), 7.39 (m, 1H), 7.28 (m, 2H), 7.11 (m, 2H), 6.22 (m, 2H), 5.65 (dd, 1H), 5.19 (s, 2H), 3.39 (t, 2H), 2.50 (t, 2H), 1.94 (m, 2H).

Example 90

Preparation of N-(3-{4-[3-chloro-4-(3-fluoro-benzyloxy)-phenylamino]-quinazolin-6-ylcarbamoyl}-propyl)-benzamide The procedure of Example 35 was repeated except for using 0.06 g of the compound obtained in (87-1) of Example 87 instead of 4-amino-N-{4-[3-chloro-4-(3-fluoro-benzyloxy)-phenylamino]-quinazolin-6-yl}-propionamide to obtain the title compound (0.05 g, 69%).

$^1$H-NMR (CD$_3$OD, 300 MHz): δ 8.95 (d, 1H), 8.84 (s, 1H), 8.12 (dd, 1H), 8.04 (d, 1H), 7.98 (dd, 2H), 7.93 (d, 1H), 7.78 (dd, 1H), 7.58 (m, 4H), 7.42 (m, 2H), 7.34 (d, 1H), 7.21 (t, 1H), 5.37 (s, 2H), 3.72 (t, 2H), 2.75 (t, 2H), 2.26 (m, 214); MS (ESI): [M+H+] 583.

Example 91

Preparation of N-(3-{4-[3-chloro-4-(3-fluoro-benzyloxy)-phenylamino]-quinazolin-6-ylcarbamoyl}-propyl)-oxalamic acid ethylester The procedure of Example 36 was repeated except for using 0.09 g of the compound obtained in (87-1) of Example 87 instead of 4-amino-N-{4-[3-chloro-4-(3-fluoro-benzyloxy)-phenylamino]-quinazolin-6-yl}-propionamide, and the resultant was subjected to column chromatography (eluent-chloroform:methanol=15:1) to obtain the title compound (0.07 g, 65%).

$^1$H-NMR (DMSO-d$_6$, 300 MHz): δ 10.21 (s, 1H), 9.76 (s, 1H), 8.66 (s, 1H), 8.47 (s, 1H), 7.95 (d, 1H), 7.69 (m, 3H), 7.45 (m, 2H), 7.30 (m, 2H), 7.22 (d, 1H), 7.16 (t, 1H), 5.23 (s, 2H), 4.20 (q, 2H), 3.20 (q, 2H), 2.37 (t, 2H), 1.82 (m, 2H), 1.24 (t, 3H).

Example 92

Preparation of cyclopropylcarboxylic acid (3-{4-[3-chloro-4-(3-fluoro-benzyloxy)-phenylamino]-quinazolin-6-ylcarbamoyl}-propyl)-amide The procedure of Example 37 was repeated except for using 0.09 g of the compound obtained in (87-1) of Example 87 instead of 4-amino-N-{4-[3-chloro-4-(3-fluoro-benzyloxy)-phenylamino]-quinazolin-6-yl}-propionamide, and the resultant was subjected to column chromatography (eluent-chloroform:methanol=15:1) to obtain the title compound (0.03 g, 30%).

$^1$H-NMR (DMSO-d$_6$, 300 MHz): δ 10.22 (s, 1H), 9.76 (s, 1H), 8.66 (s, 1H), 8.47 (s, 1H), 7.95 (d, 1H), 7.73 (m, 3H), 7.46 (m, 2H), 7.28 (m, 2H), 7.21 (d, 1H), 7.15 (t, 1H), 5.23 (s, 2H), 3.13 (q, 2H), 2.39 (t, 2H), 1.76 (m, 2H), 1.50 (m, 1H), 0.76 (m, 2H), 0.62 (m, 2H).

Example 93

Preparation of N-{4-[3-chloro-4-(3-fluoro-benzyloxy)-phenylamino]-quinazolin-6-yl}-4-(2-cyano-acetylamino)-butyramide The procedure of Example 31 was repeated except for using 0.06 g of the compound obtained in (87-1) of Example 87 instead of 4-amino-N-{4-[3-chloro-4-(3-fluoro-benzyloxy)-phenylamino]-quinazolin-6-yl}-propionamide, and the resultant was subjected to column chromatography (eluent-chloroform:methanol=15:1) to obtain the title compound (0.03 g, 44%).

$^1$H-NMR (CD$_3$OD, 300 MHz): δ 8.48 (s, 1H), 8.33 (s, 1H), 7.76 (d, 1H), 7.59 (s, 2H), 7.46 (dd, 1H), 7.28 (m, 1H), 7.17 (m, 2H), 6.99 (d, 1H), 6.92 (t, 1H), 5.06 (s, 2H), 3.22 (m, 4H), 2.40 (t, 2H), 1.84 (m, 2H).

Example 94

Preparation of furan-3-carboxylic acid (3-{4-[3-chloro-4-(3-fluoro-benzyloxy)-phenylamino]-quinazolin-6-ylcarbamoyl}-propyl)-amide The procedure of Example 33 was repeated except for using 0.06 g of the compound obtained in (87-1) of Example 87 instead of 4-amino-N-{4-[3-chloro-4-(3-fluoro-benzyloxy)-phenylamino]-quinazolin-6-yl}-propionamide, and the resultant was subjected to column chromatography (eluent-chloroform:methanol=15:1) to obtain the title compound (0.04 g, 56%).

$^1$H-NMR (CD$_3$OD, 300 MHz): δ 8.57 (d, 1H), 8.44 (s, 1H), 8.05 (dd, 1H), 7.88 (d, 1H), 7.71 (m, 2H), 7.57 (dd, 1H), 7.53 (t, 1H), 7.39 (m, 1H), 7.27 (m, 2H), 7.10 (d, 1H), 7.04 (t, 1H), 6.79 (t, 1H), 5.17 (s, 2H), 3.48 (t, 2H), 2.54 (t, 2H), 2.04 (m, 2H).

Example 95

Preparation of 1H-pyrazol-4-carboxylic acid (3-{4-[3-chloro-4-(3-fluoro-benzyloxy)-phenylamino]-quinazolin-6-ylcarbamoyl}-propyl)-amide The procedure of Example 34 was repeated except for using 0.09 g of the compound obtained in (87-1) of Example 87 instead of 4-amino-N-{4-[3-chloro-4-(3-fluoro-benzyloxy)-phenylamino]-quinazolin-6-yl}-propionamide, and the resultant was subjected to column chromatography (eluent-chloroform:methanol=15:1) to obtain the title compound (0.04 g, 37%).

$^1$H-NMR (CD$_3$OD, 300 MHz): δ 8.80 (d, 1H), 8.67 (s, 1H), 8.01 (s, 2H), 7.96 (dd, 1H), 7.86 (d, 1H), 7.76 (d, 1H), 7.59 (dd, 1H), 7.38 (m, 1H), 7.26 (m, 2H), 7.17 (d, 1H), 7.03 (t, 1H), 5.20 (s, 2H), 3.45 (t, 2H), 2.55 (t, 2H), 2.03 (m, 2H).

Example 96

Preparation of {3-[4-(3-chloro-4-fluoro-phenylamino)-quinazolin-6-ylcarbamoyl]-propyl}-carbamic acid t-butylester The procedure of Example 86 was repeated except for using 0.5 g of N$^4$-(3-chloro-4-fluoro-phenyl)-quinazolin-4,6-diamine instead of the compound obtained in (1-4) of Example 1, and the resultant was subjected to column chromatography (eluent-chloroform:methanol=15:1) to obtain the title compound (0.39 g, 57%).

$^1$H-NMR (DMSO-d$_6$, 300 MHz): δ 10.21 (s, 1H), 9.89 (s, 1H), 8.70 (s, 1H), 8.52 (s, 1H), 8.10 (dd, 1H), 7.78 (m, 3H), 7.40 (t, 1H), 6.84 (bt, 1H), 2.98 (q, 2H), 2.36 (t, 2H), 1.72 (m, 2H), 1.35 (s, 9H).

Example 97

Preparation of N-[4-(3-chloro-4-fluoro-phenylamino)-quinazolin-6-yl]-4-(2-methanesulfonyl-acetylamino)-butyramide (97-1) Preparation of 4-amino-N-[4-(3-chloro-4-fluoro-phenylamino)-quinazolin-6-yl]-butyramide The procedure of (87-1) of Example 87 was repeated except for using 0.08 g of the compound obtained in Example 96 instead of the compound obtained in Example 86 to obtain the title compound (0.06 g, 96%).

¹H-NMR (DMSO-d₆, 300 MHz): δ 8.75 (d, 1H), 8.51 (s, 1H), 8.12 (bt, 1H), 7.82 (m, 3H), 7.40 (t, 1H), 2.80 (m, 2H), 2.43 (m, 2H), 1.72 (m, 2H).

(97-2) Preparation of N-[4-(3-chloro-4-fluoro-phenylamino)-quinazolin-6-yl]-4-(2-methanesulfonyl-acetylamino)-butyramide The procedure of Example 21 was repeated except for using 0.05 g of the compound obtained in (97-1) instead of 4-amino-N-{4-[3-chloro-4-(3-fluoro-benzyloxy)-phenylamino]-quinazolin-6-yl}-propionamide, and the resultant was subjected to column chromatography (eluent-chloroform methanol=15:1) to obtain the title compound (0.03 g, 44%).

¹H-NMR (CDCl₃, 300 MHz): δ 8.69 (s, 2H), 7.98 (dd, 1H), 7.85 (d, 1H), 7.61 (m, 2H), 7.16 (t, 1H), 6.92 (m, 1H), 3.48 (m, 2H), 3.15 (s, 2H), 2.52 (t, 2H), 2.17 (s, 3H), 1.60 (m, 2H); MS (ESI): [M+H+] 494.09.

Example 98

Preparation of 4-acryloylamino-N-[4-(3-chloro-4-fluoro-phenylamino)-quinazolin-6-yl]-butyramide The procedure of Example 22 was repeated except for using 0.1 g of the compound obtained in (97-1) of Example 97 instead of 4-amino-N-{4-[3-chloro-4-(3-fluoro-benzyloxy)-phenylamino]-quinazolin-6-yl}-propionamide to obtain the title compound (0.04 g, 35%).

¹H-NMR (DMSO-d₆, 300 MHz): δ 10.26 (s, 1H), 9.90 (s, 1H), 8.70 (s, 1H), 8.52 (s, 1H), 8.11 (m, 2H), 7.78 (m, 3H), 7.40 (t, 1H), 6.20 (m, 1H), 6.04 (m, 1H), 5.55 (dd, 1H), 3.19 (q, 2H), 2.40 (t, 2H), 1.79 (m, 2H); MS (ESI): [M+H+] 428.07.

Example 99

Preparation of (3-{4-[3-methyl-4-(6-methyl-pyridin-3-yloxy)-phenylamino]-quinazolin-6-ylcarbonyl}-propyl)-carbamic acid t-butylester The procedure of Example 86 was repeated except for using 1.2 g of N⁴-[3-methyl-4-(6-methyl-pyridin-3-yloxy)-phenyl]-quinazolin-4,6-diamine instead of the compound obtained in (1-4) of Example 1, and the resultant was subjected to column chromatography (eluent-chloroform:methanol=15:1) to obtain the title compound (1.58 g, 87%).

¹H-NMR (DMSO-d₆, 300 MHz): δ 10.17 (s, 1H), 9.74 (s, 1H), 8.67 (d, 1H), 8.47 (s, 1H), 8.15 (d, 1H), 7.78 (dd, 1H), 7.70 (m, 2H), 7.63 (dd, 1H), 7.18 (m, 2H), 6.92 (d, 1H), 6.84 (bt, 1H), 2.98 (q, 2H), 2.41 (s, 3H), 2.36 (t, 2H), 2.18 (s, 3H), 1.72 (m, 2H), 1.35 (s, 9H).

Example 100

Preparation of 4-(2-methanesulfonyl-acetylamino)-N-{4-[3-methyl-4-(6-methyl-pyridin-3-yloxy)-phenylamino]-quinazolin-6-yl}-butyramide (100-1) Preparation of 4-amino-N-{4-[3-methyl-4-(6-methyl-pyridin-3-yloxy)-phenylamino]-quinazolin-6-yl}-butyramide The procedure of (87-1) of Example 87 was repeated except for using 1.51 g of the compound obtained in Example 99 instead of the compound obtained in example 86 to obtain the title compound (1.21 g, 98%).

¹H-NMR (DMSO-d₆, 300 MHz): δ 12.60 (bs, 1H), 10.64 (s, 1H), 9.55 (s, 1H), 8.61 (d, 1H), 8.47 (s, 1H), 8.26 (m, 2H), 8.17 (d, 1H), 7.63 (d, 1H), 7.20 (m, 2H), 6.92 (d, 2H), 3.12 (m, 2H), 2.40 (m, 5H), 2.17 (s, 3H), 1.75 (m, 2H).

(100-2) Preparation of 4-(2-methanesulfonyl-acetylamino)-N-{4-[3-methyl-4-(6-methyl-pyridin-3-yloxy)-phenylamino]-quinazolin-6-yl}-butyramide The procedure of Example 88 was repeated except for using 0.1 g of the compound obtained in (100-1) instead of the compound obtained in (87-1) of Example 87 to obtain the title compound (0.04 g, 32%).

¹H-NMR (DMSO-d₆, 300 MHz): δ 10.22 (s, 1H), 9.75 (s, 1H), 8.68 (s, 1H), 8.47 (s, 1H), 8.39 (bt, 1H), 8.15 (d, 1H), 7.70 (m, 4H), 7.17 (m, 2H), 6.91 (d, 1H), 4.03 (s, 2H), 3.19 (q, 2H), 3.09 (s, 3H), 2.39 (m, 5H), 2.18 (s, 3H), 1.78 (m, 2H); MS (ESI [M+H+] 563.19.

Example 101

Preparation of 4-acryloylamino-N-{4-[3-methyl-4-(6-methyl-pyridin-3-yloxy)-phenylamino]-quinazolin-6-yl}-butyramide The procedure of Example 89 was repeated except for using 0.15 g of the compound obtained in (100-1) of Example 100 instead of the compound obtained in (87-1) of Example 87 to obtain the title compound (0.03 g, 18%).

¹H-NMR (CD₃OD, 300 MHz): δ 8.64 (d, 1H), 8.44 (s, 1H), 8.11 (d, 1H), 7.75 (m, 2H), 7.66 (d, 1H), 7.58 (dd, 1H), 7.28 (m, 2H), 6.97 (d, 1H), 6.23 (d, 1H), 6.20 (s, 1H), 5.63 (dd, 1H), 3.38 (t, 2H), 2.52 (m, 5H), 2.24 (s, 3H), 1.96 (m, 2H); MS (ESI): [M+H+] 497.19.

Example 102

Preparation of 4-(2-chloro-acetylamino)-N-{4-[3-chloro-4-(3-fluoro-benzyloxy)-phenylamino]-quinazolin-6-yl}-butyramide The procedure of Example 61 was repeated except for using 0.3 g of the compound obtained in (87-1) of Example 87 instead of the compound obtained in (20-1) of Example 20 to obtain the title compound (0.33 g, 95%).

¹H-NMR (CD₃OD, 300 MHz): δ 8.63 (d, 1H), 8.46 (s, 1H), 7.87 (d, 1H), 7.74 (m, 2H), 7.58 (dd, 1H), 7.39 (m, 1H), 7.27 (m, 2H), 7.14 (d, 1H), 7.04 (t, 1H), 5.20 (s, 2H), 4.05 (s, 2H), 3.36 (t, 2H), 2.50 (t, 2H), 1.98 (m, 2H).

Example 103

Preparation of N-{4-[3-chloro-4-(3-fluoro-benzyloxy)-phenylamino]-quinazolin-6-yl}-4-(2-morpholin-4-yl-acetylamino)-butyramide The procedure of Example 62 was repeated except for using 0.04 g of the compound obtained in Example 102 instead of the compound obtained in Example 61 to obtain the title compound (0.02 g, 42%).

¹H-NMR (CD₃OD, 300 MHz): δ 8.61 (d, 1H), 8.45 (s, 1H), 7.88 (d, 1H), 7.75 (m, 2H), 7.58 (dd, 1H), 7.40 (m, 1H), 7.27 (m, 2H), 7.14 (d, 1H), 7.05 (t, 1H), 5.20 (s, 2H), 3.68 (m, 4H), 3.35 (t, 2H), 3.00 (s, 2H), 2.50 (m, 6H), 1.95 (m, 2H).

Example 104

Preparation of N-{4-[3-chloro-4-(3-fluoro-benzyloxy)-phenylamino]-quinazolin-6-yl}-4-(2-dimethylamino-acetylamino)-butyramide The procedure of Example 63 was repeated except for using 0.04 g of the compound obtained in Example 102 instead of the compound obtained in Example 61 to obtain the title compound (0.02 g, 45%).

$^1$H-NMR (CD$_3$OD, 300 MHz): δ 8.63 (s, 1H), 8.46 (s, 1H), 7.90 (d, 1H), 7.76 (m, 2H), 7.60 (dd, 1H), 7.40 (m, 1H), 7.28 (m, 2H), 7.15 (d, 1H), 7.07 (t, 1H), 5.22 (s, 2H), 3.37 (t, 2H), 3.02 (s, 2H), 2.51 (t, 2H), 2.32 (s, 6H), 1.97 (m, 2H).

Example 105

Preparation of N-{4-[3-chloro-4-(3-fluoro-benzyloxy)-phenylamino]-quinazolin-6-yl}-4-[2-(4-methyl-piperazin-1-yl)-acetylamino]-butyramide The procedure of Example 64 was repeated except for using 0.02 g of the compound obtained in Example 102 instead of the compound obtained in Example 61 to obtain the title compound (0.01 g, 10%).

$^1$H-NMR (CDCl$_3$, 300 MHz): δ 8.57 (s, 1H), 8.52 (s, 1H), 7.88 (d, 1H), 7.80 (m, 2H), 7.66 (dd, 1H), 7.37 (m, 1H), 7.24 (m, 2H), 7.04 (m, 2H), 5.18 (s, 2H), 3.41 (t, 2H), 3.07 (s, 2H), 2.63 (bs, 4H), 2.46 (t, 2H), 2.03 (m, 6H), 1.43 (s, 3H).

Example 106

Preparation of N-{4-[3-chloro-4-(3-fluoro-benzyloxy)-phenylamino]-quinazolin-6-yl}-4-[2-(2-methoxy-ethylamino)-acetylamino]-butyramide The procedure of Example 65 was repeated except for using 0.07 g of the compound obtained in Example 102 instead of the compound obtained in Example 61 to obtain the title compound (0.02 g, 28%).

$^1$H-NMR (CD$_3$OD, 300 MHz): δ 8.61 (d, 1H), 8.45 (s, 1H), 7.88 (d, 1H), 7.73 (m, 2H), 7.58 (dd, 1H), 7.39 (m, 1H), 7.28 (m, 2H), 7.13 (d, 1H), 7.05 (t, 1H), 5.19 (s, 2H), 3.47 (t, 2H), 3.35 (t, 2H), 3.30 (s, 3H), 3.28 (s, 2H), 2.75 (t, 2H), 2.50 (t, 2H), 1.98 (m, 2H).

Example 107

Preparation of N-{4-[3-chloro-4-(3-fluoro-benzyloxy)-phenylamino]-quinazolin-6-yl}-4-[2-(2-methanesulfonyl-ethylamino)-acetylamino]-butyramide The procedure of Example 66 was repeated except for using 0.09 g of the compound obtained in Example 102 instead of the compound obtained in Example 61 to obtain the title compound (0.02 g, 20%).

$^1$H-NMR (CD$_3$OD, 300 MHz): δ 8.60 (d, 1H), 8.45 (s, 1H), 7.88 (d, 1H), 7.75 (m, 2H), 7.58 (dd, 1H), 7.40 (m, 1H), 7.27 (m, 2H), 7.14 (d, 1H), 7.05 (t, 1H), 5.20 (s, 2H), 3.37 (m, 4H), 3.27 (s, 2H), 3.05 (m, 5H), 2.50 (t, 2H), 1.98 (m, 2H).

Example 108

Preparation of 4-(2-chloro-acetylamino)-N-{4-[3-methyl-4-(6-methyl-pyridin-3-yloxy)-phenylamino]-quinazolin-6-yl}-butyramide 1 g of the compound obtained in (100-1) of Example 100 dissolved in 20 ml of THF was cooled to 0° C., and reacted with 0.4 ml of pyridine and 0.3 ml of chloroacetylchloride at room temperature for 5 hours. Saturated sodium bicarbonate solution was added to the reacted solution, and the resulting solution was extracted with chloroform, washed with saturate saline solution, dried over magnesium sulfate, filtered and distilled under a reduced pressure. The resulting residue was vacuum dried to obtain the title compound (0.4 g, 35%).

$^1$H-NMR (DMSO-d$_6$, 300 MHz): δ 9.89 (s, 1H), 9.01 (s, 1H), 8.71 (s, 1H), 8.50 (s, 1H), 8.14 (m, 2H), 7.75 (m, 4H), 7.21 (m, 2H), 6.92 (d, 1H), 4.04 (s, 2H), 3.18 (m, 2H), 2.42 (m, 5H), 2.18 (s, 3H), 1.75 (m, 2H); MS (ESI): [M+H+] 519.08.

Example 109

Preparation of N-{4-[3-methyl-4-(6-methyl-pyridin-3-yloxy)-phenylamino]-quinazolin-6-yl}-4-(2-morpholin-4-yl-acetylamino)-butyramide 0.07 g of the compound obtained in Example 108 dissolved in 5 ml of N,N'-dimethylformamide was reacted with 0.02 ml of morpholine and 0.04 g of potassium carbonate for 10 hours while heating to 100° C. The reacted solution was diluted with distilled water, extracted with ethylacetate, washed with saturated saline solution, dried over anhydrous magnesium sulfate, filtered and distilled under a reduced pressure, and the resulting residue was subjected to column chromatography (eluent-chloroform:methanol=15:1) to obtain the title compound (0.03 g, 38%).

$^1$H-NMR (CD$_3$OD, 300 MHz): δ 8.62 (s, 1H), 8.42 (s, 1H), 8.10 (d, 1H), 7.72 (m, 2H), 7.63 (d, 1H), 7.57 (d, 1H), 7.24 (m, 2H), 6.94 (d, 1H), 3.67 (m, 4H), 3.35 (t, 2H), 2.99 (s, 2H), 2.48 (m, 9H), 2.22 (s, 3H), 1.94 (m, 2H); MS (ESI): [M+H+] 570.28.

Example 110

Preparation of 4-(2-dimethylamino-acetylamino)-N-{4-[3-methyl-4-(6-methyl-pyridin-3-yloxy)-phenylamino]-quinazolin-6-yl}-butyramide The procedure of Example 109 was repeated except for using dimethylamine 2 M THF instead of morpholine to obtain the title compound (0.03 g, 37%).

$^1$H-NMR (CDCl$_3$, 300 MHz): δ 10.27 (s, 1H), 8.76 (s, 1H), 8.66 (s, 1H), 8.25 (d, 1H), 8.12 (bs, 1H), 7.80 (s, 2H), 7.58 (m, 3H), 7.11 (m, 2H), 6.87 (d, 1H), 3.44 (q, 2H), 2.88 (s, 2H), 2.52 (s, 3H), 2.40 (m, 2H), 2.32 (s, 6H), 2.24 (s, 3H), 1.94 (m, 2H).

Example 111

Preparation of N-{4-[3-methyl-4-(6-methyl-pyridin-3-yloxy)-phenylamino]-quinazolin-6-yl}-4-[2-(4-methyl-piperazin-1-yl)-acetylamino]-butyramide The procedure of Example 109 was repeated except for using 1-methyl-piperazine instead of morpholine to obtain the title compound (0.05 g, 56%).

$^1$H-NMR (CDCl$_3$, 300 MHz): δ 10.22 (s, 1H), 8.65 (s, 1H), 8.53 (s, 1H), 8.24 (s, 2H), 7.79 (s, 2H), 7.53 (m, 3H), 7.10 (m, 2H), 6.87 (d, 1H), 3.44 (m, 2H), 3.07 (s, 2H), 2.57 (bs, 4H), 2.51 (s, 3H), 2.40 (m, 6H), 2.29 (s, 3H), 2.23 (s, 3H), 1.92 (m, 2H).

Example 112

Preparation of 4-[2-(2-methanesulfonyl-ethylamino)-acetylamino]-N-{4-[3-methyl-4-(6-methyl-pyridin-3-yloxy)-phenylamino]-quinazolin-6-yl}-butyramide The procedure of Example 109 was repeated except for using 2-methanesulfonylethylamine instead of morpholine to obtain the title compound (0.04 g, 33%).

$^1$H-NMR (CDCl$_3$, 300 MHz): δ 9.83 (s, 1H), 8.64 (s, 2H), 8.23 (d, 1H), 7.80 (m, 3H), 7.64 (s, 1H), 7.54 (d, 1H), 7.12 (m, 2H), 6.88 (d, 1H), 3.42 (m, 2H), 3.34 (s, 2H), 3.20 (m, 4H), 3.02 (s, 3H), 2.52 (s, 3H), 2.42 (m, 2H), 2.25 (s, 3H), 1.96 (m, 2H).

Example 113

Preparation of 4-[2-(2-methoxy-ethylamino)-acetylamino]-N-{4-[3-methyl-4-(6-methyl-pyridin-3-yloxy)-phenylamino]-quinazolin-6-yl}-butyramide The procedure of Example 109 was repeated except for using 2-methoxyethylamine instead of morpholine to obtain the title compound (0.05 g, 60%).

$^1$H-NMR (CDCl$_3$, 300 MHz): δ 10.27 (s, 1H), 8.71 (s, 1H), 8.64 (s, 1H), 8.23 (d, 1H), 7.82 (m, 3H), 7.61 (d, 1H), 7.53 (dd, 1H), 7.08 (m, 2H), 6.86 (d, 1H), 3.44 (m, 4H), 3.35 (s, 5H), 2.78 (m, 2H), 2.51 (s, 3H), 2.39 (m, 2H), 2.23 (s, 3H), 1.91 (m, 2H).

Example 114

Preparation of (4-{4-[3-chloro-4-(3-fluoro-benzyloxy)-phenylamino]-quinazolin-6-ylcarbamoyl}-butyl)-carbamic acid t-butylester The procedure of Example 19 was repeated except for using 0.4 g of 5-t-buthoxycarbonylamino-pentanoic acid instead of 3-t-buthoxycarbonylamino-propionic acid to obtain the title compound (0.6 g, 40%).

$^1$H-NMR (DMSO-d$_6$, 300 MHz): δ 10.19 (s, 1H), 9.77 (s, 1H), 8.69 (s, 1H), 8.48 (s, 1H), 7.97 (d, 1H), 7.71 (m, 2H), 7.45 (m, 1H), 7.33 (m, 2H), 7.24 (d, 1H), 7.16 (t, 1H), 6.81 (s, 1H), 5.25 (s, 2H), 2.94 (m, 2H), 2.38 (t, 2H), 1.61 (m, 2H), 1.44 (m, 2H), 1.36 (s, 9H).

Example 115

Preparation of 5-(2-methoxy-acetylamino)-pentanoic acid {4-[3-chloro-4-(3-fluoro-benzyloxy)-phenylamino]-quinazolin-6-yl}-amide (115-1) Preparation of 5-amino-pentanoic acid {4-[3-chloro-4-(3-fluoro-benzyloxy)-phenylamino]-quinazolin-6-yl}-amide The procedure of (20-1) of Example 20 was repeated except for using 0.42 g of the compound obtained in Example 114 instead of the compound obtained in Example 19 to obtain the title compound (0.34 g, 98%).

$^1$H-NMR (DMSO-d$_6$, 300 MHz): δ 10.25 (s, 1H), 8.68 (s, 1H), 8.47 (s, 1H), 7.96 (s, 1H), 7.83 (m, 1H), 7.68 (m, 2H), 7.44 (m, 1H), 7.25 (m, 4H), 5.24 (s, 2H), 3.35 (m, 2H), 2.37 (t, 2H), 1.65 (m, 2H), 1.42 (m, 2H).

(115-2) Preparation of 5-(2-methoxy-acetylamino)-pentanoic acid {4-[3-chloro-4-(3-fluoro-benzyloxy)-phenylamino]-quinazolin-6-yl}-amide The procedure of (20-2) of Example 20 was repeated except for using 0.09 g of the compound obtained in (115-1) instead of the compound obtained in (20-1) of Example 20 to obtain the title compound (0.06 g, 59%).

$^1$H-NMR (DMSO-d$_6$, 300 MHz): δ 10.20 (s, 1H), 9.77 (s, 1H), 8.69 (s, 1H), 8.49 (s, 1H), 7.96 (d, 1H), 7.71 (m, 4H), 7.46 (m, 1H), 7.32 (m, 2H), 7.24 (d, 1H), 7.18 (t, 1H), 5.25 (s, 2H), 3.77 (s, 2H), 3.29 (s, 3H), 3.13 (q, 2H), 2.39 (t, 2H), 1.62 (m, 2H), 1.50 (m, 2H).

Example 116

Preparation of 5-(2-methanesulfonyl-acetylamino)-pentanoic acid {4-[3-chloro-4-(3-fluoro-benzyloxy)-pentylamino]-quinazolin-6-yl}-amide The procedure of Example 21 was repeated except for using 0.09 g of the compound obtained in (115-1) of Example 115 instead of the compound obtained in (20-1) of Example 20 to obtain the title compound (0.05 g, 45%).

$^1$H-NMR (DMSO-d$_6$, 300 MHz): δ 10.19 (s, 1H), 9.76 (s, 1H), 8.67 (s, 1H), 8.48 (s, 1H), 8.34 (d, 1H), 7.96 (s, 1H), 7.70 (m, 3H), 7.45 (m, 1H), 7.25 (m, 4H), 5.24 (s, 2H), 4.02 (s, 2H), 3.13 (m, 2H), 3.05 (s, 3H), 2.40 (m, 2H), 1.65 (m, 2H), 1.39 (m, 2H).

Example 117

Preparation of N-{4-[3-chloro-4-(3-fluoro-benzyloxy)-phenylamino]-quinazolin-6-yl}-3-(2-methanesulfanyl-acetylamino)-propionamide The procedure of Example 21 was repeated except for using 0.19 ml of methylthioacetic acid instead of methanesulfonylacetic acid to obtain the title compound (520 mg, 87%).

$^1$H-NMR (DMSO-d$_6$, 300 MHz): δ 10.31 (s, 1H), 9.80 (s, 1H), 8.69 (s, 1H), 8.51 (s, 1H), 8.13 (t, 1H), 7.99 (d, 1H), 7.83 (dd, 1H), 7.72 (m, 2H), 7.47 (m, 1H), 7.31 (m, 2H), 7.26 (d, 1H), 7.20 (t, 1H), 5.26 (s, 2H), 3.42 (q, 2H), 3.33 (s, 3H), 3.08 (s, 2H), 2.61 (t, 2H).

Example 118

Preparation of N-{4-[3-chloro-4-(3-fluoro-benzyloxy)-phenylamino]-quinazolin-6-yl}-3-(2-methanesulfinyl-acetylamino)-propionamide 100 mg of the compound obtained in (20-1) of Example 20 dissolved in 5 ml of THF and 5 ml of saturated aqueous sodium bicarbonate solution was reacted with 40 mg of m-CPBA at room temperature for 27 hours, and the reacted solution was diluted with distilled water and chloroform, and filtered under a reduced pressure to obtain the title compound as solid (80 mg, 78%).

$^1$H-NMR (DMSO-d$_6$, 300 MHz): δ 10.23 (s, 1H), 9.75 (s, 1H), 8.66 (s, 1H), 8.48 (s, 1H), 8.34 (t, 1H), 7.92 (s, 1H), 7.79 (dd, 1H), 7.65 (m, 2H), 7.43 (m, 1H), 7.29 (m, 2H), 7.19 (m,

2H), 5.21 (s, 2H), 3.60 (dd, 2H), 3.39 (q, 2H), 2.56 (s, 3H), 2.52 (t, 2H); MS (ESI): [M+H+] 569.99.

Example 119

Preparation of N-{4-[3-chloro-4-(3-fluoro-benzyloxy)-phenylamino]-quinazolin-6-yl}-3-(2,2,2-trifluoro-acetylamino)-propionamide 80 mg of the compound obtained in (20-1) of Example 20 dissolved in 3 ml of THF at 0° C. was reacted with 0.03 mg of pyridine and 0.03 ml of anhydrous trifluoroacetic acid for 4 hours while heating to room temperature. The reacted solution was diluted with saturated sodium bicarbonate solution, extracted with ethylacetate, dried over anhydrous magnesium sulfate, filtered and distilled under a reduced pressure, and the resulting residue was subjected to column chromatography (eluent-chloroform:methanol=15:1) to obtain the title compound (40 mg, 42%).
$^1$H-NMR (CD$_3$OD, 300 MHz): δ 8.58 (s, 1H), 8.42 (s, 1H), 7.84 (d, 1H), 7.66 (m, 2H), 7.54 (dd, 1H), 7.35 (m, 1H), 7.21 (m, 2H), 7.05 (m, 2H), 5.15 (s, 2H), 3.67 (t, 2H), 2.74 (t, 2H).

Example 120

Preparation of 3-acetylamino-N-{4-[3-chloro-4-(3-fluoro-benzyloxy)-phenylamino]-quinazolin-6-yl}-propionamide The procedure of Example 119 was repeated except for using 0.03 ml of anhydrous acetic acid instead of trifluoroacetic acid to obtain the title compound (60 mg, 69%).
$^1$H-NMR (DMSO-d$_6$, 300 MHz): δ 10.25 (s, 1H), 9.76 (s, 1H), 8.65 (s, 1H), 8.46 (s, 1H), 7.94 (m, 2H), 7.79 (dd, 1H), 7.66 (m, 2H), 7.43 (m, 1H), 7.30 (m, 2H), 7.21 (d, 1H), 7.13 (t, 1H), 5.22 (s, 2H), 3.38 (t, 2H), 2.52 (t, 2H), 1.77 (s, 3H).

Example 121

Preparation of acetic acid (2-{4-[3-chloro-4-(3-fluoro-benzyloxy)-phenylamino]-quinazolin-6-ylcarbamoyl}-ethylcarbamoyl)-methylester The procedure of Example 119 was repeated except for using 0.03 ml of acetoxyacetylchloride instead of trifluoroacetic acid to obtain the title compound (80 mg, 74%).
$^1$H-NMR (DMSO-d$_6$, 300 MHz): δ 10.35 (s, 1H), 9.81 (s, 1H), 8.70 (s, 1H), 8.50 (s, 1H), 8.16 (t, 1H), 7.99 (d, 1H), 7.83 (dd, 1H), 7.74 (m, 2H), 7.46 (m, 1H), 7.32 (m, 2H), 7.25 (d, 1H), 7.16 (t, 1H), 5.25 (s, 2H), 4.44 (s, 2H), 3.43 (t, 2H), 2.60 (t, 2H), 2.10 (s, 3H).

Example 122

Preparation of N-{4-[3-chloro-4-(3-fluoro-benzyloxy)-phenylamino]-quinazolin-6-yl}-3-[2-(2-dimethylamino-ethoxy)-acetylamino]-propionamide 44 mg of sodium hydride (60%, oil suspension) dissolved in 2 ml of THF was reacted with 0.03 ml of dimethylethanol for 30 mins, 100 mg of the compound obtained (20-1) of Example 20 dissolved in 5 ml of THF was added thereto at 0° C., and the resulting solution was reacted for 3 hours while heating to room temperature. The reacted solution was diluted with saturated sodium bicarbonate solution, extracted with chloroform, dried over anhydrous magnesium sulfate, filtered and distilled under a reduced pressure, and the resulting residue was subjected to column chromatography (eluent-chloroform:methanol=15:1) to obtain the title compound (70 mg, 64%).
$^1$H-NMR (CD$_3$OD, 300 MHz): δ 8.53 (d, 1H), 8.37 (s, 1H), 7.81 (d, 1H), 7.67 (m, 2H), 7.51 (dd, 1H), 7.36 (m, 1H), 7.21 (m, 2H), 7.02 (m, 2H), 5.09 (s, 2H), 3.91 (s, 2H), 3.62 (t, 2H), 3.56 (t, 2H), 2.66 (t, 2H), 2.48 (t, 2H), 2.20 (s, 6H).

Example 123

Preparation of N-{4-[3-chloro-4-(3-fluoro-benzyloxy)-phenylamino]-quinazolin-6-yl}-3-(3-ethyl-ureido)-propionamide 80 mg of the compound obtained in (20-1) of Example 20 dissolved in 5 ml of chloroform was reacted with 0.02 ml of ethylisocyanate at room temperature for 2 hours. The reacted mixture was subjected to column chromatography (eluent-chloroform:methanol=15:1) to obtain the title compound (70 mg, 77%).
$^1$H-NMR (DMSO-d$_6$, 300 MHz): δ 10.26 (s, 1H), 9.77 (s, 1H), 8.66 (s, 1H), 8.47 (s, 1H), 7.95 (d, 1H), 7.79 (dd, 1H), 7.72 (d, 1H), 7.68 (dd, 1H), 7.45 (m, 1H), 7.30 (m, 2H), 7.22 (d, 1H), 7.16 (t, 1H), 5.88 (q, 2H), 5.23 (s, 2H), 2.97 (m, 2H), 2.51 (m, 2H), 0.94 (t, 3H).

Example 124

Preparation of N-{4-[3-chloro-4-(3-fluoro-benzyloxy)-phenylamino]-quinazolin-6-yl}-3-(3-phenyl-ureido)-propionamide The procedure of Example 123 was repeated except for using 0.02 ml of phenylisocyanate instead of ethylisocyanate to obtain the title compound (73 mg, 73%).
$^1$H-NMR (DMSO-d$_6$, 300 MHz): δ 10.40 (s, 1H), 9.82 (s, 1H), 8.71 (s, 1H), 8.68 (s, 1H), 8.51 (s, 1H), 8.00 (d, 1H), 7.89 (dd, 1H), 7.72 (m, 2H), 7.30 (m, 8H), 6.92 (m, 2H), 6.39 (t, 1H), 5.23 (s, 2H), 3.42 (q, 2H), 2.60 (t, 2H).

Example 125

Preparation of N-{4-[3-chloro-4-(3-fluoro-benzyloxy)-phenylamino]-quinazolin-6-yl}-3-(3-furan-2-ylmethyl-ureido)-propionamide The procedure of Example 123 was repeated except for using 0.02 ml of furfurylisocyanate instead of ethylisocyanate to obtain the title compound (80 mg, 80%).
$^1$H-NMR (DMSO-d$_6$, 300 MHz): δ 10.34 (s, 1H), 9.80 (s, 1H), 8.70 (s, 1H), 8.48 (s, 1H), 7.98 (d, 1H), 7.83 (dd, 1H), 7.69 (m, 2H), 7.51 (s, 1H), 7.44 (m, 1H), 7.30 (m, 2H), 7.22 (d, 1H), 7.16 (t, 1H), 6.38 (t, 1H), 6.16 (d, 1H), 6.05 (t, 1H), 5.23 (s, 2H), 4.16 (d, 2H), 3.38 (m, 2H), 2.56 (m, 2H).

Example 126

Preparation of (2-{4-[3-chloro-4-(3-fluoro-benzyloxy)-phenylamino]-quinazolin-6-ylcarbamoyl}-ethyl)-carbamic acid methylester The procedure of Example 119 was repeated except for using 0.02 ml of methylchloroformate instead of ethylisocyanate to obtain the title compound (60 mg, 67%).

¹H-NMR (CD₃OD, 300 MHz): δ 8.64 (s, 1H), 8.45 (s, 1H), 7.87 (d, 1H), 7.81 (s, 2H), 7.57 (dd, 1H), 7.38 (m, 1H), 7.29 (m, 2H), 7.12 (d, 1H), 7.04 (t, 1H), 5.20 (s, 2H), 3.64 (s, 3H), 3.51 (t, 2H), 2.66 (t, 2H).

Example 127

Preparation of (2-{4-[3-chloro-4-(3-fluoro-benzyloxy)-phenylamino]-quinazolin-6-ylcarbamoyl}-ethyl)-carbamic acid phenylester The procedure of Example 119 was repeated except for using 0.03 ml of phenylchloroformate instead of ethylisocyanate to obtain the title compound (20 mg, 20%).
¹H-NMR (CD₃OD, 300 MHz): δ 8.54 (s, 1H), 8.07 (s, 1H), 7.80 (d, 1H), 7.69 (d, 1H), 7.57 (m, 2H), 7.30 (m, 3H), 7.13 (m, 2H), 6.98 (m, 5H), 5.08 (s, 2H), 3.56 (t, 2H), 2.68 (t, 2H).

Example 128

Preparation of (2-{4-[3-chloro-4-(3-fluoro-benzyloxy)-phenylamino]-quinazolin-6-ylcarbamoyl}-ethyl)-carbamic acid benzylester The procedure of Example 119 was repeated except for using 0.04 ml of benzylchloroformate instead of ethylisocyanate to obtain the title compound (50 mg, 49%).
¹H-NMR (DMSO-d₆, 300 MHz): δ 10.27 (s, 1H), 9.77 (s, 1H), 8.68 (s, 1H), 8.49 (s, 1H), 7.96 (d, 1H), 7.83 (dd, 1H), 7.75 (d, 1H), 7.70 (dd, 1H), 7.49 (m, 1H), 7.37 (m, 6H), 7.28 (d, 1H), 7.20 (t, 1H), 5.14 (s, 2H), 5.00 (s, 2H), 3.38 (q, 2H), 2.60 (t, 2H).

Example 129

Preparation of N-{4-[3-chloro-4-(pyridin-2-ylmethoxy)-phenylamino]-quinazolin-6-yl}-3-(2-methoxy-acetylamino)-propionamide (129-1) Preparation of 3-amino-N-{4-[3-chloro-4-(pyridin-2-ylmethoxy)-phenylamino]-quinazolin-6-yl}-propionamide 350 mg of 2-{4-[3-chloro-4-(pyridin-2-ylmethoxy)-phenylamino]-quinazolin-6-ylcarbamoyl}-ethyl)-carbamic acid t-butylester dissolved in 7 ml of methylene chloride was reacted with 7 ml of trifluoroacetic acid at room temperature for 4 hours. The residue obtained from distillation of the reacted solution under a reduced pressure was stirred with 50 ml of saturated aqueous sodium bicarbonate solution for 30 mins, filtered under a reduced pressure and dried to obtain the title compound (280 mg, 97%).
¹H-NMR (CD₃OD, 300 MHz): δ 8.65 (s, 1H) 8.57 (s, 1H), 8.50 (s, 1H), 7.92-7.94 (m, 2H), 7.72-7.78 (m, 3H), 7.59-7.62 (m, 1H), 7.40 (t, J=5 Hz, 1H), 7.19 (d, J=9 Hz, 1H), 5.29 (s, 2H), 3.53 (bs, 2H), 2.65 (bs, 2H).

(129-2) Preparation of N-{4-[3-chloro-4-(pyridin-2-ylmethoxy)-phenylamino]-quinazolin-6-yl}-3-(2-methoxy-acetylamino)-propionamide 30 mg of 1-hydroxylbenzotriazole and 85 mg of 1-(3-dimethylaminopropyl)-3-ethylcarbodiimide hydrochloride were added to 17 μl of methoxyacetic acid dissolved in 3 ml of THF, and reacted at room temperature for 12 hours after adding 50 mg of the compound obtained in (129-1). The reacted solution was extracted with ethylacetate 3 times after adding 5 ml of water, dried over anhydrous magnesium sulfate, distilled under a reduced pressure, and the resulting residue was subjected to column chromatography (eluent-chloroform:methanol=15:1) to obtain the title compound (15 mg, 26%).
¹H-NMR (CD₃OD, 300 MHz): δ 8.90 (s, 1H), 8.71-8.75 (m, 2H), 8.08-8.11 (m, 2H), 7.92-7.95 (m, 3H), 7.79 (m, 1H), 7.63 (t, J=5 Hz, 1H), 7.39 (d, J=9 Hz, 1H), 5.47 (s, 2H), 4.08 (s, 2H), 3.85 (t, J=6 Hz, 2H) 3.53 (s, 3H), 2.93 (bs, 2H).

Example 130

Preparation of N-{4-[3-chloro-4-(pyridin-2-ylmethoxy)-phenylamino]-quinazolin-6-yl}-3-(2-methanesulfonyl-acetylamino)-propionamide 56 mg of 1-hydroxylbenzotriazole and 85 mg of 1-(3-dimethylaminopropyl)-3-ethylcarbodiimide hydrochloride were added to 31 mg of methanesulfonylacetic acid dissolved in 2 ml of THF, and the solution was reacted at room temperature for 12 hours after adding 50 mg of the compound obtained in (129-1) of Example 129. The reacted solution was extracted with 10 ml of ethylacetate 3 times after adding 5 ml of water, dried over anhydrous magnesium sulfate, filtered and distilled under a reduced pressure, and the resulting residue was subjected to column chromatography (eluent-chloroform:methanol=15:1) to obtain the title compound (5.2 mg, 8%).
¹H-NMR (CD₃OD, 300 MHz): δ 8.66 (s, 1H), 8.54 (bs, 1H), 8.47 (s, 1H), 7.93 (m, 2H), 7.70-7.75 (m, 3H), 7.58 (m, 1H), 7.39 (t, J=5 Hz, 1H), 7.17 (d, J=9 Hz, 1H), 5.29 (s, 2H), 4.03 (s, 2H), 3.64 (t, J=6 Hz, 2H), 3.29 (s, 3H), 2.72 (t, J=6 Hz, 2H).

Example 131

Preparation of N-(2-{4-[3-chloro-4-(pyridin-2-ylmethoxy)-phenylamino]-quinazolin-6-ylcarbamoyl}-ethyl)-acrylamide 85 mg of 1-(3-dimethylaminopropyl)-3-ethylcarbodiimide hydrochloride and 46 μl of pyridine were added to 31 μl of acrylic acid dissolved in 3 ml of THF, and reacted with 100 mg of the compound obtained in (129-1) of Example 129 at 0° C. for 30 mins; The reacted solution was extracted with 6 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (7 mg, 6%).
¹H-NMR (CD₃OD, 300 MHz): δ 8.67 (s, 1H), 8.56 (bs, 1H), 8.48 (s, 1H), 7.89-7.94 (m, 2H), 7.72-7.76 (m, 3H), 7.64 (dd, J=6.9 Hz, 1H), 7.42 (t, J=5 Hz, 1H), 7.17 (d, J=9 Hz, 1H), 6.24-6.26 (m, 2H), 5.66-5.68 (m, 1H), 5.29 (s, 2H), 3.69 (t, J=6 Hz, 2H), 2.76 (t, J=6 Hz, 2H).

Example 132

Preparation of N-{4-[3-chloro-4-(pyridin-3-ylmethoxy)-phenylamino]-quinazolin-6-yl}-3-(2-methoxy-acetylamino)-propionamide (132-1) Preparation of 3-amino-N-{4-[3-chloro-4-(pyridin-3-ylmethoxy)-phenylamino]-quinazolin-6-yl}-propionamide 280 mg of 2-{4-[3-chloro-4-(pyridin-3-ylmethoxy)-phenylamino]-quinazolin-6-ylcarbamoyl}-ethyl)-carbamic acid t-butylester dissolved in 6 ml of methylene chloride was reacted with 6 ml of trifluoroacetic acid at room temperature for 4 hours. The residue obtained from distillation of the reacted solution under a reduced pressure was stirred with 50 ml of saturated aqueous sodium bicarbonate solution for 30 mins, filtered under a reduced pressure and dried to obtain the title compound (220 mg, 96%).

$^1$H-NMR (CD$_3$OD, 300 MHz): δ 8.69 (bs, 1H), 8.63 (s, 1H), 8.50 (bs, 1H), 8.44 (s, 1H), 8.00 (d, J=8 Hz, 1H), 7.90 (d, J=2.5 Hz, 1H), 7.72-7.77 (m, 2H), 7.63 (dd, J=9, 2.5 Hz, 1H), 7.46-7.50 (m, 1H), 7.19 (d, J=9 Hz, 1H), 5.24 (s, 2H), 3.30 (bs, 2H), 2.63 (bs, 2H).

(132-2) Preparation of N-{4-[3-chloro-4-(pyridin-3-ylmethoxy)-phenylamino]-quinazolin-6-yl}-3-(2-methoxy-acetylamino)-propionamide 30 mg of 1-hydroxylbenzotriazole and 85 mg of 1-(3-dimethylaminopropyl)-3-ethylcarbodiimide hydrochloride were added to 17 μl of methoxyacetic acid dissolved in 3 ml of THF, and reacted at room temperature for 12 hours after adding 50 mg of the compound obtained in (132-1). The reacted solution was extracted with 10 ml of ethylacetate 3 times after adding 5 ml of water, dried over anhydrous magnesium sulfate, filtered and distilled under a reduced pressure, and the resulting residue was subjected to column chromatography (eluent-chloroform:methanol=15:1) to obtain the title compound (5 mg, 9%).

$^1$H-NMR (CD$_3$OD, 300 MHz): δ 8.69 (bs, 1H), 8.63 (s, 1H), 8.50 (bs, 1H), 8.44 (s, 1H), 8.00 (d, J=8 Hz, 1H), 7.90 (d, J=2.5 Hz, 1H), 7.72-7.77 (m, 2H), 7.63 (dd, J=9, 2.5 Hz, 1H), 7.46-7.50 (m, 1H), 7.19 (d, J=9 Hz, 1H), 5.24 (s, 2H), 3.30 (bs, 2H), 2.63 (bs, 2H).

Example 133

Preparation of N-{4-[3-chloro-4-(pyridin-3-ylmethoxy)-phenylamino]-quinazolin-6-yl}-3-(2-methanesulfonyl-acetylamino)-propionamide 56 mg of 1-hydroxylbenzotriazole and 85 mg of 1-(3-dimethylaminopropyl)-3-ethylcarbodiimide hydrochloride were added to 31 mg of methansulfonylacetic acid dissolved in 2 ml of THF, and reacted at room temperature for 12 hours after adding 50 mg of the compound obtained in (132-1) of Example 132. The reacted solution was extracted with 10 ml of ethylacetate 3 times after adding 5 ml of water, dried over anhydrous magnesium sulfate, filtered and distilled under a reduced pressure, and the resulting residue was subjected to column chromatography (eluent-chloroform:methanol=15:1) to obtain the title compound (16 mg, 25%).

$^1$H-NMR (DMSO-d$_6$, 300 MHz): δ 8.74 (s, 1H), 8.70 (s, 1H), 8.66 (d, J=2 Hz, 1H), 8.50 (s, 1H), 8.21 (d, J=8 Hz, 1H), 8.11 (d, J=2.5 Hz, 1H), 7.93-7.98 (m, 2H), 7.85 (dd, J=9, 2.5 Hz, 1H), 7.69 (bs, 1H), 7.43 (d, J=9 Hz, 1H), 5.29 (s, 2H), 4.11 (s, 2H), 3.71 (t, J=6 Hz, 2H), 3.16 (s, 3H), 2.79 (t, J=6 Hz, 2H).

Example 134

Preparation of N-(2-{4-[3-chloro-4-(pyridin-3-ylmethoxy)-phenylamino]-quinazolin-6-ylcarbamoyl}-ethyl)-acrylamide 46 μl of pyridine and 85 mg of 1-(3-dimethylaminopropyl)-3-ethylcarbodiimide hydrochloride were added to 31 μl of acrylic acid dissolved in 3 ml of THF at 0° C., reacted with 100 mg of the compound (132-1) of Example 132 for 30 mins, and stirred for 2 hours while heating to room temperature. The reacted solution was extracted with 6 ml of ethylacetate 3 times after adding 4 ml of water, dried over anhydrous magnesium sulfate, filtered and distilled under a reduced pressure, and the resulting residue was subjected to column chromatography (eluent-chloroform:methanol=15:1) to obtain the title compound (20 mg, 18%).

$^1$H-NMR (CD$_3$OD, 300 MHz): δ 8.86 (bs, 1H), 8.85 (s, 1H), 8.73 (bs, 1H), 8.72 (s, 1H), 8.21 (d, J=8 Hz, 1H), 8.11 (d, J=2.5 Hz, 1H), 7.93-7.98 (m, 2H), 7.85 (dd, J=9, 2.5 Hz, 1H), 7.69 (bs, 1H), 7.43 (d, J=9 Hz, 1H), 6.37-6.44 (m, 2H), 5.82-5.86 (m, 1H), 5.46 (s, 2H), 3.87 (t, J=6 Hz, 2H), 2.94 (t, J=6 Hz, 2H).

Example 135

Preparation of N-{4-[3-chloro-4-(3-fluoro-benzyloxy)-phenylamino]-quinazolin-6-yl}-3-[2-(2-methoxy-ethoxy)-acetylamino]-propionamide 0.04 ml of 2-(2-methoxyethoxy)acetic acid, 0.05 g of 1-hydroxylbenzotriazole and 0.13 g of 1-(3-dimethylaminopropyl)-3-ethylcarbodiimide hydrochloride dissolved in 5 ml of dichloromethane were reacted at room temperature for 21 hours after adding 0.08 g of the compound obtained in (20-1) of Example 20. The reacted solution was extracted with chloroform 2 times after adding saturated sodium bicarbonate, washed with saturated saline solution, dried over anhydrous magnesium sulfate, filtered and distilled under a reduced pressure, and the resulting residue was subjected to column chromatography (eluent-chloroform:methanol=15:1) to obtain the title compound (0.07 g, 71%).

$^1$H-NMR (CD$_3$OD, 300 MHz): δ 8.50 (s, 1H), 8.35 (s, 1H), 7.78 (d, 1H), 7.59 (d, 2H), 7.48 (dd, 1H), 7.28 (m, 1H), 7.15 (m, 2H), 6.94 (m, 2H), 5.07 (s, 2H), 3.90 (s, 2H), 3.53 (m, 4H), 3.42 (m, 2H), 3.20 (s, 3H), 2.62 (t, 2H).

Example 136

Preparation of 5-methyl-isoxazol-4-carboxylic acid (2-{4-[(3-chloro-4-(3-fluoro-benzyloxy)-phenylamino]-quinazolin-6-ylcarbamoyl}-ethyl)-amide The procedure of Example 140 was repeated except for using 0.05 g of 5-methylisoxazol-4-carboxylic acid instead of 2-(2-methoxyethoxy)acetic acid to obtain the title compound (0.05 g, 51%).

$^1$H-NMR (CD$_3$OD, 300 MHz): δ 8.56 (s, 1H), 8.53 (s, 1H), 8.38 (s, 1H), 7.80 (m, 1H), 7.65 (m, 2H), 7.50 (dd, 1H), 7.32 (m, 1H), 7.19 (m, 2H), 7.07 (d, 1H), 6.98 (t, 1H), 5.13 (s, 2H), 3.65 (t, 2H), 2.70 (t, 2H), 2.57 (s, 3H).

Example 137

Preparation of N-{4-[3-chloro-4-(3-fluoro-benzyloxy)phenylamino]-quinazolin-6-yl}-4-(2-methanesulfanyl-acetylamino)-butyramide The procedure of Example 135 was repeated except for using 0.3 g of the compound obtained in (20-1) of Example 20 and 0.11 ml of methylthioacetic acid 0.11 ml to obtain the title compound (0.3 g, 85%).

$^1$H-NMR (CD$_3$OD, 300 MHz): δ 8.65 (s, 1H), 8.47 (s, 1H), 7.89 (d, 1H), 7.73 (m, 2H), 7.59 (dd, 1H), 7.40 (m, 1H), 7.27 (m, 2H), 7.17 (d, 1H), 7.02 (t, 1H), 5.23 (s, 2H), 3.15 (s, 2H), 2.51 (t, 2H), 2.15 (s, 3H), 1.96 (t, 2H).

Example 138

Preparation of N-{4-[3-chloro-4-(3-fluoro-benzyloxy)-phenylamino]-quinazolin-6-yl}-4-(2-methanesulfinyl-acetylamino)-butyramide The procedure of Example 118 was repeated except for using 0.11 g of the compound obtained in Example 137 instead of the compound obtained in Example 117 to obtain the title compound (70 mg, 61%).

$^1$H-NMR (CD$_3$OD, 300 MHz): δ 8.57 (d, 1H), 8.43 (s, 1H), 7.88 (d, 1H), 7.69 (m, 2H), 7.57 (dd, 1H), 7.38 (m, 1H), 7.25 (m, 2H), 7.08 (d, 1H), 7.02 (t, 1H), 5.16 (s, 2H), 3.82 (d, 1H), 3.63 (d, 1H), 3.38 (m, 2H), 2.75 (s, 3H), 2.51 (t, 2H), 1.95 (m, 2H).

Example 139

Preparation of N-[2-({4-[3-chloro-4-(3-fluoro-benzyloxy)-phenylamino]-quinazolin-6-yl}-methyl-carbamoyl)-ethyl]-acrylamide

(139-1) Preparation of N-{4-[3-chloro-4-(3-fluoro-benzyloxy)-phenylamino]-quinazolin-6-yl}-formamide 2 g of the compound obtained in (1-4) of Example 1 and 0.78 ml of formic acid dissolved in 20 ml of dichloromethane was reacted with 1.64 ml of pyridine and 3.88 g of 1-(3-dimethylaminopropyl)-3-ethylcarbodiimide hydrochloride at room temperature for 3 hours. The reacted solution was filtered under a reduced pressure after adding saturated sodium bicarbonate to obtain the title compound as solid (1.8 g, 84%).

$^1$H-NMR (CD$_3$OD, 300 MHz): δ 8.64 (d, 1H), 8.46 (d, 1H), 8.30 (d, 1H), 7.88 (d, 1H), 7.76 (d, 1H), 7.72 (d, 1H), 7.58 (dd, 1H), 7.39 (m, 1H), 7.27 (m, 2H), 7.12 (d, 1H), 7.03 (t, 1H), 5.21 (s, 2H).

(139-2) Preparation of N$^4$-[3-chloro-4-(3-fluoro-benzyloxy)-phenyl]-N6-methyl-quinazolin-4,6-diamine 1 g of the compound obtained in (139-1) dissolved in 20 ml of THF was added to 0.45 g of lithium aluminum hydride dissolved in 5 ml of THF at 0° C., and reacted for 4 hour while heating the solution slowly to 60° C. The reacted solution was dried over magnesium sulfate after adding 0.5 ml of distilled water, 2.8 ml of 1 N aqueous sodium hydroxide solution and 1 ml of distilled water sequentially, filtered and distilled under a reduced pressure, and the resulting residue was subjected to column chromatography (eluent-chloroform methanol=15:1) to obtain the title compound (0.6 g, 62%).

$^1$H-NMR (CDCl$_3$, 300 MHz): δ 8.57 (s, 1H), 7.79 (s, 1H), 7.71 (d, 1H), 7.52 (dd, 1H), 7.32 (m, 1H), 7.15 (m, 3H), 6.98 (m, 3H), 6.52 (s, 1H), 5.14 (s, 2H), 2.96 (s, 3H).

(139-3) Preparation of [2-({4-[3-chloro-4-(3-fluoro-benzyloxy)-phenylamino]-quinazolin-6-yl}-methyl-carbamoyl)-ethyl]-carbamic acid t-butylester 0.55 g of the compound obtained in (139-2) and 1.02 g of 3-t-buthoxycarbonylamino-propionic acid dissolved in 15 ml of pyridine were reacted with 1.29 g of 1-(3-dimethylaminopropyl)-3-ethylcarbodiimide hydrochloride at room temperature for 2 hours. The reacted solution was distilled under a reduced pressure to remove solvent, and saturated sodium bicarbonate was added thereto. The resultant was extracted with chloroform 2 times, washed with saturated saline solution, dried over magnesium sulfate, filtered and distilled under a reduced pressure, and the resulting residue was subjected to column chromatography (eluent-chloroform:methanol=15:1) to obtain the title compound (0.62 g, 80%).

$^1$H-NMR (CDCl$_3$, 300 MHz): δ 8.78 (s, 1H), 8.38 (s, 1H), 7.91 (m, 2H), 7.70 (d, 1H), 7.59 (m, 1H), 7.34 (m, 1H), 7.23 (m, 2H), 6.97 (m, 2H), 5.17 (s, 2H), 3.42 (m, 2H), 3.35 (s, 3H), 2.55 (m, 2H), 1.25 (s, 9H).

(139-4) Preparation of 3-amino-N-{4-[3-chloro-4-(3-fluoro-benzyloxy)-phenylamino]-quinazolin-6-yl}-N-methyl-propionamide 0.58 g of the compound obtained in (139-3) dissolved in 10 ml of dichloromethane and 10 ml of trifluoroacetic acid was stirred at room temperature for 1 hour. The residue obtained from distillation of the reacted solution under a reduced pressure was dissolved in small amount of dichloromethane and stirred while adding saturated sodium bicarbonate. The resulting solution was extracted with chloroform, washed with saturated saline solution, dried over magnesium sulfate, and filtered and distilled under a reduced pressure to obtain the title compound (0.4 g, 83%).

$^1$H-NMR (CDCl$_3$, 300 MHz): δ 8.75 (s, 1H), 8.38 (s, 1H), 7.97 (m, 3H), 7.59 (m, 2H), 7.33 (m, 1H), 7.20 (m, 2H), 6.98 (m, 2H), 5.15 (s, 2H), 3.36 (s, 3H), 2.98 (m, 2H), 2.37 (m, 2H); MS (ESI): [M+H+] 480.

(139-5) Preparation of N-[2-({4-[3-chloro-4-(3-fluoro-benzyloxy)-phenylamino]-quinazolin-6-yl}-methyl-carbamoyl)-ethyl]-acrylamide The procedure of Example 22 was repeated except for using 0.5 g of the compound obtained in (139-4) instead of the compound obtained in (20-1) of Example 20 to obtain the title compound (0.25 g, 45%).

$^1$H-NMR (CDCl$_3$, 300 MHz): δ 9.30 (s, 1H), 8.74 (s, 1H), 8.13 (s, 1H), 7.93 (m, 2H), 7.71 (d, 1H), 7.57 (dd, 1H), 7.35 (m, 1H), 7.23 (m, 2H), 6.98 (m, 3H), 6.15 (m, 2H), 5.63 (dd, 1H), 5.15 (s, 2H), 3.55 (m, 2H), 3.34 (s, 3H), 2.55 (t, 2H).

Example 140

Preparation of N-[2-({4-[3-chloro-4-(3-fluoro-benzyloxy)-phenylamino]-quinazolin-6-yl}-ethyl-carbamoyl)-ethyl]-acrylamide The procedure of (139-5) of Example 139 was repeated except for using 3-amino-N-{4-[3-chloro-4-(3-fluoro-benzyloxy)-phenylamino]-quinazolin-6-yl}-N-ethyl-propionamide instead of the compound obtained in (139-4) of Example 139 to obtain the title compound (15 mg, 5%).

$^1$H-NMR (CDCl$_3$, 300 MHz): δ 9.21 (s, 1H), 8.77 (s, 1H), 7.95 (s, 2H), 7.88 (d, 1H), 7.72 (dd, 1H), 7.56 (dd, 1H), 7.33 (m, 1H), 7.22 (m, 2H), 7.00 (m, 2H), 6.71 (bt, 1H), 6.18 (m, 2H), 5.67 (dd, 1H), 5.17 (s, 2H), 3.84 (m, 2H), 3.57 (m, 2H), 2.50 (m, 2H), 1.09 (t, 3H).

Example 141

Preparation of N-{2-[{4-[3-chloro-4-(3-fluoro-benzyloxy)-phenylamino]-quinazolin-6-yl}-(3-dimethylamino-propyl)-carbamoyl]-ethyl}-acrylamide

(141-1) Preparation of N-{4-[3-chloro-4-(3-fluoro-benzyloxy)-phenylamino]-quinazolin-6-yl}-acrylamide The procedure of Example 22 was repeated except for using 8.8 g of the compound obtained in (1-4) of Example 1 instead of the compound obtained in (139-4) of Example 139 to obtain the title compound (5 g, 50%).

$^1$H-NMR (DMSO-d$_6$, 300 MHz): δ 10.77 (s, 1H), 10.01 (s, 1H), 8.95 (s, 1H), 8.66 (s, 1H), 8.15 (s, 1H), 8.09 (d, 1H), 7.86-7.92 (m, 2H), 7.58-7.63 (m, 1H), 7.32-7.46 (m, 4H), 6.61-6.65 (m, 1H), 6.50 (d, 1H), 5.99 (d, 1H), 5.39 (s, 2H).

(141-2) Preparation of N-{4-[3-chloro-4-(3-fluoro-benzyloxy)-phenylamino]-quinazolin-6-yl}-3-dimethylamino-propionamide 6 ml of dimethylamine 2 M THF was added to 534 mg of the compound obtained in (141-1) and 113 mg of p-toluene sulfonic acid dissolved in 15 ml of THF, and reacted for 5 hour while heating the solution slowly to 50° C. The reacted solution was cooled to room temperature, extracted with ethylacetate 3 times after adding saturated sodium bicarbonate, washed with saturated saline solution, dried over magnesium sulfate, filtered and distilled under a reduced pressure, and the resulting residue was subjected to column chromatography (eluent-chloroform:methanol=15:1) to obtain the title compound (0.4 g, 68%).

$^1$H-NMR (CD$_3$OD, 300 MHz): δ 8.50 (s, 1H), 8.40 (s, 1H), 7.83 (d, 1H), 7.63 (s, 2H), 7.52 (dd, 1H), 7.3 (m, 1H), 7.19 (m, 2H), 6.97 (m, 2H), 5.08 (s, 2H), 2.76 (t, 2H), 2.61 (t, 2H), 2.33 (s, 6H).

(141-3) Preparation of N$^4$-[3-chloro-4-(3-fluoro-benzyloxy)-phenyl]-N$^6$-(3-dimethylamino-propyl)-quinazolin-4,6-diamine The procedure of (139-2) of Example 139 was repeated except for using 0.13 g of the compound obtained in (141-2) instead of the compound obtained in (139-1) of Example 139 to obtain the title compound (0.12 g, 93%).

$^1$H-NMR (CD$_3$OD, 300 MHz): δ 8.22 (s, 1H), 7.80 (s, 1H), 7.48 (m, 3H), 7.31 (m, 1H), 7.22 (m, 3H), 7.04 (m, 2H), 5.06 (s, 2H), 3.19 (bt, 2H), 2.41 (t, 2H), 2.25 (s, 6H), 1.83 (m, 2H).

(141-4) Preparation of N-{2-[{4-[3-chloro-4-(3-fluoro-benzyloxy)-phenylamino]-quinazolin-6-yl}-(3-dimethylamino-propyl)-carbamoyl]-ethyl}-acrylamide The procedure of Example 139 was repeated except for using 335 mg of the compound obtained in (141-3) instead of the compound obtained in (139-2) of Example 139 to obtain the title compound (80 mg, 23%).

$^1$H-NMR (CD$_3$OD, 300 MHz): δ 8.55 (s, 1H), 8.30 (s, 1H), 7.91 (s, 1H), 7.85 (d, 1H), 7.74 (d, 1H), 7.6 (d, 1H), 7.37 (m, 1H), 7.25 (m, 2H), 7.14 (d, 1H), 7.03 (t, 1H), 6.14 (m, 2H), 5.57 (m, 1H), 5.19 (s, 2H), 3.84 (t, 2H), 3.46 (t, 2H), 2.37 (m, 4H), 2.24 (s, 6H), 1.77 (m, 2H).

Example 142

Preparation of N-(2-{4-[3-chloro-4-(3-fluoro-benzyloxy)-phenylamino]-quinazolin-6-ylcarbamoyl}-ethyl)-N-methyl-acrylamide (142-1) Preparation of N-{4-[3-chloro-4-(3-fluoro-benzyloxy)-phenylamino]-quinazolin-6-yl}-3-methylamino-propionamide The procedure of (141-2) of Example 141 was repeated except for using methylamine instead of dimethylamine to obtain the title compound (0.41 g, 96%).

$^1$H-NMR (CD$_3$OD, 300 MHz): δ 8.56 (d, 1H), 8.35 (s, 1H), 7.78 (d, 1H), 7.66 (m, 2H), 7.49 (dd, 1H), 7.32 (m, 1H), 7.16 (m, 2H), 7.08 (d, 1H), 6.96 (t, 1H), 5.13 (s, 2H), 2.85 (t, 2H), 2.57 (t, 2H), 2.34 (s, 3H).

(142-2) Preparation of N-(2-{4-[3-chloro-4-(3-fluoro-benzyloxy)-phenylamino]-quinazolin-6-ylcarbamoyl}-ethyl)-N-methyl-acrylamide The procedure of Example 22 was repeated except for using 0.38 g of the compound obtained in (142-1) instead of the compound obtained in (20-1) of Example 20 to obtain the title compound (0.04 g, 10%).

$^1$H-NMR (CDCl$_3$, 300 MHz): δ 10.06 (s, 1H), 8.61 (s, 1H), 8.47 (s, 1H), 8.08 (bs, 1H), 7.81 (d, 1H), 7.71 (m, 2H), 7.53 (dd, 1H), 7.36 (m, 1H), 7.22 (m, 2H), 7.02 (t, 1H), 6.92 (d, 1H), 6.59 (m, 1H), 6.36 (d, 1H), 5.77 (d, 1H), 5.12 (s, 2H), 3.87 (t, 2H), 3.12 (s, 3H), 2.79 (t, 2H).

Example 143

Preparation of N-(2-{4-[3-chloro-4-(pyridin-2-ylmethoxy)-phenylamino]-quinazolin-6-ylcarbamoyl}-ethyl)-N-methyl-acrylamide The procedure of Example 22 was repeated except for using N-{4-[3-chloro-4-(pyridin-2-ylmethoxy)-phenylamino]-quinazolin-6-yl}-3-methylamino-propionamide instead of the compound obtained in (20-1) of Example 20 to obtain the title compound (80 mg, 14%).

$^1$H-NMR (CDCl$_3$, 300 MHz): δ 9.80 (s, 1H), 8.38 (m, 3H), 7.64 (d, 1H), 7.52 (m, 3H), 7.43 (d, 1H), 7.28 (d, 1H), 7.02 (t, 1H), 6.77 (d, 1H), 6.39 (m, 1H), 6.18 (d, 1H), 5.57 (d, 1H), 5.06 (s, 2H), 3.66 (t, 2H), 2.96 (s, 3H), 2.61 (t, 2H).

Example 144

Preparation of N-(2-{4-[3-chloro-4-(6-methyl-pyridin-2-ylmethoxy)-phenylamino]-quinazolin-6-ylcarbamoyl}-ethyl)-acrylamide The procedure of Example 22 was repeated except for using 3-amino-N-{4-[3-chloro-4-(6-methyl-pyridin-2-ylmethoxy)-phenylamino]-quinazolin-6-yl}-propionamide instead of the compound obtained in (20-1) of Example 20 to obtain the title compound (47 mg, 12%).

$^1$H-NMR (CD$_3$OD, 300 MHz): δ 8.61 (s, 1H), 8.42 (s, 1H), 7.88 (d, 1H), 7.70 (m, 3H), 7.55 (dd, 1H), 7.47 (d, 1H), 7.21 (d, 1H), 7.10 (d, 1H), 6.19 (m, 2H), 5.62 (dd, 1H), 5.18 (s, 2H), 3.60 (t, 2H), 2.70 (t, 2H), 2.51 (s, 3H).

Example 145

Preparation of (2S)-1-acryloyl-pyrrolidine-2-carboxylic acid {4-[3-chloro-4-(pyridin-2-ylmethoxy)-phenylamino]-quinazolin-6-yl}-amide (145-1) Preparation of [3-chloro-4-(pyridin-2-ylmethoxy)-phenyl]-(6-nitro-quinazolin-4-yl)-amine hydrochloride salt The procedure of (1-3) of Example 1 was repeated except for using 3.13 g of the compound obtained in (1-2) of Example 1 and 2.99 g of 3-chloro-4-(pyridin-2-ylmethoxy)-phenylamine instead of 3-chloro-4-(3-fluorobenzyloxy)-phenylamine to obtain the title compound (5 g, 88%).

¹H-NMR (DMSO-d₆, 300 MHz): δ 9.80 (s, 1H), 8.95 (s, 1H), 8.75 (dd, 1H), 8.69 (d, 1H), 8.11 (d, 1H), 8.05 (t, 1H), 7.97 (d, 1H), 7.72 (m, 2H), 7.68 (t, 1H), 7.36 (d, 1H), 5.41 (s, 2H).

(145-2) Preparation of N⁴-[3-chloro-4-(pyridin-2-ylmethoxy)-phenyl]-quinazolin-4,6-diamine The procedure of (1-4) of Example 1 was repeated except for using 4.5 g of the compound obtained in (145-1) instead of the compound obtained in (1-3) of Example 3 to obtain the title compound (2 g, 47%).
¹H-NMR (DMSO-d₆, 300 MHz): δ 9.33 (s, 1H), 8.60 (d, 1H), 8.30 (s, 1H), 8.06 (d, 1H), 7.88 (t, 1H), 7.74 (dd, 1H), 7.59 (d, 1H), 7.50 (d, 1H), 7.38 (m, 2H), 7.22 (d, 2H), 5.41 (s, 2H), 5.56 (bs, 2H), 5.27 (s, 2H).

(145-3) Preparation of (2S)-2-{4-[3-chloro-4-(pyridin-2-ylmethoxy)-phenylamino]-quinazolin-6-ylcarbamoyl}-pyrrolidine-1-carboxylic acid t-butylester The procedure of (1-5) of Example 1 was repeated except for using 414 mg of (2S)-pyrrolidine-1,2-dicarboxylic acid-1-t-butylester instead of 2-t-butoxycarbonylamino-ethanoic acid and 368 mg of the compound obtained in (145-2) to obtain the title compound (200 mg, 35%).
¹H-NMR (CD₃OD, 300 MHz): δ 8.69 (s, 1H), 8.58 (d, 1H), 8.49 (s, 1H), 7.90-7.93 (m, 2H), 7.72-7.79 (m, 2H), 7.63 (dd, 1H), 7.42 (t, 1H), 7.20 (d, 1H), 5.29 (s, 2H), 4.35 (m, 1H), 3.59 (m, 2H), 2.04 (m, 4H), 1.43 (m, 9H).

(145-4) Preparation of (2S)-pyrrolidine-2-carboxylic acid{4-[3-chloro-4-(pyridin-2-ylmethoxy)-phenylamino]-quinazolin-6-yl}-amide The procedure of (2-3) of Example 2 was repeated except for using 200 mg of the compound obtained in (145-3) instead of the compound obtained in (1-5) of Example 1 to obtain the title compound (130 mg, 79%).
¹H-NMR (CD₃OD, 300 MHz): δ 8.57 (s, 2H), 8.49 (s, 1H), 7.93 (m, 3H), 7.75 (t, 1H), 7.60 (d, 1H), 7.39 (t, 1H), 7.10 (d, 1H), 5.26 (s, 2H), 4.85 (m, 1H), 3.85 (m, 1H), 3.75 (m, 1H), 1.80-2.20 (m, 4H).

(145-5) Preparation of (2S)-1-acryloyl-pyrrolidine-2-carboxylic acid {4-[3-chloro-4-(pyridin-2-ylmethoxy)-phenylamino]-quinazolin-6-yl}-amide The procedure of Example 18 was repeated except for using the compound obtained in (145-4) instead of the compound obtained in (16-1) of Example 16 to obtain the title compound (32 mg, 22%).
¹H-NMR (CD₃OD, 300 MHz): δ 8.65 (d, 1H), 8.65 (d, 1H), 8.58 (s, 1H), 7.88-7.93 (m, 3H), 7.70-7.80 (m, 2H), 7.65 (t, 1H), 7.40 (t, 1H), 7.20 (d, 1H), 6.55-6.79 (m, 1H), 6.30 (dd, 1H), 5.80 (dd, 1H), 5.27 (s, 2H), 4.60-4.70 (m, 1H), 3.80 (m, 2H), 2.26 (m, 4H).

Example 146

Preparation of (2S)-1-(1-oxo-butyn-2-yl)-pyrrolidine-2-carboxylic acid {4-[3-chloro-4-(pyridin-2-ylmethoxy)-phenylamino]-7-methoxy-quinazolin-6-yl}-amide The procedure of Example 18 was repeated except for using 2-butynoic acid instead of acrylic acid to obtain the title compound (43 mg, 13%).
¹H-NMR (CDCl₃, 300 MHz): δ 9.70 (s, 1H), 8.92 (s, 1H), 8.61 (s, 2H), 7.85 (s, 1H), 7.75 (t, 1H), 7.67 (d, 2H), 7.51 (dd, 1H), 7.43 (s, 1H), 6.92 (d, 1H), 7.26 (m, 2H), 5.77 (t, 1H), 5.29 (s, 2H), 4.82 (d, 1H), 4.05 (s, 3H), 3.77 (m, 2H), 2.60 (m, 1H), 1.92-2.13 (m, 3H), 2.02 (s, 3H).

Example 147

Preparation of (2S)-1-acryloyl-pyrrolidine-2-carboxylic acid {4-[3-chloro-4-(6-methyl-pyridin-2-ylmethoxy)-phenylamino]-quinazolin-6-yl}-amide The procedure of Example 145 was repeated except for using N⁴-[3-chloro-4-(6-methyl-pyridin-2-ylmethoxy)-phenyl]-quinazolin-4,6-diamine as a starting material to obtain the title compound (250 mg, 66%).
¹H-NMR (CDCl₃, 300 MHz): δ 10.59 (s, 1H), 8.48 (s, 1H), 8.15 (bs, 1H), 7.95 (d, 1H), 7.79 (m, 2H), 7.62 (t, 1H), 7.51 (bs, 1H), 7.46 (d, 1H), 7.36 (d, 1H), 7.08 (d, 1H), 6.98 (d, 1H), 6.60 (m, 1H), 6.39 (dd, 1H), 5.78 (dd, 1H), 5.26 (s, 2H), 5.02 (m, 1H), 3.93 (m, 1H), 3.74 (m, 1H), 2.58 (s, 3H), 2.39 (m, 2H), 2.28 (m, 1H), 2.15 (m, 1H).

Example 148

Preparation of (3R,5S)-acetic acid 1-acryloyl-5-{4-[3-chloro-4-(pyridin-2-ylmethoxy)-phenylamino]-quinazolin-6-ylcarbamoyl}-pyrrolidin-3-ylester The procedure of Example 145 was repeated except for using (2S,4R)-4-acetoxy-pyrrolidine-1,2-dicarboxylic acid-1-t-butylester instead of (2S)-pyrrolidine-1,2-dicarboxylic acid-1-t-butylester to obtain the title compound (300 mg, 46%).
¹H-NMR (CDCl₃, 300 MHz): δ 10.50 (s, 1H), 8.60 (d, 1H), 8.47 (s, 1H), 8.18 (bs, 1H), 7.94 (d, 1H), 7.75 (m, 4H), 7.50 (s, 1H), 7.34 (d, 1H), 7.25 (t, 1H), 7.06 (d, 1H), 6.53 (m, 1H), 6.40 (m, 1H), 5.81 (d, 1H), 5.57 (m, 1H), 5.29 (s, 2H), 5.08 (t, 1H), 4.20 (m, 1H), 3.89 (d, 1H), 2.67 (m, 1H), 2.52 (m, 1H), 2.12 (s, 3H).

Example 149

Preparation of (2S,4R)-1-acryloyl-4-hydroxyl-pyrrolidine-2-carboxylic acid {4-[3-chloro-4-(pyridin-2-ylmethoxy)-phenylamino]-quinazolin-6-yl}-amide 0.32 ml of ammonia water was added to 130 mg of the compound obtained in Example 148 diluted with 10 ml of methanol, and the solution was refluxed with stirring at 80° C. for 26 hours. The reacted solution was cooled to room temperature, and filtered under a reduced pressure to obtain solid. The solid was subjected to column chromatography (eluent-chloroform:methanol=15:1) to obtain the title compound (80 mg, 66%).
¹H-NMR (CDCl₃, 300 MHz): δ 10.48 (s, 1H), 8.59 (d, 1H), 8.52 (s, 1H), 7.97 (m, 1H), 7.88 (m, 2H), 7.76 (m, 2H), 7.66 (m, 2H), 7.45 (d, 1H), 7.01 (d, 1H), 6.52 (m, 1H), 6.40 (d, 1H), 5.79 (d, 1H), 5.29 (s, 2H), 5.12 (t, 1H), 4.78 (m, 1H), 3.92 (m, 1H), 3.75 (m, 1H), 2.60 (m, 1H), 2.17 (m, 1H).

Example 150

Preparation of (2S,4R)-1-acryloyl-4-ethylsulfanyl-pyrrolidine-2-carboxylic acid {4-[3-chloro-4-(pyridin-2-ylmethoxy)-phenylamino]-quinazolin-6-yl}-amide The procedure of Example 145 was repeated except for using (2S,4R)-4-ethylsulfanyl-pyrrolidine-1,2-dicarboxylic acid-1-t-butylester instead of (2S)-pyrrolidine-1,2-dicarboxylic acid-1-t-butylester to obtain the title compound (70 mg, 36%).
¹H-NMR (CDCl₃, 300 MHz): δ 10.35 (s, 1H), 8.60 (d, 1H), 8.50 (s, 1H), 8.04 (bs, 1H), 7.97 (d, 1H), 7.70 (m, 5H), 7.42 (d, 1H), 7.25 (t, 1H), 7.01 (d, 1H), 6.68 (m, 1H), 6.40 (dd, 1H), 5.82 (dd, 1H), 5.30 (s, 2H), 4.92 (t, 1H), 4.18 (m, 1H), 3.70 (t, 1H), 3.47 (m, 1H), 2.73 (m, 1H), 2.68 (m, 2H), 2.43 (m, 1H), 1.33 (t, 3H).

Example 151

Preparation of (2S,4R)-1-acryloyl-4-dimethylamino-pyrrolidine-2-carboxylic acid {4-[3-chloro-4-(pyridin-2-ylmethoxy)-phenylamino]-quinazolin-6-yl}-amide The procedure of Example 145 was repeated except for using (2S,4R)-4-dimethylamino-pyrrolidine-1,2-dicarboxylic acid-1-t-butylester instead of (2S)-pyrrolidine-1,2-dicarboxylic acid-1-t-butylester to obtain the title compound (60 mg, 25%).
¹H-NMR (CDCl₃, 300 MHz): δ 10.28 (s, 1H), 8.64 (d, 1H), 8.59 (s, 1H), 7.97 (d, 1H), 7.76 (m, 6H), 7.56 (d, 1H), 7.30 (t, 1H), 7.05 (d, 1H), 6.55 (m, 2H), 5.89 (dd, 1H), 5.40 (m, 1H), 5.34 (s, 2H), 5.10 (m, 1H), 4.14 (m, 1H), 3.95 (m, 1H), 2.95 (s, 3H), 2.87 (s, 3H), 2.80 (m, 1H), 2.58 (m, 1H).

Example 152

Preparation of (2S)-1-acryloyl-pyrrolidine-2-carboxylic acid {4-[3-chloro-4-(pyridin-3-ylmethoxy)-phenylamino]-quinazolin-6-yl}-amide The procedure of Example 145 was repeated except for using N⁴-[3-chloro-4-(pyridin-3-ylmethoxy)-phenyl]-quinazolin-4,6-diamine instead of the compound obtained in (145-2) of Example 145 to obtain the title compound (19 mg, 14%).
¹H-NMR (CD₃OD, 300 MHz): δ 8.72 (s, 1H), 8.67 (s, 1H), 8.55 (m, 1H), 8.51 (s, 1H), 7.93 (t, 1H), 7.92 (d, 1H), 7.82 (d, 1H), 7.80 (m, 1H), 7.60 (dd, 1H), 7.50 (dd, 1H), 7.26 (d, 1H), 6.35 (dd, 1H), 5.84 (d, 1H), 5.45 (d, 1H), 5.29 (s, 2H), 4.70 (m, 1H), 3.70 (m, 2H), 2.00-2.20 (m, 4H).

Example 153

Preparation of (2S)-1-acryloyl-pyrrolidine-2-carboxylic acid {4-[3-chloro-4-(pyridin-4-ylmethoxy)-phenylamino]-quinazolin-6-yl}-amide The procedure of Example 145 was repeated except for using N⁴-[3-chloro-4-(pyridin-4-ylmethoxy)-phenyl]-quinazolin-4,6-diamine instead of the compound obtained in (145-2) of Example 145 to obtain the title compound (8.3 mg, 10%).
¹H-NMR (CD₃OD, 300 MHz): δ 8.77 (s, 1H), 8.60 (m, 3H), 7.94 (dd, 2H), 7.80 (d, 1H), 7.60 (m, 3H), 7.20 (d, 1H), 6.70 (dd, 1H), 6.30 (d, 1H), 5.80 (d, 1H), 5.20 (s, 2H), 4.80 (m, 1H), 3.80 (m, 2H), 2.20 (m, 4H).

Example 154

Preparation of 2-(1-acryloyl-pyrrolidin-2-yl)-N-{4-[3-chloro-4-(pyridin-2-ylmethoxy)-phenylamino]-quinazolin-6-yl}-acetamide The procedure of Example 145 was repeated except for using 2-carboxymethyl-pyrrolidine-1-carboxylic acid t-butylester (see, J. Med. Chem. 1991, 34(2):717) instead of (2S)-pyrrolidine-1,2-dicarboxylic acid-1-t-butylester to obtain the title compound (50 mg, 13%).
¹H-NMR (CDCl₃, 300 MHz): δ 10.23 (br s, 1H), 8.66 (s, 1H), 8.60 (br s, 2H), 7.89 (d, 1H), 7.65-7.83 (m, 3H), 7.56 (m, 2H), 7.24 (t, 1H), 7.01 (d, 1H), 6.48 (m, 2H), 5.79 (m, 1H), 5.30 (s, 2H), 4.50 (m, 1H), 3.68 (m, 1H), 3.59 (m, 1H), 2.92 (dd, 1H), 2.60 (dd, 1H), 2.11 (m, 4H).

Example 155

Preparation of 1-acryloyl-pyrrolidine-3-carboxylic acid {4-[3-chloro-4-(pyridin-2-ylmethoxy)-phenylamino]-quinazolin-6-yl}-amide The procedure of Example 145 was repeated except for using pyrrolidine-1,3-dicarboxylic acid-1-t-butylester instead of (2S)-pyrrolidine-1,2-dicarboxylic acid-1-t-butylester to obtain the title compound (29 mg, 10%).
¹H-NMR (CDCl₃, 300 MHz): δ 8.59 (m, 3H), 7.61-7.76 (m, 5H), 7.45 (d, 1H), 7.23 (t, 1H), 6.93 (d, 1H), 6.32 (m, 2H), 5.68 (m, 1H), 5.24 (s, 2H), 4.88 (br s, 1H), 3.80 (m, 2H), 3.58 (m, 1H), 3.15 (m, 1H), 2.40 (m, 1H), 2.20 (m, 1H).

Example 156

Preparation of 1-acryloyl-piperidine-4-carboxylic acid {4-[3-chloro-4-(pyridin-2-ylmethoxy)-phenylamino]-quinazolin-6-yl}-amide The procedure of Example 145 was repeated except for using piperidine-1,4-dicarboxylic acid-1-t-butylester instead of (2S)-pyrrolidine-1,2-dicarboxylic acid-1-t-butylester to obtain the title compound (35 mg, 11%).
¹H-NMR (CDCl₃, 300 MHz): δ 8.76 (s, 1H), 8.69 (s, 1H), 8.60 (d, 1H), 7.85 (m, 2H), 7.75 (m, 1H), 7.66 (m, 1H), 7.50 (m, 2H), 7.42 (d, 1H), 7.01 (d, 1H), 6.58 (dd, 1H), 6.30 (dd, 1H), 5.73 (dd, 1H), 5.29 (s, 2H), 4.70 (br s, 1H), 3.20 (m, 1H), 2.80 (m, 2H), 2.50 (m, 1H), 1.82 (m, 4H).

Example 157

Preparation of (2S)-1-acryloyl-pyrrolidine-2-carboxylic acid {4-[3-methyl-4-(6-methyl-pyridin-3-yloxy)-phenylamino]-quinazolin-6-yl}-amide The procedure of Example 145 was repeated except for using N-[3-methyl-4-(6-methyl-pyridin-3-ylmethoxy)-phenyl]-quinazolin-4,6-diamine instead of the compound obtained in (145-2) of Example 145 to obtain the title compound (170 mg, 29%).
¹H-NMR (DMSO-d₆, 300 MHz): δ 9.79 (s, 1H), 8.70 (d, 1H), 8.49 (s, 1H), 8.17 (d, 1H), 7.84 (dd, 1H), 7.74 (m, 2H), 7.65 (dd, 1H), 7.22 (m, 2H), 6.95 (d, 1H), 6.60 (dd, 1H), 6.18 (d, 1H), 5.69 (d, 1H), 4.50 (m, 1H), 3.60 (m, 2H), 2.44 (s, 3H), 2.21 (m, 1H), 2.20 (s, 3H), 2.01 (m, 3H).

Example 158

Preparation of (2S)-1-acryloyl-pyrrolidine-2-carboxylic acid [4-(3-ethynyl-phenylamino)-quinazolin-6-yl]-amide The procedure of Example 145 was repeated except for using N⁴-(3-ethynyl-phenyl)-quinazolin-4,6-diamine instead of the compound obtained in (145-2) of Example 145 to obtain the title compound (69 mg, 10%).

¹H-NMR (DMSO-d₆, 300 MHz): δ 10.32 (br s, 1H), 9.81 (s, 1H), 8.65 (s, 1H), 8.48 (s, 1H), 7.93 (s, 1H), 7.79 (m, 2H), 7.73 (m, 2H), 7.31 (t, 1H), 7.13 (d, 1H), 6.61 (m, 1H), 6.08 (dd, 1H), 5.66 (dd, 1H), 4.53 (t, 1H), 4.11 (s, 1H), 3.63 (m, 2H), 1.96 (m, 4H).

Example 159

Preparation of (2S)-1-acryloyl-pyrrolidine-2-carboxylic acid [4-(3-chloro-4-fluoro-phenylamino)-quinazolin-6-yl]-amide The procedure of Example 145 was repeated except for using N⁴-(3-chloro-4-fluoro-phenyl)-quinazolin-4,6-diamine instead of the compound obtained in (145-2) of Example 145 to obtain the title compound (109 mg, 19%).
¹H-NMR (DMSO-d₆, 300 MHz): δ 10.38 (br s, 1H), 9.92 (s, 1H), 8.72 (s, 1H), 8.71 (s, 1H), 8.31 (m, 1H), 7.81 (m, 3H), 6.66 (m, 1H), 6.16 (dd, 1H), 5.70 (dd, 1H), 4.60 (t, 1H), 3.69 (m, 2H), 2.09 (m, 2H), 1.98 (m, 2H).

Example 160

Preparation of (2S,4R)-1-acryloyl-4-ethanesulfonyl-pyrrolidine-2-carboxylic acid {4-[3-chloro-4-(pyridin-2-ylmethoxy)-phenylamino]-quinazolin-6-yl}-amide The procedure of Example 145 was repeated except for using (2S,4R)-4-ethanesulfonyl-pyrrolidine-1,2-dicarboxylic acid-1-t-butylester instead of (2S)-pyrrolidine-1,2-dicarboxylic acid-1-t-butylester to obtain the title compound (10 mg, 9%).
¹H-NMR (CDCl₃, 300 MHz): δ 8.42 (m, 3H), 7.79 (d, 1H), 7.65 (m, 3H), 7.46 (m, 2H), 7.16 (t, 1H), 6.90 (d, 1H), 6.32 (m, 1H), 5.98 (m, 1H), 5.68 (m, 1H), 5.15 (s, 2H), 4.69 (m, 1H), 4.28 (t, 1H), 4.05 (m, 2H), 3.75 (m, 1H), 2.72 (m, 1H), 2.53 (m, 2H), 1.32 (t, 3H).

Example 161

Preparation of (2S,4R)-1-acryloyl-4-methoxy-pyrrolidine-2-carboxylic acid {4-[3-chloro-4-(pyridin-2-ylmethoxy)-phenylamino]-quinazolin-6-yl}-amide The procedure of Example 145 was repeated except for using (2S,4R)-4-methoxy-pyrrolidine-1,2-dicarboxylic acid-1-t-butylester instead of (2S)-pyrrolidine-1,2-dicarboxylic acid-1-t-butylester to obtain the title compound (70 mg, 42%).
¹H-NMR (CDCl₃, 300 MHz): δ 9.96 (s, 1H), 8.61 (d, 1H), 8.60 (s, 1H), 8.17 (s, 1H), 7.91 (dd, 1H), 7.76 (m, 2H), 7.69 (s, 1H), 7.59 (s, 1H), 7.25 (t, 1H), 7.01 (d, 1H), 6.50 (m, 2H), 5.82 (m, 1H), 5.30 (s, 2H), 5.01 (t, 1H), 4.93 (m, 1H), 4.35 (m, 1H), 4.02 (m, 1H), 3.43 (s, 3H), 2.75 (m, 1H), 2.48 (m, 1H).

Example 162

Preparation of 1-acryloyl-piperidine-3-carboxylic acid {4-[3-chloro-4-(pyridin-2-ylmethoxy)-phenylamino]-quinazolin-6-yl}-amide The procedure of Example 145 was repeated except for using piperidine-1,3-dicarboxylic acid-1-t-butylester instead of (2S)-pyrrolidine-1,2-dicarboxylic acid-1-t-butylester to obtain the title compound (130 mg, 43%).
¹H-NMR (CDCl₃, 300 MHz): δ 9.63 (s, 1H), 8.76 (s, 1H), 8.68 (s, 1H), 8.60 (d, 1H), 7.84 (m, 2H), 7.76 (m, 2H), 7.66 (d, 1H), 7.55 (m, 2H), 7.02 (d, 1H), 6.59 (dd, 1H), 6.39 (d, 1H), 5.81 (d, 1H), 5.30 (s, 2H), 4.43 (d, 1H), 6.39 (d, 1H), 5.81 (d, 1H), 5.30 (s, 2H), 4.43 (d, 1H), 3.77 (m, 1H), 3.64 (m, 1H), 3.49 (m, 1H), 2.80 (m, 1H), 2.48 (m, 1H), 1.70 (m, 3H).

Example 163

Preparation of 1-acryloyl-azetidine-3-carboxylic acid {4-[3-chloro-4-(pyridin-2-ylmethoxy)-phenylamino]-quinazolin-6-yl}-amide The procedure of Example 145 was repeated except for using azetidine-1,3-dicarboxylic acid-1-t-butylester instead of (2S)-pyrrolidine-1,2-dicarboxylic acid-1-t-butylester to obtain the title compound (85 mg, 34%).
¹H-NMR (CDCl₃, 300 MHz): δ 8.76 (s, 1H), 8.67 (s, 1H), 8.63 (d, 1H), 8.30 (s, 1H), 7.8 (m, 3H), 7.67 (d, 1H), 7.49 (t, 2H), 6.99 (d, 1H), 6.31 (d, 1H), 6.23 (dd, 1H), 5.73 (d, 1H), 5.29 (s, 2H), 4.60 (m, 1H), 4.29 (m, 3H), 3.49 (m, 1H).

Example 164

Preparation of 1-acryloyl-piperidine-2-carboxylic acid {4-[3-chloro-4-(pyridin-2-ylmethoxy)-phenylamino]-quinazolin-6-yl}-amide The procedure of Example 145 was repeated except for using piperidine-1,2-dicarboxylic acid-1-t-butylester instead of (2S)-pyrrolidine-1,2-dicarboxylic acid-1-t-butylester to obtain the title compound (67 mg, 19%).
¹H-NMR (CDCl₃, 300 MHz): δ 9.27 (s, 1H), 8.65 (s, 1H), 8.60 (d, 1H), 8.45 (s, 1H), 7.90 (d, 1H), 7.76 (t, 2H), 7.67 (d, 1H), 7.54 (m, 3H), 7.30 (d, 1H), 6.65 (dd, 1H), 6.44 (dd, 1H), 5.85 (dd, 1H), 4.00 (d, 1H), 3.25 (t, 1H), 2.30 (d, 1H), 1.58-2.03 (m, 6H).

Example 165

Preparation of (2S)-1-acryloyl-pyrrolidine-2-carboxylic acid {4-[3-chloro-4-(pyridin-2-ylmethoxy)-phenylamino]-7-fluoro-quinazolin-6-yl}-amide (165-1) Preparation of 4-chloro-7-fluoro-6-nitro-quinazoline Preparation of the Compound was Carried Out in Accordance with Examples of International patent publication WO 00/031048.

(165-2) Preparation of [3-chloro-4-(pyridin-2-ylmethoxy)-phenyl]-(7-fluoro-6-nitro-quinazolin-4-yl)-amine hydrochloride salt 72 g of the compound obtained in (165-1) and 74 g of 3-chloro-4-(pyridin-2-ylmethoxy)-phenylamine was stirred at 100° C. for 17 hours after adding 1,000 ml of isopropanol. The reacted solution was cooled, filtered under a reduced pressure, washed with acetone and dried at 40° C. for 15 hours to obtain the title compound (118 g, 91%).

(165-3) Preparation of N⁴-[3-chloro-4-(pyridin-2-ylmethoxy)-phenyl]-7-fluoro-quinazolin-4,6-diamine The procedure of (1-4) of Example 1 was repeated except for using 1.5 g of the compound obtained in (165-2) instead of the compound obtained in (1-3) of Example 1 to obtain the title compound (1.3 g, 91%).

¹H-NMR (DMSO-d₆, 300 MHz): δ 9.23 (s, 1H), 8.59 (d, 1H), 8.32 (s, 1H), 8.03 (s, 1H), 7.91 (s, 1H), 7.71 (t, 1H), 7.58 (dd, 1H), 7.35 (m, 2H), 7.22 (t, 1H), 7.05 (m, 1H), 5.32 (s, 2H), 5.25 (s, 2H).

(165-4) Preparation of (2S)-2-{4-[3-chloro-4-(pyridin-2-ylmethoxy)-phenylamino]-7-fluoro-quinazolin-6-ylcarbamoyl}-pyrrolidine-1-carboxylic acid t-butylester The procedure of (145-3) of Example 145 was repeated except for using 1.74 g of (2S)-pyrrolidine-1,2-dicarboxylic acid 1-t-butylester and 0.8 g of the compound obtained in (165-3) instead of the compound obtained in (145-2) of Example 145 to obtain the title compound (1.1 g, 89%).

¹H-NMR (DMSO-d₆, 300 MHz): δ 9.71 (s, 1H), 9.49 (d, 1H), 8.90 (d, 1H), 8.65 (d, 1H), 8.41 (s, 1H), 8.20 (s, 1H), 7.90 (s, 1H), 7.88 (t, 1H), 7.67 (dd, 1H), 7.59 (d, 1H), 7.38 (t, 1H), 7.21 (m, 2H), 5.25 (s, 2H), 4.50 (m, 1H), 1.80-2.18 (m, 6H).

(165-5) Preparation of (2S)-pyrrolidine-2-carboxylic acid {4-[3-chloro-4-(pyridin-2-ylmethoxy)-phenylamino]-7-fluoro-quinazolin-6-yl}-amide The procedure of (145-4) of Example 145 was repeated except for using 1.1 g of the compound obtained in (165-4) instead of the compound obtained in (145-3) of Example 145 to obtain the title compound (0.8 g, 90%).

¹H-NMR (DMSO-d₆, 300 MHz): δ 10.40 (s, 1H), 9.75 (s, 1H), 9.06 (s, 1H), 8.60 (d, 1H), 8.45 (s, 1H), 7.93 (s, 1H), 7.88 (t, 1H), 7.65 (dd, 1H), 7.59 (d, 1H), 7.35 (t, 1H), 7.21 (m, 2H), 5.28 (s, 2H), 4.01 (s, 3H), 2.99 (m, 1H), 2.84 (m, 1H), 1.85 (m, 1H), 1.72 (m, 1H), 1.61 (m, 2H).

(165-6) Preparation of (2S)-1-acryloyl-pyrrolidine-2-carboxylic acid {4-[3-chloro-4-(pyridin-2-ylmethoxy)-phenylamino]-7-fluoro-quinazolin-6-yl}-amide The procedure of (145-5) of Example 145 was repeated except for using 474 mg of the compound obtained in (165-5) instead of the compound obtained in (145-5) of Example 145 to obtain the title compound (260 mg, 49%).

¹H-NMR (CD₃OD, 300 MHz): δ 8.70 (s, 1H), 8.51 (d, 1H), 8.35 (s, 1H), 7.88 (m, 2H), 7.71 (d, 1H), 7.55 (dd, 1H), 7.30 (t, 1H), 7.12 (m, 2H), 6.71 (dd, 1H), 6.35 (d, 1H), 5.81 (d, 1H), 5.21 (s, 2H), 4.80 (m, 1H), 3.80 (m, 2H), 2.03-2.30 (m, 4H).

Example 166

Preparation of (2S)-1-acryloyl-pyrrolidine-2-carboxylic acid {4-[3-chloro-4-(pyridin-2-ylmethoxy)-phenylamino]-7-methoxy-quinazolin-6-yl}-amide (166-1) Preparation of [3-chloro-4-(pyridin-2-ylmethoxy)-phenyl]-(7-methoxy-6-nitro-quinazolin-4-yl)-amine 100 ml of dimethylsulfoxide and 5.84 g of sodium methoxide were added to 5 g of the compound obtained in (165-2) of Example 165, and the mixture was stirred at room temperature for 20 hours. The resultant was stirred for 30 mins after adding water, filtered under a reduced pressure and dried 40° C. to obtain the title compound (4.7 g, 99%).

¹H-NMR (DMSO-d₆, 300 MHz): δ 9.13 (s, 1H) 8.45 (d, 1H) 8.49 (s, 1H) 7.91 (s, 1H) 7.81 (t, 1H) 7.55 (m, 2H) 7.23 (m, 2H) 7.07 (m, 1H) 5.24 (s, 2H) 3.99 (s, 3H)

(166-2) Preparation of N⁴-[3-chloro-4-(pyridin-2-ylmethoxy)-phenyl]-7-methoxy-quinazolin-4,6-diamine 3 g of iron was refluxed with stirring at 100° C. for 1 hour after adding 100 ml of 50% aqueous ethanol solution and 0.358 ml of HCl, the mixture was refluxed with stirring after adding 4.7 g of the compound obtained in (166-1) for 1 hour. The resultant was filtered under a reduced pressure through celite pad, and the pad was washed with ethylacetate. The organic layer was dried over magnesium sulfate, and distilled under a reduced pressure to obtain the title compound (3.4 g, 79%).

¹H-NMR (DMSO-d₆, 300 MHz): δ 9.23 (s, 1H), 8.59 (d, 1H), 8.32 (s, 1H), 8.03 (s, 1H), 7.87 (s, 1H), 7.70 (t, 1H), 7.58 (dd, 1H), 7.36 (m, 2H), 7.22 (t, 1H), 7.07 (m, 1H), 5.31 (s, 2H), 5.28 (s, 2H), 3.95 (s, 3H).

(166-3) Preparation of (2S)-2-{4-[3-chloro-4-(pyridin-2-ylmethoxy)-phenylamino]-7-methoxy-quinazolin-6-ylcarbamoyl}-pyrrolidine-1-carboxylic acid t-butylester 3.75 g of (2S)-pyrrolidine-1,2-dicarboxylic acid 1-t-butylester and 30 ml of pyridine were added to 3.4 g of the compound obtained in (166-2), and the mixture was stirred for 5 hours after adding 3.53 g of 1-(3-dimethylaminopropyl)-3-ethylcarbodiimide hydrochloride. The reacted solution was extracted with ethylacetate after adding water, dried over anhydrous magnesium sulfate, filtered and distilled under a reduced pressure, and the resulting residue was subjected to column chromatography (eluent-chloroform:methanol=15:1) to obtain the title compound (3.4 g, 68%).

¹H-NMR (DMSO-d₆, 300 MHz): δ 9.71 (s, 1H), 9.49 (d, 1H), 8.95 (d, 1H), 8.60 (d, 1H), 8.46 (s, 1H), 8.30 (s, 1H), 7.93 (s, 1H), 7.88 (t, 1H), 7.67 (dd, 1H), 7.59 (d, 1H), 7.38 (t, 1H), 7.21 (m, 2H), 5.28 (s, 2H), 4.51 (m, 1H), 4.03 (s, 3H), 1.80-2.18 (m, 6H).

(166-4) Preparation of (2S)-pyrrolidine-2-carboxylic acid {4-[3-chloro-4-(pyridin-2-ylmethoxy)-phenylamino]-7-methoxy-quinazolin-6-yl}-amide 60 ml of dimethylene chloride and 60 ml of trifluoroacetic acid were added to 3.3 g of the compound obtained in (166-3). After 4 hours, the reacted solution was distilled under a reduced pressure, distilled with small amount of water, and neutralized with saturated aqueous sodium bicarbonate solution. The solution was filtered under a reduced pressure and dried at 40° C. for 15 hours to obtain the title compound (2.8 g, 99%).

¹H-NMR (DMSO-d₆, 300 MHz): δ 10.46 (s, 1H), 9.71 (s, 1H), 9.06 (s, 1H), 8.60 (d, 1H), 8.45 (s, 1H), 7.93 (s, 1H), 7.88 (t, 1H), 7.67 (dd, 1H), 7.59 (d, 1H), 7.38 (t, 1H), 7.21 (m, 2H), 5.28 (s, 2H), 4.03 (s, 3H), 3.81 (s, 1H), 2.99 (m, 1H), 2.84 (m, 1H), 1.89 (m, 1H), 1.69 (m, 1H), 1.64 (m, 2H).

(166-5) Preparation of (2S)-1-acryloyl-pyrrolidine-2-carboxylic acid {4-[3-chloro-4-(pyridin-2-ylmethoxy)-phenylamino]-7-methoxy-quinazolin-6-yl}-amide 0.489 ml of acrylic acid dissolved in 50 ml of THF was reacted with 1.77 ml of pyridine, 1.37 g of 1-(3-dimethylaminopropyl)-3-ethylcarbodiimide hydrochloride and 1.8 g of the compound obtained in (166-4) for 4 hours. The reacted solution was diluted with water, extracted with ethylacetate, dried over anhydrous magnesium sulfate, and the resulting residue was subjected to column chromatography (eluent-chloroform:methanol=15:1) to obtain the title compound (743 mg, 37%).

$^1$H-NMR (CD$_3$OD, 300 MHz): δ 8.76 (s, 1H), 8.55 (d, 1H), 8.40 (s, 1H), 7.88 (m, 2H), 7.71 (d, 1H), 7.55 (dd, 1H), 7.33 (t, 1H), 7.12 (m, 2H), 6.71 (dd, 1H), 6.36 (d, 1H), 5.82 (d, 1H), 5.23 (s, 2H), 4.85 (m, 1H), 4.02 (s, 3H), 3.81 (m, 2H), 2.03-2.27 (m, 4H).

Example 167

Preparation of N-(2-{4-[3-chloro-4-(pyridin-2-yl-methoxy)-phenylamino]-7-methoxy-quinazolin-6-ylcarbamoyl}-ethyl)-acrylamide The procedure of Example 166 was repeated except for using 3-t-buthoxycarbonylamino-propionic acid instead of (2S)-pyrrolidine-1,2-dicarboxylic acid 1-t-butylester to obtain the title compound (80 mg, 21%).

$^1$H-NMR (CD$_3$OD, 300 MHz): δ 8.85 (s, 1H), 8.57 (t, 1H), 8.45 (s, 1H), 7.93 (m, 2H), 7.75 (d, 1H), 7.60 (dd, 1H), 7.41 (t, 1H), 7.22 (s, 1H), 7.19 (d, 1H), 6.26 (m, 2H), 5.69 (dd, 1H), 5.29 (s, 2H), 4.07 (s, 3H), 3.69 (t, 2H), 2.01 (t, 2H).

Example 168

Preparation of (2S)-1-acryloyl-pyrrolidine-2-carboxylic acid {7-methoxy-4-[3-methyl-4-(pyridin-2-ylmethoxy)-phenylamino]-quinazolin-6-yl}-amide The procedure of Example 166 was repeated except for using N$^4$-[3-methyl-4-(pyridin-2-ylmethoxy)-phenyl]-7-methoxy-quinazolin-4,6-diamine instead of the compound obtained in (166-2) of Example 166 to obtain the title compound (230 mg, 23%).

$^1$H-NMR (CDCl$_3$, 300 MHz): δ 9.85 (s, 1H), 9.02 (s, 1H), 8.67 (m, 2H), 7.79 (m, 1H), 7.64 (d, 1H), 7.50 (m, 2H), 7.41 (s, 1H), 7.28 (m, 2H), 6.96 (d, 1H), 6.60 (m, 2H), 5.89 (m, 1H), 5.31 (s, 2H), 4.98 (m, 1H), 4.09 (s, 3H), 3.80 (m, 1H), 3.71 (m, 1H), 2.60 (m, 1H), 2.44 (s, 3H), 2.20 (m, 3H).

Example 169

Preparation of 2-(1-acryloyl-pyrrolidin-2-yl)-N-{4-[3-chloro-4-(pyridin-2-ylmethoxy)-phenylamino]-7-methoxy-quinazolin-6-yl}-acetamide The procedure of Example 166 was repeated except for using 2-carboxymethyl-pyrrolidine-1-carboxylic acid t-butylester instead of (2S)-pyrrolidine-1,2-dicarboxylic acid-1-t-butylester to obtain the title compound (72 mg, 14%).

$^1$H-NMR (CDCl$_3$, 300 MHz): δ 8.56 (s, 2H), 8.00 (s, 1H), 7.79 (s, 1H), 7.72 (m, 1H), 7.61 (m, 1H), 7.48 (d, 1H), 7.29 (m, 1H), 7.19 (t, 1H), 6.91 (d, 1H), 6.43 (m, 2H), 5.69 (dd, 1H), 5.23 (s, 2H), 4.42 (br s, 1H), 3.95 (s, 3H), 3.55 (m, 2H), 3.05 (m, 1H), 2.59 (m, 1H), 2.02 (m, 4H).

Example 170

Preparation of (2S)-1-acryloyl-pyrrolidine-2-carboxylic acid {4-[3-chloro-4-(pyridin-2-ylmethoxy)-phenylamino]-7-ethoxy-quinazolin-6-yl}-amide The procedure of Example 166 was repeated except for using N$^4$-[3-chloro-4-(pyridin-2-ylmethoxy)-phenyl]-7-ethoxy-quinazolin-4,6-diamine instead of the compound obtained in (166-2) of Example 166 to obtain the title compound (170 mg, 28%).

$^1$H-NMR (CDCl$_3$, 300 MHz): δ 9.81 (s, 1H), 8.79 (s, 1H), 8.57 (m, 2H), 8.08 (s, 1H), 7.80 (d, 1H), 7.73 (td, 1H), 7.64 (d, 1H), 7.52 (dd, 1H), 7.22 (t, 1H), 6.99 (s, 1H), 6.94 (d, 1H), 6.48 (m, 2H), 5.78 (dd, 1H), 5.25 (s, 2H), 4.98 (d, 1H), 3.96 (m, 2H), 3.73 (m, 1H), 3.62 (m, 1H), 2.52 (m, 1H), 2.07 (m, 3H), 1.44 (t, 3H).

Example 171

Preparation of (2S)-1-acryloyl-pyrrolidine-2-carboxylic acid {4-[3-chloro-4-(pyridin-2-ylmethoxy)-phenylamino]-7-ethylsulfanyl-quinazolin-6-yl}-amide The procedure of Example 166 was repeated except for using N$^4$-[3-methyl-4-(pyridin-2-ylmethoxy)-phenyl]-7-ethylsulfanyl-quinazolin-4,6-diamine instead of the compound obtained in (166-2) of Example 166 to obtain the title compound (250 mg, 32%).

$^1$H-NMR (CDCl$_3$, 300 MHz): δ 9.95 (s, 1H), 8.58 (d, 1H), 8.46 (s, 1H), 8.17 (s, 1H), 8.00 (s, 1H), 7.74 (m, 2H), 7.63 (m, 2H), 7.35 (s, 1H), 7.23 (t, 1H), 6.94 (d, 1H), 6.54 (m, 1H), 6.37 (dd, 1H), 5.74 (dd, 1H), 5.27 (s, 2H), 5.12 (m, 1H), 3.88 (m, 1H), 3.70 (m, 1H), 2.71 (m, 2H), 2.60 (m, 1H), 2.25 (m, 3H), 1.29 (t, 3H).

Example 172

Preparation of (2S)-1-acryloyl-pyrrolidine-2-carboxylic acid {4-[3-chloro-4-(pyridin-2-ylmethoxy)-phenylamino]-7-cyclopropylmethoxy-quinazolin-6-yl}-amide The procedure of Example 166 was repeated except for using N$^4$-[3-methyl-4-(pyridin-2-ylmethoxy)-phenyl]-7-ethylsulfanyl-quinazolin-4,6-diamine instead of the compound obtained in (166-2) of Example 166 to obtain the title compound (250 mg, 32%).

The procedure of Example 166 was repeated except for using N$^4$-[3-methyl-4-(pyridin-2-ylmethoxy)-phenyl]-7-cyclopropylmethoxy-quinazolin-4,6-diamine instead of the compound obtained in (166-2) of Example 166 to obtain the title compound (19 mg, 5%).

$^1$H-NMR (CDCl$_3$, 300 MHz): δ 8.61 (m, 1H), 7.92 (s, 1H), 7.77 (m, 2H), 7.69 (d, 2H), 7.20-7.40 (m, 3H), 7.01 (m, 1H), 6.43 (d, 1H), 6.19 (dd, 1H), 5.92 (d, 1H), 5.25 (s, 2H), 4.45 (m, 1H), 4.02 (m, 2H), 3.74 (m, 1H), 2.77 (m, 1H), 2.00 (m, 5H), 0.89 (t, 2H), 0.63 (d, 2H), 0.40 (q, 2H).

Example 173

Preparation of (2S)-1-acryloyl-pyrrolidine-2-carboxylic acid {4-[3-chloro-4-(pyridin-2-ylmethoxy)-phenylamino]-7-cyclopentyloxy-quinazolin-6-yl}-amide The procedure of Example 166 was repeated except for using N-[3-methyl-4-(pyridin-2-ylmethoxy)-phenyl]-7-cyclopentyloxy-quinazolin-4,6-diamine instead of the compound obtained in (166-2) of Example 166 to obtain the title compound (300 mg, 61%).

$^1$H-NMR (CDCl$_3$, 300 MHz): δ 9.86 (s, 1H), 8.88 (s, 1H), 8.52 (s, 2H), 7.76 (s, 1H), 7.67 (m, 1H), 7.57 (d, 2H), 7.41 (dd,

1H), 7.21 (m, 3H), 6.92 (d, 1H), 6.89 (m, 2H), 5.77 (t, 1H), 5.21 (s, 2H), 4.90 (m, 2H), 3.55 (m, 2H), 2.55 (m, 1H), 1.60-2.10 (m, 10H).

Example 174

Preparation of N-(2-{4-[3-chloro-4-(pyridin-4-ylmethoxy)-phenylamino]-quinazolin-6-ylcarbamoyl}-ethyl)-acrylamide The procedure of Example 22 was repeated except for using $N^4$-[3-chloro-4-(pyridin-4-ylmethoxy)-phenyl]-quinazolin-4,6-diamine instead of the compound obtained in (1-4) of Example 1 to obtain the title compound (10 mg, 13%).

$^1$H-NMR (CD$_3$OD, 300 MHz): δ 8.77 (s, 1H), 8.60 (m, 3H), 7.94 (dd, 2H), 7.80 (d, 1H), 7.60 (m, 3H), 7.20 (d, 1H), 6.90 (m, 1H), 6.50 (d, 1H), 6.20 (m, 1H), 5.30 (s, 2H), 3.60 (t, 2H), 2.80 (t, 2H).

Example 175

Preparation of (2S)-1-(4-dimethylamino-buten-2-oyl)-pyrrolidine-2-carboxylic acid {4-[3-chloro-4-(pyridin-2-ylmethoxy)-phenylamino]-7-methoxy-quinazolin-6-yl}-amide The procedure of Example 166 was repeated except for using 4-dimethylamino-buten-2-oic acid instead of acrylic acid to obtain the title compound (100 mg, 22%).

$^1$H-NMR (CDCl$_3$, 300 MHz): δ: 9.84 (s, 1H), 8.88 (s, 1H), 8.59 (s, 2H), 7.83 (s, 1H), 7.77 (t, 1H), 7.68 (d, 1H), 7.57 (s, 1H), 7.51 (d, 1H), 7.26 (m, 1H), 7.15 (s, 1H), 7.06 (m, 2H), 6.36 (d, 1H), 5.28 (s, 2H), 4.92 (d, 2H), 3.95 (s, 3H), 3.73 (m, 2H), 3.13 (d, 2H), 2.52 (m, 1H), 2.27 (s, 6H), 1.92-2.13 (m, 3H).

Example 176

Preparation of (2S)-1-acryloyl-pyrrolidine-2-carboxylic acid {7-chloro-4-[3-chloro-4-(pyridin-2-ylmethoxy)-phenylamino]-quinazolin-6-yl}-amide The procedure of Example 166 was repeated except for using $N^4$-[3-methyl-4-(pyridin-2-ylmethoxy)-phenyl]-7-chloro-quinazolin-4,6-diamine instead of the compound obtained in (166-2) of Example 166 to obtain the title compound (250 mg, 31%).

$^1$H-NMR (CDCl$_3$, 300 MHz): δ 8.71 (s, 1H), 8.60 (m, 2H), 8.20 (s, 1H), 7.74 (m, 2H), 7.68 (m, 1H), 7.60 (s, 1H), 7.49 (m, 1H), 7.23 (m, 1H), 6.96 (d, 1H), 6.27 (m, 1H), 6.00 (m, 1H), 5.72 (m, 1H), 5.31 (s, 2H), 4.90 (m, 1H), 4.16 (m, 2H), 4.00 (m, 1H), 3.33 (m, 1H), 3.07 (m, 1H), 2.65 (m, 1H).

Example 177

Preparation of (2S)-1-acryloyl-pyrrolidine-2-carboxylic acid {7-fluoro-4-[3-methyl-4-(pyridin-2-ylmethoxy)-phenylamino]-quinazolin-6-yl}-amide The procedure of Example 166 was repeated except for using $N^4$-[3-methyl-4-(pyridin-2-ylmethoxy)-phenyl]-7-fluoro-quinazolin-4,6-diamine instead of the compound obtained in (166-2) of Example 166 to obtain the title compound (220 mg, 36%).

$^1$H-NMR (CDCl$_3$, 300 MHz): δ 10.35 (s, 1H), 8.90 (d, 1H), 8.65 (m, 2H), 7.77 (m, 1H), 7.61 (m, 2H), 7.53 (d, 1H), 7.46 (m, 2H), 7.26 (m, 1H), 6.92 (d, 1H), 6.57 (m, 2H), 5.88 (m, 1H), 5.28 (s, 2H), 5.02 (m, 1H), 3.80 (m, 1H), 3.66 (m, 1H), 2.68 (m, 1H), 2.41 (s, 3H), 2.20 (m, 1H), 2.02 (m, 2H).

Example 178

Preparation of N-(2-{7-fluoro-4-[3-methyl-4-(pyridin-2-ylmethoxy)-phenylamino]-quinazolin-6-ylcarbamoyl}-ethyl)-acrylamide The procedure of Example 22 was repeated except for using $N^4$-[3-methyl-4-(pyridin-2-ylmethoxy)-phenyl]-7-fluoro-quinazolin-4,6-diamine instead of the compound obtained in (20-1) of Example 20 to obtain the title compound (100 mg, 19%).

$^1$H-NMR (CDCl$_3$, 300 MHz): δ 8.98 (bd, 1H), 8.82 (bs, 1H), 8.60 (m, 2H), 7.74 (m, 2H), 7.67 (bs, 1H), 7.54 (m, 2H), 7.41 (m, 2H), 7.26 (m, 1H), 6.88 (d, 1H), 6.61 (m, 1H), 6.30 (m, 1H), 5.72 (m, 1H), 5.23 (s, 2H), 3.80 (m, 2H), 2.82 (m, 2H), 2.36 (s, 3H).

Example 179

Preparation of (2S)-1-acryloyl-2,5-dihydro-1H-pyrrol-2-carboxylic acid {4-[3-chloro-4-(pyridin-2-ylmethoxy)-phenylamino]-7-methoxy-quinazolin-6-yl}-amide The procedure of Example 166 was repeated except for using (2S)-dihydro-1H-pyrrol-1,2-dicarboxylic acid-1-t-butylester instead of (2S)-pyrrolidine-1,2-dicarboxylic acid-1-t-butylester to obtain the title compound (15 mg, 3%).

$^1$H-NMR (CDCl$_3$, 300 MHz): δ 9.43 (bs, 1H), 8.92 (s, 1H), 8.60 (m, 2H), 7.85 (d, 1H), 7.74 (m, 1H), 7.65 (d, 1H), 7.48 (m, 2H), 7.19 (m, 2H), 6.98 (d, 1H), 6.52 (d, 2H), 6.07 (m, 2H), 5.85 (t, 1H), 5.54 (m, 1H), 5.28 (s, 2H), 4.52 (m, 2H), 4.00 (s, 3H).

Example 180

Preparation of (4R)-3-acryloyl-thiazolidin-4-carboxylic acid {4-[3-chloro-4-(pyridin-2-ylmethoxy)-phenylamino]-7-methoxy-quinazolin-6-yl}-amide The procedure of Example 166 was repeated except for using (4R)-thiazolidin-3,4-dicarboxylic acid-3-t-butylester instead of (2S)-pyrrolidine-1,2-dicarboxylic acid-1-t-butylester to obtain the title compound (150 mg, 19%).

$^1$H-NMR (CDCl$_3$, 300 MHz): δ 9.48 (bs, 1H), 8.91 (s, 1H), 8.60 (m, 2H), 7.83 (d, 1H), 7.74 (t, 1H), 7.65 (d, 1H), 7.56 (bs, 1H), 7.48 (dd, 1H), 7.23 (m, 1H), 7.21 (s, 1H), 6.98 (d, 1H), 6.55 (m, 2H), 5.89 (m, 1H), 5.33 (m, 1H), 5.28 (s, 2H), 4.81 (m, 1H), 4.68 (m, 1H), 4.00 (s, 3H), 3.67 (m, 1H), 3.23 (m, 1H).

Example 181

Preparation of 1-acryloyl-azetidine-2-carboxylic acid {4-[3-chloro-4-(pyridin-2-ylmethoxy)-phenylamino]-quinazolin-6-yl}-amide The procedure of Example 145 was repeated except for using azetidine-1,2-dicarboxylic acid-1-t-butylester instead of (2S)-pyrrolidine-1,2-dicarboxylic acid-1-t-butylester to obtain the title compound (153 mg, 33%).

$^1$H-NMR (CDCl$_3$, 300 MHz): δ 10.81 (s, 1H), 8.67 (s, 1H), 8.60 (d, 1H), 8.50 (s, 1H), 7.90 (d, 1H), 7.82 (d, 1H), 7.73 (td,

1H), 7.68 (m, 2H), 7.55 (m, 2H), 7.02 (d, 1H), 6.51 (d, 1H), 6.26 (dd, 1H), 5.87 (dd, 1H), 5.30 (s, 2H), 5.22 (m, 1H), 4.27 (t, 2H), 2.90 (m, 1H), 2.59 (m, 1H).

Example 182

Preparation of 1-acryloyl-azetidine-2-carboxylic acid {4-[3-chloro-4-(pyridin-2-ylmethoxy)-phenylamino]-7-methoxy-quinazolin-6-yl}-amide The procedure of Example 181 was repeated except for using the compound obtained in (166-2) of Example 166 instead of the compound obtained in (145-2) of Example 145 to obtain the title compound (106 mg, 17%).

$^1$H-NMR (CDCl$_3$, 300 MHz): δ 10.34 (s, 1H), 8.97 (s, 1H), 8.63 (s, 1H), 8.60 (d, 1H), 7.87 (d, 1H), 7.76 (td, 1H), 7.67 (d, 1H), 7.51 (dd, 1H), 7.42 (s, 1H), 7.23 (s, 1H), 7.01 (d, 1H), 6.51 (dd, 1H), 6.26 (dd, 1H), 5.83 (dd, 1H), 5.30 (s, 2H), 5.16 (m, 1H), 4.25 (t, 2H), 4.04 (s, 3H), 2.87 (m, 1H), 2.62 (m, 1H).

Example 183

Preparation of (2S)-1-acryloyl-pyrrolidine-2-carboxylic acid [4-[3-chloro-4-(pyridin-2-ylmethoxy)-phenylamino]-7-(2,2,2-trifluoro-ethoxy)-quinazolin-6-yl]-amide The procedure of Example 166 was repeated except for using N$^4$-[3-methyl-4-(pyridin-2-ylmethoxy)-phenyl]-7-(2,2,2-trifluoro-ethoxy)-quinazolin-4,6-diamine instead of the compound obtained in (166-2) of Example 166 to obtain the title compound (70 mg, 15%).

$^1$H-NMR (CDCl$_3$, 300 MHz): δ 9.96 (s, 1H), 8.80 (s, 1H), 8.60 (m, 2H), 7.86 (d, 1H), 7.76 (m, 2H), 7.66 (d, 1H), 7.53 (dd, 1H), 7.12 (s, 1H), 7.00 (d, 1H), 6.52 (m, 2H), 5.82 (t, 1H), 5.30 (s, 2H), 4.98 (m, 1H), 4.43 (m, 2H), 3.77 (m, 1H), 3.65 (m, 1H), 2.53 (m, 1H), 2.09 (m, 1H).

Example 184

Preparation of (2S)-1-acryloyl-pyrrolidine-2-carboxylic acid {4-[3-chloro-4-(pyridin-2-ylmethoxy)-phenylamino]-7-dimethylamino-quinazolin-6-yl}-amide The procedure of Example 166 was repeated except for using N$^4$-[3-methyl-4-(pyridin-2-ylmethoxy)-phenyl]-7-dimethylamino-quinazolin-4,6-diamine instead of the compound obtained in (166-2) of Example 166 to obtain the title compound (190 mg, 44%).

$^1$H-NMR (CDCl$_3$, 300 MHz): δ 9.61 (s, 1H), 8.84 (s, 1H), 8.55 (s, 1H), 8.53 (d, 1H), 7.79 (d, 1H), 7.68 (td, 1H), 7.59 (d, 1H), 7.52 (m, 3H), 7.17 (d, 1H), 6.94 (d, 1H), 6.45 (m, 2H), 5.76 (dd, 1H), 5.23 (s, 2H), 4.86 (m, 1H), 3.69 (m, 1H), 3.60 (m, 1H), 2.70 (s, 6H), 2.47 (m, 1H), 2.06 (m, 3H).

Example 185

Preparation of (2S)-1-acryloyl-pyrrolidine-2-carboxylic acid [7-methoxy-4-(1-pyridin-2-ylmethyl-1H-indazol-5-ylamino)-quinazolin-6-yl]-amide The procedure of Example 166 was repeated except for using 7-methoxy-N$^4$-(1-pyridin-2-ylmethyl-1H-indazol-5-yl)-quinazolin-4,6-diamine instead of the compound obtained in (166-2) of Example 166 to obtain the title compound (160 mg, 29%).

$^1$H-NMR (CDCl$_3$, 300 MHz): δ 9.74 (s, 1H), 8.97 (s, 1H), 8.58 (s, 1H), 8.05 (m, 2H), 7.88 (bs, 1H), 7.55 (dd, 1H), 7.27 (m, 2H), 7.23 (s, 1H), 6.99 (m, 2H), 6.88 (m, 1H), 6.51 (m, 2H), 5.80 (m, 1H), 5.57 (s, 2H), 4.92 (m, 1H), 3.98 (s, 3H), 3.74 (m, 1H), 3.60 (m, 1H), 3.22 (m, 2H), 2.53 (m, 1H), 2.12 (m, 1H).

Example 186

Preparation of (2S)-1-acryloyl-pyrrolidine-2-carboxylic acid {4-[3-methyl-4-(pyridin-2-ylmethoxy)-phenylamino]-7-ethoxy-quinazolin-6-yl}-amide The procedure of Example 166 was repeated except for using N$^4$-[3-methyl-4-(pyridin-2-ylmethoxy)-phenyl]-7-ethoxy-quinazolin-4,6-diamine instead of the compound obtained in (166-2) of Example 166 to obtain the title compound (130 mg, 15%).

$^1$H-NMR (CDCl$_3$, 300 MHz): δ 9.81 (s, 1H), 9.45 (s, 1H), 8.95 (s, 1H), 8.57 (m, 2H), 7.66 (m, 1H), 7.50 (d, 1H), 7.22 (d, 1H), 7.18 (d, 2H), 6.75 (d, 1H), 6.54 (m, 2H), 5.84 (m, 1H), 5.18 (s, 2H), 4.95 (d, 1H), 4.24 (m, 2H), 3.76 (m, 1H), 3.64 (m, 1H), 2.39 (s, 1H), 2.28 (s, 3H), 2.04 (m, 3H), 1.27 (t, 3H).

Example 187

Preparation of (2S)-1-acryloyl-pyrrolidine-2-carboxylic acid [4-[3-chloro-4-(pyridin-2-ylmethoxy)-phenylamino]-7-(2-fluoro-ethoxy)-quinazolin-6-yl]-amide The procedure of Example 166 was repeated except for using N$^4$-[3-chloro-4-(pyridin-2-ylmethoxy)-phenyl]-7-(2-fluoro-ethoxy)-quinazolin-4,6-diamine instead of the compound obtained in (166-2) of Example 166 to obtain the title compound (155 mg, 33%).

$^1$H-NMR (CDCl$_3$, 300 MHz): δ 10.05 (s, 1H), 8.85 (s, 1H), 8.52 (m, 2H), 7.77 (d, 1H), 7.68 (td, 1H), 7.59 (d, 1H), 7.55 (m, 1H), 7.44 (dd, 1H), 7.18 (d, 1H), 7.12 (d, 1H), 6.94 (d, 1H), 6.48 (d, 2H), 5.76 (t, 1H), 5.22 (s, 2H), 4.92 (m, 2H), 4.80 (m, 1H), 4.34 (m, 1H), 4.25 (m, 1H), 3.70 (m, 1H), 3.56 (q, 1H), 2.55 (m, 1H), 2.05 (m, 3H).

Example 188

Preparation of (2S)-1-acryloyl-pyrrolidine-2-carboxylic acid {4-[1-(3-fluoro-benzyl)-1H-indazol-5-ylamino]-7-methoxy-quinazolin-6-yl}-amide The procedure of Example 166 was repeated except for using-N$^4$-[1-(3-fluoro-benzyl)-1H-indazol-5-yl)-7-methoxy-quinazolin-4,6-diamine instead of the compound obtained in (166-2) of Example 166 to obtain the title compound (150 mg, 25%).

$^1$H-NMR (CDCl$_3$, 300 MHz): δ 9.71 (s, 1H), 8.92 (s, 1H), 8.52 (s, 1H), 7.98 (m, 2H), 7.73 (bs, 1H), 7.48 (dd, 1H), 7.19 (m, 3H), 6.91 (m, 2H), 6.82 (m, 1H), 6.46 (m, 2H), 5.74 (m, 1H), 5.51 (s, 2H), 4.84 (m, 1H), 4.01 (s, 3H), 3.73 (m, 1H), 3.55 (m, 1H), 2.98 (m, 2H), 2.47 (m, 1H), 2.05 (m, 1H).

Example 189

Preparation of (1R)—N-(1-{4-[3-chloro-4-(pyridin-2-ylmethoxy)-phenylamino]-7-methoxy-quinazolin-6-ylcarbamoyl}-ethyl)-acrylamide The procedure of Example 166 was repeated except for using (2S)-2-t-buthoxycarbonylamino-propionic acid instead of (2S)-pyrrolidine-1,2-dicarboxylic acid-1-t-butylester to obtain the title compound (49 mg, 6%).

$^1$H-NMR (CD$_3$OD, 300 MHz): δ 8.69 (s, 1H), 8.49 (d, 1H), 8.35 (s, 1H), 7.81 (m, 2H), 7.64 (d, 1H), 7.51 (dd, 1H), 7.33 (m, 1H), 7.10 (d, 1H), 6.30 (d, 1H), 6.26 (d, 1H), 5.68 (dd, 2H), 5.20 (s, 2H), 4.67 (q, 1H), 4.01 (s, 3H), 1.44 (d, 3H).

Example 190

Preparation of (1S)—N-(1-{4-[3-chloro-4-(pyridin-2-ylmethoxy)-phenylamino]-7-methoxy-quinazolin-6-ylcarbamoyl}-ethyl)-acrylamide The procedure of Example 166 was repeated except for using (2R)-2-t-buthoxycarbonylamino-propionic acid instead of (2S)-pyrrolidine-1,2-dicarboxylic acid-1-t-butylester to obtain the title compound (32 mg, 7%).

$^1$H-NMR (CD$_3$OD, 300 MHz): δ 8.72 (s, 1H), 8.45 (d, 1H), 8.32 (s, 1H), 7.80 (td, 2H), 7.78 (d, 1H), 7.62 (d, 1H), 7.47 (dd, 1H), 7.30 (m, 1H), 7.10 (s, 1H), 7.05 (d, 1H), 6.25 (d, 2H), 6.23 (d, 1H), 5.66 (dd, 1H), 5.17 (s, 2H), 4.64 (m, 1H), 3.95 (s, 3H), 1.39 (d, 3H).

Example 191

Preparation of (1S)—N-(1-{4-[3-chloro-4-(pyridin-2-ylmethoxy)-phenylamino]-7-methoxy-quinazolin-6-ylcarbamoyl}ethyl)-N-methyl-acrylamide The procedure of Example 166 was repeated except for using (2R)-2-(t-buthoxycarbonyl-methyl-amino)-propionic acid instead of (2S)-pyrrolidine-1,2-dicarboxylic acid-1-t-butylester to obtain the title compound (24 mg, 6%).

$^1$H-NMR (CD$_3$OD, 300 MHz): δ 8.56 (s, 1H), 8.43 (d, 1H), 8.26 (s, 1H), 7.79 (td, 2H), 7.72 (d, 1H), 7.58 (d, 1H), 7.41 (dd, 1H), 7.26 (m, 1H), 6.97 (s, 1H), 6.94 (dd, 1H), 6.68 (d, 1H), 5.73 (d, 1H), 5.24 (m, 1H), 5.22 (s, 3H), 4.45 (br s, 1H), 3.87 (s, 3H), 3.20 (s, 3H), 1.41 (d, 3H).

Example 192

Preparation of N-(2-{4-[3-chloro-4-(pyridin-2-ylmethoxy)-phenylamino]-7-fluoro-quinazolin-6-ylcarbamoyl}-ethyl)-acrylamide The procedure of Example 165 was repeated except for using (3-t-buthoxycarbonylamino-propionic acid instead of (2S)-pyrrolidine-1,2-dicarboxylic acid-1-t-butylester to obtain the title compound (60 mg, 19%).

$^1$H-NMR (CDCl$_3$, 300 MHz): δ 8.79 (m, 1H), 8.55 (m, 2H), 7.86 (s, 1H), 7.76 (t, 1H), 7.66 (m, 2H), 7.52 (m, 3H), 7.22 (m, 1H), 7.01 (d, 1H), 6.30 (m, 1H), 6.10 (m, 1H), 5.65 (m, 1H), 5.26 (s, 2H), 3.65 (m, 2H), 2.74 (m, 2H); MS (ESI): [M+Na]+ 543.

Example 193

Preparation of (2S)-1-acryloyl-pyrrolidine-2-carboxylic acid [7-methoxy-4-(1-penta-2,4-dienyl-1H-indazol-5-ylamino)-quinazolin-6-yl]-amide The procedure of Example 166 was repeated except for using N$^4$-[1-benzyl-1H-indazol-5-yl)-7-methoxy-quinazolin-4,6-diamine instead of the compound obtained in (166-2) of Example 166 to obtain the title compound (52 mg, 22%).

$^1$H-NMR (CDCl$_3$, 300 MHz): δ 9.81 (s, 1H), 8.99 (s, 1H), 8.61 (s, 1H), 8.00 (s, 2H), 7.72-7.69 (m, 2H), 7.55-7.51 (m, 2H), 7.37 (m, 5H), 6.54 (dd, 2H), 5.84 (d, 1H), 5.60 (s, 2H), 4.23 (m, 1H), 4.04 (s, 3H), 3.75-3.63 (m, 2H), 2.54 (m, 1H), 1.98 (m, 3H).

Example 194

Preparation of (2S)-1-acryloyl-pyrrolidine-2-carboxylic acid {4-[3-chloro-4-(6-methyl-pyridin-2-ylmethoxy)-phenylamino]-7-methoxy-quinazolin-6-yl}-amide The procedure of Example 166 was repeated except for using N$^4$-[3-chloro-4-(6-methyl-pyridin-2-ylmethoxy)-phenyl]-7-methoxy-quinazolin-4,6-diamine instead of the compound obtained in (166-2) of Example 166 to obtain the title compound (113 mg, 21%).

$^1$H-NMR (CDCl$_3$, 300 MHz): δ 9.76 (s, 1H), 8.89 (s, 1H), 8.59 (s, 1H), 7.83 (d, 1H), 7.71 (s, 1H), 7.50 (t, 1H), 7.49 (dd, 1H), 7.43 (d, 1H), 7.25 (s, 1H), 7.19 (s, 1H), 7.09 (d, 1H), 6.95 (d, 1H), 6.51 (m, 2H), 5.83 (dd, 1H), 5.78 (s, 2H), 4.92 (d, 1H), 3.99 (s, 3H) 3.75-3.62 (m, 2H) 2.57 (s, 3H) 2.55 (m, 1H) 2.08 (m, 3H).

Example 195

Preparation of 1-acryloyl-azetidine-2-carboxylic acid {4-[3-chloro-4-(pyridin-2-ylmethoxy)-phenylamino]-7-fluoro-quinazolin-6-yl}-amide The procedure of Example 165 was repeated except for using azetidine-1,2-dicarboxylic acid-1-t-butylester instead of (2S)-pyrrolidine-1,2-dicarboxylic acid-1-t-butylester to obtain the title compound (82 mg, 20%).

$^1$H-NMR (CD$_3$OD, 300 MHz): δ 8.97 (d, 1H), 8.57 (d, 1H), 8.49 (s, 1H), 7.92 (m, 2H), 7.73 (d, 1H), 7.60 (dd, 1H), 7.51 (d, 1H), 7.40 (m, 1H), 7.17 (d, 1H), 6.39 (m, 2H), 5.84 (dd, 1H), 5.29 (s, 2H), 5.20 (m, 1H), 4.35 (t, 2H), 2.66 (m, 2H).

Example 196

Preparation of 1-acryloyl-piperidine-2-carboxylic acid {4-[3-chloro-4-(pyridin-2-ylmethoxy)-phenylamino]-7-methoxy-quinazolin-6-yl}-amide The procedure of Example 166 was repeated except for using piperidine-1,2-dicarboxylic acid-1-t-butylester instead of (2S)-pyrrolidine-1,2-dicarboxylic acid-1-t-butylester to obtain the title compound (50 mg, 9%).

$^1$H-NMR (CDCl$_3$, 300 MHz): δ 9.07 (bs, 1H), 8.95 (s, 1H), 8.60 (m, 2H), 7.86 (d, 1H), 7.76 (m, 2H), 7.67 (d, 1H), 7.52 (dd, 1H), 7.23 (m, 2H), 6.99 (d, 1H), 6.70 (m, 1H), 6.41 (m, 1H), 5.82 (m, 1H), 5.48 (m, 1H), 5.29 (s, 2H), 4.00 (m, 1H), 3.97 (s, 3H), 3.20 (m, 1H), 2.39 (m, 1H), 1.70 (m, 5H).

Example 197

Preparation of 1-acryloyl-piperidine-4-carboxylic acid {4-[3-chloro-4-(pyridin-2-ylmethoxy)-phenylamino]-7-methoxy-quinazolin-6-yl}-amide The procedure of Example 166 was repeated except for using piperidine-1,4-dicarboxylic acid-1-t-butylester instead of (2S)-pyrrolidine-1,2-dicarboxylic acid-1-t-butylester to obtain the title compound (210 mg, 17%).

$^1$H-NMR (CDCl$_3$, 300 MHz): δ 8.96 (s, 1H), 8.58 (m, 2H), 8.15 (s, 1H), 7.93 (bs, 1H), 7.84 (d, 1H), 7.75 (m, 1H), 7.65 (d, 1H), 7.47 (dd, 1H), 7.28 (s, 1H), 7.22 (m, 1H), 6.97 (d, 1H), 6.59 (m, 1H), 6.29 (m, 1H), 5.71 (m, 1H), 5.27 (s, 2H), 4.70 (m, 1H), 4.04 (s, 3H), 3.24 (m, 1H), 2.85 (m, 1H), 2.34 (m, 4H), 1.82 (m, 2H).

Example 198

Preparation of 1-acryloyl-pyrrolidine-3-carboxylic acid {4-[3-chloro-4-(pyridin-2-ylmethoxy)-phenylamino]-7-methoxy-quinazolin-6-yl}-amide The procedure of Example 166 was repeated except for using piperidine-1,3-dicarboxylic acid-1-t-butylester instead of (2S)-pyrrolidine-1,2-dicarboxylic acid-1-t-butylester to obtain the title compound (110 mg, 27%).
$^1$H-NMR (CDCl$_3$, 300 MHz): δ 8.86 (s, 1H), 8.53 (m, 2H), 8.15 (d, 1H), 7.86 (bs, 1H), 7.75 (m, 1H), 7.65 (m, 1H), 7.58 (d, 1H), 7.41 (dd, 1H), 7.17 (m, 2H), 6.88 (d, 1H), 6.35 (m, 2H), 5.64 (m, 1H), 5.19 (s, 2H), 3.94 (s, 3H), 3.81 (m, 3H), 3.55 (m, 1H), 3.14 (m, 1H), 2.27 (m, 2H).

Example 199

Preparation of 1-acryloyl-azetidine-2-carboxylic acid {4-[3-chloro-4-(pyridin-2-ylmethoxy)-phenylamino]-7-ethoxy-quinazolin-6-yl}-amide The procedure of Example 170 was repeated except for using azetidine-1,2-dicarboxylic acid-1-t-butylester instead of (2S)-pyrrolidine-1,2-dicarboxylic acid-1-t-butylester to obtain the title compound (85 mg, 25%).
$^1$H-NMR (CD$_3$OD, 300 MHz): δ 9.10 (d, 1H), 8.74 (d, 1H), 8.64 (d, 1H), 8.09 (m, 2H), 7.90 (d, 1H), 7.77 (m, 2H), 7.57 (m, 1H), 7.35 (m, 1H), 6.53 (m, 2H), 6.02 (dd, 1H), 5.46 (s, 2H), 5.36 (m, 1H), 4.51 (m, 2H), 2.84 (m, 2H).

Example 200

Preparation of 1-acryloyl-azetidine-3-carboxylic acid {4-[3-chloro-4-(pyridin-2-ylmethoxy)-phenylamino]-7-methoxy-quinazolin-6-yl}-amide The procedure of Example 166 was repeated except for using azetidine-1,3-dicarboxylic acid-1-t-butylester instead of (2S)-pyrrolidine-1,2-dicarboxylic acid-1-t-butylester to obtain the title compound (70 mg, 26%).
$^1$H-NMR (CDCl$_3$, 300 MHz): δ 9.04 (s, 1H), 8.64 (m, 2H), 8.20 (s, 1H), 7.98 (bs, 1H), 7.89 (d, 1H), 7.80 (m, 1H), 7.70 (d, 1H), 7.54 (dd, 1H), 7.27 (m, 2H), 7.02 (d, 1H), 6.43 (m, 1H), 6.26 (m, 1H), 5.76 (m, 1H), 5.32 (s, 2H), 4.61 (m, 1H), 4.40 (m, 3H), 4.07 (s, 3H), 3.61 (m, 1H).

Example 201

Preparation of (3S)-1-acryloyl-piperidine-3-carboxylic acid {4-[3-chloro-4-(pyridin-2-ylmethoxy)-phenylamino]-7-methoxy-quinazolin-6-yl}-amide The procedure of Example 166 was repeated except for using (3S)-piperidine-1,3-dicarboxylic acid-1-t-butylester instead of (2S)-pyrrolidine-1,2-dicarboxylic acid-1-t-butylester to obtain the title compound (50 mg, 30%).
$^1$H-NMR (CDCl$_3$, 300 MHz): δ 8.95 (bs, 1H), 8.60 (m, 3H), 8.29 (bs, 1H), 7.84 (d, 1H), 7.75 (m, 1H), 7.66 (d, 1H), 7.50 (dd, 1H), 7.24 (m, 2H), 6.98 (d, 1H), 6.57 (m, 1H), 6.31 (m, 1H), 5.73 (m, 1H), 5.28 (s, 2H), 4.78 (m, 1H), 4.02 (m, 1H), 3.97 (s, 3H), 3.20 (m, 1H), 2.57 (m, 1H), 2.18 (m, 3H), 1.90 (m, 1H), 1.57 (m, 1H).

Example 202

Preparation of N-((1S)-1-{4-[3-chloro-4-(pyridin-2-ylmethoxy)-phenylamino]-7-methoxy-quinazolin-6-ylcarbamoyl}-ethyl)-N-ethyl-acrylamide The procedure of Example 166 was repeated except for using (2S)-2-(t-buthoxycarbonyl-ethyl-amino)-propionic acid instead of (2S)-pyrrolidine-1,2-dicarboxylic acid-1-t-butylester to obtain the title compound (7 mg, 7%).
$^1$H-NMR (CDCl$_3$, 300 MHz): δ 9.17 (s, 1H), 8.83 (s, 1H), 8.53 (m, 2H), 7.78 (m, 1H), 7.70 (td, 1H), 7.61 (s, 1H), 7.58 (d, 1H), 7.45 (dd, 1H), 7.16 (s, 1H), 7.14 (s, 1H), 6.92 (d, 1H), 6.53 (m, 1H), 5.75 (dd, 1H), 5.21 (s, 2H), 4.08 (m, 1H), 3.95 (s, 3H), 3.48 (q, 2H), 1.45 (d, 3H), 1.19 (t, 3H).

Example 203

Preparation of (2S)-1-acryloyl-pyrrolidine-2-carboxylic acid {4-[3-chloro-4-(2-fluoro-ethoxy)-phenylamino]-7-methoxy-quinazolin-6-yl}-amide The procedure of Example 166 was repeated except for using N$^4$-[3-chloro-4-(2-fluoro-ethoxy)-phenyl]-7-methoxy-quinazolin-4,6-diamine instead of the compound obtained in (166-2) of Example 166 to obtain the title compound (110 mg, 34%).
$^1$H-NMR (CDCl$_3$, 300 MHz): δ 8.99 (s, 1H) 8.62 (s, 1H), 7.83 (d, 1H), 7.60 (s, 1H), 7.56 (dd, 1H), 7.00 (d, 1H), 6.51 (m, 2H), 5.83 (dd, 1H), 4.88 (t, 1H), 4.73 (t, 1H), 4.50 (m, 1H), 4.35 (t, 1H), 4.26 (t, 1H), 3.98 (s, 3H), 3.48 (m, 2H), 2.20 (m, 1H), 1.98 (m, 1H), 1.89 (m, 2H).

Example 204

Preparation of (2S)-1-acryloyl-pyrrolidine-2-carboxylic acid {4-[3-chloro-4-(pyridin-3-ylmethoxy)-phenylamino]-7-methoxy-quinazolin-6-yl}-amide The procedure of Example 166 was repeated except for using N$^4$-[3-chloro-4-(pyridin-3-ylmethoxy)-phenyl]-7-methoxy-quinazolin-4,6-diamine instead of the compound obtained in (166-2) of Example 166 to obtain the title compound (19 mg, 11%).
$^1$H-NMR (CD$_3$OD, 300 MHz): δ 8.86 (s, 1H), 8.85 (s, 1H), 8.73 (s, 1H), 8.72 (s, 1H), 8.21 (d, 1H), 8.11 (d, 1H), 7.93-7.98 (m, 2H), 7.85 (dd, 1H), 7.43 (d, 1H), 6.37-6.44 (m, 2H), 5.82-5.86 (m, 1H), 5.46 (s, 2H), 4.80 (m, 1H), 3.96 (s, 3H), 3.51 (m, 2H), 2.24 (m, 1H), 1.78-1.99 (m, 3H).

Example 205

Preparation of (2S)-2-acryloylamino-N-{4-[3-chloro-4-(pyridin-2-ylmethoxy)-phenylamino]-7-methoxy-quinazolin-6-yl}-butyramide The procedure of Example 166 was repeated except for using (2S)-2-(t-buthoxycarbonylamino)-butanoic acid instead of (2S)-pyrrolidine-1,2-dicarboxylic acid-1-t-butylester to obtain the title compound (180 mg, 32%).
$^1$H-NMR (CDCl$_3$, 300 MHz): δ 8.86 (s, 1H), 8.73 (s, 1H), 8.59 (m, 2H), 7.76 (m, 3H), 7.65 (d, 1H), 7.49 (m, 1H), 7.25 (m, 1H), 7.19 (s, 1H), 6.96 (d, 1H), 6.39 (m, 1H), 6.23 (m, 1H), 5.75 (m, 1H), 5.27 (s, 2H), 4.66 (m, 1H), 4.00 (s, 3H), 2.04 (m, 2H), 1.05 (t, 3H).

Example 206

Preparation of N-(2-{4-[3-chloro-4-(pyridin-2-yl-methoxy)-phenylamino]-7-methoxy-quinazolin-6-ylcarbamoyl}-2-fluoro-ethyl)-acrylamide The procedure of Example 166 was repeated except for using 3-t-buthoxycarbonylamino-2-fluoro-propionic acid instead of (2S)-pyrrolidine-1,2-dicarboxylic acid-1-t-butylester to obtain the title compound (59 mg, 17%).

$^1$H-NMR (CD$_3$OD, 300 MHz): δ 8.65 (s, 1H), 8.34 (d, 1H), 8.22 (s, 1H), 7.70 (td, 1H), 7.67 (s, 1H), 7.50 (d, 1H), 7.37 (dd, 1H), 7.18 (m, 1H), 7.02 (s, 1H), 6.94 (d, 1H), 6.03 (m, 2H), 5.45 (dd, 1H), 5.15 (m, 1H), 5.06 (s, 2H), 3.86 (s, 3H), 3.75 (m, 1H), 3.66 (m, 1H).

Example 207

Preparation of (2S)-1-acryloyl-pyrrolidine-2-carboxylic acid {4-[3-chloro-4-(pyridin-3-ylmethoxy)-phenylamino]-7-(1-methyl-piperidin-4-ylmethoxy)-quinazolin-6-yl}-amide 385 mg of (2S)-pyrrolidine-2-carboxylic acid [4-[3-chloro-4-(pyridin-2-ylmethoxy)-phenylamino-7-(1-methyl-piperidin-4-ylmethoxy)-quinazolin-6-yl]-amide as a starting material was dissolved in 10 ml of THF, and cooled to 0° C. 0.09 ml of acrylic acid and 0.1 ml of pyridine were added thereto, and the resulting solution was reacted with 0.37 g of 1-(3-dimethylaminopropyl)-3-ethylcarbodiimide hydrochloride at 0° C. for 30 mins and then stirred for 2 hours while heating to room temperature. The reacted solution was extracted with a mixture of chloroform and isopropanol after adding water, washed with water and saturated saline solution, dried over anhydrous sodium sulfate, filtered and distilled under a reduced pressure, and the resulting residue was subjected to column chromatography (eluent-chloroform:methanol=15:1) to obtain the title compound (68 mg, 16%).

$^1$H-NMR (CD$_3$OD, 300 MHz): δ 8.71 (s, 1H), 8.55 (d, 1H), 8.40 (s, 1H), 7.89 (m, 2H), 7.70 (d, 1H), 7.56 (dd, 1H), 7.38 (m, 1H), 7.13 (m, 2H), 6.72 (m, 1H), 6.35 (m, 1H), 5.83 (m, 1H), 5.24 (s, 2H), 3.99 (d, 2H), 2.91 (m, 2H), 2.32 (s, 3H), 2.15 (m, 3H), 1.94 (m, 2H), 1.48 (m, 2H).

Example 208

Preparation of (1R)—N-(1-{4-[3-chloro-4-(pyridin-2-ylmethoxy)-phenylamino]-7-(2-methoxy-ethoxy)-quinazolin-6-ylcarbamoyl}-ethyl)-acrylamide 75 µl of acrylic acid was dissolved in 4 ml of THF, and cooled to 0° C. 180 µl of pyridine and 520 ml of 1-(3-dimethylaminopropyl)-3-ethylcarbodiimide hydrochloride were added thereto, the resulting solution was reacted with 284 mg of 2-amino-N-[4-[3-chloro-4-(pyridin-2-ylmethoxy)-phenylamino]-7-(2-methoxy-ethoxy)-quinazolin-6-yl]-propionamide dissolved in 4 ml of THF as a starting material for 30 mins, and then stirred for 3 hours while heating to room temperature. The reacted solution was washed with saturated sodium bicarbonate solution, extracted with a mixture of chloroform and methanol, dried over sodium sulfate, filtered and distilled under a reduced pressure, and the resulting residue was subjected to column chromatography (eluent-chloroform:methanol=15:1) to obtain the title compound (87 mg, 28%).

$^1$H-NMR (DMSO-d$_6$ 300 MHz): δ 9.71 (s, 1H), 9.42 (s, 1H), 8.84 (s, 1H), 8.61 (m, 1H), 8.59 (s, 1H), 8.47 (s, 1H), 7.96 (d, 1H), 7.88 (td, 1H), 7.67 (dd, 1H), 7.58 (d, 1H), 7.36 (m, 1H), 7.28 (s, 1H), 7.23 (d, 1H), 6.38 (m, 1H), 6.17 (m, 1H), 5.69 (m, 1H), 5.29 (s, 1H), 4.70 (m, 1H), 4.32 (t, 2H), 3.77 (t, 2H), 3.35 (s, 3H), 1.41 (d, 3H).

Example 209

Preparation of (2S)-1-acryloyl-pyrrolidine-2-carboxylic acid {4-[3-chloro-4-(pyridin-3-ylmethoxy)-phenylamino]-7-(3-morpholin-4-yl-propoxy)-quinazolin-6-yl}-amide 230 mg of (2S)-pyrrolidine-2-carboxylic acid [4-[3-chloro-4-(pyridin-2-ylmethoxy)-phenylamino-7-(3-morpholin-4-ylpropoxy)-quinazolin-6-yl]-amide as a starting material was dissolved in 10 ml of THF, and cooled to 0° C. The solution was reacted with 0.05 ml of acrylic acid, 0.06 ml of pyridine and 0.21 g of 1-(3-dimethylaminopropyl)-3-ethylcarbodiimide hydrochloride at 0° C. for 30 min and at room temperature for 3 hours. The reacted solution was extracted with a mixture of isopropanol and chloroform (1:3) after adding water, washed with saturated saline solution, dried over anhydrous sodium sulfate, filtered and distilled under a reduced pressure, and the resulting residue was subjected to column chromatography (eluent-chloroform:methanol=15:1) to obtain the title compound (120 mg, 48%).

$^1$H-NMR (CDCl$_3$, 300 MHz): δ 9.98 (s, 1H), 8.91 (s, 1H), 8.59 (m, 2H), 7.95 (bs, 1H), 7.84 (d, 1H), 7.76 (m, 1H), 7.65 (d, 1H), 7.52 (dd, 1H), 7.26 (m, 1H), 7.18 (s, 1H), 6.96 (d, 1H), 6.53 (m, 2H), 5.81 (m, 1H), 5.27 (s, 2H), 4.95 (m, 1H), 4.18 (t, 2H), 3.73 (m, 5H), 3.61 (m, 1H), 2.65 (m, 4H), 2.52 (m, 4H), 2.15 (m, 2H), 2.04 (m, 1H), 1.95 (m, 1H).

Example 210

Preparation of N-({4-[3-chloro-4-(pyridin-2-yl-methoxy)-phenylamino]-7-methoxy-quinazolin-6-ylcarbamoyl}-methyl)-acrylamide The procedure of Example 145 was repeated except for using tert-buthoxycarbonylamino-acetic acid instead of (2S)-pyrrolidine-1,2-dicarboxylic acid-1-t-butylester to obtain the title compound (36 mg, 10%).

$^1$H-NMR (CDCl$_3$, 300 MHz): δ 8.78 (s, 1H), 8.59 (s, 1H), 8.58 (d, 1H), 7.91 (d, 1H), 7.78 (td, 1H), 7.69 (d, 1H), 7.58 (dd, 1H), 7.25 (m, 1H), 7.22 (s, 1H), 7.03 (d, 1H), 6.42 (dd, 1H), 6.26 (dd, 1H), 5.79 (dd, 1H), 5.30 (s, 2H), 4.22 (s, 2H), 4.05 (s, 3H).

Example 211

Preparation of N-({4-[3-chloro-4-(3-fluoro-benzyloxy)-phenylamino]-7-methoxy-quinazolin-6-ylcarbamoyl}-methyl)-acrylamide 170 mg of 2-amino-N-{4-[3-chloro-4-(3-fluoro-benzyloxy)-phenylamino]-7-methoxy-quinazolin-6-yl}-acetamide as a starting material was dissolved in 5 ml of THF, and cooled to 0° C. The solution was reacted with 0.04 ml of acrylic acid, 0.06 ml of pyridine and 134 mg of 1-(3-dimethylaminopropyl)-3-ethylcarbodiimide hydrochloride at 0° C. for 1 hour and at room temperature for 5 hours. The reacted solution was extracted with chloroform after adding saturated sodium bicarbonate, dried over anhydrous sodium sulfate, filtered and distilled under a reduced pressure, and the resulting residue was subjected to column chromatography (eluent-ethylacetate methanol=10:1) to obtain the title compound (51 mg, 27%).

¹H-NMR (CDCl₃, 300 MHz): δ 8.75 (s, 1H), 8.58 (s, 1H), 7.86 (d, 1H), 7.56 (dd, 1H), 7.36 (m, 1H), 7.24 (d, 2H), 7.19 (s, 1H), 6.99 (t, 1H), 6.96 (d, 1H), 6.40 (dd, 1H), 6.27 (dd, 1H), 5.79 (dd, 1H), 5.15 (s, 2H), 4.22 (s, 2H), 4.01 (s, 3H).

Example 212

Preparation of (3S)-3-acryloylamino-N-{4-[3-chloro-4-(pyridin-2-ylmethoxy)-phenylamino]-7-methoxy-quinazolin-6-yl}-butyramide 36 mg of (3S)-amino-N-{4-[3-chloro-4-(pyridin-2-ylmethoxy)-phenylamino]-7-methoxy-quinazolin-6-yl}-butyramide as a starting material was dissolved in 3 ml of THF, and cooled to 0° C. The solution was reacted with 0.01 ml of acrylic acid, 0.01 ml of pyridine and 0.042 g of 1-(3-dimethylaminopropyl)-3-ethylcarbodiimide hydrochloride at 0° C. for 30 mins and at room temperature for 2 hours. The reacted solution was extracted with a mixture of chloroform and isopropanol after adding water, washed with saturated saline solution, dried over anhydrous sodium sulfate, filtered and distilled under a reduced pressure, and the resulting residue was subjected to column chromatography (eluent-ethylacetate:methanol=15:1) to obtain the title compound (6 mg, 15%).

¹H-NMR (CDCl₃, 300 MHz): δ 9.09 (s, 1H), 8.61 (m, 2H), 7.89 (d, 1H), 7.76 (m, 1H), 7.66 (m, 1H), 7.51 (dd, 1H), 7.24 (m, 2H), 7.01 (d, 1H), 6.42 (m, 1H), 6.36 (m, 1H), 5.87 (dd, 1H), 5.30 (s, 2H), 4.05 (s, 3H), 4.03 (m, 1H), 2.03 (d, 2H), 1.25 (d, 3H).

Example 213

Preparation of (2S)-1-acryloyl-pyrrolidine-2-carboxylic acid {4-[3-chloro-4-(pyridin-2-ylmethoxy)-phenylamino]-7-(2-methoxyethoxy)-quinazolin-6-yl}-amide 302 mg of (2S)-pyrrolidine-2-carboxylic acid {4-[3-chloro-4-(pyridin-2-ylmethoxy)-phenylamino]-7-(2-methoxyethoxy)-quinazolin-6-yl}-amide as a starting material was dissolved in 10 ml of THF, and cooled to 0° C. The solution was reacted with 0.15 ml of acrylic acid, 0.18 ml of pyridine and 0.53 g of 1-(3-dimethylaminopropyl)-3-ethylcarbodiimide hydrochloride at 0° C. for 30 mins and at room temperature for 2 hours. The reacted solution was extracted with a mixture of chloroform and isopropanol after adding water, washed with saturated saline solution, dried over anhydrous sodium sulfate, filtered and distilled under a reduced pressure, and the resulting residue was subjected to column chromatography (eluent-ethylacetate:methanol=30:1) to obtain the title compound (31 mg, 9%).

¹H-NMR (CD₃OD, 300 MHz): δ 9.71 (s, 1H), 8.79 (d, 1H), 8.66 (s, 1H), 8.13 (m, 2H), 7.95 (d, 1H), 7.81 (dd, 1H), 7.62 (m, 1H), 7.45 (s, 1H), 7.38 (d, 1H), 6.93 (m, 1H), 6.61 (m, 1H), 6.07 (m, 1H), 5.50 (s, 2H), 4.58 (t, 2H), 4.12 (t, 2H), 4.02 (m, 1H), 2.49 (m, 2H), 2.32 (m, 2H).

Example 214

Preparation of (1S)—N-(1-{4-[3-chloro-4-(3-fluoro-benzyloxy)-phenylamino]-7-(2-methoxyethoxy)-quinazolin-6-ylcarbamoyl}-ethyl)-acrylamide 205 mg of (2S)-amino-N-{4-[3-chloro-4-(3-fluoro-benzyloxy)-phenylamino]-7-(2-methoxyethoxy)-quinazolin-6-yl}-propionamide as a starting material was dissolved in 10 ml of a mixture of THF and water (3:1), and reacted with 0.047 ml of acryloylchloride at room temperature for 1 hour after adding 97 mg of sodium bicarbonate. The reacted solution was extracted with a mixture of chloroform and isopropanol after adding water, washed with saturated saline solution, dried over anhydrous sodium sulfate, filtered and distilled under a reduced pressure, and the resulting residue was subjected to column chromatography (eluent-ethylacetate:methanol=30:1) to obtain the title compound (55 mg, 24%).

¹H-NMR (DMSO-d₆, 300 MHz): δ 9.71 (s, 1H), 9.42 (s, 1H), 8.83 (s, 1H), 8.61 (d, 1H), 8.47 (s, 1H), 7.49 (d, 1H), 7.66 (dd, 1H), 7.46 (m, 1H), 7.25 (m, 5H), 6.34 (m, 1H), 6.21 (m, 1H), 5.68 (m, 1H), 5.24 (s, 2H), 4.70 (m, 1H), 4.32 (t, 2H), 3.78 (t, 2H), 1.41 (d, 3H).

Example 215

Preparation of (2S)-1-acryloyl-pyrrolidine-2-carboxylic acid {4-[3-chloro-4-(3-fluoro-benzyloxy)-phenylamino]-7-(2-methoxyethoxy)-quinazolin-6-yl}-amide 288 mg of (2S)-pyrrolidine-2-carboxylic acid {4-[3-chloro-4-(3-fluoro-benzyloxy)-phenylamino]-7-(2-methoxyethoxy)-quinazolin-6-yl}-amide as a starting material was dissolved in 10 ml of THF, and cooled to 0° C. The solution was reacted with 0.07 ml of acrylic acid, 0.17 ml of pyridine and 0.29 g of 1-(3-dimethylaminopropyl)-3-ethylcarbodiimide hydrochloride at 0° C. for 30 mins and at room temperature for 2 hours. The reacted solution was extracted with a mixture of chloroform and isopropanol after adding water, washed with saturated saline solution, dried over anhydrous sodium sulfate, filtered and distilled under a reduced pressure, and the resulting residue was subjected to column chromatography (eluent-ethylacetate:methanol=30:1) to obtain the title compound (52 mg, 17%).

¹H-NMR (DMSO-d₆, 300 MHz): δ 9.78 (s, 1H), 9.54 (s, 1H), 8.82 (s, 1H), 8.47 (d, 1H), 7.67 (m, 1H), 7.43 (m, 1H), 7.26 (m, 5H), 6.69 (m, 1H), 6.23 (m, 1H), 5.78 (m, 1H), 5.24 (s, 2H), 4.76 (m, 1H), 4.35 (t, 2H), 3.78 (t, 2H), 3.64 (m, 2H), 2.11 (m, 2H), 2.01 (m, 2H).

Example 216

Preparation of (1S)—N-(1-{4-[3-chloro-4-(pyridin-2-ylmethoxy)-phenylamino]-7-methoxy-quinazolin-6-ylcarbamoyl}-ethyl)-acrylamide 300 mg of (2S)-amino-N-{4-[3-chloro-4-(pyridin-2-ylmethoxy)-phenylamino]-7-ethoxy-quinazolin-6-yl}-propionamide as a starting material was dissolved in 9 ml of THF and 3 ml of water, and reacted with 0.06 ml of acryloylchloride at room temperature for 1 hour after adding 153 mg of sodium bicarbonate. The reacted solution was extracted with a mixture of chloroform and isopropanol after adding water, washed with saturated saline solution, dried over anhydrous sodium sulfate, filtered and distilled under a reduced pressure, and the resulting residue was subjected to column chromatography (eluent-ethylacetate:methanol=15:1) to obtain the title compound (11 mg, 3%).

¹H-NMR (CDCl₃, 300 MHz): δ 9.05 (bs, 1H), 8.90 (s, 1H), 8.60 (m, 2H), 7.84 (d, 1H), 7.76 (m, 1H), 7.66 (m, 1H), 7.49 (m, 2H), 7.23 (m, 2H), 6.98 (d, 1H), 6.41 (m, 1H), 6.19 (m, 2H), 5.77 (m, 1H), 5.29 (s, 2H), 4.84 (m, 1H), 4.23 (m, 2H), 2.02 (d, 3H), 1.55 (t, 3H).

Example 217

Preparation of N-({4-[3-chloro-4-(3-fluoro-benzyloxy)-phenylamino]-7-(2-methoxyethoxy)-quinazolin-6-ylcarbamoyl}-methyl)-acrylamide 320 mg of 2-amino-N-{4-[3-chloro-4-(3-fluoro-benzyloxy)-phenylamino]-7-(2-methoxyethoxy)-quinazolin-6-yl}-acetamide as a starting material was dissolved in 10 ml of THF, and cooled to 0° C. The solution was reacted with 0.06 ml of acrylic acid, 0.1 ml of pyridine and 234 mg of 1-(3-dimethylaminopropyl)-3-ethylcarbodiimide hydrochloride at 0° C. for 1 hour and at room temperature for 5 hours. The reacted solution was extracted with a mixture of chloroform and isopropanol after adding saturated sodium bicarbonate, dried over anhydrous sodium sulfate, filtered and distilled under a reduced pressure, and the resulting residue was subjected to column chromatography (eluent-ethylacetate:methanol=30:1) to obtain the title compound (96 mg, 27%).

$^1$H-NMR (CDCl$_3$, 300 MHz): δ 8.78 (s, 1H), 8.52 (s, 1H), 7.84 (d, 1H), 7.55 (dd, 1H), 7.35 (m, 1H), 7.23 (m, 2H), 7.15 (s, 1H), 7.02 (t, 1H), 6.98 (d, 1H), 6.38 (dd, 1H), 6.30 (dd, 1H), 5.76 (dd, 1H), 5.15 (s, 2H), 4.31 (m, 2H), 4.24 (s, 2H), 3.87 (m, 2H), 3.50 (s, 3H).

Example 218

Preparation of N-({4-[3-chloro-4-(pyridin-2-ylmethoxy)-phenylamino]-7-(2-methoxyethoxy)-quinazolin-6-ylcarbamoyl}-methyl)-acrylamide 320 mg of 2-amino-N-{4-[3-chloro-4-(3-pyridin-2-ylmethoxy)-phenylamino]-7-(2-methoxyethoxy)-quinazolin-6-yl}-acetamide as a starting material was dissolved in 10 ml of THF, and cooled to 0° C. The solution was reacted with 0.07 ml of acrylic acid, 0.11 ml of pyridine and 257 mg of 1-(3-dimethylaminopropyl)-3-ethylcarbodiimide hydrochloride at 0° C. for 1 hour and at room temperature for 5.5 hours. The reacted solution was extracted with a mixture of chloroform and isopropanol after adding saturated sodium bicarbonate, dried over anhydrous sodium sulfate, filtered and distilled under a reduced pressure, and the resulting residue was subjected to column chromatography (eluent-ethylacetate:methanol=10:1) to obtain the title compound (45 mg, 12%).

$^1$H-NMR (CDCl$_3$, 300 MHz): δ 8.80 (s, 1H), 8.57 (d, 1H), 8.55 (s, 1H), 7.89 (d, 1H), 7.79 (td, 1H), 7.70 (d, 1H), 7.57 (dd, 1H), 7.28 (m, 1H), 7.18 (s, 1H), 7.02 (d, 1H), 6.42 (dd, 1H), 6.29 (dd, 1H), 5.77 (dd, 1H), 5.29 (s, 2H), 4.32 (m, 2H), 4.25 (s, 2H), 3.87 (m, 2H), 3.50 (s, 3H).

Example 219

Preparation of (1S)—N-(1-{4-[3-chloro-4-(pyridin-2-ylmethoxy)-phenylamino]-7-(3-morpholin-4-ylpropoxy)-quinazolin-6-ylcarbamoyl}-ethyl)-acrylamide 500 mg of (2S)-2-amino-N-{4-[3-chloro-4-(pyridin-2-ylmethoxy)-phenylamino]-7-(3-morpholin-4-ylpropoxy)-quinazolin-6-yl}-propionamide as a starting material was dissolved in 12 ml of THF and 4 ml of water, and reacted with 0.08 ml of acryloylchloride at room temperature for 1.5 hours after adding 213 mg of sodium bicarbonate. The reacted solution was extracted with a mixture of chloroform and isopropanol after adding water, washed with water and saturated saline solution, dried over anhydrous sodium sulfate, filtered and distilled under a reduced pressure, and the resulting residue was subjected to column chromatography (eluent-ethylacetate:methanol=15:1) to obtain the title compound (180 mg, 33%).

$^1$H-NMR (CDCl$_3$, 300 MHz): δ 9.12 (s, 1H), 8.83 (s, 1H), 8.58 (d, 1H), 8.55 (s, 1H), 7.90 (s, 1H), 7.75 (m, 2H), 7.64 (d, 1H), 7.45 (dd, 1H), 7.24 (m, 1H), 7.13 (s, 1H), 6.91 (d, 1H), 6.79 (d, 1H), 6.37 (m, 1H), 6.20 (m, 1H), 5.72 (m, 1H), 5.23 (s, 2H), 4.80 (m, 1H), 4.14 (t, 2H), 3.71 (m, 4H), 2.56 (t, 2H), 2.47 (m, 4H), 2.06 (m, 2H), 1.50 (d, 3H).

Example 220

Preparation of (1S)—N-(1-{4-[3-chloro-4-(pyridin-2-ylmethoxy)-phenylamino]-7-(3-methoxypropoxy)-quinazolin-6-ylcarbamoyl}-ethyl)-acrylamide 400 mg of (2S)-2-amino-N-{4-[3-chloro-4-(pyridin-2-ylmethoxy)-phenylamino]-7-(3-methoxypropoxy)-quinazolin-6-yl}-propionamide as a starting material was dissolved in 10 ml of THF and 3 ml of water, and reacted with 0.07 ml of acryloylchloride at room temperature for 1.5 hours after adding 188 mg of sodium bicarbonate. The reacted solution was extracted with a mixture of chloroform and isopropanol after adding water, washed with water and saturated saline solution, dried over anhydrous sodium sulfate, filtered and distilled under a reduced pressure, and the resulting residue was subjected to column chromatography (eluent-ethylacetate:methanol=15:1) to obtain the title compound (110 mg, 25%).

$^1$H-NMR (CDCl$_3$, 300 MHz): δ 9.12 (s, 1H), 8.86 (s, 1H), 8.58 (m, 2H), 7.75 (m, 2H), 7.64 (m, 2H), 7.45 (dd, 1H), 7.26 (m, 1H), 7.17 (s, 1H), 6.94 (d, 1H), 6.53 (d, 1H), 6.39 (m, 1H), 6.20 (m, 1H), 5.75 (m, 1H), 5.26 (s, 2H), 4.82 (m, 1H), 4.22 (t, 2H), 3.63 (t, 2H), 3.37 (s, 3H), 2.17 (m, 2H), 1.52 (d, 3H); [M+H]+: 591.3.

Example 221

Preparation of (2S)-2-acryloylamino-N-{4-[3-chloro-4-(3-fluoro-benzyloxy)-phenylamino]-7-methoxy-quinazolin-6-yl}-4-methylsulfanyl-butyramide 297 mg of (2S)-2-amino-N-{4-[3-chloro-4-(pyridin-2-ylmethoxy)-phenylamino]-7-methoxy-quinazolin-6-yl}-4-methylsulfanyl-butyramide as a starting material was dissolved in 9 ml of THF and 3 ml of water, and reacted with 0.05 ml of acryloylchloride at room temperature for 1.5 hours after adding 139 mg of sodium bicarbonate. The reacted solution was extracted with a mixture of chloroform and isopropanol after adding water, washed with water and saturated saline solution, dried over anhydrous sodium sulfate, filtered and distilled under a reduced pressure, and the resulting residue was subjected to column chromatography (eluent-ethylacetate:methanol=15:1) to obtain the title compound (81 mg, 25%).

$^1$H-NMR (CDCl$_3$, 300 MHz): δ 8.90 (s, 1H), 8.82 (s, 1H), 8.59 (m, 2H), 7.75 (m, 2H), 7.65 (m, 2H), 7.48 (dd, 1H), 7.24 (m, 1H), 7.16 (s, 1H), 6.96 (d, 1H), 6.84 (d, 1H), 6.38 (m, 1H), 6.20 (m, 1H), 5.75 (m, 1H), 5.27 (s, 2H), 4.95 (m, 1H), 3.96 (s, 3H), 2.66 (m, 2H), 2.22 (m, 2H), 2.14 (s, 3H); [M+H]+: 593.2.

Example 222

Preparation of (2S)-2-acryloylamino-N-{4-[3-chloro-4-(3-fluoro-benzyloxy)-phenylamino]-7-(2-methoxyethoxy)-quinazolin-6-yl}-4-methylsulfanyl-butyramide 300 mg of (2S)-2-amino-N-{4-[3-chloro-4-(pyridin-2-ylmethoxy)-phenylamino]-7-(2-methoxyethoxy)-quinazolin-6-yl}-4-methylsulfanyl-butyramide as a starting material was dissolved in 9 ml of THF and 3 ml of water, and reacted with 0.05 ml of acryloylchloride at room temperature for 1.5 hours after adding 130 mg of sodium bicarbonate. The reacted solution was extracted with a mixture of chloroform and isopropanol after adding water, washed with water and saturated saline solution, dried over anhydrous sodium sulfate, filtered and distilled under a reduced pressure, and the resulting residue was subjected to column chromatography (eluent-ethylacetate:methanol=15:1) to obtain the title compound (80 mg, 25%).

$^1$H-NMR (CDCl$_3$, 300 MHz): δ 8.79 (s, 1H), 8.56 (m, 2H), 7.88 (d, 1H), 7.78 (m, 1H), 7.70 (d, 1H), 7.56 (dd, 1H), 7.28 (m, 1H), 7.19 (s, 1H), 7.02 (d, 1H), 6.50 (m, 1H), 6.28 (m, 1H), 5.76 (dd, 1H), 5.28 (s, 2H), 4.92 (m, 1H), 4.32 (m, 2H), 3.88 (m, 2H), 3.06 (s, 3H), 2.65 (m, 2H), 2.25 (m, 2H), 2.14 (s, 3H); [M+H]+: 637.3.

Example 223

Preparation of (2S)-2-acryloylamino-N-{4-[3-chloro-4-(3-fluoro-benzyloxy)-phenylamino]-7-methoxy-quinazolin-6-yl}-4-methanesulfinyl-butyramide 81 mg of 2-amino-N-{4-[3-chloro-4-(pyridin-2-ylmethoxy)-phenylamino]-7-methoxy-quinazolin-6-yl}-4-methylsulfanyl-butyramide as a starting material was dissolved in 3 ml of THF and 1 ml of water, and reacted with 0.05 ml of acryloylchloride at room temperature for 1 hour after adding 37 mg of sodium bicarbonate. The reacted solution was extracted with a mixture of chloroform and isopropanol after adding water, washed with water and saturated saline solution, dried over anhydrous sodium sulfate, filtered and distilled under a reduced pressure, and the resulting residue was subjected to column chromatography (eluent-ethylacetate:methanol=15:1) to obtain the title compound (62 mg, 70%).

$^1$H-NMR (CDCl$_3$, 300 MHz): δ 8.73 (s, 1H), 8.56 (m, 2H), 7.84 (d, 1H), 7.76 (m, 1H), 7.69 (d, 1H), 7.55 (dd, 1H), 7.28 (m, 1H), 7.13 (s, 1H), 7.01 (d, 1H), 6.35 (m, 2H), 5.78 (dd, 1H), 5.27 (s, 2H), 4.87 (m, 1H), 3.97 (s, 3H), 2.96 (m, 2H), 2.65 (s, 3H), 2.48 (m, 2H); [M+H]+: 609.3.

Example 224

Preparation of (2S)-2-acryloylamino-N-{4-[3-chloro-4-(pyridin-2-ylmethoxy)-phenylamino]-quinazolin-6-yl}-3-methyl-butyramide 474 mg of (2S)-2-amino-N-{4-[3-chloro-4-(pyridin-2-yll-methoxy)-phenylamino]-quinazolin-6-yl}-3-methyl-butyramide as a starting material was dissolved in 10 ml of THF, and cooled to 0° C. The solution was reacted with 0.11 ml of acrylic acid, 0.16 ml of pyridine and 380 mg of 1-(3-dimethylaminopropyl)-3-ethylcarbodiimide hydrochloride at 0° C. for 1 hour and at room temperature for 1.5 hours. The reacted solution was extracted with chloroform after adding saturated sodium bicarbonate, dried over anhydrous sodium sulfate, filtered and distilled under a reduced pressure, and the resulting residue was stirred in ethylacetate and filtered under a reduced pressure to obtain the title compound (178 mg, 34%).

$^1$H-NMR (DMSO-d$_6$, 300 MHz): δ 10.42 (s, 1H), 9.76 (s, 1H), 8.60 (s, 1H), 8.54 (d, 1H), 8.44 (s, 1H), 8.30 (d, 1H), 7.90 (d, 1H), 7.82 (m, 2H), 7.69 (d, 1H), 7.61 (dd, 1H), 7.52 (d, 1H), 7.31 (m, 1H), 7.19 (d, 1H), 6.40 (dd, 1H), 6.09 (dd, 1H), 5.58 (dd, 1H), 5.23 (s, 2H), 4.38 (t, 1H), 2.05 (m, 1H), 0.91 (m, 6H).

Example 225

Preparation of (2S)-2-acryloylamino-4-methyl-pentanoic acid {4-[3-chloro-4-(pyridin-2-ylmethoxy)-phenylamino]-quinazolin-6-yl}-amide 480 mg of (2S)-2-amino-4-methyl-pentanoic acid {4-[3-chloro-4-(pyridin-2-ylmethoxy)-phenylamino]-quinazolin-6-yl}-amide was dissolved in 10 ml of THF, cooled to 0° C., and the resulting solution was treated with 0.1 ml of acrylic acid, 0.16 ml of pyridine and 376 mg of 1-(3-dimethylaminopropyl)-3-ethylcarbodiimide hydrochloride at 0° C. for 1 hour and at room temperature for 2 hours. The resulting solution was treated with saturated sodium bicarbonate, extracted with chloroform, dried over anhydrous sodium sulfate, filtered and distilled under a reduced pressure. The resulting residue was subjected to column chromatography (eluent-ethylacetate:methanol=30:1) to obtain the title compound of formula (162 mg, 31%).

$^1$H-NMR (DMSO-d$_6$, 300 MHz): δ 10.43 (s, 1H), 9.76 (s, 1H), 8.60 (s, 1H), 8.53 (d, 1H), 8.44 (s, 1H), 8.39 (d, 1H), 7.92 (d, 1H), 7.82 (td, 2H), 7.70 (d, 1H), 7.60 (dd, 1H), 7.52 (d, 1H), 7.30 (m, 1H), 7.19 (d, 1H), 6.30 (dd, 1H), 6.08 (dd, 1H), 5.57 (dd, 1H), 5.22 (s, 2H), 4.57 (m, 1H), 1.50 (m, 3H), 0.87 (m, 6H).

The inventive compounds prepared in the Examples were formulated as follows:

PREPARATION EXAMPLE 1

Tablets for oral administration comprising each of the compounds of formula (I) obtained in Examples 1 to 225 as an active ingredient were prepared based on the recipes of Table 1.

TABLE 1

| Ingredient | Amount per formulation |
| --- | --- |
| Active compound | 100 mg |
| Corn starch | 80 mg |
| Lactose | 80 mg |
| Magnesium stearate | 5 mg |

PREPARATION EXAMPLE 2

Gelatin capsules for oral administration comprising each of the compounds of formula (I) obtained in Examples 1 to 225 as an active ingredient were prepared based on the recipes of Table 2.

TABLE 2

| Ingredient | Amount per formulation |
| --- | --- |
| Active compound | 100 mg |
| Corn starch | 40 mg |

TABLE 2-continued

| Ingredient | Amount per formulation |
| --- | --- |
| Lactose | 80 mg |
| Crystalline cellulose | 80 mg |
| Magnesium stearate | 5 mg |

PREPARATION EXAMPLE 3

Injection formulations comprising each of the compounds of formula (I) obtained in Examples 1 to 225 as an active ingredient were prepared based on the recipes of Table 3, wherein in case a salt of the compound of formula (I) was used, pH values was not manipulated.

TABLE 3

| Ingredient | Amount per formulation |
| --- | --- |
| Active compound | 20 mg |
| 5% glucose solution | 10 ml |
| HCl (1N) | to adjust pH 4 |

PREPARATION EXAMPLE 4

Injection formulations comprising each of the compounds of formula (I) obtained in Examples 1 to 225 as an active ingredient were prepared based on the recipes of Table 4.

TABLE 4

| Ingredient | Amount per formulation |
| --- | --- |
| Active compound | 20 mg |
| Polyethyleneglycol 400 | 2 ml |
| Sterile water | 8 ml |

TEST EXAMPLE 1

Inhibition of EGFR Enzyme

10 μl of EGFR (EGFR type 1 kinase) was added to each well of a 96-well microplate. As an EGFR inhibitor, 10 μl each of the serially diluted solution of the compounds obtained in Examples 1 to 225, Iressa (astrazeneca) or Tarceba (Roche) was added to each well, and the plate was incubated at room temperature for 10 mins. 10 μl of Poly (Glu, Tyr) 4:1 and 10 μl of ATP were successively added thereto to initiate kinase reaction, and the resulting mixture was incubated at room temperature for 1 hour. 10 μl of 100 mM EDTA was added to each well and stirred for 5 mins to terminate the kinase reaction. 10 μl of 10× anti-phosphotyrosine antibody (PanVera), 10 μl of 10×PTK (protein tyrosine kinase) green tracer (PanVera) and 30 μl of FP (fluorescence polarization) diluted buffer were added to the reacted solution, and incubated in dark at room temperature for 30 mins. FP values of each well were determined using VICTORIII fluorescence meter (Perkin Elmer) at 488 nm, and $IC_{50}$, the concentration at which 50% inhibition was observed, was determined, wherein the maximum value was the polarized light value measured for the well untreated with EGFR inhibitor and the minimum value corresponded to 100% inhibition. The calculation and analysis of $IC_{50}$ were carried out by using Microsoft Excel, and the results were shown in Table 5.

TEST EXAMPLE 2

Test of Cancer Cell Growth Inhibition

A skin cancer cell line, A431 (ATCC: CRL-1555), a skin cancer cell line, SK-Br3 (ATCC: HTB-30), and a colon and rectal cancer cell line, SW-620 (ATCC: CCL-227) were used to test the degrees of cancer cell growth inhibition using a culture medium, DEME (Dulbecco's Modified Eagle's Medium) including 4.5 g/l of glucose and 1.5 g/l of sodium bicarbonate and supplemented with 10% FBS (fetal bovine serum).

The cancer cell lines stored in a liquid nitrogen tank were each quickly thawed at 37° C., and centrifuged to remove the medium. The resulting cell pellet was mixed with a culture medium, incubated in a culture flask at 37° C. under 5% $CO_2$ for 2 to 3 days, and the medium was removed. The remaining cells were washed with DPBS (Dulbecco's Phosphate Buffered Saline) and separaed from the flask by using Tripsin-EDTA, and the separated cells were diluted with a culture medium to a concentration of 100,000 A431 cells/ml or in case of SK-Br3, 200,000 cells/ml. 100 μl of the diluted cell solution was added to each well of a 96-well plate, which was incubated at 37° C. under 5% $CO_2$ for 1 day.

The compounds obtained in Examples 1 to 225 as well as conventional EGFR inhibitors, Iressa and Tarceva were each dissolved in 99.5% DMSO to a concentration of 25 mM. In case that the test compound was not soluble in DMSO, a small amount of 1% HCl was added thereto and treated in a 40° C. water bath for 30 mins until complete dissolution was attained. The test compound solution was diluted with a culture medium to a final concentration of 100 μM, then diluted 10 time serially to $10^{-6}$ (final concentration of DMSO was less than 1%).

The medium was removed from each well of the 96-well microplate, 100 μl of a diluted test compound solution was added to each well holding cultured cells, and the microplate was incubated at 37° C. under 5% $CO_2$ for 72 hours. After removing the medium from the plate, 50 μl of 10% trichloracetic acid was added to each well, and the plate was kept at 37° C. for 1 hour to fix the cells to the bottom of the plate. 10% trichloroacetic acid was removed from each well, the plate was dried, 100 μl of an SRB (Sulforhodamine-B) dye solution was added thereto, and reacted for 10 mins. The SRB dye solution was prepared by dissolving SRB in 1% acetic acid to a concentration of 0.4%. After removing the dye solution, the plate was washed with water, and dried. When the dye solution was not removed by water, 1% acetic acid was used. 150 μl of 10 mM trisma base was added to each well, and the absorbance at 570 nm was determined with a microplate reader. $IC_{50}$, the concentration at which 50% inhibition occurs, was evaluated by regarding the difference between the final concentration of cells and the initial concentration of the cells incubated in a well untreated with the test compound as 100%. The calculation of $IC_{50}$ was carried out by using Microsoft Excel, and the results are shown in Table 5.

TABLE 5

| | $IC_{50}$ (μM) | | | |
| --- | --- | --- | --- | --- |
| Example | EGFR | A431 | SK-Br-3 | SW-620 |
| 1-5 | — | 0.408 | 0.359 | — |
| 2-4 | — | 0.206 | 0.245 | >10 |
| 4 | — | 0.179 | 0.010 | >10 |
| 5-3 | — | 0.315 | 0.106 | >10 |
| 7-2 | — | 0.740 | 0.261 | — |

TABLE 5-continued

| Example | IC$_{50}$ (μM) | | | |
|---|---|---|---|---|
| | EGFR | A431 | SK-Br-3 | SW-620 |
| 8 | — | 0.308 | 0.190 | — |
| 9 | — | 0.060 | 0.007 | >10 |
| 11 | — | 0.252 | 0.113 | — |
| 17 | — | 0.713 | 0.182 | — |
| 18 | — | 0.157 | 0.29 | >10 |
| 19 | — | 0.335 | 0.427 | — |
| 20-2 | 0.030 | 0.948 | 0.151 | — |
| 21 | — | 0.455 | 0.016 | >10 |
| 22 | 0.003 | 0.058 | 0.003 | >10 |
| 23 | — | 0.316 | 0.359 | — |
| 24 | — | 0.232 | 0.105 | >10 |
| 25 | — | 0.138 | 0.133 | >10 |
| 26 | — | 0.801 | 0.872 | — |
| 27 | — | 0.085 | 0.010 | >10 |
| 28 | — | 0.197 | 0.065 | >10 |
| 29 | — | 0.310 | 0.054 | >10 |
| 30 | — | 0.119 | 0.038 | >10 |
| 32 | — | 0.312 | 0.163 | — |
| 33 | — | 0.348 | 0.131 | — |
| 34 | — | 0.896 | 0.141 | — |
| 37 | — | 0.137 | 0.160 | — |
| 39-2 | — | 0.482 | 0.045 | >10 |
| 40 | — | 0.327 | 0.084 | >10 |
| 41 | — | 0.936 | 0.172 | — |
| 42-2 | — | 0.340 | 0.102 | >10 |
| 43 | — | 0.390 | 0.115 | — |
| 44 | — | 0.043 | 0.006 | >10 |
| 48 | — | 0.828 | 0.131 | — |
| 50-2 | — | 0.845 | 0.099 | — |
| 53-2 | — | 0.124 | 0.258 | — |
| 54 | — | 0.321 | 0.046 | >10 |
| 56 | — | 0.613 | 0.051 | — |
| 57 | — | 0.625 | 0.043 | — |
| 61 | — | 0.168 | 0.098 | >10 |
| 64 | — | 0.698 | 0.212 | — |
| 77 | — | 0.208 | 0.086 | >10 |
| 79 | — | 0.065 | 0.003 | >10 |
| 85-2 | — | 0.012 | 0.003 | >10 |
| 87-2 | — | 0.095 | 0.035 | >10 |
| 88 | — | 0.732 | 0.062 | — |
| 89 | — | 0.173 | 0.019 | >10 |
| 90 | — | 0.423 | 0.628 | — |
| 91 | — | 0.603 | 0.445 | — |
| 92 | — | 0.293 | 0.080 | — |
| 93 | — | 0.324 | 0.033 | >10 |
| 94 | — | 0.245 | 0.070 | — |
| 95 | — | 0.994 | 0.331 | — |
| 98 | — | 0.079 | 0.184 | — |
| 101 | — | 0.786 | 0.021 | >10 |
| 102 | — | 0.345 | 0.080 | >10 |
| 103 | — | 0.227 | 0.042 | >10 |
| 104 | — | 0.254 | 0.022 | >10 |
| 106 | — | 0.359 | 0.048 | — |
| 107 | — | 0.641 | 0.051 | — |
| 114 | — | 0.136 | 0.216 | — |
| 115-2 | — | 0.117 | 0.038 | >10 |
| 117 | — | 0.336 | 0.040 | >10 |
| 118 | — | 0.735 | 0.161 | — |
| 119 | — | 0.161 | 0.069 | — |
| 121 | — | 0.616 | 0.069 | — |
| 122 | — | 0.617 | 0.085 | — |
| 123 | — | 0.240 | 0.036 | >10 |
| 124 | — | 0.584 | 0.107 | — |
| 125 | — | 0.272 | 0.083 | — |
| 126 | — | 0.099 | 0.091 | — |
| 128 | — | 0.489 | 0.585 | — |
| 129-2 | — | 0.490 | 0.345 | — |
| 131 | 0.004 | 0.037 | 0.003 | — |
| 132-2 | — | 0.880 | 0.662 | — |
| 133 | — | 7.261 | 1.110 | — |
| 134 | — | 0.193 | 0.004 | — |
| 135 | — | 0.123 | 0.092 | — |
| 136 | — | 0.828 | 1.713 | — |
| 137 | — | 0.100 | 0.044 | — |
| 138 | — | 0.102 | 0.054 | — |
| 139-5 | 0.005 | 0.069 | 0.047 | — |
| 140 | — | 0.102 | 0.102 | — |
| 141-4 | — | 1.327 | 0.804 | — |
| 142-2 | 0.002 | 0.019 | 0.004 | — |
| 143 | 0.001 | 0.010 | 0.002 | — |
| 144 | — | 0.073 | 0.008 | — |
| 145 | 0.004 | 0.032 | 0.025 | — |
| 146 | 0.004 | 0.032 | 0.040 | — |
| 147 | 0.002 | 0.021 | 0.019 | — |
| 148 | — | 0.034 | 0.004 | — |
| 149 | — | 0.054 | 0.002 | — |
| 150 | — | 0.036 | 0.006 | — |
| 151 | — | 0.105 | 0.003 | — |
| 152 | — | 0.166 | 0.004 | — |
| 153 | — | 0.394 | 0.029 | — |
| 154 | — | 0.086 | 0.005 | — |
| 155 | — | 0.350 | 0.012 | — |
| 156 | — | 0.513 | 0.019 | — |
| 157 | — | 5.592 | 0.123 | — |
| 158 | — | 0.583 | 0.048 | — |
| 159 | — | 0.462 | 0.223 | — |
| 160 | — | 6.934 | 0.437 | — |
| 161 | — | 0.680 | 0.019 | — |
| 162 | — | 0.286 | 0.028 | — |
| 163 | — | 1.400 | 0.060 | — |
| 164 | — | 0.105 | 0.012 | — |
| 165 | — | 0.215 | 0.005 | — |
| 166 | 0.003 | 0.027 | 0.003 | — |
| 167 | 0.002 | 0.017 | 0.004 | — |
| 168 | — | 0.068 | 0.006 | — |
| 169 | — | 0.079 | 0.024 | — |
| 170 | — | 0.199 | 0.002 | — |
| 171 | — | 0.306 | 0.031 | — |
| 172 | — | 10 | 4.519 | — |
| 173 | — | 0.552 | 0.029 | — |
| 174 | — | 0.956 | 0.035 | — |
| 175 | — | 0.048 | 0.026 | — |
| 176 | — | 0.517 | 0.034 | — |
| 177 | — | 0.078 | 0.009 | — |
| 178 | 0.004 | 0.050 | 0.003 | — |
| 179 | — | 0.121 | 0.017 | — |
| 180 | — | 0.438 | 0.063 | — |
| 181 | — | 0.218 | 0.013 | — |
| 182 | — | 0.128 | 0.009 | — |
| 183 | 0.002 | 0.013 | 0.003 | — |
| 184 | — | 1.425 | 0.114 | — |
| 185 | — | 0.022 | 0.003 | — |
| 186 | — | 0.026 | 0.008 | — |
| 187 | — | 0.022 | 0.003 | — |
| 188 | — | 0.024 | 0.006 | — |
| 189 | 0.001 | 0.009 | 0.002 | — |
| 190 | 0.002 | 0.013 | 0.006 | — |
| 191 | — | 0.056 | 0.003 | — |
| 192 | — | 0.036 | 0.006 | — |
| 193 | — | 0.075 | 0.022 | — |
| 194 | — | 0.093 | 0.056 | — |
| 195 | — | 0.119 | 0.044 | — |
| 196 | — | 0.088 | 0.025 | — |
| 197 | — | 0.259 | 0.196 | — |
| 198 | — | 0.047 | 0.024 | — |
| 199 | — | 0.145 | 0.096 | — |
| 200 | — | 0.332 | 0.008 | — |
| 201 | — | 0.148 | 0.025 | — |
| 202 | — | 0.105 | 0.006 | — |
| 203 | — | 0.269 | 0.034 | — |
| 204 | — | 0.085 | 0.030 | — |
| 205 | 0.002 | 0.017 | 0.019 | — |
| 206 | — | 0.017 | 0.010 | — |
| 208 | 0.002 | 0.011 | 0.003 | — |
| 209 | — | 0.044 | 0.003 | — |
| 211 | 0.002 | 0.016 | 0.006 | — |
| 212 | — | 0.098 | 0.009 | — |
| 213 | — | 0.034 | 0.004 | — |
| 214 | — | 0.022 | 0.006 | — |
| 215 | — | 0.059 | 0.011 | — |
| 216 | 0.002 | 0.013 | 0.008 | — |
| 217 | 0.002 | 0.014 | 0.003 | — |

TABLE 5-continued

| Example | IC$_{50}$ (μM) | | | |
|---|---|---|---|---|
| | EGFR | A431 | SK-Br-3 | SW-620 |
| 218 | 0.002 | 0.016 | 0.004 | — |
| 219 | 0.002 | 0.017 | 0.007 | — |
| 220 | — | 0.022 | 0.021 | — |
| 221 | — | 0.028 | 0.023 | — |
| 222 | — | 0.025 | 0.009 | — |
| 223 | — | 0.054 | 0.032 | — |
| 224 | — | 0.049 | 0.012 | — |
| 225 | — | 0.042 | 0.021 | — |
| Iressa | 1.147 | 0.028 | 0.206 | >10 |
| Tarceva | >1.7 | 0.059 | 0.891 | >10 |

As shown in Table 5, each of the inventive compounds showed an excellent anticancer activity by effectively inhibiting EGFR kinase, arresting the growth of EGFR overexpressed A431 and Erb-B2 overexpressed SK-Br3 at a low drug concentration, while the inventive compounds did not inhibit the growth of SW-620 not having overexpressed EGFR and Erb-B2.

Therefore, the compounds of formula (I) of the present invention can selectively inhibit the growth of specific cancer cells induced by epithelial growth factor with reduced side effects.

While the invention has been described with respect to the above specific embodiments, it should be recognized that various modifications and changes may be made and also fall within the scope of the invention as defined by the claims that follow.

What is claimed is:

1. A quinazoline derivative of formula (I) or a pharmaceutically acceptable salt thereof:

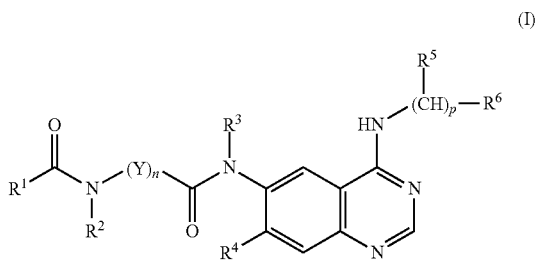

(I)

wherein,
R$^1$ is hydrogen, C$_{1-6}$alkyl, C$_{3-7}$cycloalkyl, C$_{2-6}$alkenyl, C$_{2-6}$alkynyl, C$_{1-6}$alkoxy, C$_{1-6}$alkylamino, C$_{1-6}$dialkylamino, C$_{1-6}$alkylthio, 2 ((N-methyl-(2'hydroxyethyl)amino)methyilvinyl, phenoxy, phenyl, dimethylaminoethoxymethyl, methoxyethoxymethyl, 4-methylpiperazinylmethyl, ethoxycarbonyl, benzamino, cyclopentenyl, 2-(4-methylpiperazinylmethylvinyl, methanesulfonylethylaminomethyl, methoxyethylaminomethyl,
2-(methanesulfonylethylaminomethyl)vinyl, or 5-membered heteroaryl having 1-2 heteroatoms selected from N, O, or S which are optionally substituted with X;
R$^2$ is hydrogen, or C$_{1-6}$alkyl;
R$^3$ is hydrogen, C$_{1-6}$alkyl or C C$_{1-6}$dialkylamino C$_{1-6}$alkyl;
Y is —(CR$^{11}$R$^{12}$)—, phenyl or a 5-membered heteroaryl having 1 sulfur atom, R$^{11}$ and R$^{12}$ being each independently hydrogen, halogen, hydroxy, carboyC$_{1-6}$alkyl, C$_{1-6}$alkyl, C$_{1-6}$alkoxy, C$_{1-6}$alkylthio, C$_{1-6}$alkylsulfinyl, C$_{1-6}$alkanoyl, C$_{1-6}$alkoxycarbonyl, phenyl, or optionally fused to each other to form a 3 membered non-aromatic ring, or R$^{11}$ or R$^{12}$ may be fused to R$^2$ to form together with the carbon and nitrogen they are attached to a 4 to 8-membered non-aromatic ring, optionally comprising additional heteroatom S;
R$^4$ is hydrogen, halogen, C$_{1-6}$alkoxy, ethylsulfanyl, cyclopropylmethoxy, cyclopentyloxy or C$_{1-6}$alkylamino optionally substituted with R$^{13}$, R$^{13}$ being halogen, trifluoromethyl, C$_{1-6}$alkoxy, 4-methylpiperidinylmethoxy, dimethylamino or a 6-membered heteroaryl having 1-2 heteroatoms selected from N and O;
R$^5$ is hydrogen or C$_{1-3}$alkyl;
R$^6$ is phenyl, 1-phenyl-ethyl, 3-ethynyl-phenyl, 1-penta-2,4-dienyl-1H-indazol-5-yl, imidazole or a 9-membered heteroaryl having 1-2 nitrogen atoms, optionally substituted with R$^{15}$, being hydrogen halogen, C$_{1-6}$alkyl, or phenyl, benzyl, a 10-membered heteroaryl C$_{1-6}$alkyl having 1 nitrogen atom, benzyloxy, a 6-membered heteroaryl C$_{1-6}$alkoxy having 1 nitrogen atom, a 6-membered heteroaryloxy having a nitrogen atom, phenylcarbamoyl, optionally substituted with R$^{16}$, wherein R$^{16}$ is halogen, nitro, C$_{1-6}$alkyl, or C$_{1-6}$alkoxy;
n is an integer in the range of 1 to 4;
p is 0 or 1;
X is a halogen, nitro, cyano, trifluoromethyl, C$_{1-6}$alkyl, C$_{1-6}$alkoxy, C$_{1-6}$dialkylamino, C$_{1-6}$alkylsulfinyl, C$_{1-6}$alkylsulfonyl, C$_{1-6}$alkyloxycarbonyl, C$_{1-6}$alkanoyl, phenyl, or a 5- to 6-membered heteroaryl having 1-2 heteroatoms selected from N and O; wherein heteroaryl is a heteroaromatic or non-aromatic.

2. The compound of claim 1, wherein R$^1$ is methyl, cyclopropyl, trifluoromethyl, cyanomethyl, chloromethyl, phenyl, methoxy, phenoxy, benzyloxy, methoxymethyl, acetoxymethyl, dimethylaminoethoxymethyl, methoxyethoxymethyl, methylthiomethyl, methanesulfinylmethyl, methanesulfonylmethyl, dimethylaminomethyl, morpholinomethyl, 4-methylpiperazinylmethyl, methanesulfonylethylaminomethyl, methoxyethylaminomethyl, ethoxycarbonyl, ethylamino, furan-3-yl, furan-2-yl-methylamino, benzamino, benzylamino, 1-buthoxy, 3-methyl-isoxazol-5-yl, 5-methyl-isoxazol-4-yl, 1H-pyrazol-4-yl, vinyl, penta-1,3-dienyl, cyclopentenyl, 2-phenylvinyl, 2-methylvinyl, 2,2-dimethylvinyl, 1-methylvinyl, 2-phenylethynyl, 2-methylethynyl, 2-(bromomethyl)vinyl, 2-(dimethylaminomethyl)vinyl, 2-(morpholinomethyl)vinyl, 2-(4-methylpiperazinylmethyl)vinyl, 2-((N-methyl-(2-hydroxyethyl)amino)methyl)vinyl or 2-(methanesulfonylethylaminomethyl)vinyl;
R$^2$ is hydrogen, methyl, ethyl;
R$^3$ is methyl, ethyl or 3-(N,N-dimethylamino)propyl;
R$^4$ is hydrogen, fluoro, chloro, methoxy, ethoxy, methoxyethoxy, methoxypropoxy, ethylsulfanyl, cyclopropylmethoxy, cyclopentyloxy, 2,2,2-trifluoroethoxy, 2-fluoroethoxy, N,N-dimethylamino, morpholinopropoxy or 4-methylpiperadinylmethoxy;
R$^5$ is hydrogen;
R$^6$ is 1 phenyl-ethyl, 3-ethynyl-phenyl, biphenyl, 3-chloro-4-fluoro-phenyl, 3-chloro-4-(3-fluoro-benzyloxy)-phenyl, 3-methyl-4-(6-methyl-pyridin-3-yloxy)-phenyl, 4-[2-(6,7-dimethoxy-3,4-dihydro-1H-isoquinolin-2-yl)-ethyl]-phenyl, N-phenyl-benzamid-4-yl, 3-chloro-4-(pyridin-2-ylmethoxy)-phenyl, 3-chloro-4-(pyridin-3-ylmethoxy)-phenyl, 3-chloro-4-(6-methyl-pyridin-2-ylmethoxy)-phenyl, 3-chloro-4-(pyridin-4-ylmethoxy)-phenyl, 3-methyl-4-(pyridin-2-ylmethoxy)-phenyl, 1-pyridin-2-ylmethyl-1H-indazol-5-yl, 1-(3-fluorobenzyl)-1H-indazol-5-yl, 1-penta-2,4-dienyl-1H-indazol-5-yl, 3-chloro-4-(2-fluoroethoxy)-phenyl, 2-methyl-1H-indol-5-yl or 1-benzyl-1H-indazol-5-yl;

Y is —(CR¹¹R¹²)—, phenyl or thiophene, R¹¹ and R¹² being each independently hydrogen, hydroxyl, halogen, $C_{1-6}$alkyl, carboxy$C_{1-3}$alkyl, $C_{1-3}$alkoxy, phenyl, or optionally, fused to each other to form a 3 membered non-aromatic ring, or R¹¹ or R¹² may be fused to R² to form together with the carbon and nitrogen they are attached to a 4 to 6-membered non-aromatic ring.

3. The compound of claim 1, which is selected from the group consisting of:
- ({-4-[3-chloro-4-(3-fluoro-benzyloxy)-phenylamino]-quinazolin-6-ylcarbamoyl}-methyl)-carbamic acid t-butylester;
- N-({-4-[3-chloro-4-(3-fluoro-benzyloxy)-phenylamino]-quinazolin-6-ylcarbamoyl}-methyl)-2-methoxy-acetamide;
- N-({-4-[3-chloro-4-(3-fluoro-benzyloxy)-phenylamino]-quinazolin-6-ylcarbamoyl}-methyl)-2-methanesulfonyl-acetamide;
- N-({-4-[3-chloro-4-(3-fluoro-benzyloxy)-phenylamino]-quinazolin-6-ylcarbamoyl}-methyl)-acrylamide;
- (2S)—N-{-4-[3-chloro-4-(3-fluoro-benzyloxy)-phenylamino]-quinazolin-6-yl}-2-(2-methoxy-acetylamino)-3-phenyl-propionamide;
- (1S)-(1-{-4-[3-chloro-4-(3-fluoro-benzyloxy)-phenylamino]-quinazolin-6-ylcarbamoyl}-3-methanesulfanyl-propyl)-carbamic acid t-butylester;
- (2S)—N-{4-[3-chloro-4-(3-fluoro-benzyloxy)-phenylamino]-quinazolin-6-yl}-2-(2-methoxy-acetylamino)-4-methanesulfanyl-butyramide;
- (2S)—N-{4-[3-chloro-4-(3-fluoro-benzyloxy)-phenylamino]-quinazolin-6-yl}-2-(2-methanesulfonyl-acetamino)-4-methanesulfanyl-butyramide;
- (2S)-2-acryloylamino-N-{-4-[3-chloro-4-(3-fluoro-benzyloxy)-phenylamino]-quinazolin-6-yl}-4-methanesulfanyl-butyramide;
- (1-{-4-[3-chloro-4-(3-fluoro-benzyloxy)-phenylamino]-quinazolin-6-ylcarbamoyl}-cyclopropyl)-carbamic acid t-butylester;
- (2S)—N-{4-[3-chloro-4-(3-fluoro-benzyloxy)-phenylamino]-quinazolin-6-yl}-2-(2-methoxy-acetylamino)-2-phenyl-acetamide;
- (4S)-4-t-buthoxycarbonylamino-4-{-4-[3-chloro-4-(3-fluoro-benzyloxy)-phenylamino]-quinazolin-6-ylcarbamoyl}-butyric acid methylester;
- 4-{-4-[3-chloro-4-(3-fluoro-benzyloxy)-phenylamino]-quinazolin-6-ylcarbamoyl}-4-(2-methoxy-acetylamino)-butyric acid methylester;
- 4-{4-[3-chloro-4-(3-fluoro-benzyloxy)-phenylamino]-quinazolin-6-ylcarbamoyl}-4-(2-methoxy-acetylamino)-butyric acid;
- 2-{-4-[3-chloro-4-(3-fluoro-benzyloxy)-phenylamino]-1-quinazolin-6-ylcarbamoyl}-pyrrolidine-1-carboxylic acid t-butylester;
- 1-(2-methoxy-acetyl)-pyrrolidine-2-carboxylic acid {-4-[3-chloro-4-(3-fluoro-benzyloxy)-phenylamino]-quinazolin-6-yl}-amide;
- 1-(2-methanesulfonyl-acetyl)-pyrrolidine-2-carboxylic acid {4-[3-chloro-4-(3-fluoro-benzyloxy)-phenylamino]-quinazolin-6-yl}-amide;
- 1-acryloyl-pyrrolidine-2-carboxylic acid {-4-[3-chloro-4-(3-fluoro-benzyloxy)-phenylamino]-quinazolin-6-yl}-amide;
- (2-{4-[3-chloro-4-(3-fluoro-benzyloxy)-phenylamino]-quinazolin-6-ylcarbamoyl}-ethyl)-carbamic acid t-butylester;
- N-{4-[3-chloro-4-(3-fluoro-benzyloxy)-phenylamino]-quinazolin-6-yl}-3-(2-methoxy-acetylamino)-propionamide;
- N-{4-[3-chloro-4-(3-fluoro-benzyloxy)-phenylamino]-quinazolin-6-yl}-3-(2-methanesulfonyl-acetylamino)-propionamide;
- N-(2-{-4-[3-chloro-4-(3-fluoro-benzyloxy)-phenylamino]-quinazolin-6-ylcarbamoyl}-ethyl)-acrylamide;
- 3-phenyl-propionylic acid (2-{-4-[3-chloro-4-(3-fluoro-benzyloxy)-phenylamino]-quinazolin-6-ylcarbarnoyl}-ethyl)-amide;
- hexa-2,4-dienonylic acid (2-{4-[3-chloro-4-(3-fluoro-benzyloxy)-phenylamino]-quinazolin-6-ylcarbamoyl}-ethyl)-amide;
- cyclopent-1-en carboxylic acid (2-{4-[3-chloro-4-(3-fluoro-benzyloxy)-phenylamino]-quinazolin-6-ylcarbamoyl}-ethyl)-amide;
- N-(2-{4-[3-chloro-4-(3-fluoro-benzyloxy)-phenylamino]-quinazolin-6-ylcarbamoyl}-ethyl)-3-phenyl-acrylamide;
- but-2-ynoylic acid (2-{4-[3-chloro-4-(3-fluoro-benzyloxy)-phenylamino]-quinazolin-6-ylcarbamoyl}-ethyl)-amide;
- but-2-enonylic acid (2-{4-[3-chloro-4-(3-fluoro-benzyloxy)-phenylamino]-quinazolin-6-ylcarbamoyl}-ethyl)-amide;
- 3-methyl-but-2-enonylic acid, (2-{4-[3-chloro-4-(3-fluoro-benzyloxy)-phenylamino]-quinazolin-6-ylcarbamoyl}-ethyl)-amide;
- N-(2-{-4-[3-chloro-4-(3-fluoro-benzyloxy)-phenylamino]-quinazolin-6-ylcarbamoyl}-ethyl)-2-methyl-acrylamide;
- N-(2-{-4-[3-chloro-4-(3-fluoro-benzyloxy)-phenylamino]-quinazolin-6-ylcarbamoyl}-ethyl)-2-cyano-acetamide;
- 3-methyl-isoxazol-5-carboxylic acid (2-{4-[3-chloro-4-(3-fluoro-benzyloxy)-phenylamino]-quinazolin-6-ylcarbamoyl}-ethyl)-amide;
- furan-3-carboxylic acid (2-{4-[3-chloro-4-(3-fluoro-benzyloxy)-phenylamino]-quinazolin-6-ylcarbamoyl}-ethyp-amide;
- 1H-pyrazol-4-carboxylic acid (2-{4-[3-chloro-4-(3-fluoro-benzyloxy)-phenylamino]-quinazolin-6-ylcarbamoyl}-ethyp-amide;
- N-(2-{4-[3-chloro-4-(3-fluoro-benzyloxy)-phenylamino]-quinazolin-6-ylcarbamoyl}-ethyl)-benzamide;
- N-(2-{4-[3-chloro-4-(3-fluoro-benzyloxy)-phenylamino]-quinazolin-6-ylcarbamoyl}-ethyl)-oxalamic acid ethylester;
- cyclopropylcarboxylic acid (2-{-4-[3-chloro-4-(3-fluoro-benzyloxy)-phenylamino]-quinazolin-6-ylcarbamoyl}-ethyl)-amide;
- acetic acid 2-t-buthoxycarbonylamino-1-{4-[3-chloro-4-(3-fluoro-benzyloxy)-phenylamino]-quinazolin-6-yl carbamoyl}-ethylester;
- acetic acid 1-{4-[3-chloro-4-(3-fluoro-benzyloxy)-phenylamino]-quinazolin-6-ylcarbamoyl}-2-(2-methoxy-acetylamino)-ethylester;
- N-{4-[3-chloro-4-(3-fluoro-benzyloxy)-phenylamino]-quinazolin-6-yl}-2-hydroxyl-3-(2-methoxy-acetylamino)-propionamide;
- (2-{4-[3-chloro-4-(3-fluoro-benzyloxy)-phenylamino]-quinazolin-6-ylcarbamoyl}-propyl)-carbamic acid t-butylester;

N-{4-[3-chloro-4-(3-fluoro-benzyloxy)-phenylamino]-quinazolin-6-yl}-3-(2-methoxy-acetylamino)-2-methyl-propionamide;
N-{4-[3-chloro-4-(3-fluoro-benzyloxy)-phenylamino]-quinazolin-6-yl}-3-(2-methanesulfonyl-acetylamino)-2-methyl-propionamide;
N-(2-{4-[3-chloro-4-(3-fluoro-benzyloxy)-phenylamino]-quinazolin-6-ylcarbamoyl}-propyl)-acrylamide;
(2-{4-[3-chloro-4-(3-fluoro-benzyloxy)-phenylamino]-quinazolin-6-ylcarbamoyl}-1-phenyl-ethyl)-carbamic acid t-butylester;
N-{4-[3-chloro-4-(3-fluoro-benzyloxy)-phenylamino]-quinazolin-6-yl}-3-(2-methoxy-acetylamino)-3-phenyl-propionamide;
N-{4-[3-chloro-4-(3-fluoro-benzyloxy)-phenylamino]-quinazolin-6-yl}-3-(2-methanesulfonyl-acetylamino)-3-phenyl-propionamide;
3-(2-methoxy-acetylamino)-thiophene-2-carboxylic acid {4-[3-chloro-4-(3-fluoro-benzyloxy)-phenylamino]-quinazolin-6-yl}-amide;
(2-{4-[3-methyl-4-(6-methyl-pyridin-3-yloxy)-phenylamino]-quinazolin-6-ylcarbamoyl}-ethyl)-carbamic acid t-butylester;
3-(2-methanesulfonyl-acetylamino)-N-{4-[3-methyl-4-(6-methyl-pyridin-3-yloxy)-phenyl amino]-quinazolin-6-yl}-propionamide;
N-(2-{4-[3-methyl-4-(6-methyl-pyridin-3-yloxy)-phenylamino]-quinazolin-6-ylcarbamoyl}-ethyl)-acrylamide;
{2-[4-(3-chloro-4-fluoro-phenylamino)-quinazolin-6-ylcarbamoyl]-ethyl}-carbamic acid t-butylester;
N-[4-(3-chloro-4-fluoro-phenylamino)-quinazolin-6-yl]-3-(2-methanesulfonyl-acetylamino)-propionamide;
N-{2-[4-(3-chloro-4-fluoro-phenylamino)-quinazolin-6-ylcarbamoyl]-ethyl}-acrylamide;
4-bromo-but-2-enonylic acid (2-{4-[3-chloro-4-(3-fluoro-benzyloxy)-phenylamino]-quinazolin-6-ylcarbamoyl}-ethyl)-amide;
4-dimethylamino-but-2-enonylic acid (2-{-4-[3-chloro-4-(3-fluoro-benzyloxy)-phenylamino]-quinazolin-6-ylcarbamoyl}-ethyl)-amide;
4-morpholin-4-yl-but-2-enonylic acid (2-{4-[3-chloro-4-(3-fluoro-benzyloxy)-phenylamino]-quinazolin-6-ylcarbamoyl}-ethyl)-amide;
4-(4-methyl-piperazin-1-yl)-but-2-enonylic acid (2-{4-[3-chloro-4-(3-fluoro-benzyloxy)-phenylamino]-quinazolin-6-ylcarbamoyl}-ethyl)-amide;
4-[(2-hydroxyl-ethyl)-methyl-amino]-but-2-enonylic acid (2-{4-[3-chloro-4-(3-fluoro-benzyloxy)-phenylamino]-quinazolin-6-ylcarbamoyl}-ethyl)-amide;
4-(2-methanesulfonyl-ethylamino)-but-2-enonylic acid (2-{4-[3-chloro-4-(3-fluoro-benzyloxy)-phenylamino]-quinazolin-6-ylcarbamoyl}-ethyl)-amide;
3-(2-chloro-acetylamide)-N-{4-[3-chloro-4-(3-fluoro-benzyloxy)-phenylamino]-quinazolin-6-yl}-propionamide;
N-{4-[3-chloro-4-(3-fluoro-benzyloxy)-phenylamino]-quinazolin-6-yl}-3-(2-morpholin-4-yl-acetylamino)-propionamide;
N-{4-[3-chloro-4-(3-fluoro-benzyloxy)-phenylamino]-quinazolin-6-yl}-3-(2-dimethylamino-acetylamino)-propionamide;
N-{4-[3-chloro-4-(3-fluoro-benzyloxy)-phenylamino]-quinazolin-6-yl}-3-[2-(4-methyl-piperazin-1-yl)-acetylamino]-propionamide;
N-{4-[3-chloro-4-(3-fluoro-benzyloxy)-phenylamino]-quinazolin-6-yl}-3-[2-(2-methoxy-ethylamino)-acetylamino]-propionamide;
N-{4-[3-chloro-4-(3-fluoro-benzyloxy)-phenylamino]-quinazolin-6-yl}-3-[2-(2-methanesulfonyl-ethylamino)-acetylamino]-propionamide;
3-(2-chloro-acetylamino)-N-{4-[3-methyl-4-(6-methyl-pyridin-3-yloxy)-phenylamin]-quinazolin-6-yl}-propionamide;
N-{4-[3-methyl-4-(6-methyl-pyridin-3-yloxy)-phenylamino]-quinazolin-6-yl}-3-(2-morpholin-4-yl-acetylamino)-propionamide;
3-(2-dimethylamino-acetylamino)-N-{4-[3-methyl-4-(6-methyl-pyridin-3-yloxy)-phenylamino]-quinazolin-6-yl}-propionamide;
N-{4-[3-methyl-4-(6-methyl-pyridin-3-yloxy)-phenylamino]-quinazolin-6-yl}-3-[2-(4-methyl-piperazin-1-yl)-acetylamino]-propionamide;
3-[2-(2-methoxy-ethylamino)-acetylamino]-N-{4-[3-methyl-4-(6-methyl-pyridin-3-yloxy)-methylamino]-quinazolin-6-yl}-propionamide;
3-[2-(2-methanesulfonyl-ethylamino)-acetylamino]-N-{4-[3-methyl-4-(6-methyl-pyridin-3-yloxy)-phenylamino]-quinazolin-6-yl}-prop ionamide;
N-{2-[4-(2-methyl-1H-indol-5-ylamino)-quinazolin-6-ylcarbamoyl]ethyl}-acrylamide;
3-(2-methanesulfonyl-acetylamino)-N-[4-(1-phenyl-ethylamino)-quinazolin-6-yl]-propionamide;
N-{2-[4-(1-phenyl-ethylamino)-quinazolin-6-ylcarbamoyl]-ethyl-acrylamide;
N-[2-(4-{4-[2-(6,7-dimethoxy-3,4-dihydro-1H-isoquinolin-2-yl)-ethyl]-phenylamino}-quinazolin-6-ylcarbamoyl)-ethyl]-acrylamide;
{2-[4-(1-benzyl-1H-indazol-5-ylamino)-quinazolin-6-ylcarbamoyl]ethyl}-carbamic acid t-butylester;
N-[4-(1-benzyl-1H-indazol-5-ylamino)-quinazolin-6-yl]-3-(2-methanesulfonyl-acetylamino)-propionamide;
N-{2-[4-(1-benzyl-1H-imidazol-5-ylamino)-quinazolin-6-ylcarbamoyl]-ethyl}-acrylamide;
{2-[4-(4-phenylcarbamoyl-phenylamino)-quinazolin-6-ylcarbamoyl]-ethyl}-carbamic acid t-butylester;
4-{6-[3-(2-methanesulfonyl-acetylamino)-propionylamino]-quinazolin-4-ylamino}-N-phenyl-benzamide;
4-[6-(3-acryloylamino-propionylamino)-quinazolin-4-ylamino]-N-phenyl-benzamide;
N-[4-(biphenyl-4-ylamino)-quinazolin-6-yl]-3-(2-methanesulfonyl-acetylamino)-propionamide;
N-{2-[4-(biphenyl-4-ylamino)-quinazolin-6-ylcarbamoyl]-ethyl}-acrylamide;
N-{2-[4-[3-chloro-4-(3-fluoro-benzyloxy)-phenylamino]-7-(3-morpholin-4-yl-propoxy)-quinazolin-6-ylcarbamoyl]-ethyl}-acrylamide;
(3-{4-[3-chloro-4-(3-fluoro-benzyloxy)-phenylamino]-quinazolin-6-ylcarbamoyl}-propyl)-carbamic acid t-butylester;
N-{4-[3-chloro-4-(3-fluoro-benzyloxy)-phenylamino]-quinazolin-6-yl}-4-(2-methoxy-acetylamino)-butyramide;
N-{4-[3-chloro-4-(3-fluoro-benzyloxy)-phenylamino]-quinazolin-6-yl}-4-(2-methanesulfonyl-acetylamino)-butyramide;
4-acryloylamino-N-{4-[3-chloro-4-(3-fluoro-benzyloxy)-phenylamino]-quinazolin-6-yl}-butyramide;
N-(3-{4-[3-chloro-4-(3-fluoro-benzyloxy)-phenylamino]-quinazolin-6-ylcarbamoyl}-propyl)-benzamide;

N-(3-{4-[3-chloro-4-(3-fluoro-benzyloxy)-phenylamino]-quinazolin-6-ylcarbamoyl}-propyl)-oxalamic acid ethylester;
cyclopropylcarboxylic acid (3-{4-[3-chloro-4-(3-fluoro-benzyloxy)-phenylamino]-quinazolin-6-ylcarbamoyl}-propyl)-amide;
N-{4-[3-chloro-4-(3-fluoro-benzyloxy)-phenylamino]-quinazolin-6-yl}-4-(2-cyano-acetyl amino)-butyramide;
furan-3-carboxylic acid (3-{4-[3-chloro-4-(3-fluoro-benzyloxy)-phenylamino]-quinazolin-6-ylcarbamoyl}-propyl)-amide;
1H-pyrazol-4-carboxylic acid (3-{4-[3-chloro-4-(3-fluoro-benzyloxy)-phenylamino]-quinazolin-6-ylcarbamoyl}-propyl)-amide;
{3-[4-(3-chloro-4-fluoro-phenylamino)-quinazolin-6-ylcarbamoyl]-propyl}-carbamic acid t-butylester;
N-[4-(3-chloro-4-fluoro-phenylamino)-quinazolin-6-yl]-4-(2-methanesulfonyl-acetylamino)-butyramide;
4-acryloylamino-N-[4-(3-chloro-4-fluoro-phenylamino)-quinazolin-6-yl]-butyramide;
(3-{4-[3-methyl-4-(6-methyl-pyridin-3-yloxy)-phenylamino]-quinazolin-6-ylcarbonyl}-propyl)-carbamic acid t-butylester;
4-(2-methanesulfonyl-acetylamino)-N-{4-[3-methyl-4-(6-methyl-pyridin-3-yloxy)-phenyl amino]-quinazolin-6-yl}-butyramide;
4-acryloylamino-N-{4-[3-methyl-4-(6-methyl-pyridin-3-yloxy)-phenylamino]-quinazolin-6-yl}-butyramide;
4-(2-chloro-acetylamino)-N-{4-[3-chloro-4-(3-fluoro-benzyloxy)-phenylamino]-quinazolin-6-yl}-butyramide;
N-{4-[3-chloro-4-(3-fluoro-benzyloxy)-phenylamino]-quinazolin-6-yl}-4-(2-morpholin-4-yl-acetylamino)-butyramide;
N-{4-[3-chloro-4-(3-fluoro-benzyloxy)-phenylamino]-quinazolin-6-yl}-4-(2-dimethylamino-acetylamino)-butyramide;
N-{-4-[3-chloro-4-(3-fluoro-benzyloxy)-phenylamino]-quinazolin-6-yl}-4-[2-(4-methyl-piperazin-1-yl)-acetylamino]-butyramide;
N-{4-[3-chloro-4-(3-fluoro-benzyloxy)-phenylamino]-quinazolin-6-yl}-4-[2-(2-methoxy-ethylamino)-acetylamino]-butyramide;
N-{4-[3-chloro-4-(3-fluoro-benzyloxy)-phenylamino]-quinazolin-6-yl}-4-[2-(2-methanesulfonyl-ethylamino)-acetylamino]-butyramide;
4-(2-chloro-acetylamino)-N-{4-[3-methyl-4-(6-methyl-pyridin-3-yloxy)-phenylamino]-quinazolin-6-yl}-butyramide;
N-{4-[3-methyl-4-(6-methyl-pyridin-3-yloxy)-phenylamino]-quinazolin-6-yl}-4-(2-morpholin-4-yl-acetylamino)-butyramide;
4-(2-dimethylamino-acetylamino)-N-{4-[3-methyl-4-(6-methyl-pyridin-3-yloxy)-phenylamino]-quinazolin-6-yl}-butyramide;
N-{4-[3-methyl-4-(6-methyl-pyridin-3-yloxy)-phenylamino]-quinazolin-6-yl}-4-[2-(4-methyl-piperazin-1-yl)-acetylamino]-butyramide;
4-[2-(2-methanesulfonyl-ethylamino)-acetylamino]-N-{4-[3-methyl-4-(6-methyl-pyridin-3-yloxy)-phenylamino]-quinazolin-6-yl}-butyramide;
4-[2-(2-methoxy-ethylamino)-acetylamino]-N-{4-[3-methyl-4-(6-methyl-pyridin-3-yloxy)-phenylamino]-quinazolin-6-yl}-butyramide;
(4-{4-[3-chloro-4-(3-fluoro-benzyloxy)-phenylamino]-quinazolin-6-ylcarbamoyl}-butyl)-carbamic acid t-butylester;
5-(2-methoxy-acetylamino)-pentanoic acid {4-[3-chloro-4-(3-fluoro-benzyloxy)-phenylamino]-quinazolin-6-yl}-amide;
5-(2-methanesulfonyl-acetylamino)-pentanoic acid {4-[3-chloro-4-(3-fluoro-benzyloxy)-pentylamino]-quinazolin-6-yl}-amide;
N-{4-[3-chloro-4-(3-fluoro-benzyloxy)-phenylamino]-quinazolin-6-yl}-3-(2-methanesulfanyl-acetylamino)-propionamide;
N-{4-[3-chloro-4-(3-fluoro-benzyloxy)-phenylamino]-quinazolin-6-yl}-3-(2-methanesulfinyl-acetylamino)-propionamide;
N-{4-[3-chloro-4-(3-fluoro-benzyloxy)-phenylamino]-quinazolin-6-yl}-3-(2,2,2-trifluoro-acetylamino)-propionamide;
3-acetylamino-N-{4-[3-chloro-4-(3-fluoro-benzyloxy)-phenylamino]-quinazolin-6-yl}-propionamide;
acetic acid (2-{4-[3-chloro-4-(3-fluoro-benzyloxy)-phenylamino]-quinazolin-6-ylcarbamoyl}-ethylcarbamoyl)-methylester;
N-{4-[3-chloro-4-(3-fluoro-benzyloxy)-phenylamino]-quinazolin-6-yl}-3-[2-(2-dimethylamino-ethoxy)-acetylamino]-propionamide;
N-{4-[3-chloro-4-(3-fluoro-benzyloxy)-phenylamino]-quinazolin-6-yl}-3-(3-ethyl-ureido)-propionamide;
N-{4-[3-chloro-4-(3-fluoro-benzyloxy)-phenylamino]-quinazolin-6-yl}-3-(3-phenyl-ureido)-propionamide;
N-{4-[3-chloro-4-(3-fluoro-benzyloxy)-phenylamino]-quinazolin-6-yl}-3-(3-furan-2-ylmethyl-ureido)-propionamide;
(2-{4-[3-chloro-4-(3-fluoro-benzyloxy)-phenylamino]-quinazolin-6-ylcarbamoyl}-ethyl)-carbamic acid methylester;
(2-{4-[3-chloro-4-(3-fluoro-benzyloxy)-phenylamino]-quinazolin-6-ylcarbamoyl}-ethyl)-carbamic acid phenylester;
(2-{4-[3-chloro-4-(3-fluoro-benzyloxy)-phenylamino]-quinazolin-6-ylcarbamoyl}-ethyl)-carbamic acid benzylester;
N-{4-[3-chloro-4-(pyridin-2-ylmethoxy)-phenylamino]-quinazolin-6-yl}-3-(2-methoxy-acetylamino)-propionamide;
N-{4-[3-chloro-4-(pyridin-2-ylmethoxy)-phenylamino]-quinazolin-6-yl}-3-(2-methanesulfonyl-acetylamino)-propionamide;
N-(2-{4-[3-chloro-4-(pyridin-2-ylmethoxy)-phenylamino]-quinazolin-6-ylcarbamoyl}-ethyl)-acrylamide;
N-{4-[3-chloro-4-(pyridin-3-ylmethoxy)-phenylamino]-quinazolin-6-yl}-3-(2-methoxy-acetylamino)-propionamide;
N-{4-[3-chloro-4-(pyridin-3-ylmethoxy)-phenylamino]-quinazolin-6-yl}-3-(2-methanesulfonyl-acetylamino)-propionamide;
N-(2-{4-[3-chloro-4-(pyridin-3-ylmethoxy)-phenylamino]-quinazolin-6-ylcarbamoyl}-ethyl)-acrylamide;
N-{4-[3-chloro-4-(3-fluoro-benzyloxy)-phenylamino]-quinazolin-6-yl}-3-[2-(2-methoxy-ethoxy)-acetylamino]-propionamide;
5-methyl-isoxazol-4-carboxylic acid (2-{4-[3-chloro-4-(3-fluoro-benzyloxy)-phenylamino]-quinazol in-6-ylcarbamoyl}-ethyl)-amide;

N-{4-[3-chloro-4-(3-fluoro-benzyloxy)-phenylamino]-quinazolin-6-yl}-4-(2-methanesulfanyl-acetylamino)-butyramide;
N-{4-[3-chloro-4-(3-fluoro-benzyloxy)-phenylamino]-quinazolin-6-yl}-4-(2-methanesulfinyl-acetylamino)-butyramide;
N-[2-({4-[3-chloro-4-(3-fluoro-benzyloxy)-phenylamino]-quinazolin-6-yl}-methyl-carbamoyl)-ethyl]-acrylamide;
N-[2-({4-[3-chloro-4-(3-fluoro-benzyloxy)-phenylamino]-quinazolin-6-yl}-ethyl-carbamoyl)-ethyl]-acrylamide;
N-{2-[{4-[3-chloro-4-(3-fluoro-benzyloxy)-phenylamino]-quinazolin-6-yl}-(3-dimethylamino-propyl)-carbamoyl]-ethyl}-acrylamide;
N-(2-{4-[3-chloro-4-(3-fluoro-benzyloxy)-phenylamino]-quinazolin-6-ylcarbamoyl}-ethyl)-N-methyl-acrylamide;
N-(2-{4-[3-chloro-4-(pyridin-2-ylmethoxy)-phenylamino]-quinazolin-6-ylcarbamoyl}-ethyl)-N-methyl-acrylamide;
N-(2-{4-[3-chloro-4-(6-methyl-pyridin-2-ylmethoxy)-phenylamino]-quinazolin-6-ylcarbamoyl}-ethyl)-acrylamide;
(2S)-1-acryloyl-pyrrolidin-2-carboxylic acid {4-[3-chloro-4-(pyridin-2-ylmethoxy)-phenylamino]-quinazolin-6-yl}-amide;
(2S)-1-(1-oxo-butyn-2-yl)-pyrrolidin-2-carboxylic acid {4-[3-chloro-4-(pyridin-2-ylmethoxy)-phenylamino]-7-methoxy-quinazolin-6-yl}-amide;
(2S)-1-acryloyl-pyrrolidine-2-carboxylic acid {4-[3-chloro-4-(6-methyl-pyridin-2-ylmethoxy)-phenylamino]-quinazolin-6-yl}-amide;
(3R,5S)-acetic acid 1-acryloyl-5-{4-[3-chloro-4-(pyridin-2-ylmethoxy)-phenylamino]-quinazolin-6-ylcarbamoyl}-pyrrolidin-3-ylester;
(2S,4R)-1-acryloyl-4-hydroxyl-pyrrolidine-2-carboxylic acid {4-[3-chloro-4-(pyridin-2-ylmethoxy)-phenylamino]-quinazolin-6-yl)-amide;
(2S,4R)-1-acryloyl-4-ethylsulfanyl-pyrrolidine-2-carboxylic acid {4-[3-chloro-4-(pyridin-2-ylmethoxy)-phenylamino]-quinazolin-6-yl}-amide;
(2S,4R)-1-acryloyl-4-dimethylamino-pyrrolidine-2-carboxylic acid {4-[3-chloro-4-(pyridin-2-ylmethoxy)-phenylamino]-quinazolin-6-yl}-amide;
(2S)-1-acryloyl-pyrrolidine-2-carboxylic acid {4-[3-chloro-4-(pyridin-3-ylmethoxy)-phenylamino]-quinazolin-6-yl}-amide;
(2S)-1-acryloyl-pyrrolidine-2-carboxylic acid {4-[3-chloro-4-(pyridin-4-ylmethoxy)-phenylamino]-quinazolin-6-yl}-amide;
2-(1-acryloyl-pyrrolidin-2-yl)-N-{4-[3-chloro-4-(pyridin-2-ylmethoxy)-phenylamino]-quinazolin-6-yl}-acetamide;
1-acryloyl-pyrrolidine-3-carboxylic acid {4-[3-chloro-4-(pyridin-2-ylmethoxy)-phenylamino]-quinazolin-6-yl}-amide;
1-acryloyl-piperidine-4-carboxylic acid {4-[3-chloro-4-(pyridin-2-ylmethoxy)-phenylamino]-quinazolin-6-yl}-amide;
(2S)-1-acryloyl-pyrrolidine-2-carboxylic acid {4-[3-methyl-4-(6-methyl-pyridin-3-yloxy)-phenylamino]-quinazolin-6-yl}-amide;
(2S)-1-acryloyl-pyrrolidine-2-carboxylic acid [4-(3-ethynyl-phenylamino)-quinazolin-6-yl]-amide;
(2S)-1-acryloyl-pyrrolidine-2-carboxylic acid [4-(3-chloro-4-fluoro-phenylamino)-quinazolin-6-yl]amide;
(2S,4R)-1-acryloyl-4-ethanesulfonyl-pyrrolidine-2-carboxylic acid {4-[3-chloro-4-(pyridin-2-ylmethoxy)-phenylamino]-quinazolin-6-yl}-amide;
(2S,4R)-1-acryloyl-4-methoxy-pyrrolidine-2-carboxylic acid {4-[3-chloro-4-(pyridin-2-ylmethoxy)-phenylamino]-quinazolin-6-yl}-amide;
1-acryloyl-piperidine-3-carboxylic acid {4-[3-chloro-4-(pyridin-2-ylmethoxy)-phenylamino]-quinazolin-6-yl}-amide;
1-acryloyl-azetidine-3-carboxylic acid {4-[3-chloro-4-(pyridin-2-ylmethoxy)-phenylamino]-quinazolin-6-yl}-amide;
1-acryloyl-piperidine-2-carboxylic acid {4-[3-chloro-4-(pyridin-2-ylmethoxy)-phenylamino]-quinazolin-6-yl}-amide;
(2S)-1-acryloyl-pyrrolidine-2-carboxylic acid {4-[3-chloro-4-(pyridin-2-ylmethoxy)-phenylamino]-7-fluoro-quinazolin-6-yl}-amide;
(2S)-1-acryloyl-pyrrolidine-2-carboxylic acid {4-[3-chloro-4-(pyridin-2-ylmethoxy)-phenylamino]-7-methoxy-quinazolin-6-yl}-amide;
N-(2-{4-[3-chloro-4-(pyridin-2-ylmethoxy)-phenylamino]-7-methoxy-quinazolin-6-ylcarbamoyl}-ethyl)-acrylamide;
(2S)-1-acryloyl-pyrrolidin-2-carboxylic acid {7-methoxy-4-[3-methyl-4-(pyridin-2-ylmethoxy)-phenylamino]-quinazolin-6-yl}-amide;
2-(1-acryloyl-pyrrolidin-2-yl)-N-{4-[3-chloro-4-(pyridin-2-ylmethoxy)-phenylamino]-7-methoxy-quinazolin-6-yl}-acetamide;
(2S)-1-acryloyl-pyrrolidine-2-carboxylic acid {4-[3-chloro-4-(pyridin-2-ylmethoxy)-phenylamino]-7-ethoxy-quinazolin-6-yl}-amide;
(2S)-1-acryloyl-pyrrolidine-2-carboxylic acid {4-[3-chloro-4-(pyridin-2-ylmethoxy)-phenylamino]-7-ethylsulfanyl-quinazolin-6-yl}-amide;
(2S)-1-acryloyl-pyrrolidine-2-carboxylic acid {4-[3-chloro-4-(pyridin-2-ylmethoxy)-phenylamino]-7-cyclopropylmethoxy-quinazolin-6-yl}-amide;
(2S)-1-acryloyl-pyrrolidine-2-carboxylic acid {4-[3-chloro-4-(pyridin-2-ylmethoxy)-phenylamino]-7-cyclopentyloxy-quinazolin-6-yl}-amide;
N-(2-{4-[3-chloro-4-(pyridin-4-ylmethoxy)-phenylamino]-quinazolin-6-ylcarbamoyl}-ethyl)-acrylamide;
(2S)-1-(4-dimethylamino-buten-2-oyl)-pyrrolidine-2-carboxylic acid {4-[3-chloro-4-(pyridin-2-ylmethoxy)-phenylamino]-7-methoxy-quinazolin-6-yl}-amide;
(2S)-1-acryloyl-pyrrolidine-2-carboxylic acid {7-chloro-4-[3-chloro-4-(pyridin-2-ylmethoxy)-phenylamino]-quinazolin-6-yl}-amide;
(2S)-1-acryloyl-pyrrolidine-2-carboxylic acid {7-fluoro-4-[3-methyl-4-(pyridin-2-ylmethoxy)-phenylamino]-quinazolin-6-yl}-amide;
N-(2-{7-fluoro-4-[3-methyl-4-(pyridin-2-ylmethoxy)-phenylamino]-quinazolin-6-ylcarbamoyl}-ethyl)-acrylamide;
(2S)-1-acryloyl-2,5-dihydro-1H-pyrrol-2-carboxylic acid {4-[3-chloro-4-(pyridin-2-ylmethoxy)-phenylamino]-7-methoxy-quinazolin-6-yl}-amide;
(4R)-3-acryloyl-thiazolidin-4-carboxylic acid {4-[3-chloro-4-(pyridin-2-ylmethoxy)-phenylamino]-7-methoxy-quinazolin-6-yl}-amide;
1-acryloyl-azetidine-2-carboxylic acid {4-[3-chloro-4-(pyridin-2-ylmethoxy)-phenylamino]-quinazolin-6-yl}-amide;

1-acryloyl-azetidine-2-carboxylic acid {4-[3-chloro-4-(pyridin-2-ylmethoxy)-phenylamino]-7-methoxy-quinazolin-6-yl}-amide;

(2S)-1-acryloyl-pyrrolidine-2-carboxylic acid [4-[3-chloro-4-(pyridin-2-ylmethoxy)-phenylamino]-7-(2,2,2-trifluoro-ethoxy)-quinazolin-6-yl]-amide;

(2S)-1-acryloyl-pyrrolidine-2-carboxylic acid {4-[3-chloro-4-(pyridin-2-ylmethoxy)-phenylamino]-7-dimethylamino-quinazolin-6-yl}-amide;

(2S)-1-acryloyl-pyrrolidine-2-carboxylic acid [7-methoxy-4-(1-pyridin-2-ylmethyl-1H-indazol-5-ylamino)-quinazolin-6-yl]-amide;

(2S)-1-acryloyl-pyrrolidine-2-carboxylic acid {4-[3-methyl-4-(pyridin-2-ylmethoxy)-phenylamino]-7-ethoxy-quinazolin-6-yl}-amide;

(2S)-1-acryloyl-pyrrolidine-2-carboxylic acid [4-[3-chloro-4-(pyridin-2-ylmethoxy)-phenylamino]-7-(2-fluoro-ethoxy)-quinazolin-6-yl]-amide;

(2S)-1-acryloyl-pyrrolidine-2-carboxylic acid {4-[1-(3-fluoro-benzyl)-1H-indazol-5-ylamino]-7-methoxy-quinazolin-6-yl}-amide;

(1R)—N-(1-{4-[3chloro-4-(pyridin-2-ylmethoxy)-phenylamino]-7-methoxy-quinazolin-6-ylcarbamoyl}-ethyl)-acrylamide;

(1S)—N-(1-{4-[3-chloro-4-(pyridin-2-ylmethoxy)-phenylamino]-7-methoxy-quinazolin-6-ylcarbamoyl}-ethyl)-acrylamide;

(1S)—N-(1-{4-[3-chloro-4-(pyridin-2-ylmethoxy)-phenylamino]-7-methoxy-quinazolin-6-ylcarbamoyl}ethyl)-N-methyl-acrylamide;

N-(2-{4-[3-chloro-4-(pyridin-2-ylmethoxy)-phenylamino]-7-fluoro-quinazolin-6-ylcarbamoyl}-ethyl)-acrylamide;

(2S)-1-acryloyl-pyrrolidine-2-carboxylic acid [7-methoxy-4-(1-penta-2,4-dienyl-1H-indazol-5-ylamino)-quinazolin-6-yl]-amide;

(2S)-1-acryloyl-pyrrolidine-2-carboxylic acid {4-[3-chloro-4-(6-methyl-pyridin-2-ylmethoxy)-phenylamino]-7-methoxy-quinazolin-6-yl}-amide;

1-acryloyl-azetidine-2-carboxylic acid {4-[3-chloro-4-(pyridin-2-ylmethoxy)-phenylamino]-7-fluoro-quinazolin-6-yl}-amide;

1-acryloyl-piperidine-2-carboxylic acid {4-[3-chloro-4-(pyridin-2-ylmethoxy)-phenylamino]-7-methoxy-quinazolin-6-yl}-amide;

1-acryloyl-piperidine-4-carboxylic acid {4-[3-chloro-4-(pyridin-2-ylmethoxy)-phenylamino]-7-methoxy-quinazolin-6-yl}-amide;

1-acryloyl-pyrrolidine-3-carboxylic acid {4-[3-chloro-4-(pyridin-2-ylmethoxy)-phenylamino]-7-methoxy-quinazolin-6-yl}-amide;

1-acryloyl-azetidine-2-carboxylic acid {4-[3-chloro-4-(pyridin-2-ylmethoxy)-phenylamino]-7-ethoxy-quinazolin-6-yl}-amide;

1-acryloyl-azetidine-3-carboxylic acid {4-[3-chloro-4-(pyridin-2-ylmethoxy)-phenylamino]-7-methoxy-quinazolin-6-yl}-amide;

(3S)-1-acryloyl-piperidine-3-carboxylic acid {4-[3-chloro-4-(pyridin-2-ylmethoxy)-phenylamino]-7-methoxy-quinazolin-6-yl}-amide;

N-((1S)-1-{4-[3-chloro-4-(pyridin-2-ylmethoxy)-phenylamino]-7-methoxy-quinazolin-6-ylcarbamoyl}-ethyl)-N-ethyl-acrylamide;

(2S)-1-acryloyl-pyrrolidine-2-carboxylic acid {4-[3-chloro-4-(2-fluoro-ethoxy)-phenylamino]-7-methoxy-quinazolin-6-yl}-amide;

(2S)-1-acryloyl-pyrrolidine-2-carboxylic acid {4-[3-chloro-4-(pyridin-3-ylmethoxy)-phenylamino]-7-methoxy-quinazolin-6-yl}-amide;

(2S)-2-acryloylamino-N-{4-[3-chloro-4-(pyridin-2-ylmethoxy)-phenylamino]-7-methoxy-quinazolin-6-yl}-butyramide;

N-(2-{4-[3-chloro-4-(pyridin-2-ylmethoxy)-phenylamino]-7-methoxy-quinazolin-6-ylcarbamoyl}-2-fluoro-ethyl)-acrylamide;

(2S)-1-acryloyl-pyrrolidine-2-carboxylic acid {4-[3-chloro-4-(pyridin-3-ylmethoxy)-phenylamino]-7-(1-methyl-piperidin-4-ylmethoxy)-quinazolin-6-yl}-amide;

(1R)—N-(1-{4-[3-chloro-4-(pyridin-2-ylmethoxy)-phenylamino]-7-(2-methoxy-ethoxy)-quinazolin-6-ylcarbamoyl}-ethyl)-acrylamide;

(2S)-1-acryloyl-pyrrolidine-2-carboxylic acid {4-[3-chloro-4-(pyridin-3-ylmethoxy)-phenylamino]-7-(3-morpholin-4-yl-propoxy)-quinazolin-6-yl}-amide;

N-({4-[3-chloro-4-(pyridin-2-ylmethoxy)-phenylamino]-7-methoxy-quinazolin-6-ylcarbamoyl}-methyl)-acrylamide N-({4-[3-chloro-4-(3-fluoro-benzyloxy)-phenylamino]-7-methoxy-quinazolin-6-ylcarbamoyl}-methyl)-acrylamide;

(3S)-3-acryloylamino-N-{4-[3-chloro-4-(pyridin-2-ylmethoxy)-phenylamino]-7-methoxy-quinazolin-6-yl}-butyramide;

(2S)-1-acryloyl-pyrrolidine-2-carboxylic acid [4-[3-chloro-4-(pyridin-2-ylmethoxy)-phenylamino]-7-(2-methoxyethoxy)-quinazolin-6-yl]-amide;

(1S)—N-{1-[4-[3-chloro-4-(3-fluoro-benzyloxy)-phenylamino]-7-(2-methoxyethoxy)-quinazolin-6-ylcarbamoyl}-ethyl)-acrylamide;

(2S)-1-acryloyl-pyrrolidine-2-carboxylic acid {4-[3-chloro-4-(3-fluoro-benzyloxy)-phenylamino]-7-(2-methoxyethoxy)-quinazolin-6-yl}-amide;

(1S)—N-(1-{4-[3-chloro-4-(pyridin-2-ylmethoxy)-phenylamino]-7-methoxy-quinazolin-6-ylcarbamoyl}-ethyl)-acrylamide;

N-{[4-[3-chloro-4-(3-fluoro-benzyloxy)-phenylamino]-7-(2-methoxyethoxy)-quinazolin-6-ylcarbamoyl]-methyl}-acrylamide;

N-({4-[3-chloro-4-(pyridin-2-ylmethoxy)-phenylamino]-7-(2-methoxyethoxy)-quinazolin-6-ylcarbamoyl}-methyl]-acrylamide;

(1S)—N-(1-{4-[3-chloro-4-(pyridin-2-ylemthoxy)-phenylamino]-7-(3-morpholin-4-yl-propoxy)-quinazolin-6-ylcarbamoyl}-ethyl-acrylamide;

(1S)—N-(1-{4-[3-chloro-4-(pyridin-2-ylmethoxy)-phenylamino]-7-(3-methoxypropoxy)-quinazolin-6-ylcarbamoyl}-ethyl)-acrylamide;

(2S)-2-acryloylamino-N-{4-[3-chloro-4-(3-fluoro-benzyloxy)-phenylamino]-7-methoxy-quinazolin-6-yl}-4-methylsulfanyl-butyramide;

(2S)-2-acryloylamino-N-{4-[3-chloro-4-(3-fluoro-benzyloxy)-phenylamino]-7-(2-methoxyethoxy)-quinazolin-6-yl}-4-methylsulfanyl-butyramide;

(2S)-2-acryloylamino-N-{4-[3-chloro-4-(3-fluoro-benzyloxy)-phenylamino]-7-methoxy-quinazolin-6-yl}-4-methylsulfanyl-butyramide;

(2S)-2-acryloylamino-N-{4-[3-chloro-4-(pyridin-2-ylmethoxy)-phenylamino]-quinazol in-6-yl}-3-methyl-butyramide; and (2S)-2-acryloylamino-4-methyl-pentanoic acid {4-[3-chloro-4-(pyridin-2-ylmethoxy)-phenylamino]-quinazolin-6-yl}-amide.

4. A process for preparing the quinazoline derivative of claim 1, which comprises the step of subjecting a compound of formula (IV) to a condensation reaction with a compound of formula (V):

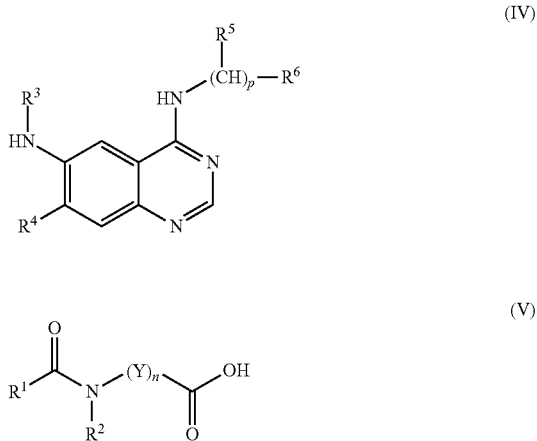

wherein,
$R^1$, $R^2$, $R^3$, $R^4$, $R^5$, $R^6$, Y, n and p have same meanings as defined in claim 1.

5. A process for preparing the quinazoline derivative of claim 1, which comprises the step of subjecting a compound of formula (II) to a condensation reaction with a compound of formula (IX):

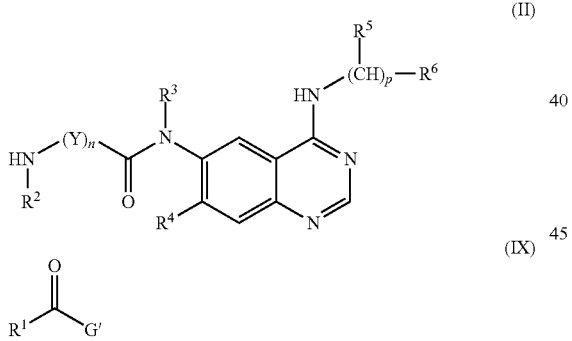

wherein,
$R^1$, $R^2$, $R^3$, $R^4$, $R^5$, $R^6$, Y, n and p have same meanings as defined in claim 1, and G' is halogen, hydroxy or $C_{1-6}$alkanoyloxy.

6. The process of claim 4, wherein the condensation reaction is carried out in the presence of a condensation reagent selected from the group consisting of 1-(3-dimethylaminopropyl)-3-ethylcarbodiimide, N,N-dicyclohexyldiimide, C1-6alkylchloroformate, carbonyldiimidazole and O-(1H-benzotriazol-1-yl)-N,N,N',N'-tetramethyluronium tetrafluoroborate.

7. The process of claim 4, wherein the condensation reaction is carried out in a solvent selected form the group consisting of methylene chloride, chloroform, N,N-dimethylformamide, THF, 1,4-dioxane, acetonitrile and a mixture thereof at a temperature ranging from −20° C. to the boiling point of the solvent.

8. The process of claim 5, wherein the compound of formula (II) is prepared by subjecting a compound of formula (IV) to a condensation reaction with a compound of formula (VIII) to obtain a compound of formula (III), followed by removing the amine protecting group P from the compound of formula (III):

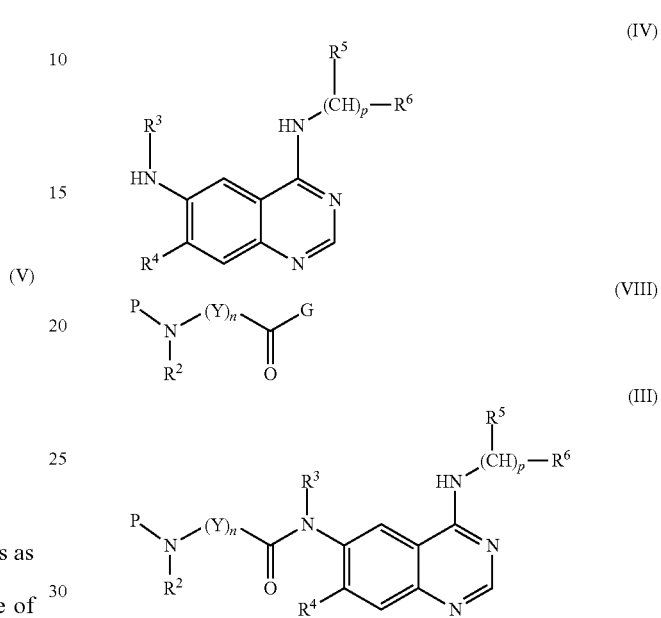

wherein,
$R^2$, $R^3$, $R^4$, $R^5$, $R^6$, Y, n and p have same meanings as defined in claim 1, P is an amine protecting group, and G is halogen, hydroxy or $C_{1-6}$alkanoyloxy.

9. The process of claim 4, wherein the compound of formula (IV) is prepared by reacting a compound of formula (XVII) with a compound of formula (XX) to obtain a compound of formula (XVI), followed by reducing the compound of formula (XVI):

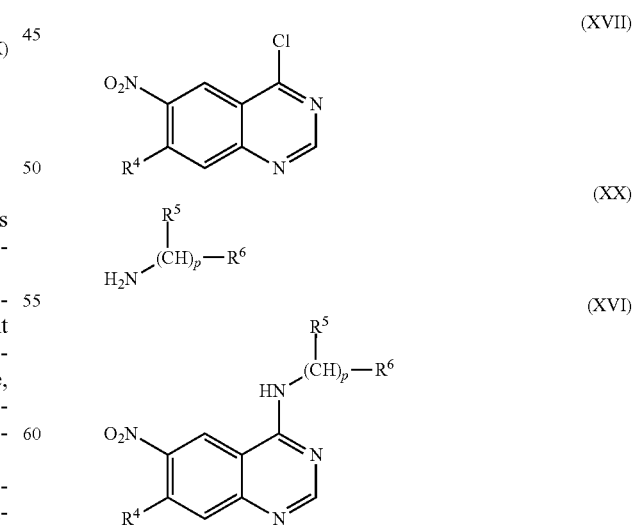

wherein,
$R^4$, $R^5$, $R^6$ and p have same meanings as defined in claim 1.

10. A pharmaceutical composition comprising the compound or salt defined in claim 1 as an active ingredient and a pharmaceutically acceptable carrier.

11. The composition of claim 10, which is administered in combination with an anticancer agent selected from the group consisting of cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents and antiandrogen.

* * * * *